US008124592B2

(12) United States Patent
Nabel et al.

(10) Patent No.: US 8,124,592 B2
(45) Date of Patent: Feb. 28, 2012

(54) DEVELOPMENT OF A PREVENTIVE VACCINE FOR FILOVIRUS INFECTION IN PRIMATES

(

OTHER PUBLICATIONS

Sato, Y. et al. "Immunostimulatory DNA sequences necessary for effective intradermal gene immunization," 1996, Science 273:352-354.

Schneider, J. et al. "Enhanced immunogenicity for CD8 + T cell induction and complete protective efficacy of malaria DNA vaccination by boosting with modified vaccinia virus Ankara," 1998, Nature Med. 4:397-402.

Sedegah, M. et al. "Boosting with recombinant vaccinia increases immunogenicity and protective efficacy of malaria DNA vaccine," 1998, PNAS USA 95:7648-7653.

Sedegah, M. et al. "Protection against malaria by immunization with plasmid DNA encoding circumsporozoite protein," 1994, PNAS USA 91:9866-9870.

Sullivan, N.J. et al. "Ebola virus pathogenesis and vaccine development" 2000, Symposium on Marburg and Ebola Viruses, Marburg, Germany, Oct. 1-4, Abstract 23, p. 35.

Sullivan, N.J. et al., "Accelerated vaccination for Ebola virus haemorrhagic fever in non-human primates," 2003, 424: 681-684.

Sullivan, N.J. et al., "Development of a preventive vaccine for Ebola virus infection in primates," 2000, Nature, 408: 605-609.

Tang, D.C. et al. "Genetic immunization is a simple method for eliciting an immune response," 1992, Nature 356:152-154.

Ulmer, J.B. et al. "Heterologous protection against influenza by injection of DNA encoding a viral protein," 1993, Science 259:1745-1749.

Vanderzanden, L. et al. "DNA vaccines expressing either the GP or NP genes of Ebola virus protect mice from lethal challenge," 1998, Virology 246:134-144.

Wang, B. et al. "Gene inoculation generates immune responses against human immunodeficiency virus type 1," 1993, PNAS USA 90:4156-4160.

Wilson, J. et al. "Epitopes involved in antibody-mediated protection from Ebola virus," 2000, Science 287:1664-1666.

Xiang, Z.Q. et al. 1996 "A replication-defective human adenovirus recombinant serves as a highly efficacious vaccine carrier," Virology 219:220-227.

Xu, L. et al. "Immunization for Ebola virus infection," 1998, Nature Med. 4:37-42.

Yang, Z. et al. "Distinct cellular interactions of secreted and transmembrane Ebola virus glycoproteins" 1998, Science 279:1034-1037.

Yang, Z. et al. "Identification of the Ebola virus glycoprotein as the main viral determinant of vascular cell cytotoxicity and injury" 2000, Nature Med. 6:886-889.

Yang, Z.Y. et al., "Overcoming immunity to a viral vaccine by DNA priming before vector boosting," 2003, J. Virol. 77(1): 799-803.

pVR1012-GP(Z)

FIG. 1 pVR1012-GP(Z) delta MUC delta FUR

- Dra III (6359)
- Xho I (6223)
- kanamycin resistance
- Pvu I (5827)
- Hin dIII (5703)
- Nde I (185)
- Nde I (571)
- CMV enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Ebola GP Zaire delta MUC, delta FUR
- Earl/3436bp
- Pst I (3130)
- Bcl I (3215)
- Kpn I (3565)
- Sph I (3784)
- Kpn I (3812)
- bovine growth hormone poly A pVRC 6003
6561 bp

FIG. 4 pVR1012-GP(Z) delta GP2 delta C-term A pVRC 6005
6887 bp

- Dra III (6685)
- Xho I (6549)
- kanamycin resistance
- Pvu I (6153)
- Hind III (6029)
- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Ebola GP Zaire(MscII/BspMI)
- Pst I (3022)
- Bsp I (3088)
- Bcl I (3414)
- MscI/BspMI
- Bsp MI (3623)
- Kpn I (3891)
- Sph I (4110)
- Kpn I (4138)
- bovine growth hormone poly A
- Bst XI (4225)

FIG. 6

FIG. 11 pAdApt Ebola GP(R) (dTM)

- Pvu I (7502)
- Amp
- Ad5(bp1-454)
- Nde I (843)
- CMV enhancer
- Pml I (1279)
- Bcl I (1283)
- Eco RV (1291)
- Bcl I (1425)
- Nde I (2001)
- Pml I (6026)
- Xho I (5823)
- Nar I (5554)
- Kas I (5553)
- VRC6110
- 8131 bp
- Ebola GP(Reston)(dTM)
- Pvu I (2784)
- Kpn I (3079)
- Xba I (3238)
- Ad5(bp3511-6093)
- Bovine Growth Hormone Poly A
- Kpn I (3494)
- LoxP

FIG. 12 pVR1012-GP(S)

pVRC 6200
7082 bp

- Dra III (6880)
- Cla I (6653)
- kanamycin resistance
- Pvu I (6348)
- Hind III (6224)
- Nde I (185)
- Msc I (248)
- Nde I (571)
- CMV enhancer
- Sac II (992)
- CMV IE 5' UTR
- Bsp EI (1436)
- CMV IE Intron
- Hpa I (1755)
- Sal I (1875)
- Pml I (1882)
- Bcl I (1886)
- Not I (1899)
- Not I (1928)
- Xmn I (4650)
- bovine growth hormone poly A
- Kpn I (4333)
- Xba I (4077)
- Hpa I (3491)
- Ebola Glycoprotein Sudan subtype (#U28134)

FIG. 13 pVR1012x/s Ebola GP(S)

VRC6201
7087 bp

- Dra III (6885)
- Xho I (6749)
- Cla I (6658)
- Xma I (6475)
- Kan r
- Pvu I (6353)
- Hin d III (6229)
- Nde I (185)
- Nde I (571)
- CMV enhancer
- Sac II (992)
- CMV IE 5' UTR
- Sph I (1092)
- CMV IE Intron
- Hpa I (1755)
- Sal I (1875)
- Pml I (1882)
- Bcl I (1886)
- Not I (1899)
- Xho I (2161)
- Xma I (2394)
- Ebola GP(S)
- Hpa I (3462)
- Xba I (4048)
- Sph I (4276)
- TbGH
- Sfi I (4646)

FIG. 14 pVR1012-GP(S) delta TM

Plasmid map of pVRC 6202 (6940 bp) showing:
- Dra III (6738)
- Cla I (6511)
- kanamycin resistance
- Pvu I (6206)
- Hind III (6082)
- Nde I (185)
- Msc I (248)
- Nde I (571)
- CMV enhancer
- Sac II (992)
- CMV IE 5' UTR
- Bsp EI (1436)
- CMV IE Intron
- Hpa I (1755)
- Sal I (1875)
- Not I (1903)
- Eco RV (1922)
- Eco RV (2191)
- Ebola Glycoprotein Sudan Subtype (#U28134)
- Hpa I (3466)
- Kpn I (4191)
- bovine growth hormone poly A
- Xmn I (4508)

FIG. 15 pVR1012-GP(IC)

Plasmid map of pVRC 6300 (7002 bp) showing restriction sites:
- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Eco RV (1894)
- Not I (1899)
- Xba I (1906)
- Xho I (2665)
- Ebola Glycoprotein Ivory Coast subtype (#U28006)
- Bst XI (2982)
- Bsp MI (3485)
- Msc I (3619)
- Xba I (3997)
- Bgl II (4018)
- Sph I (4225)
- Kpn I (4253)
- bovine growth hormone poly A
- Bst XI (4340)
- Xmn I (4570)
- Hind III (6144)
- Pvu I (6268)
- kanamycin resistance
- Cla I (6573)
- Xho I (6664)
- Dra III (6800)

FIG. 16 pVR1012x/s Ebola GP(IC)

*Dra* III (6834)
*Xho* I (6698)
*Cla* I (6607)
*Xma* I (6424)
Kan r
*Pvu* I (6302)
*Hin* d III (6178)

*Nde* I (185)
*Nde* I (571)
CMV enhancer
*Sac* II (992)
CMV IE 5' UTR
*Sph* I (1092)
CMV IE Intron
*Hpa* I (1755)
*Pst* I (1865)
*Sal* I (1875)
*Pml* I (1882)
*Eco* RV (1894)
*Not* I (1899)
*Xba* I (1906)
*Eco* RI (1910)
*Xho* I (2665)
Ebola GP(IC)

VRC6301
7036 bp

*Sfi* I (4595)
TbGH
*Sph* I (4225)
*Bgl* II (4018)
*Xba* I (3997)
*Eco* RI (3993)

FIG. 17 pVR1012x/s Ebola GP(IC)(dTM)

- Nde I (185)
- Nde I (571)
- CMV Enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Bam HI (2536)
- Xho I (2645)
- Ebola GP(Ivory Coast)(dTM)
- Bam HI (3397)
- Bgl II (3871)
- Sph I (4078)
- Kpn I (4106)
- Bovine Growth Hormone Poly A
- Sfi I (4448)
- Hin d III (6031)
- Pvu I (6155)
- Kan
- Cla I (6460)
- Xho I (6551)
- Dra III (6687)

VRC6303
6889 bp

FIG. 19 pVR1012x/s-sGP(IC)

Plasmid map of pVRC 6351 (7023 bp) with the following features labeled:

- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Eco RV (1894)
- Not I (1899)
- Xba I (1906)
- Xho I (2665)
- Ebola Secreted Glycoprotein Ivory Coast (#U28006)
- Bst XI (2982)
- Bsp MI (3485)
- Msc I (3619)
- Xba I (3997)
- Bgl II (4018)
- Sph I (4225)
- Kpn I (4253)
- bovine growth hormone poly A
- Bst XI (4340)
- Sfi I (4582)
- Hind III (6165)
- Pvu I (6289)
- kanamycin resistance
- Cla I (6594)
- Xho I (6685)
- Dra III (6821)

FIG. 21 pVR1012-NP

Dra III (7093)
Xho I (6957)
Cla I (6866)
kanamycin resistance
Pvu I (6561)
Hind III (6437)

CMV enhancer
Sac II (992)
CMV IE 5' UTR
Bsp EI (1436)
CMV IE Intron
Pvu II (1701)
Hpa I (1755)
Pst I (1865)
Sal I (1875)
Pml I (1882)
Eco RV (1894)
Not I (1899)
Xba I (1906)
BamH I (1921)
Cla I (1930)
Kas I (1970)
Nar I (1971)
Bgl II (2008)
Bsp MI (2010)
Bsp MI (2115)
Bst XI (2509)

pVRC 6400
7295 bp

Xmn I (4863)
Bst XI (4633)
bovine growth hormone poly A
Kpn I (4546)
Xmn I (4128)

Xba I (3401)
Ebola Nucleoprotein (#J04337)

FIG. 22 pVR1012x/s Ebola-NP

Dra III (7127)
Xho I (6991)
Cla I (6900)
Xma I (6717)
Kan r
Pvu I (6595)
Hin d III (6471)

CMV enhancer
Sac II (992)
CMV IE 5' UTR
CMV IE Intron
Pvu II (1701)
Hpa I (1755)
Pst I (1865)
MCS
Sal I (1875)
Pml I (1882)
Eco RV (1894)
Not I (1899)
Xba I (1906)
Bam H I (1921)
Cla I (1930)
Bgl II (2008)

VRC6401
7329 bp

Sfi I (4888)
TbGH
Untranslated NP
Ebola NP
Xba I (3401)

FIG. 31 pVR1012x/s Lassa GP

Dra III (6245)
Xho I (6109)
Cla I (6018)
Kan
Pvu I (5713)
Hin d III (5589)
Nde I (185)
Nde I (571)
CMV Enhancer
Sac II (992)
CMV IE 5' UTR
Sph I (1092)
CMV IE/Intron
Pvu II (1701)
Hpa I (1755)
Pst I (1865)
Sal I (1875)
Pml I (1882)
Eco RV (1894)
Not I (1899)
Xba I (1906)
Eco RI (1950)

VRC6800
6447 bp

Sfi I (4006)
Bovine Growth Poly A
Sph I (3649)
Bgl II (3442)
Bam H I (3436)
Hin d III (3273)
Lassa GP(Strain LP)
Dra III (2785)
Pvu II (2848)

FIG. 38 pVR1012x/s Marburg (codon optimized)

VRC6703
6902 bp

- Dra III (6700)
- Xho I (6564)
- Cla I (6473)
- Xma I (6290)
- kanamycin resistance
- Pvu I (6168)
- Hin d III (6044)
- Sfi I (4461)
- bovine growth hormone poly A
- Bgl II (3884)
- Bam HI (3878)
- Pml I (3874)
- Dra III (3207)
- Nde I (185)
- Nde I (571)
- CMV enhancer
- Nco I (697)
- Sac II (992)
- CMV IE 5' UTR
- CMV IE Intron
- Pvu II (1701)
- Hpa I (1755)
- Nco I (1848)
- Sal I (1875)
- Pml I (1882)
- Eco RV (1894)
- Not I (1899)
- Xba I (1906)
- Eco RV (1914)
- Hpa I (2433)
- Marburg (codon optimized)

DEVELOPMENT OF A PREVENTIVE VACCINE FOR FILOVIRUS INFECTION IN PRIMATES

This application is a division of U.S. patent application Ser. No. 10/491,121, filed Aug. 23, 2004, which is a 371 national phase of PCT/US02/30251, filed Sep. 24, 2002, which claims priority to U.S. Provisional Patent Application No. 60/326,476, filed Oct. 1, 2001, the contents of both are incorporated herein in the entirety for all purposes.

FIELD OF THE INVENTION

The present invention relates generally to viral vaccines and, more particularly, to filovirus vaccines and methods of eliciting an immune response against a filovirus or a disease caused by infection with filovirus.

BACKGROUND OF THE INVENTION

The Ebola viruses, and the genetically-related Marburg virus, are filoviruses associated with outbreaks of highly lethal hemorrhagic fever in humans and primates in North America, Europe, and Africa (Peters, C. J. et al. in: *Fields Virology*, eds. Fields, B. N. et al. 1161-1176, Philadelphia, Lippincott-Raven, 1996; Peters, C. J. et al. 1994 *Semin Virol* 5:147-154). Ebola viruses are negative-stranded RNA viruses comprised of four subtypes, including those described in the Zaire, Sudan, Reston, and Ivory Coast episodes (Sanchez, A. et al. 1996 *PNAS USA* 93:3602-3607). Although several subtypes have been defined, the genetic organization of these viruses is similar, each containing seven linearly arrayed genes. Among the viral proteins, the envelope glycoprotein exists in two alternative forms, a 50-70 kilodalton (kDa) secreted protein of unknown function encoded by the viral genome and a 130 kDa transmembrane glycoprotein generated by RNA editing that mediates viral entry (Peters, C. J. et al. in: *Fields Virology*, eds. Fields, B. N. et al. 1161-1176, Philadelphia, Lippincott-Raven, 1996; Sanchez, A. et al. 1996 *PNAS USA* 93:3602-3607). Other structural gene products include the nucleoprotein (NP), matrix proteins VP24 and VP40, presumed nonstructural proteins VP30 and VP35, and the viral polymerase (reviewed in Peters, C. J. et al. in: *Fields Virology*, eds. Fields, B. N. et al. 1161-1176, Philadelphia, Lippincott-Raven, 1996). Although spontaneous variation of its RNA sequence does occur in nature, there appears to be less nucleotide polymorphism within Ebola subtypes than among other RNA viruses (Sanchez, A. et al. 1996 *PNAS USA* 93:3602-3607), suggesting that immunization may be useful in protecting against this disease. Previous attempts to elicit protective immune responses against Ebola virus using traditional active and passive immunization approaches have, however, not succeeded in primates (Peters, C. J. et al. in: *Fields Virology*, eds. Fields, B. N. et al. 1161-1176, Philadelphia, Lippincott-Raven, 1996; Clegg, J. C. S. et al. 1997 *New Generation Vaccines*, eds.: Levine, M. M. et al. 749-765, New York, N.Y. Marcel Dekker, Inc.; Jahrling, P. B. et al. 1996 *Arch Virol Suppl* 11:135-140). It would thus be desirable to provide a vaccine to elicit an immune response against a filovirus or disease caused by infection with filovirus. It would further be desirable to provide methods of making and using said vaccine.

SUMMARY OF THE INVENTION

Outbreaks of hemorrhagic fever caused by the Ebola virus are associated with high mortality rates that are a distinguishing feature of this human pathogen. The highest lethality is associated with the Zaire subtype, one of four strains identified to date (Feldmann, H. et al. 1994 *Virology* 199:469-473; Sanchez, A. et al. 1996 *PNAS USA* 93:3602-3607). Its rapid progression allows little opportunity to develop natural immunity, and there is currently no effective anti-viral therapy. Therefore, vaccination offers a promising intervention to prevent infection and limit spread. Here we describe a highly effective vaccine strategy for Ebola virus infection in primates. A combination of DNA immunization and boosting with adenoviral vectors that encode viral proteins generated cellular and humoral immunity in cynomolgus macaques. Challenge with a lethal dose of the highly pathogenic, wild-type, 1976 Mayinga strain of Ebola Zaire virus resulted in uniform infection in controls, who progressed to a moribund state and death in less than one week. In contrast, all vaccinated animals were asymptomatic for more than six months, with no detectable virus after the initial challenge. These findings demonstrate that it is possible to develop a preventive vaccine against Ebola virus infection in primates.

BRIEF DESCRIPTION OF THE DRAWINGS

Figure 1:
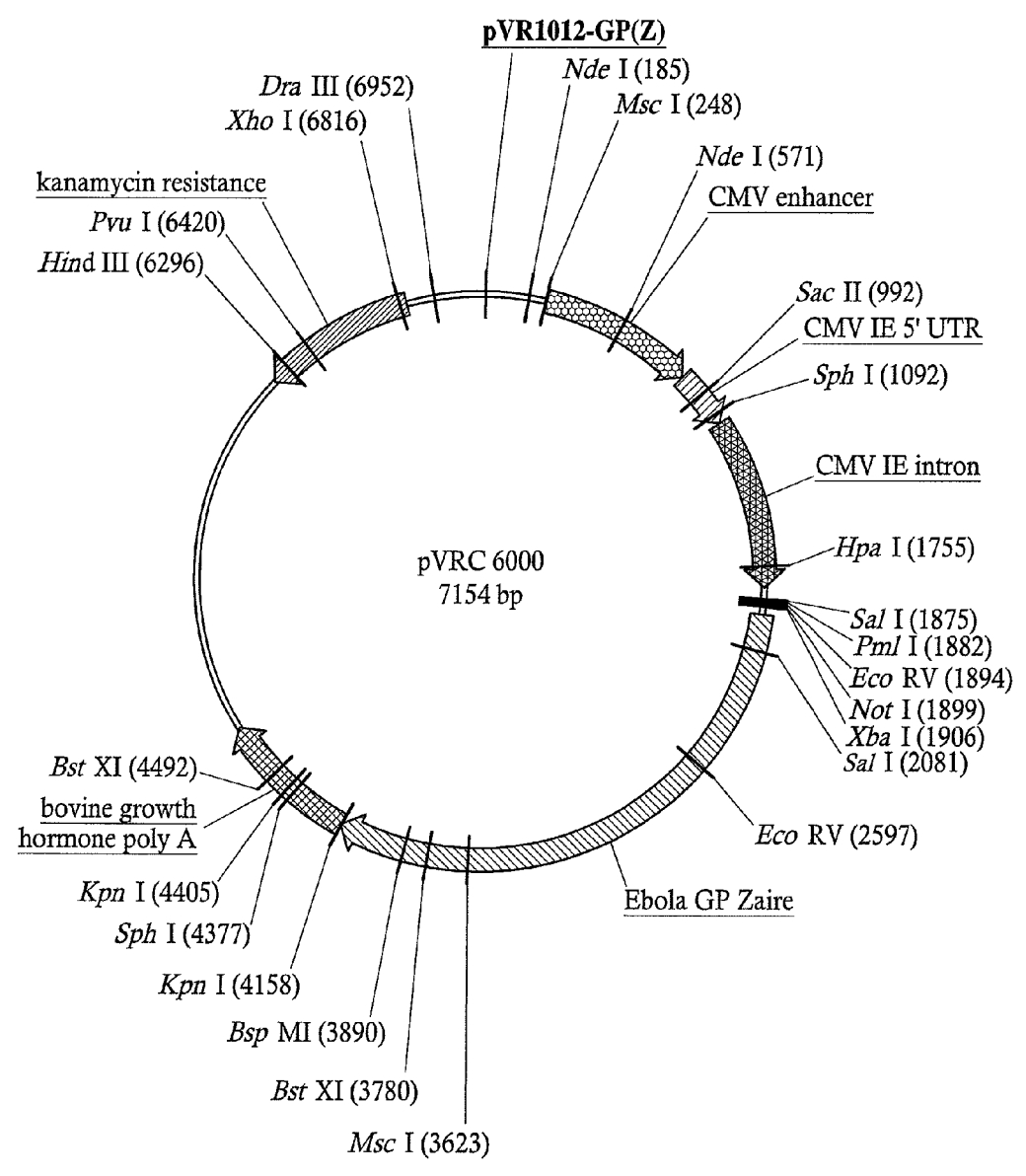

FIG. 1 shows VRC6000 (pVR1012-GP(Z)) construct map (see, Ebola/Marburg/Lassa Plasmids, and Recombinant Adenoviruses in Table 2).

FIG. 4 shows VRC6003 (pVR1012-GP(Z) delta MUC delta FUR) construct map (see, Ebola/Marburg/Lassa Plasmids, and Recombinant Adenoviruses in Table 2).

FIG. 6 shows VRC6005 (pVR1012-GP(Z) delta GP2 delta C-term A) construct map (see, Ebola/Marburg/Lassa Plasmids, and Recombinant Adenoviruses in Table 2).

Figure 11:
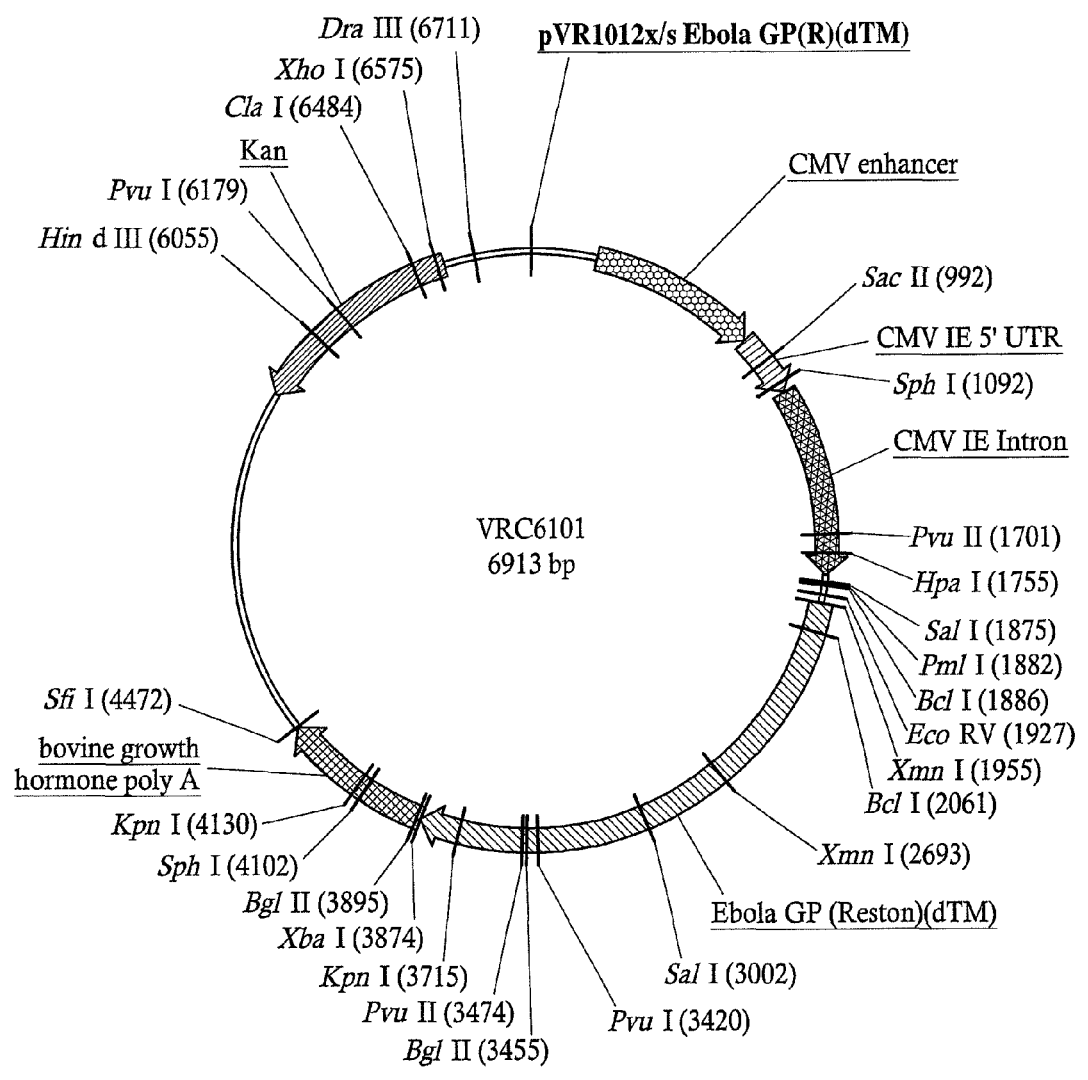

FIG. 11 shows VRC 6101 (pVR1012x/s Ebola GP(R) (dTM)) construct map (see, Ebola/Marburg/Lassa Plasmids, and Recombinant Adenoviruses in Table 2).

FIG. 12 shows VRC 6110 (pAdApt Ebola GP(R) (dTM)) construct map (see, Ebola/Marburg/Lassa Plasmids, and Recombinant Adenoviruses in Table 2).

FIG. 13 shows VRC6200 (pVR1012-GP(S)) construct map (see, Ebola/Marburg/Lassa Plasmids, and Recombinant Adenoviruses in Table 2).

FIG. 14 shows VRC 6201 (pVR1012x/s Ebola GP(S)) construct map (see, Ebola/Marburg/Lassa Plasmids, and Recombinant Adenoviruses in Table 2).

FIG. 15 shows VRC6202 (pVR1012-GP(S) delta TM) construct map (see, Ebola/Marburg/Lassa Plasmids, and Recombinant Adenoviruses in Table 2).

FIG. 16 shows VRC6300 (pVR1012-GP(IC)) construct map (see, Ebola/Marburg/Lassa Plasmids, and Recombinant Adenoviruses in Table 2).

FIG. 17 shows VRC6301 (pVR1012x/s-GP(IC)) construct map (see, Ebola/Marburg/Lassa Plasmids, and Recombinant Adenoviruses in Table 2).

FIG. 19 shows VRC6303 (pVR1012x/s Ebola GP (IC) (dTM)) construct map (see, Ebola/Marburg/Lassa Plasmids, and Recombinant Adenoviruses in Table 2).

FIG. 21 shows VRC6351 (pVR1012x/s-SGP(IC)) construct map (see, Ebola/Marburg/Lassa Plasmids, and Recombinant Adenoviruses in Table 2).

FIG. 22 shows VRC6400 (pVR1012-NP) construct map (see, Ebola/Marburg/Lassa Plasmids, and Recombinant Adenoviruses in Table 2).

FIG. 23 shows VRC6401 (pVR1012x/s-NP) construct map (see, Ebola/Marburg/Lassa Plasmids, and Recombinant Adenoviruses in Table 2).

Figure 27:
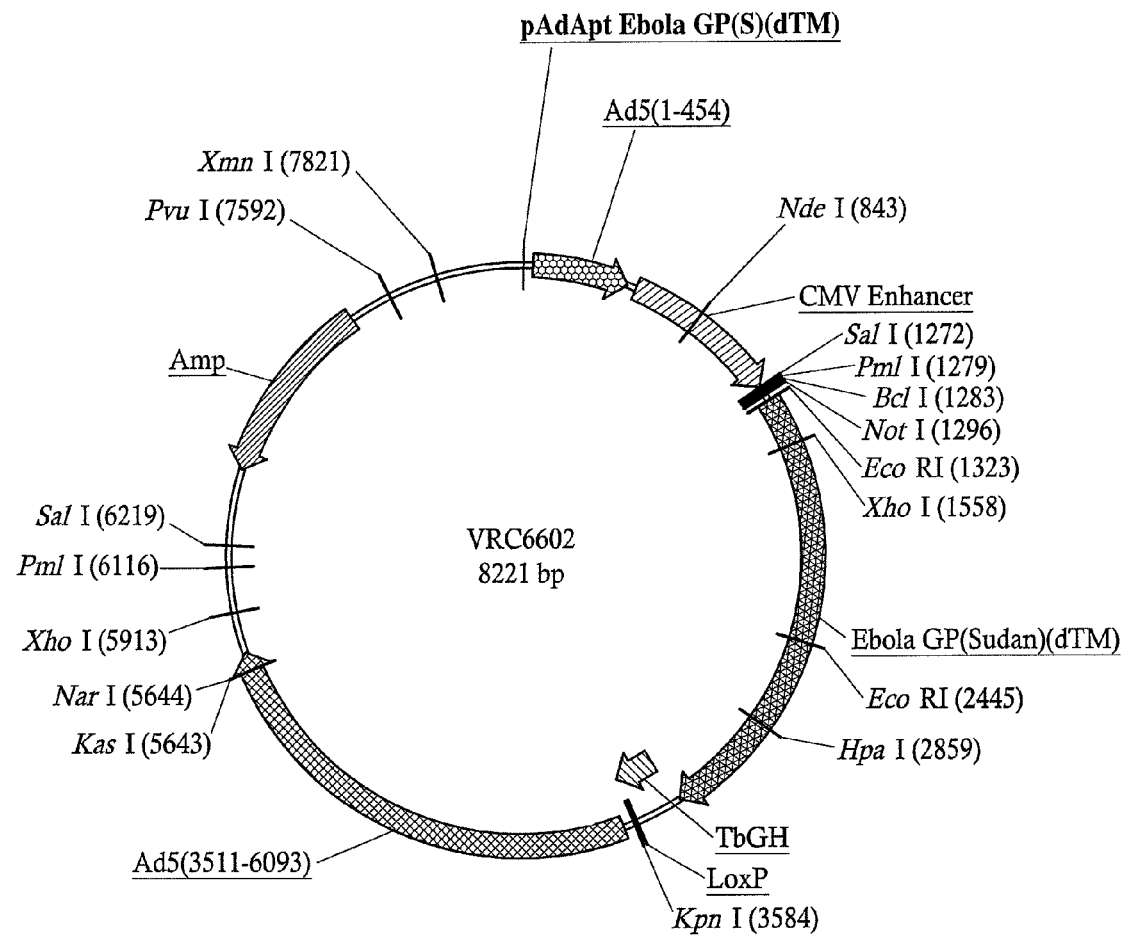

FIG. 27 shows VRC6602 (pAdApt Ebola GP(S)(dTM)) construct map (see, Ebola/Marburg/Lassa Plasmids, and Recombinant Adenoviruses in Table 2).

Figure 30:
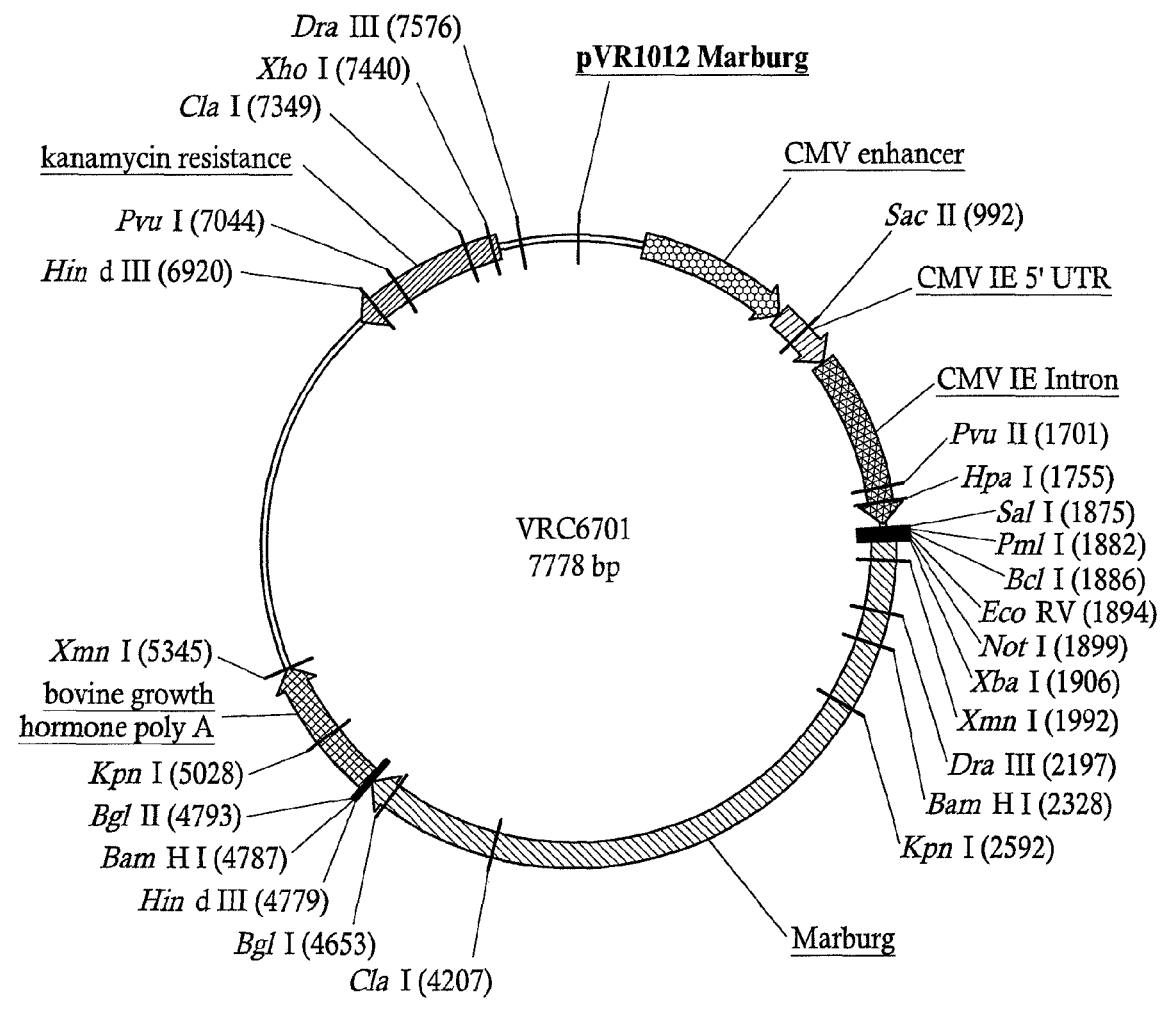

FIG. 30 shows VRC6701 (pVR1012-Marburg) construct map (see, Ebola/Marburg/Lassa Plasmids, and Recombinant Adenoviruses in Table 2).

Figure 31:
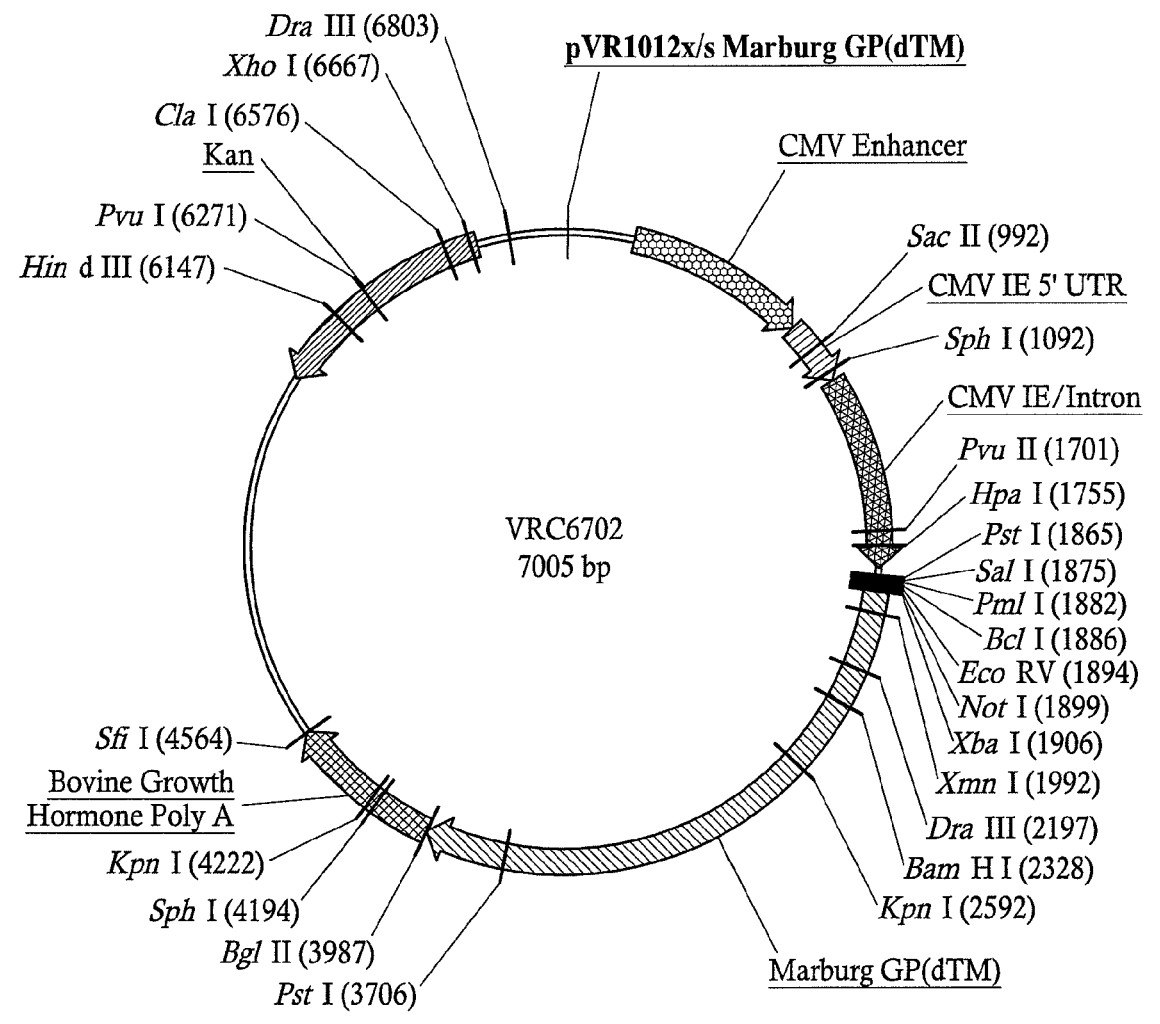

FIG. 31 shows VRC6702 (pVR1012x/s Marburg GP (dTM)) construct map (see, Ebola/Marburg/Lassa Plasmids, and Recombinant Adenoviruses in Table 2).

FIG. 33 shows VRC6800 (pVR1012x/s Lassa GP) construct map (see, Ebola/Marburg/Lassa Plasmids, and Recombinant Adenoviruses in Table 2).

Figure 37:
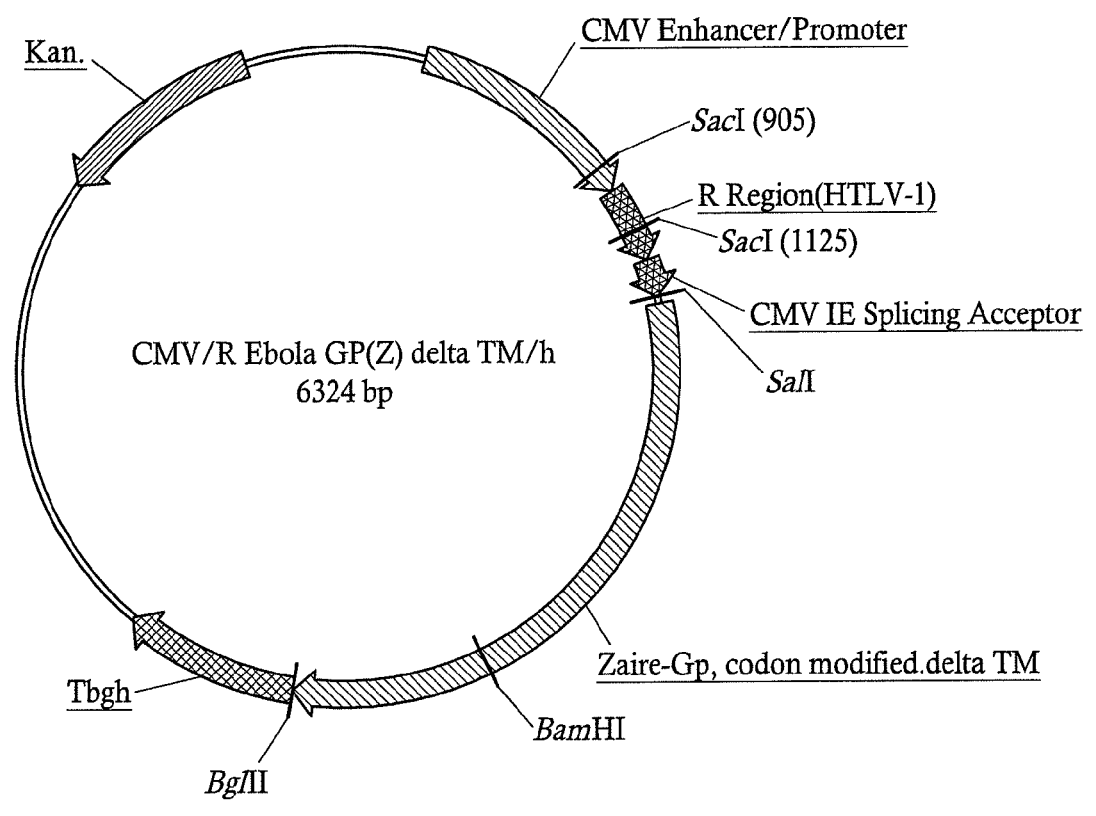

FIG. 37 shows CMV/R Ebola GP (Z) deltaTM/h (codon optimized) construct map (see, Ebola/Marburg/Lassa Plasmids, and Recombinant Adenoviruses in Table 2).

Figure 38:
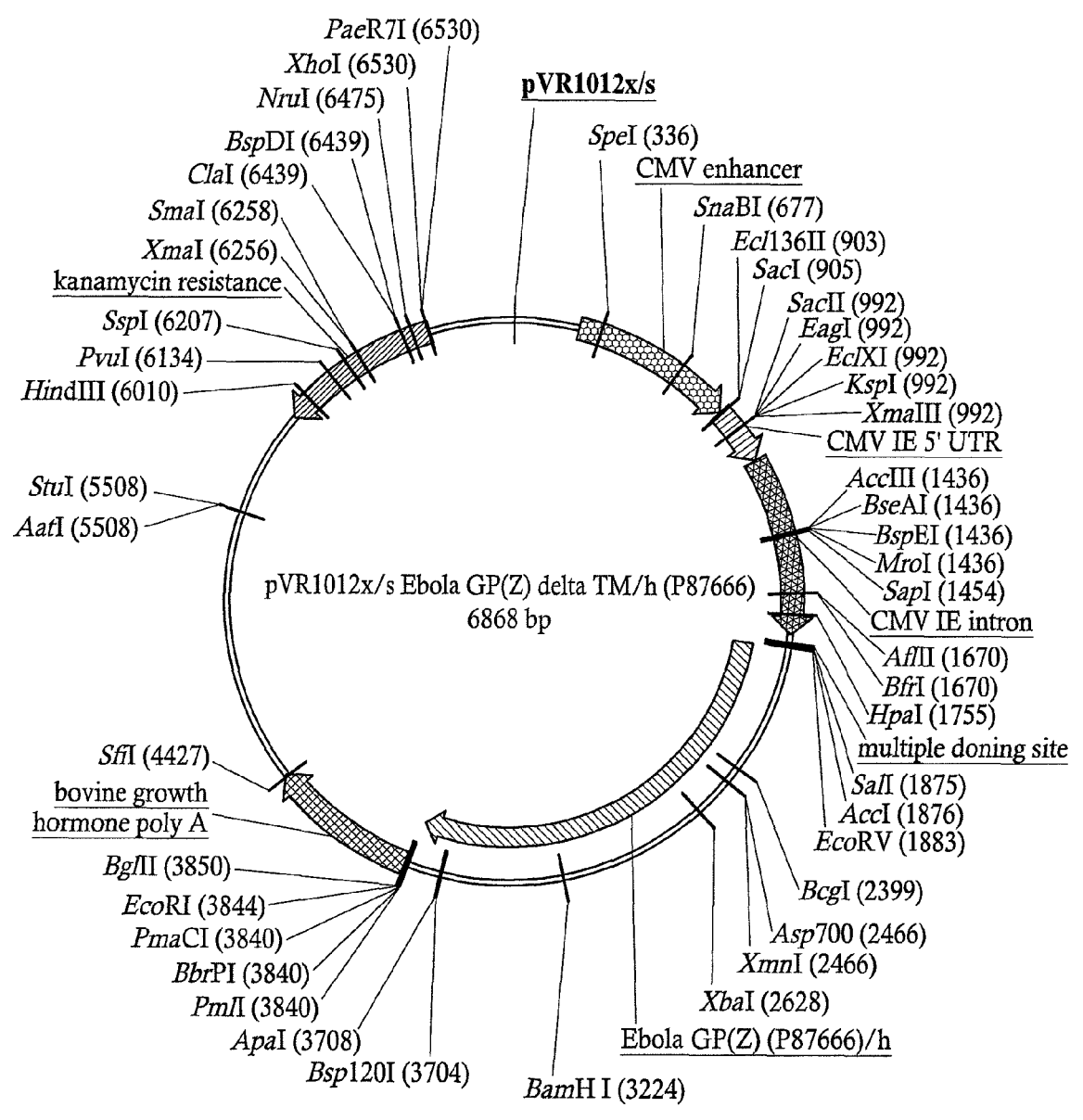

FIG. 38 shows pVR1012 Ebola GP (Z, P87666) delta TM/h (codon optimized) construct map (see, Ebola/Marburg/Lassa Plasmids, and Recombinant Adenoviruses in Table 2).

FIG. 42 shows VRC6703, pVR1012x/s Marburg delta TM/h (codon optimized) construct map (see, Ebola/Marburg/Lassa Plasmids, and Recombinant Adenoviruses in Table 2).

Figure 43:
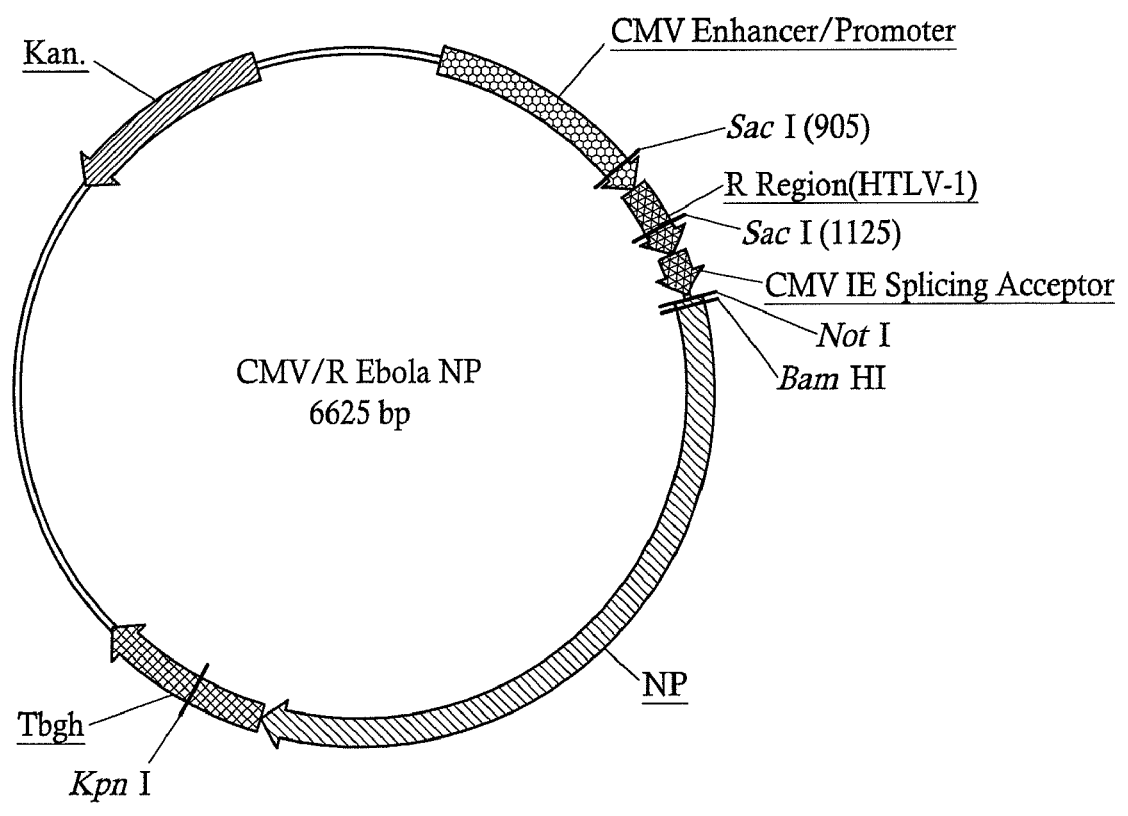

FIG. 43 shows CMV/R Ebola NP construct map (see, Ebola/Marburg/Lassa Plasmids, and Recombinant Adenoviruses in Table 2).

TABLE 1

Figure 2:
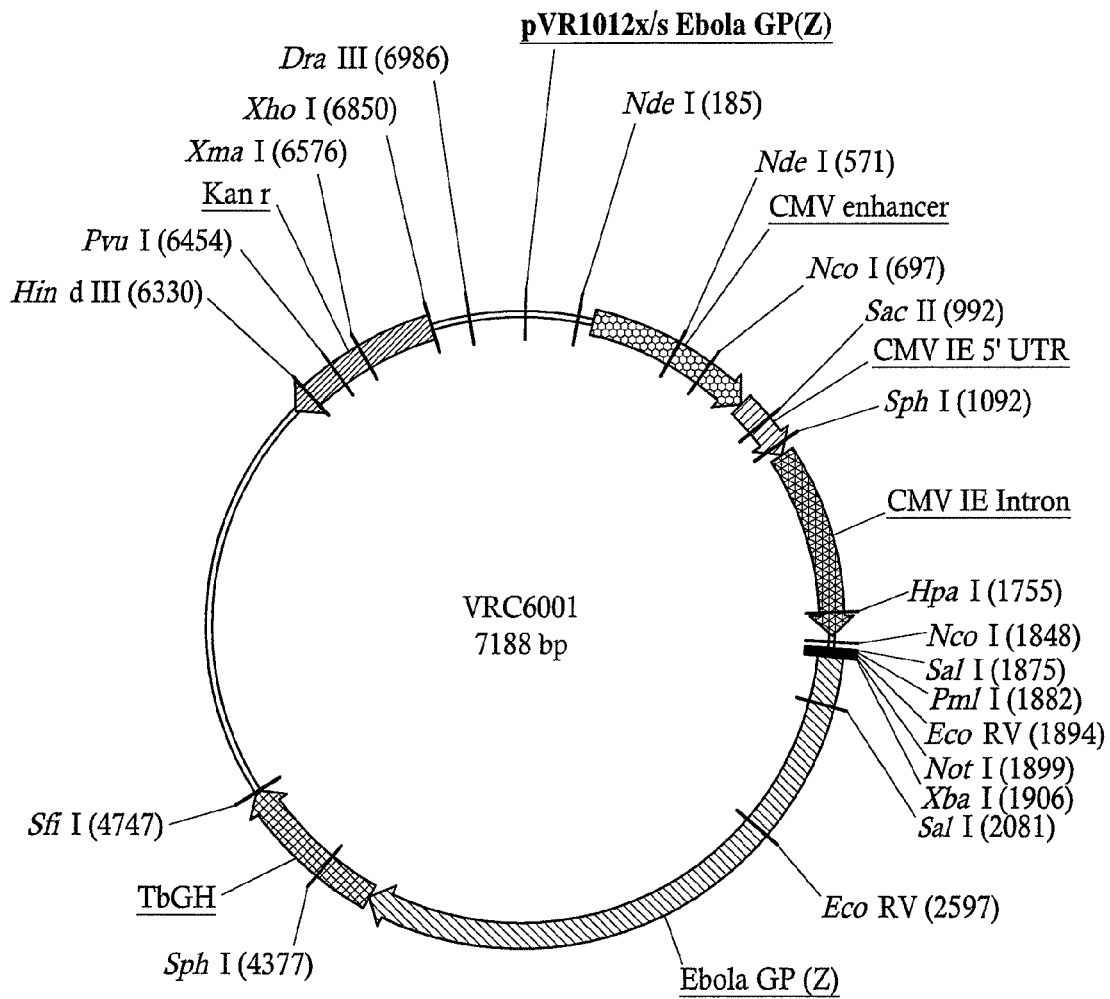
FIG. 2 shows VRC6001 (pVR1012x/s-GP(Z)) construct map (see, Ebola/Marburg/Lassa Plasmids, and Recombinant Adenoviruses in Table 2).
Figure 3:
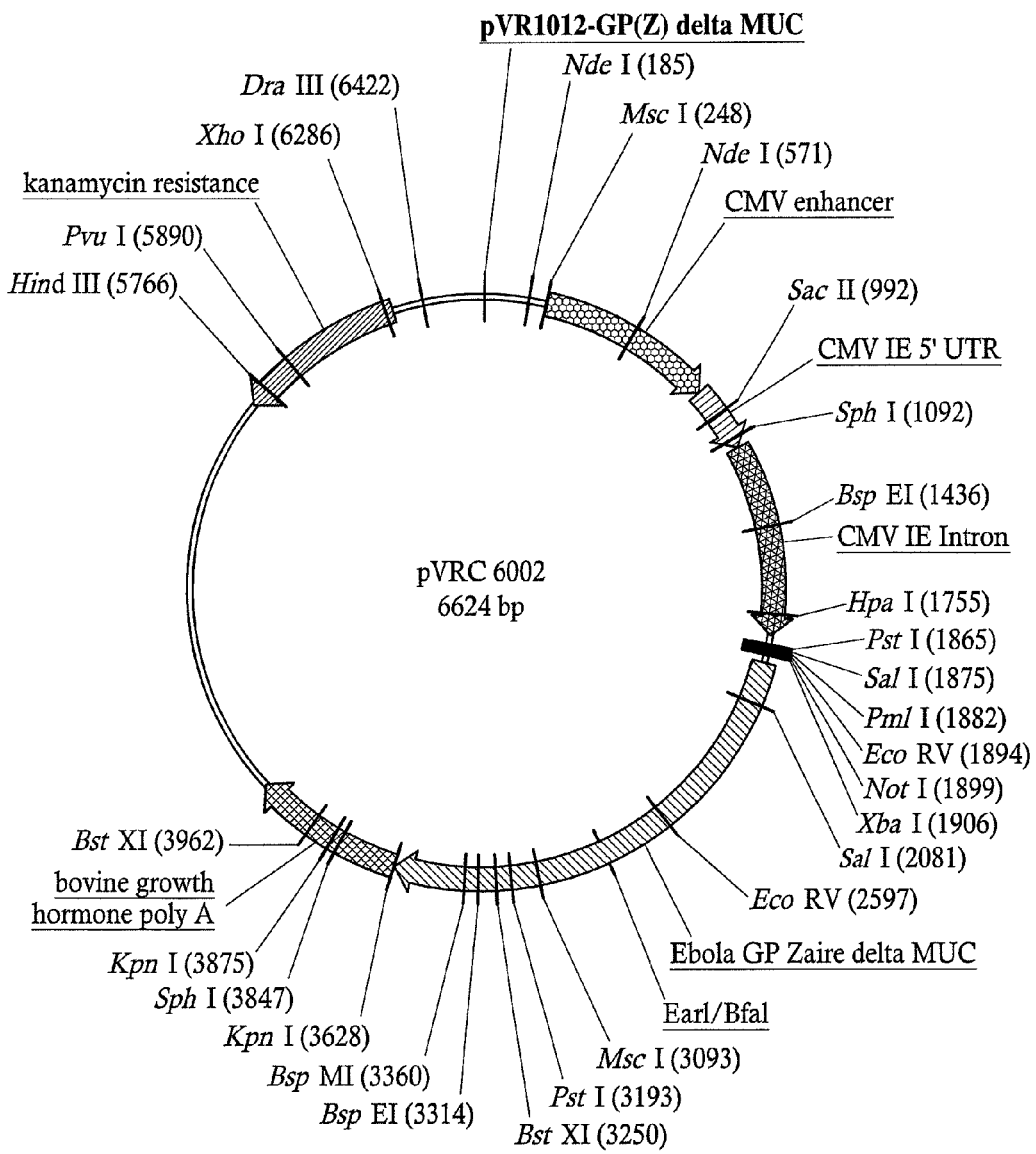
FIG. 3 shows VRC6002 (pVR1012-GP(Z) delta MUC) construct map (see, Ebola/Marburg/Lassa Plasmids, and Recombinant Adenoviruses in Table 2).
Figure 5:
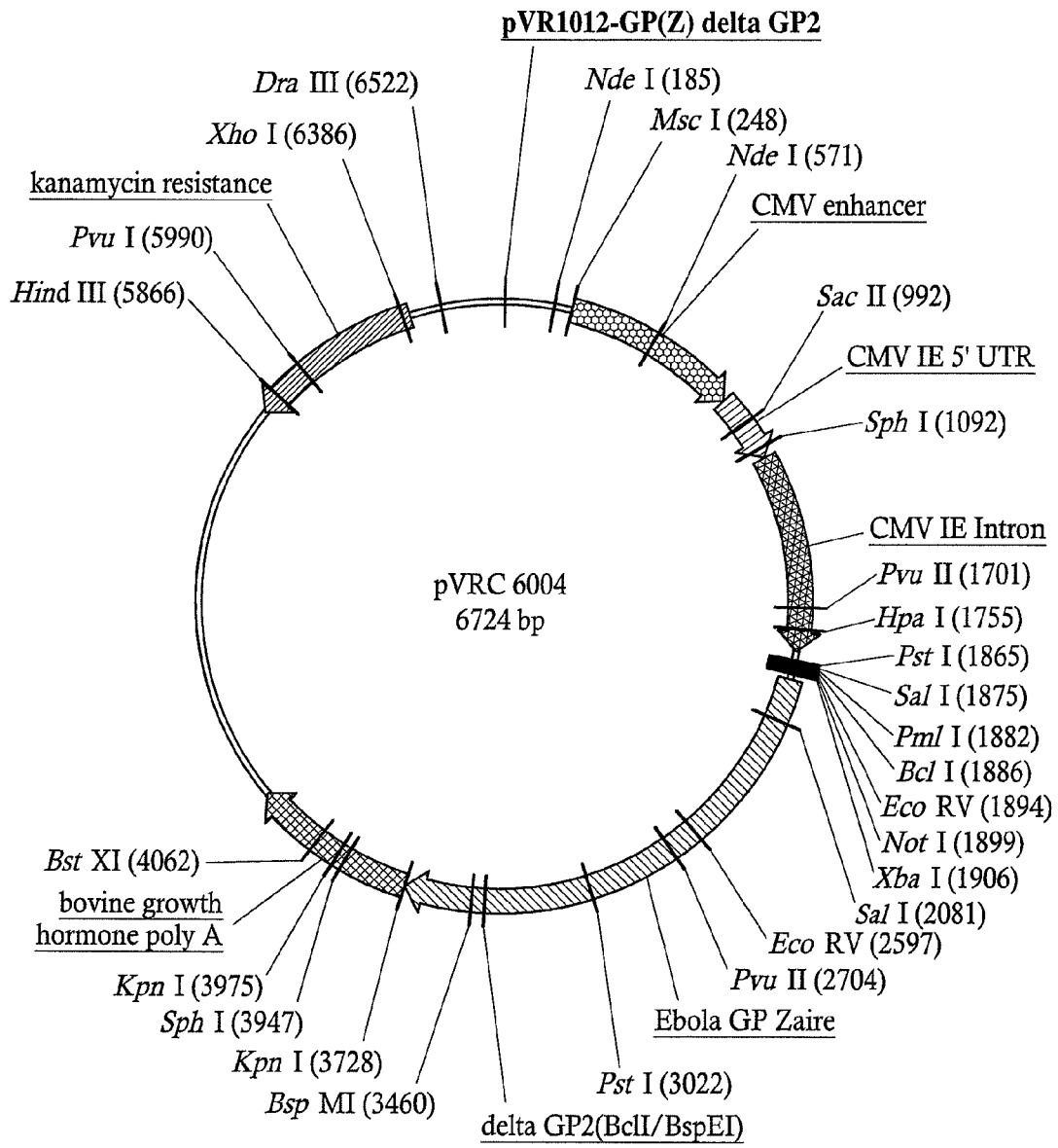
FIG. 5 shows VRC6004 (pVR1012-GP(Z) delta GP2) construct map (see, Ebola/Marburg/Lassa Plasmids, and Recombinant Adenoviruses in Table 2).
Figure 7:
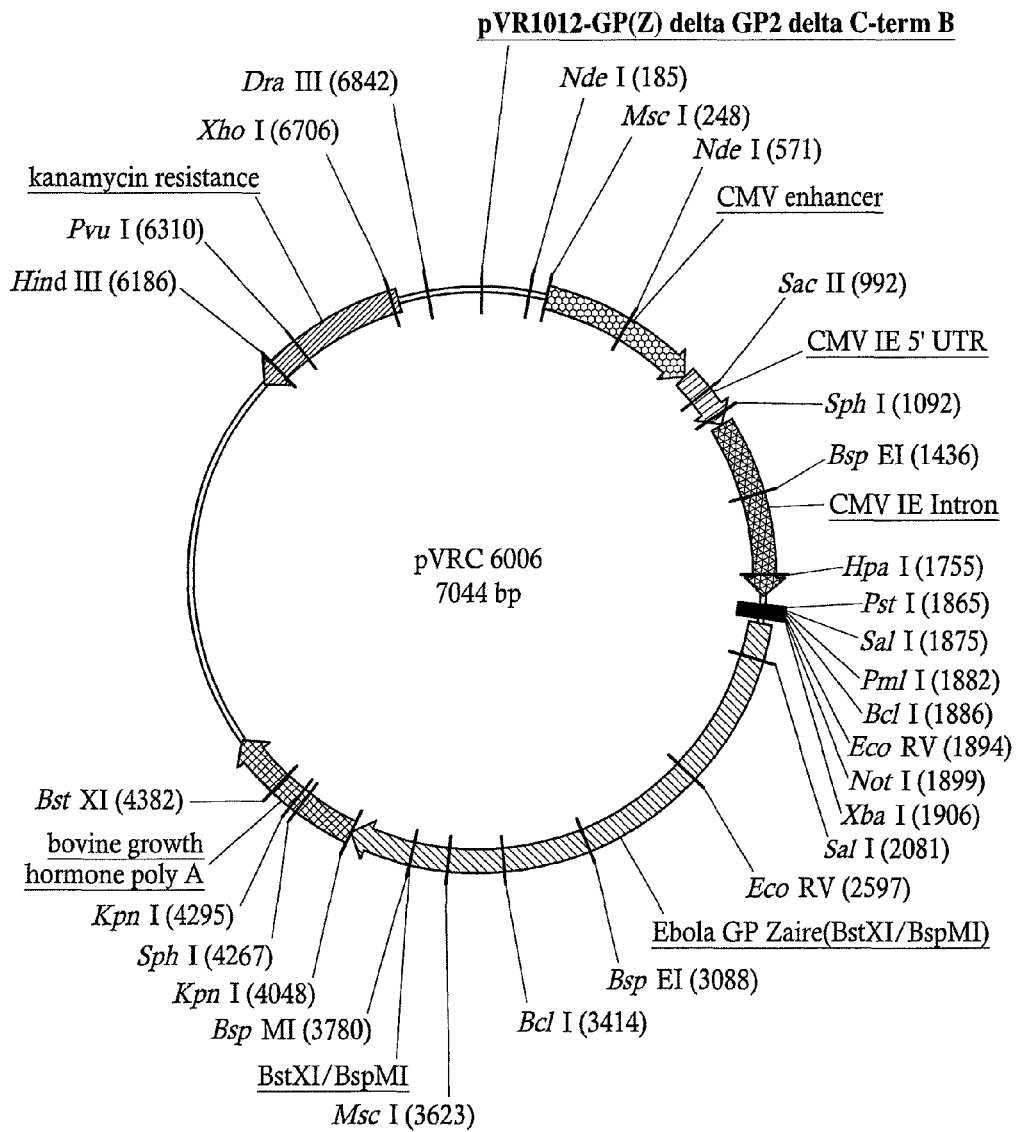
FIG. 7 shows VRC6006 (pVR1012-GP(Z) delta GP2 delta C-term B) construct map (see, Ebola/Marburg/Lassa Plasmids, and Recombinant Adenoviruses in Table 2).
Figure 8:
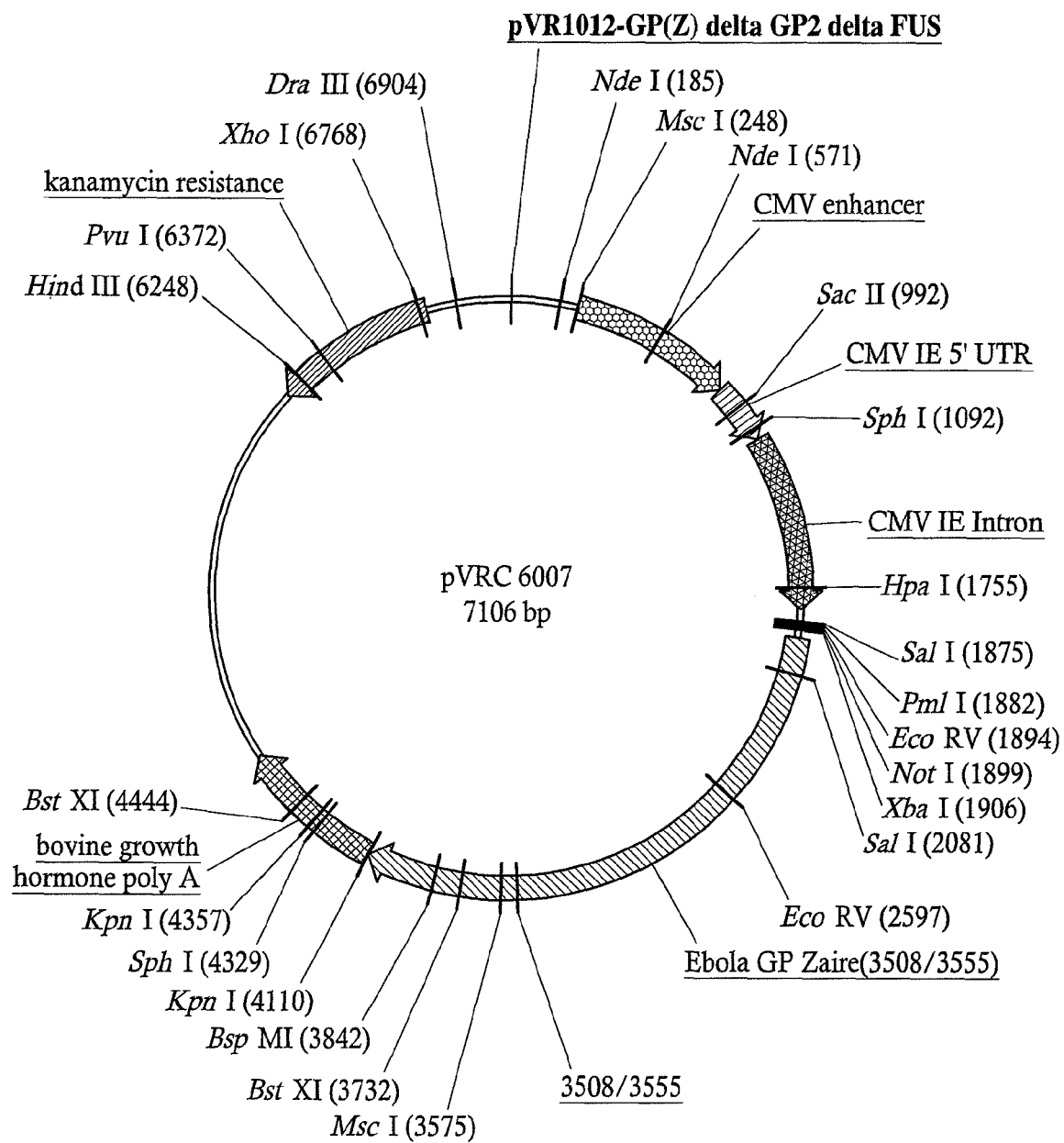
FIG. 8 shows VRC6007 (pVR1012-GP(Z) delta GP2 delta FUS) construct map (see, Ebola/Marburg/Lassa Plasmids, and Recombinant Adenoviruses in Table 2).
Figure 9:
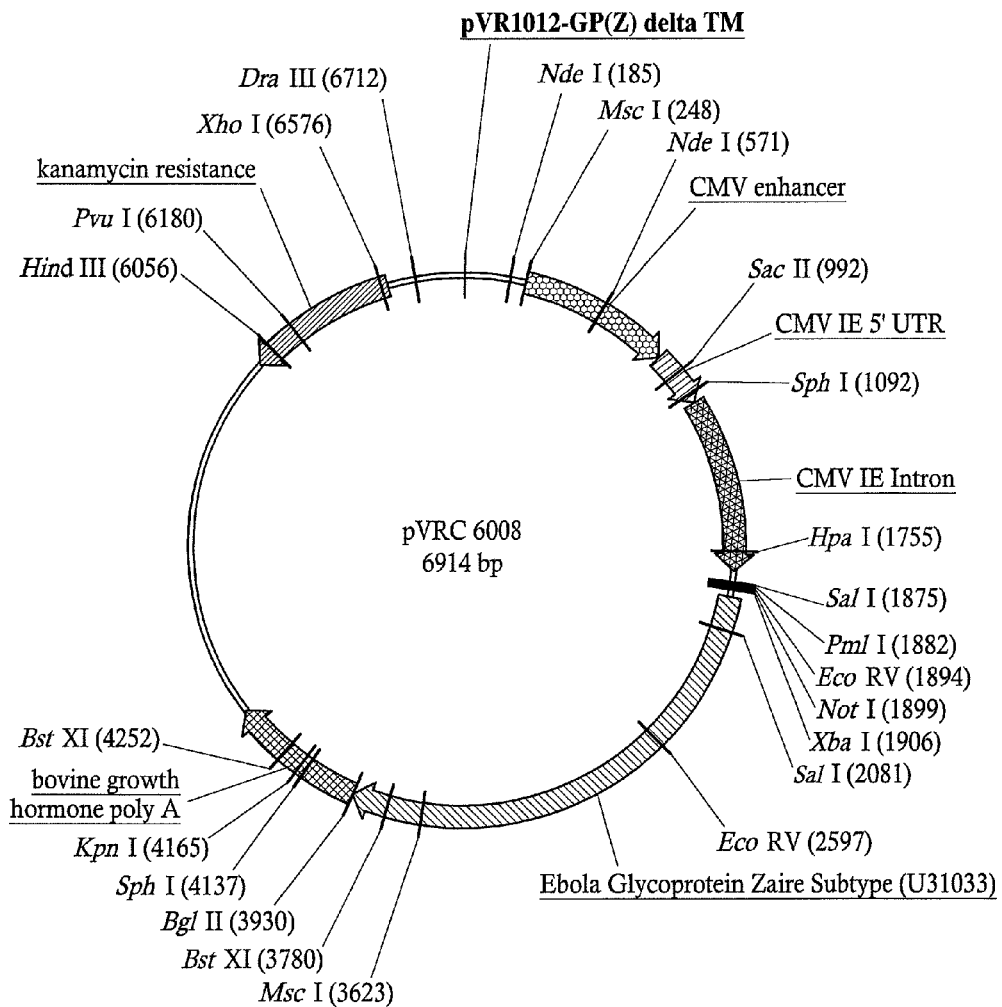
FIG. 9 shows VRC6008 (pVR1012-GP(Z) delta TM) construct map (see, Ebola/Marburg/Lassa Plasmids, and Recombinant Adenoviruses in Table 2).
Figure 10:
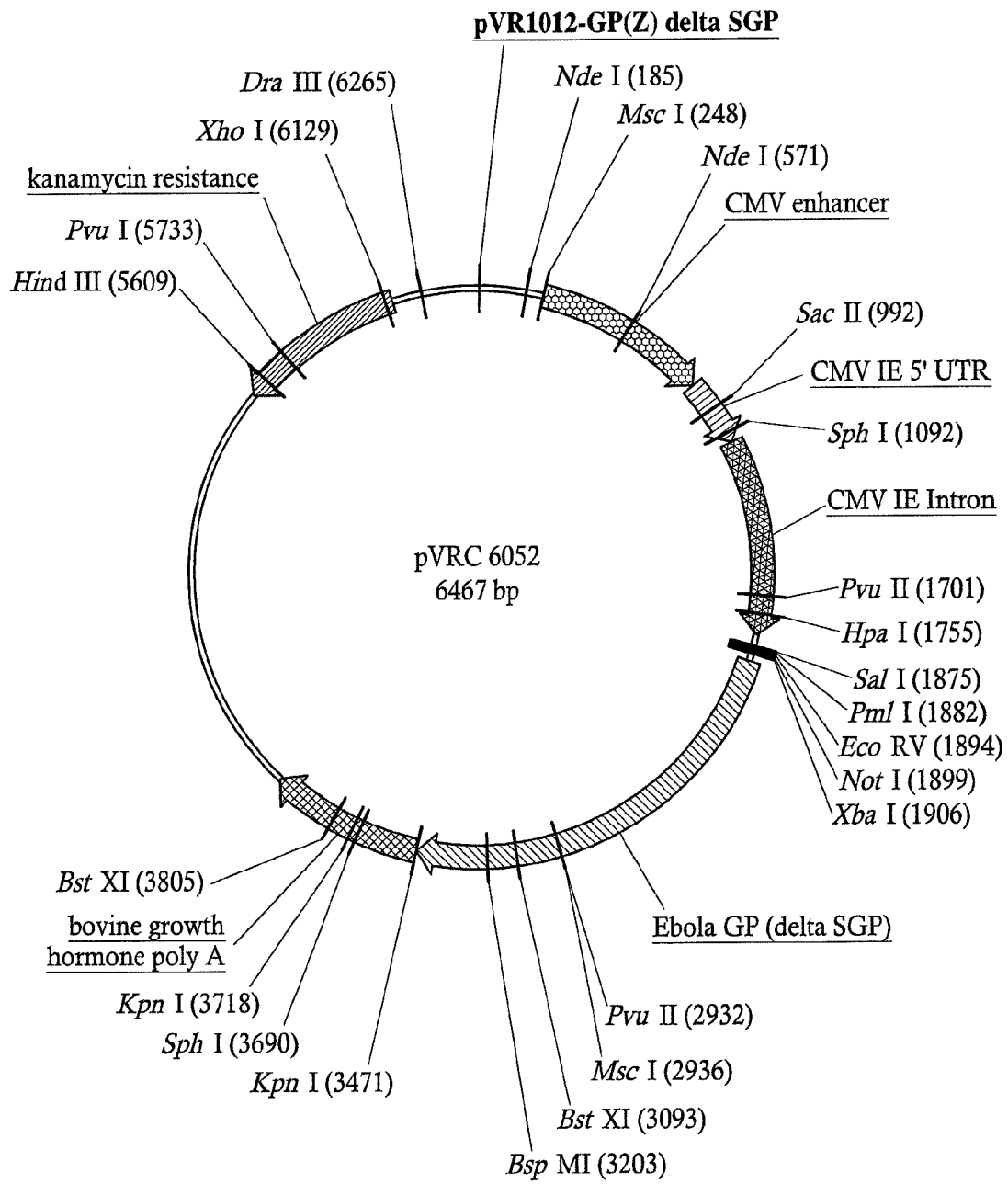
FIG. 10 shows VRC 6052 (pVR1012-GP(Z) delta SGP) construct map (see, Ebola/Marburg/Lassa Plasmids, and Recombinant Adenoviruses in Table 2).
Figure 18:
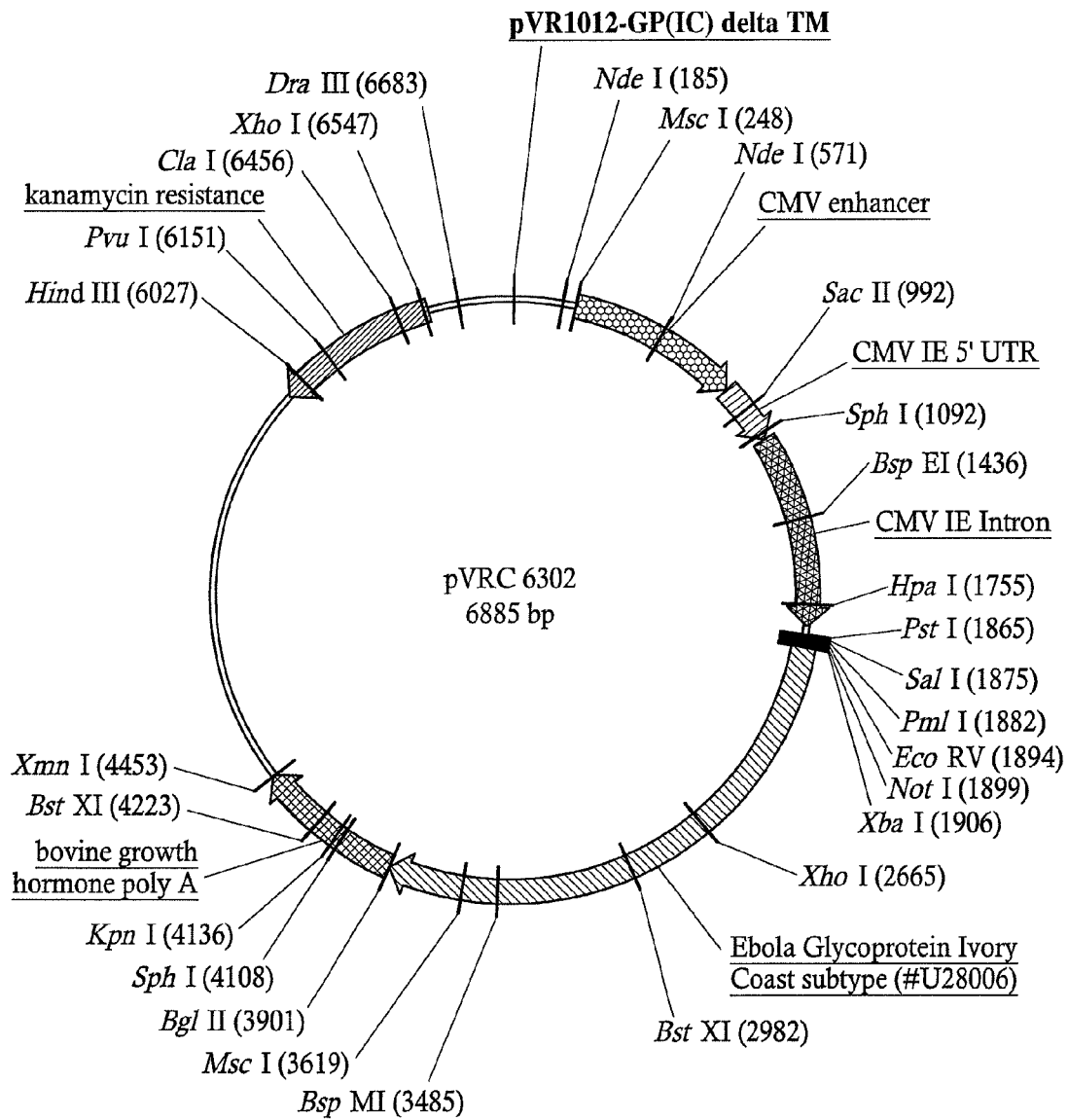
FIG. 18 shows VRC6302 (pVR1012-GP(IC) delta TM) construct map (see, Ebola/Marburg/Lassa Plasmids, and Recombinant Adenoviruses in Table 2).
Figure 20:
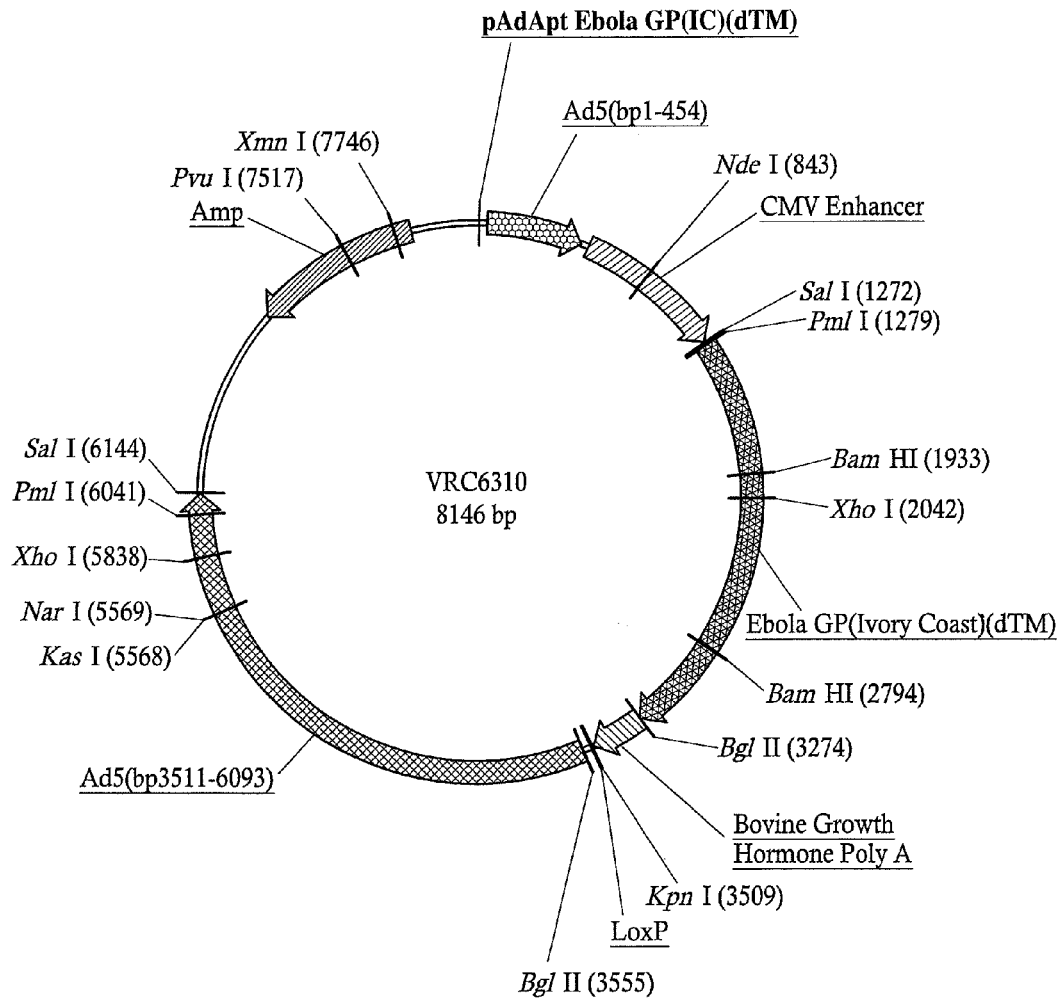
FIG. 20 shows VRC6310 (pAdApt Ebola GP (IC) (dTM)) construct map (see, Ebola/Marburg/Lassa Plasmids, and Recombinant Adenoviruses in Table 2).
Figure 24:
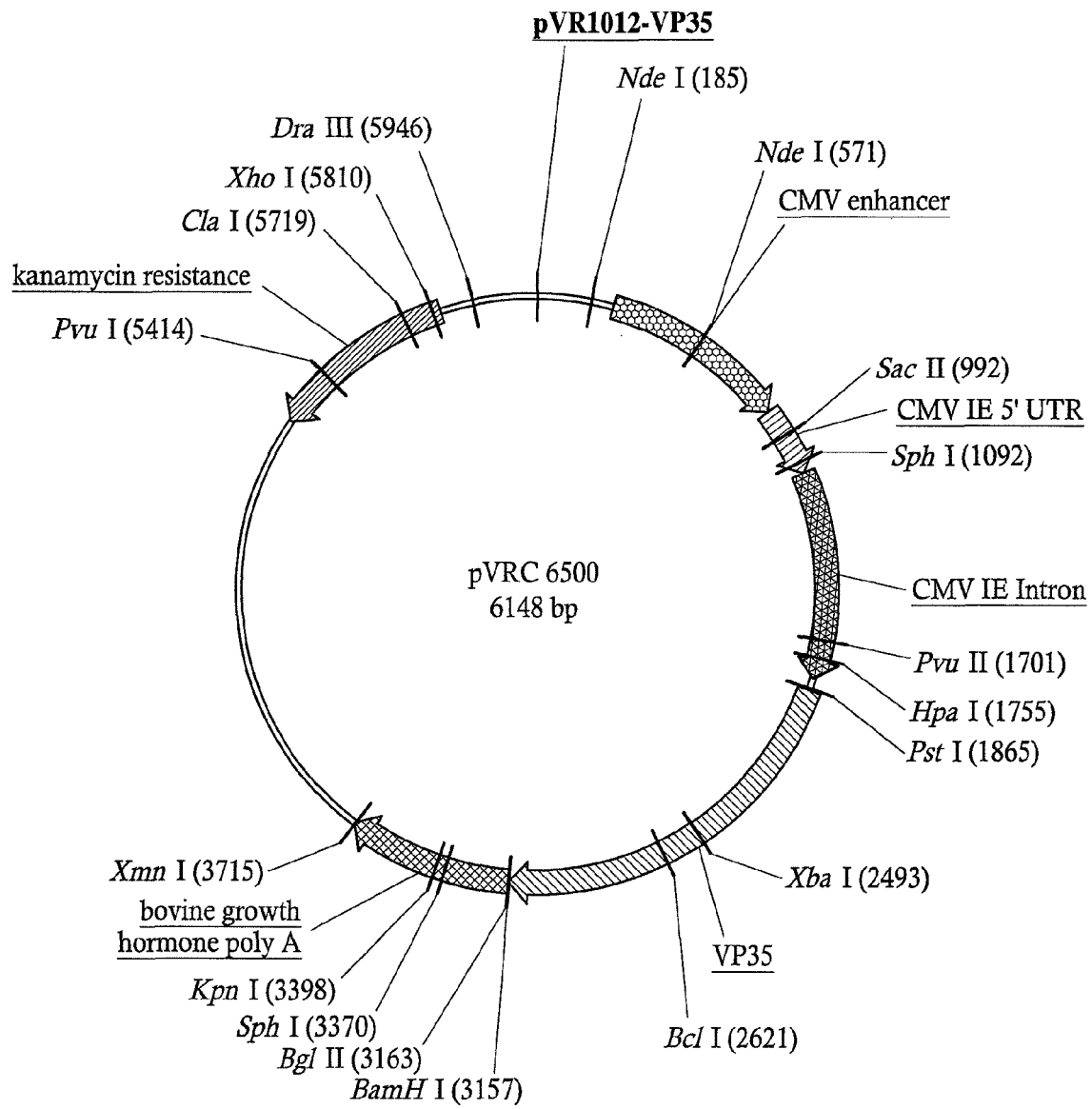
FIG. 24 shows VRC6500 (pVR1012-VP35) construct map (see, Ebola/Marburg/Lassa Plasmids, and Recombinant Adenoviruses in Table 2).
Figure 25:
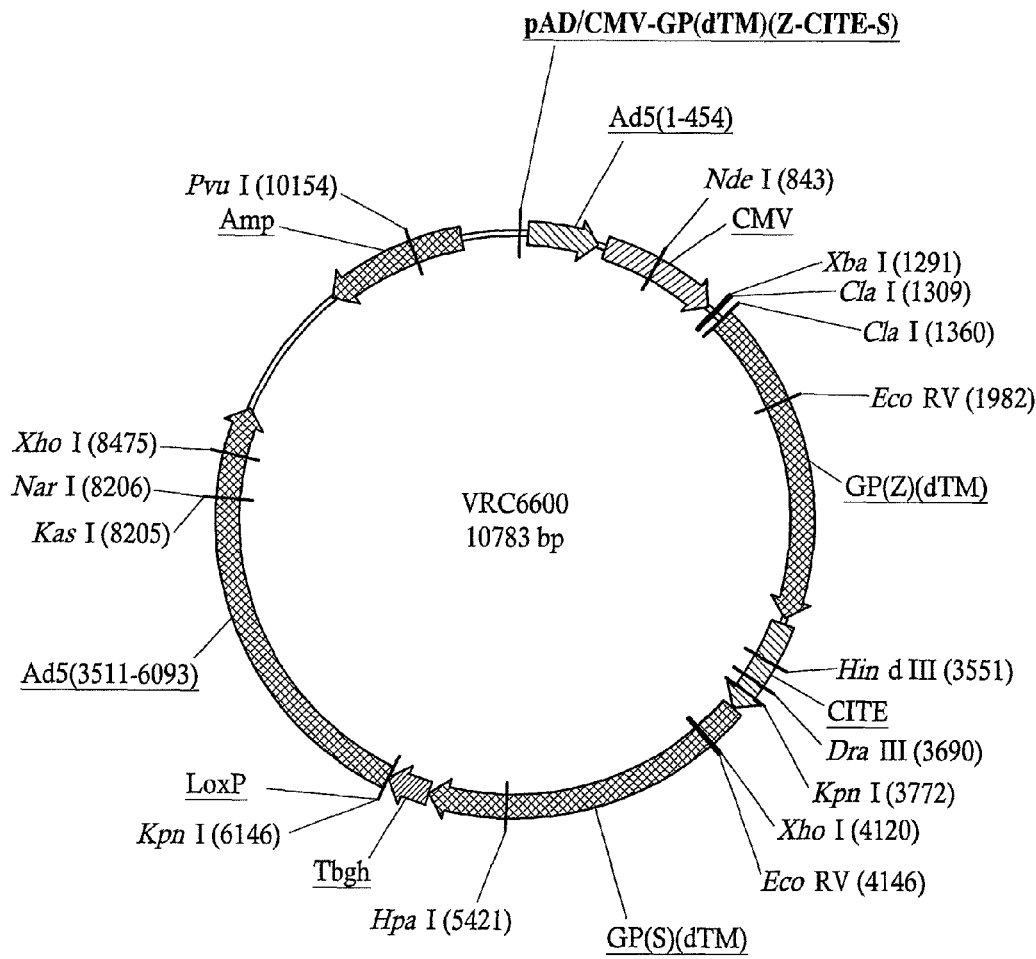
FIG. 25 shows VRC6600 (pAD/CMV-GP(dTM)(Z-CITE-S) construct map (see, Ebola/Marburg/Lassa Plasmids, and Recombinant Adenoviruses in Table 2).
Figure 26:
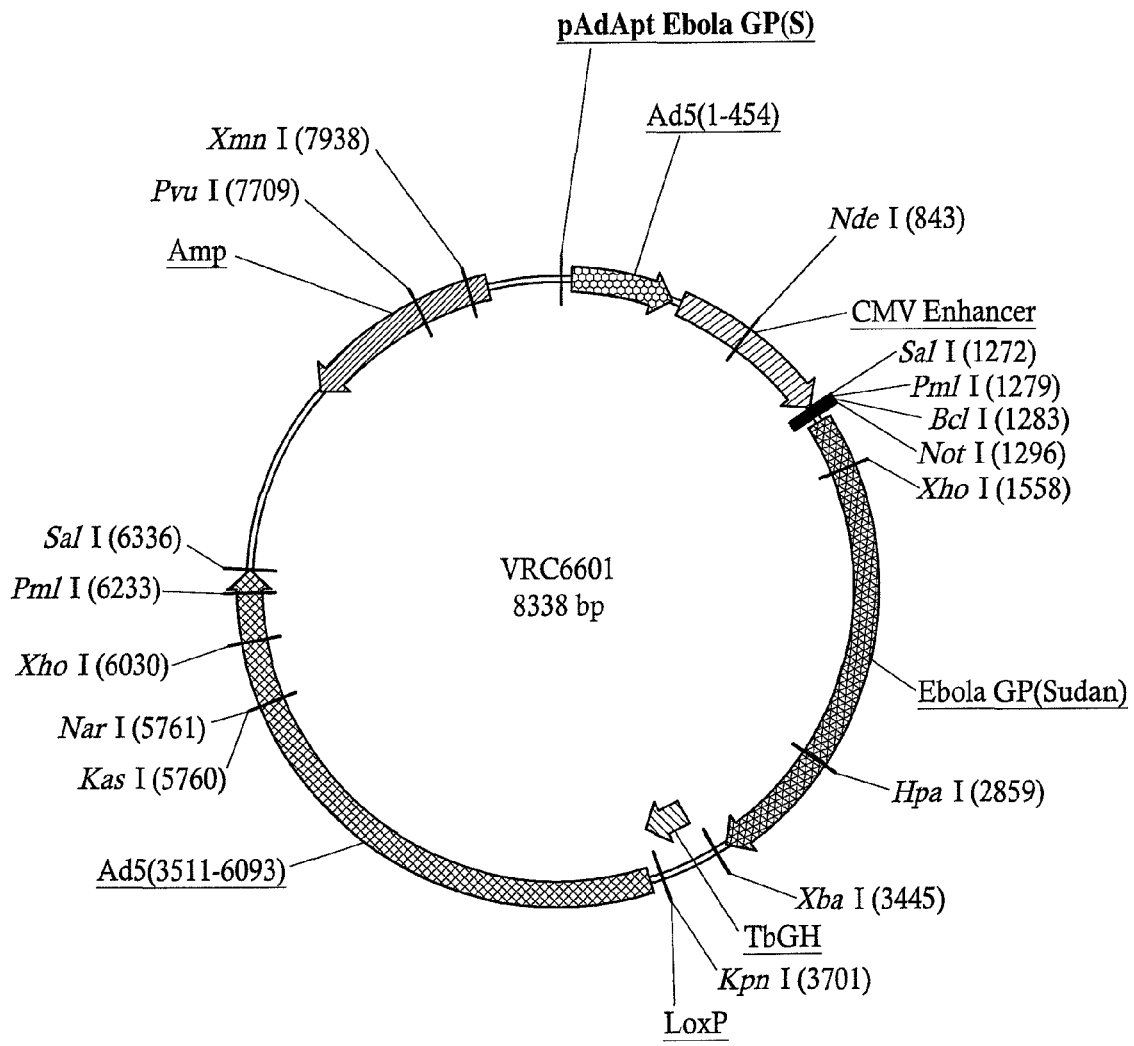
FIG. 26 shows VRC6601 (pAdApt Ebola GP(S)) construct map (see, Ebola/Marburg/Lassa Plasmids, and Recombinant Adenoviruses in Table 2).
Figure 28:
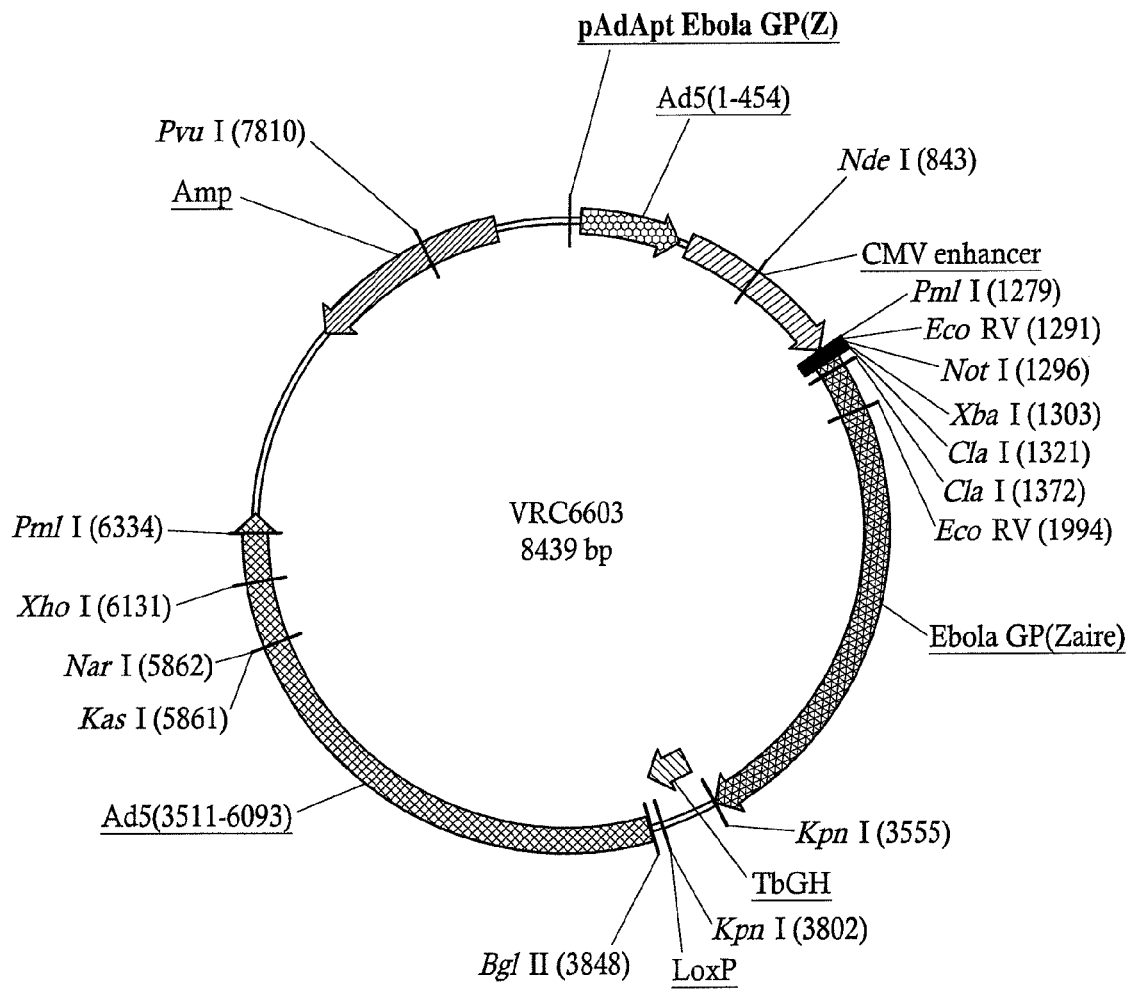
FIG. 28 shows VRC6603 (pAdApt Ebola GP(Z)) construct map (see, Ebola/Marburg/Lassa Plasmids, and Recombinant Adenoviruses in Table 2).
Figure 29:
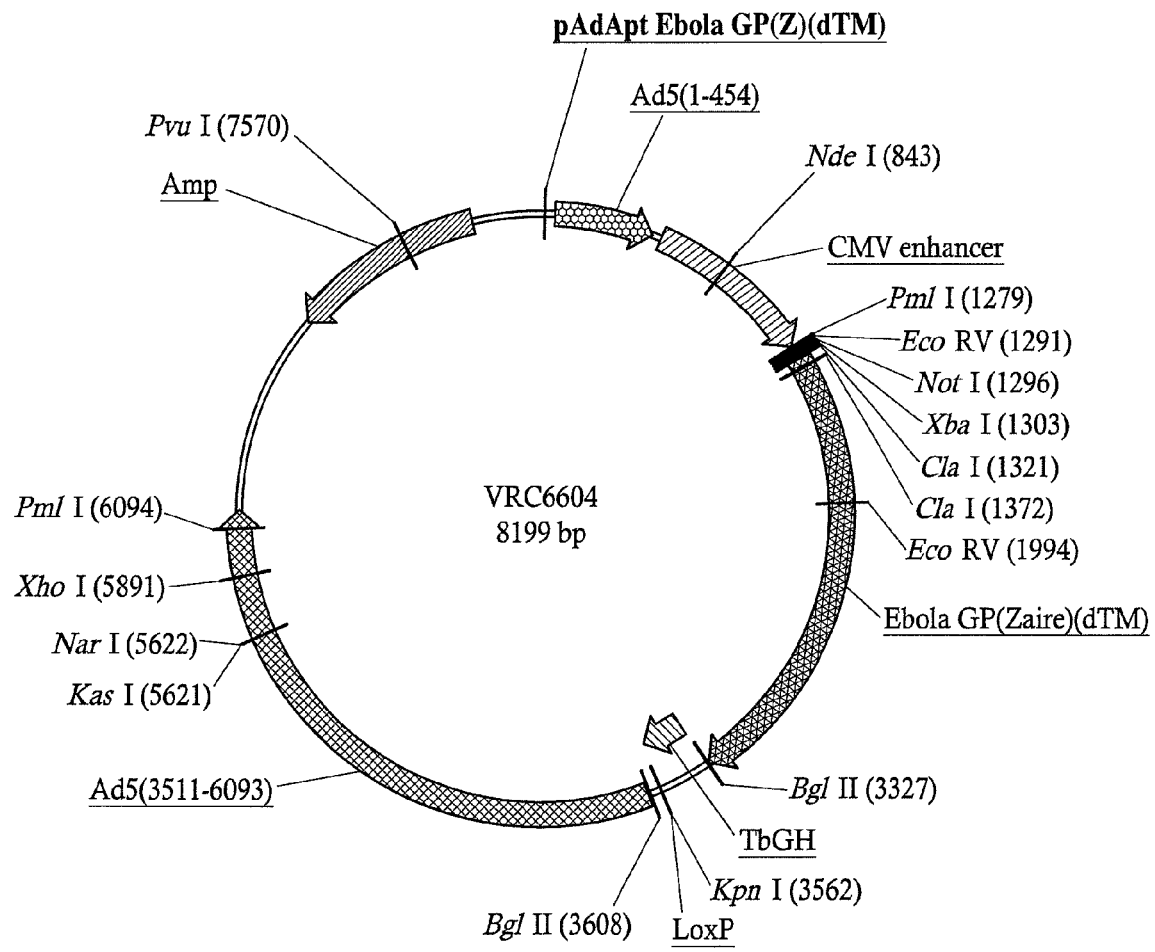
FIG. 29 shows VRC6604 (pAdApt Ebola GP(Z)(dTM)) construct map (see, Ebola/Marburg/Lassa Plasmids, and Recombinant Adenoviruses in Table 2).
Figure 32:
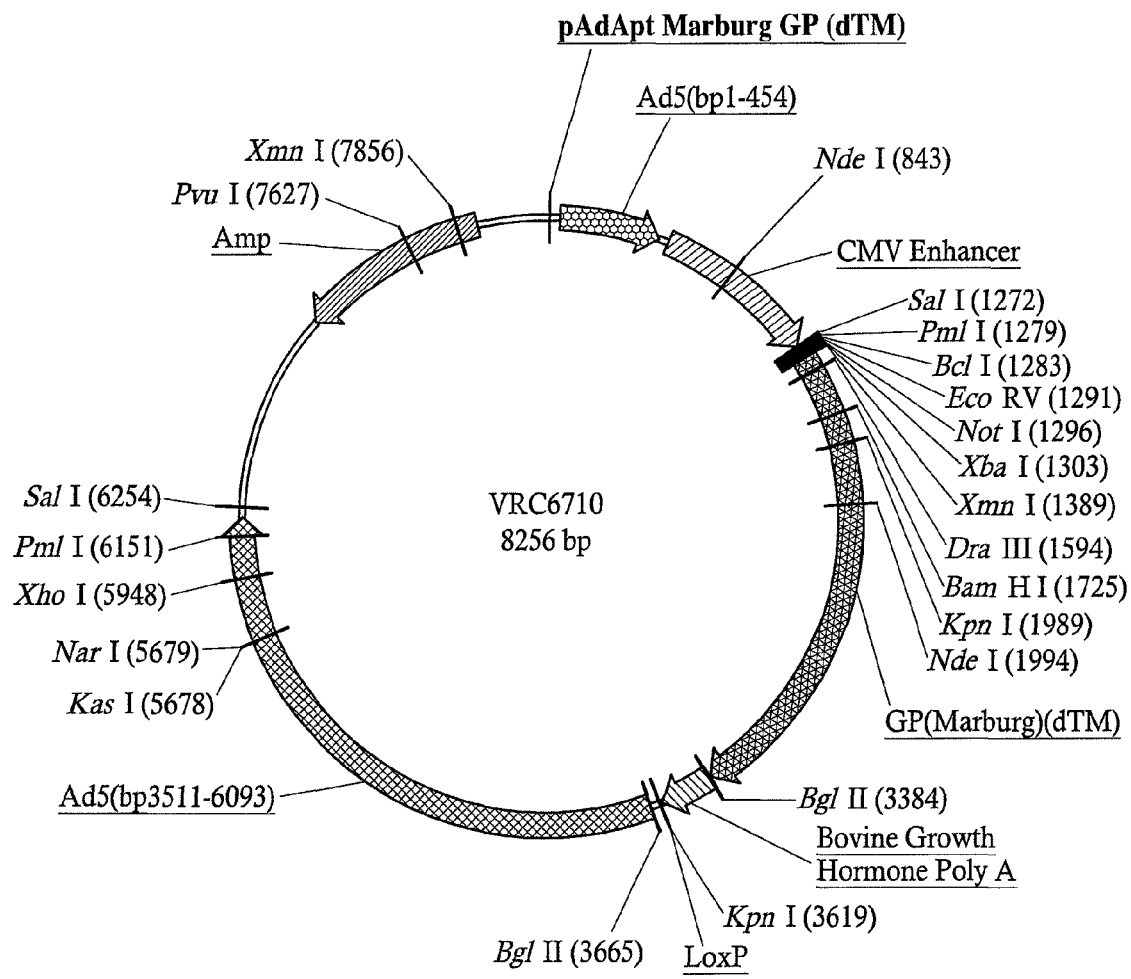
FIG. 32 shows VRC6710 (pAdApt Marburg GP (dTM)) construct map (see, Ebola/Marburg/Lassa Plasmids, and Recombinant Adenoviruses in Table 2).
Figure 34:
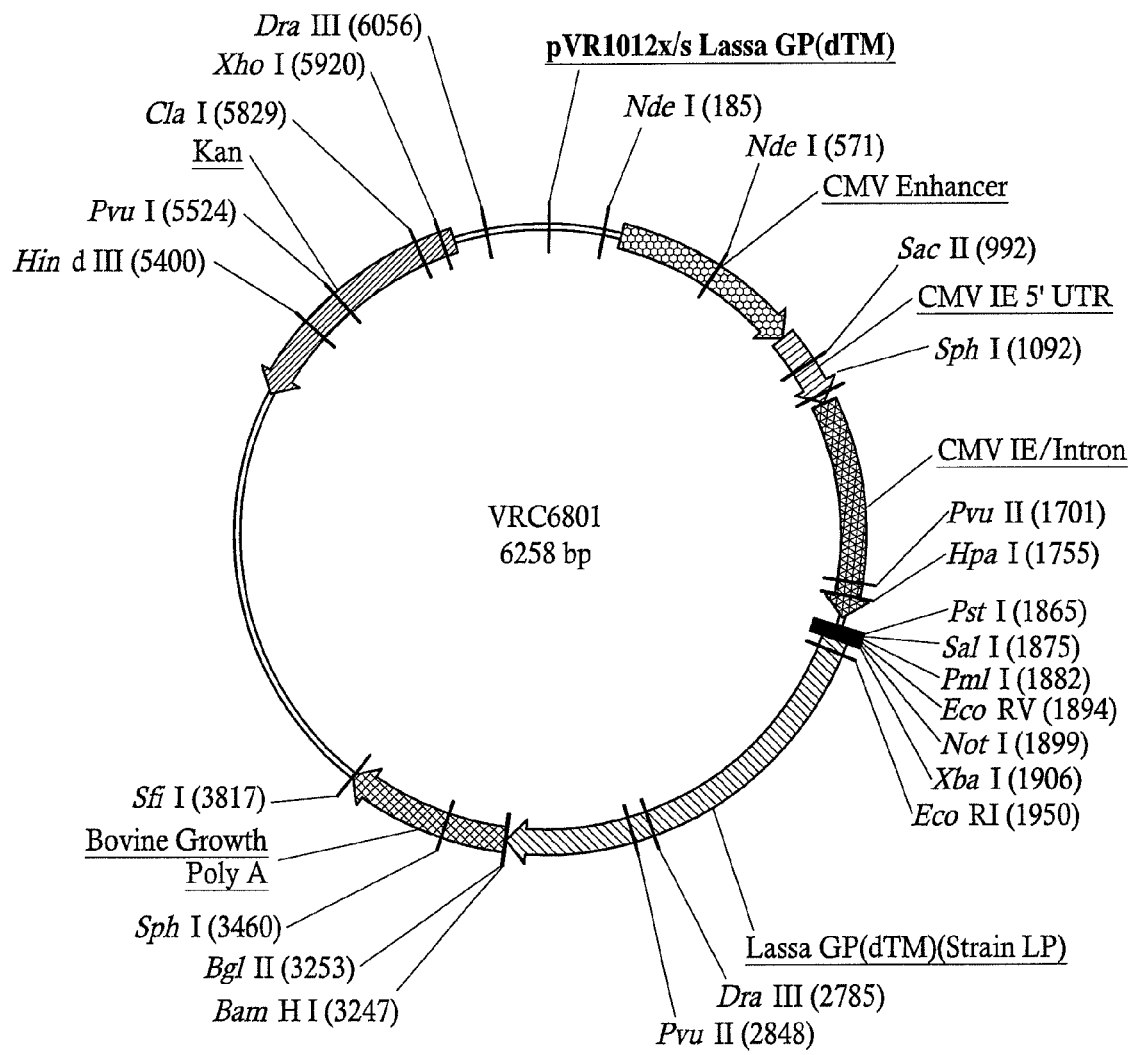
FIG. 34 shows VRC6801 (pVR1012x/s Lassa GP (dTM) construct map (see, Ebola/Marburg/Lassa Plasmids, and Recombinant Adenoviruses in Table 2).
Figure 35:
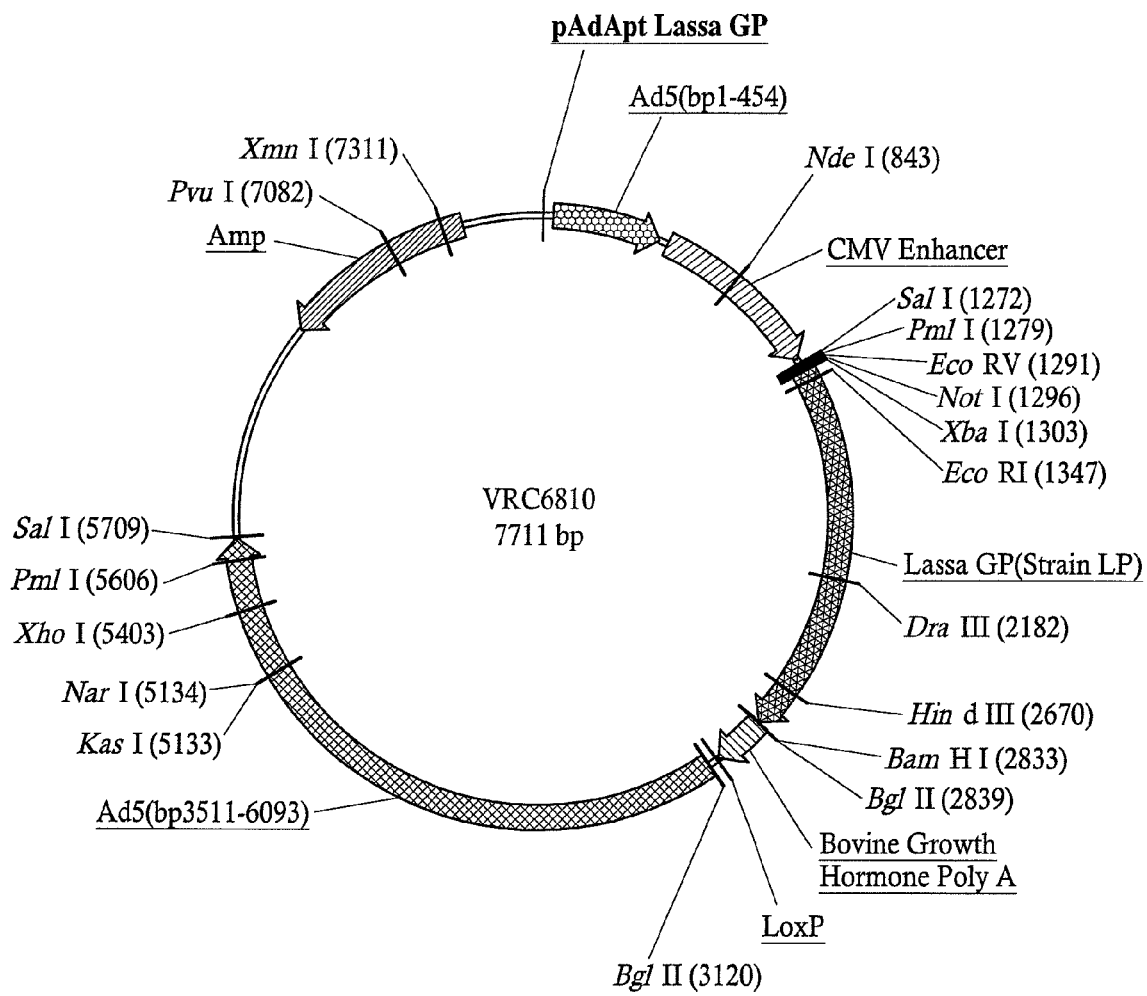
FIG. 35 shows VRC6810 (pAdApt Lassa GP) construct map (see, Ebola/Marburg/Lassa Plasmids, and Recombinant Adenoviruses in Table 2).
Figure 36:
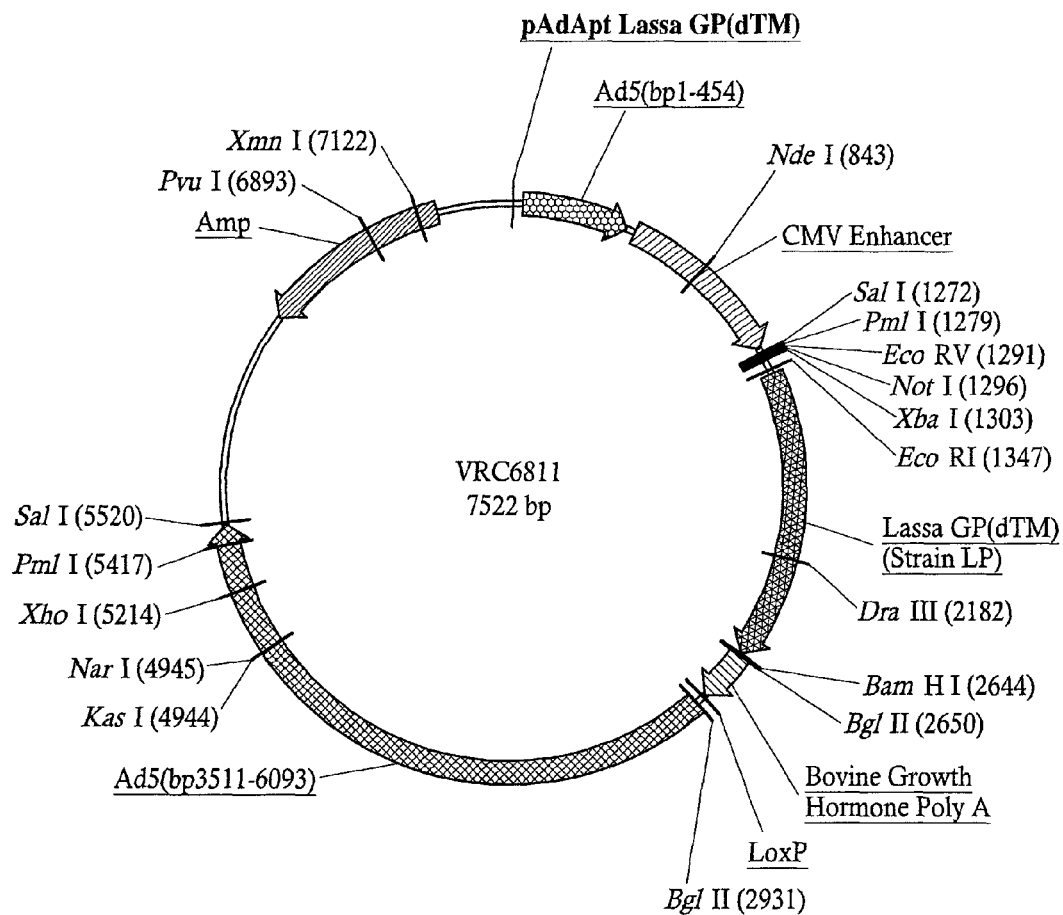
FIG. 36 shows VRC6811 (pAdApt Lassa GP (dTM)) construct map (see, Ebola/Marburg/Lassa Plasmids, and Recombinant Adenoviruses in Table 2).
Figure 39:
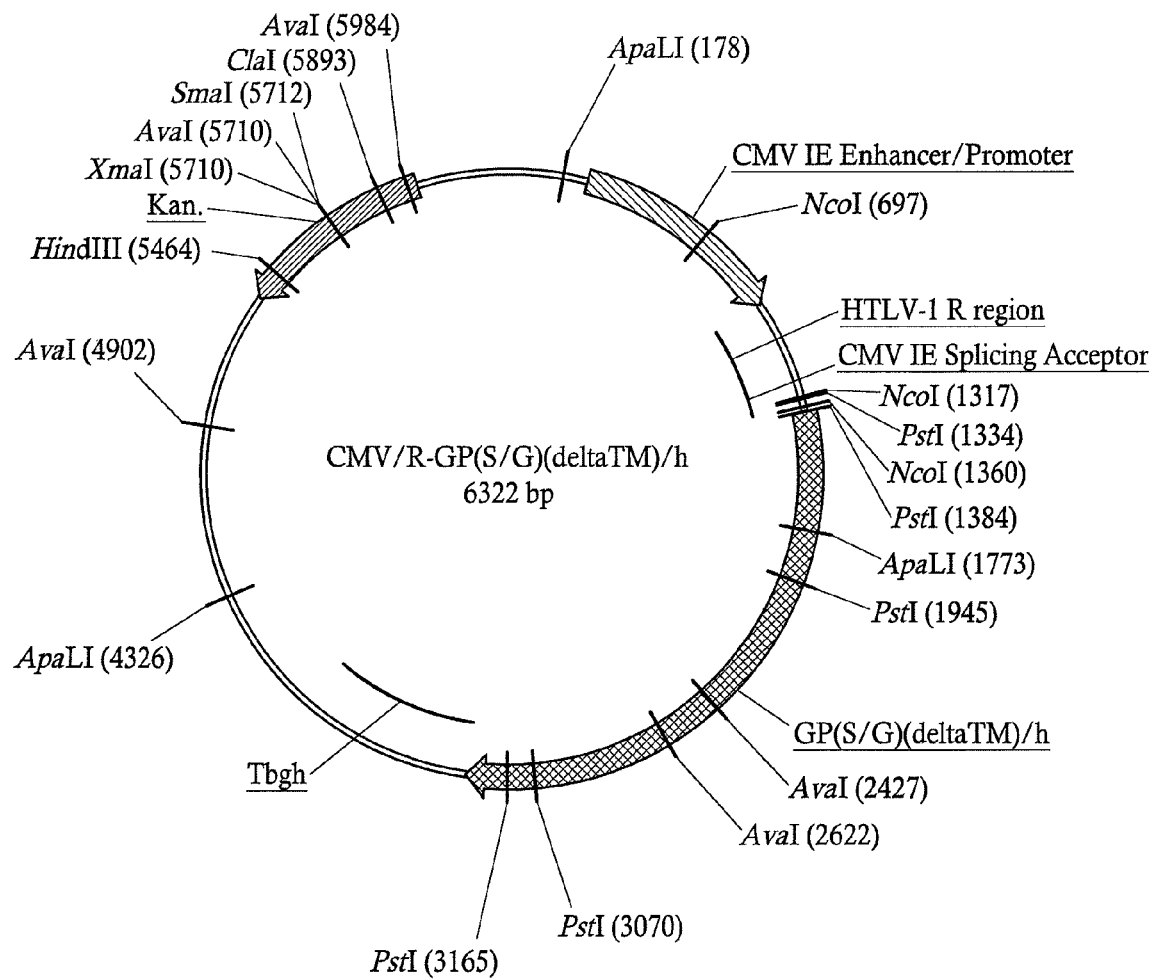
FIG. 39 shows CMV/R Ebola GP (S/Gulu) delta TM/h (codon optimized) construct map (see, Ebola/Marburg/Lassa Plasmids, and Recombinant Adenoviruses in Table 2).
Figure 40:
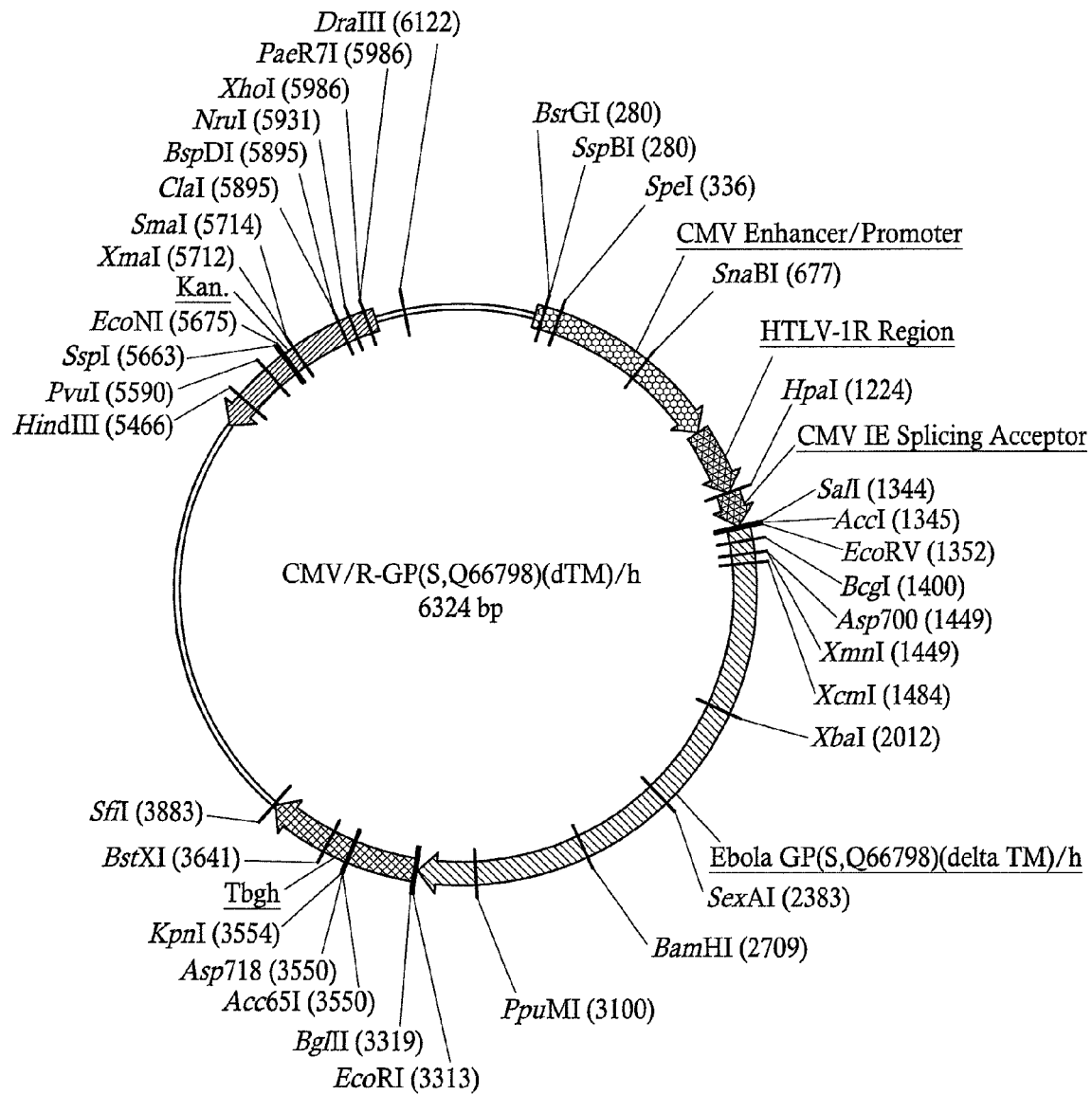
FIG. 40 shows CMV/R Ebola GP (S,Q66798) delta TM/h (codon optimized) construct map (see, Ebola/Marburg/Lassa Plasmids, and Recombinant Adenoviruses in Table 2).
Figure 41:
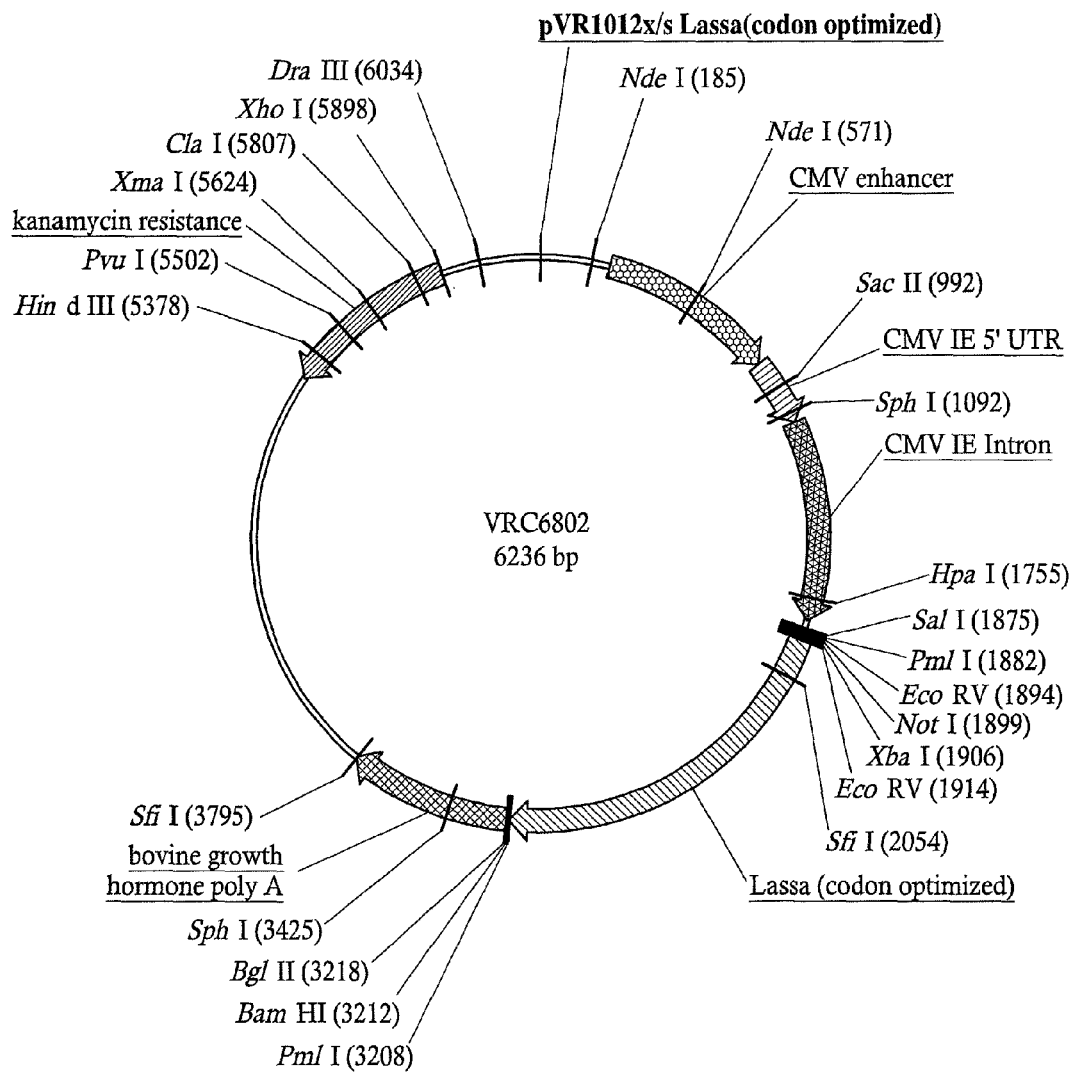
FIG. 41 shows VRC6802, pVR1012x/s Lassa delta TM/h (codon optimized) construct map (see, Ebola/Marburg/Lassa Plasmids, and Recombinant Adenoviruses in Table 2).

Ebola/Marburg/Lassa GenBank Accession Numbers.

| Gene | GenBank Accession number |
|---|---|
| Ebola Zaire GP | U23187, P87666 |
| Ebola Zaire NP | J04337 |
| Ebola Sudan GP | U28134, Q66798 |
| Ebola Sudan NP | AF173836 |
| Ebola Ivory Coast GP | U28006 |
| Ebola Ivory Coast NP | J04336 |
| Ebola Reston GP | U23152 |
| Ebola Reston NP | |
| Marburg GP | Z12132 |
| Marburg NP | X68495 |
| Lassa GP | AF181853 |
| Lassa NP | AF246121 |

TABLE 2

Ebola/Marburg/Lassa Plasmids, and Recombinant Adenoviruses

| Construct | Construct Name/Description | Construct Map Name | SEQ ID NO | Figure |
|---|---|---|---|---|
| VRC6000 | VRC6000 (pVR1012-GP(Z)) | pVR1012-GP(Z) | 1 | 1 |
| VRC6001 | VRC6001 (pVR1012x/s-GP(Z)) | pVR1012x/s Ebola GP(Z) | 2 | 2 |
| VRC6002 | VRC6002 (pVR1012-GP(Z) delta MUC) | pVR1012-GP(Z) delta MUC | 3 | 3 |
| VRC6003 | VRC6003 (pVR1012-GP(Z) delta MUC delta FUR) | pVR1012-GP(Z) delta MUC delta FUR | 4 | 4 |
| VRC6004 | VRC6004 (pVR1012-GP(Z) delta GP2) | pVR1012-GP(Z) delta GP2 | 5 | 5 |
| VRC6005 | VRC6005 (pVR1012-GP(Z) delta GP2 delta C-term A) | pVR1012-GP(Z) delta GP2 delta C-term A | 6 | 6 |
| VRC6006 | VRC6006 (pVR1012-GP(Z) delta GP2 delta C-term B) | pVR1012-GP(Z) delta GP2 delta C-term B | 7 | 7 |
| VRC6007 | VRC6007 (pVR1012-GP(Z) delta GP2 delta FUS) | pVR1012-GP(Z) delta GP2 delta FUS | 8 | 8 |
| VRC6008 | VRC6008 (pVR1012-GP(Z) delta TM) | pVR1012-GP(Z) delta TM | 9 | 9 |
| VRC6052 | VRC 6052 (pVR1012-GP(Z) delta SGP) | pVR1012-GP(Z) delta SGP | 10 | 10 |
| VRC6101 | VRC 6101 (pVR1012x/s Ebola GP(R) (dTM)) | pVR1012x/s Ebola GP(R)(dTM) | 11 | 11 |
| VRC6110 | VRC 6110 (pAdApt Ebola GP(R) (dTM)) | pAdApt Ebola GP(R) (dTM) | 12 | 12 |
| VRC6200 | VRC6200 (pVR1012-GP(S)) | pVR1012-GP(S) | 13 | 13 |
| VRC6201 | VRC 6201 (pVR1012x/s Ebola GP(S)) | pVR1012x/s Ebola GP(S) | 14 | 14 |
| VRC6202 | VRC6202 (pVR1012-GP(S) delta TM) | pVR1012-GP(S) delta TM | 15 | 15 |
| VRC6300 | VRC6300 (pVR1012-GP(IC)) | pVR1012-GP(IC) | 16 | 16 |
| VRC6301 | VRC6301 (pVR1012x/s-GP(IC)) | pVR1012x/s Ebola GP(IC) | 17 | 17 |
| VRC6302 | VRC6302 (pVR1012-GP(IC) delta TM) | pVR1012-GP(IC) delta TM | 18 | 18 |
| VRC6303 | VRC 6303 (pVR1012x/s Ebola GP (IC) (dTM)) | pVR1012x/s Ebola GP(IC)(dTM) | 19 | 19 |
| VRC6310 | VRC 6310 (pAdApt Ebola GP (IC) (dTM)) | pAdApt Ebola GP(IC)(dTM) | 20 | 20 |
| VRC6351 | VRC6351 (pVR1012x/s-sGP(IC)) | pVR1012x/s-sGP(IC) | 21 | 21 |
| VRC6400 | VRC6400 (pVR1012-NP) | pVR1012-NP | 22 | 22 |
| VRC6401 | VRC6401 (pVR1012x/s-NP) | pVR1012x/s Ebola-NP | 23 | 23 |
| VRC6500 | VRC6500 (pVR1012-VP35) | pVR1012-VP35 | 24 | 24 |
| VRC6600 | VRC6600 (pAD/CMV-GP(dTM)(Z-CITE-S) | pAD/CMV-GP(dTM)(Z-CITE-S) | 25 | 25 |
| VRC6601 | VRC6601 (pAdApt Ebola GP(S)) | pAdApt Ebola GP(S) | 26 | 26 |
| VRC6602 | VRC 6602 (pAdApt Ebola GP(S)(dTM)) | pAdApt Ebola GP(S)(dTM) | 27 | 27 |
| VRC6603 | VRC6603 (pAdApt Ebola GP(Z)) | pAdApt Ebola GP(Z) | 28 | 28 |
| VRC6604 | VRC 6604 (pAdApt Ebola GP(Z)(dTM)) | pAdApt Ebola GP(Z)(dTM) | 29 | 29 |
| VRC6701 | VRC6701 (pVR1012-Marburg) | pVR1012 Marburg | 30 | 30 |
| VRC6702 | VRC 6702 (pVR1012x/s Marburg GP (dTM)) | pVR1012x/s Marburg GP(dTM) | 31 | 31 |
| VRC6710 | VRC 6710 (pAdApt Marburg GP (dTM)) | pAdApt Marburg GP (dTM) | 32 | 32 |
| VRC6800 | VRC6800 (pVR1012x/s Lassa GP) | pVR1012x/s Lassa GP | 33 | 33 |
| VRC6801 | VRC6801 (pVR1012x/s Lassa GP (dTM) | pVR1012x/s Lassa GP (dTM) | 34 | 34 |
| VRC6810 | VRC6810 (pAdApt Lassa GP) | pAdApt Lassa GP | 35 | 35 |
| VRC6811 | VRC6811 (pAdApt Lassa GP (dTM)) | pAdApt Lassa GP (dTM) | 36 | 36 |
| | CMV/R Ebola GP (Z) deltaTM/h (codon optimized) | CMV/R Ebola GP(Z) delta TM/h | 37 | 37 |
| | pVR1012 EbolaGP(Z, P87666)delta TM/h (codon optimized) | pVR1012x/s Ebola GP(Z) delta TM/h (P87666) | 38 | 38 |
| | CMV Ebola GP (S/Gulu) delta TM/h (codon optimized) | CMV/R-GP(S/G)(deltaTM)/h | 39 | 39 |
| | CMV/R Ebola GP (S, Q66798) delta TM/h (codon optimized) | CMV/R-GP(S, Q66798)(dTM)/h | 40 | 40 |

TABLE 2-continued

Ebola/Marburg/Lassa Plasmids, and Recombinant Adenoviruses

| Construct | Construct Name/Description | Construct Map Name | SEQ ID NO | Figure |
|---|---|---|---|---|
| VRC6802 | VRC6802, pVR1012x/s Lassa delta TM/h (codon optimized) | pVR1012x/s Lassa (codon optimized) | 41 | 41 |
| VRC6703 | VRC6703, pVR1012x/sMarburgdeltaTM/h (codon optimized) | PVR1012x/s Marburg (codon optimized) | 42 | 42 |
| | CMV/R Ebola NP | CMV/R Ebola NP | 43 | 43 |

DETAILED DESCRIPTION OF THE INVENTION

Filovirus vaccines are provided comprising a nucleic acid molecule encoding a filoviral structural protein operatively-linked to a control sequence in a pharmaceutically acceptable excipient. In one embodiment, the nucleic acid molecule encodes the transmembrane form of the viral glycoprotein (GP). In another embodiment, the nucleic acid molecule encodes the secreted form of the viral glycoprotein (SGP). In yet another embodiment, the nucleic acid molecule encodes the viral nucleoprotein (NP).

The present invention further includes vaccines comprising nucleic acid molecules encoding filoviral structural proteins other than GP, SGP, and NP, e.g., other structural gene products which elicit an immune response against a filovirus or disease caused by infection with filovirus. The nucleic acid molecules of the vaccines of the present invention encode structural gene products of any Ebola viral strain including the Zaire, Sudan, Ivory Coast and Reston strains. Nucleic acid molecules encoding structural gene products of the genetically-related Marburg virus strains may also be employed. Moreover, the nucleic acid molecules of the present invention may be modified, e.g., the nucleic acid molecules set forth herein may be mutated, as long as the modified expressed protein elicits an immune response against a pathogen or disease. For example, the nucleic acid molecule may be mutated so that the expressed protein is less toxic to cells. The present invention also includes vaccines comprising a combination of nucleic acid molecules. For example, and without limitation, nucleic acid molecules encoding GP, SGP and NP of the Zaire, Sudan and Ivory Coast Ebola strains may be combined in any combination, in one vaccine composition.

The present invention also provides methods for immunizing a subject against disease caused by infection with filovirus comprising administering to the subject an immunoeffective amount of a filovirus vaccine. Methods of making and using filovirus vaccines are also provided by the present invention including the preparation of pharmaceutical compositions.

Biochemical Analysis of Secreted and Virion Glycoproteins of Ebola Virus.

Ebola (EBO) viruses are members of the Filoviridae and cause a severe, often fatal form of hemorrhagic fever disease in human and/or non-human primates. The glycoprotein (GP) gene of filoviruses is the fourth gene (of seven) from the 3' end of the negative-strand RNA genome. All EBO viruses characterized thus far have the same unconventional type of GP gene organization that results in the expression of a secreted, nonstructural glycoprotein (SGP) in preference to the structural GP. The SGP is encoded in a single frame (0 frame), while the GP is encoded in two frames (0 and −1 frames). Expression of the GP occurs when the two frames are connected through a transcriptional editing event that results in the insertion of a single extra adenosine (added to a run of seven adenosines).

Figure 44:
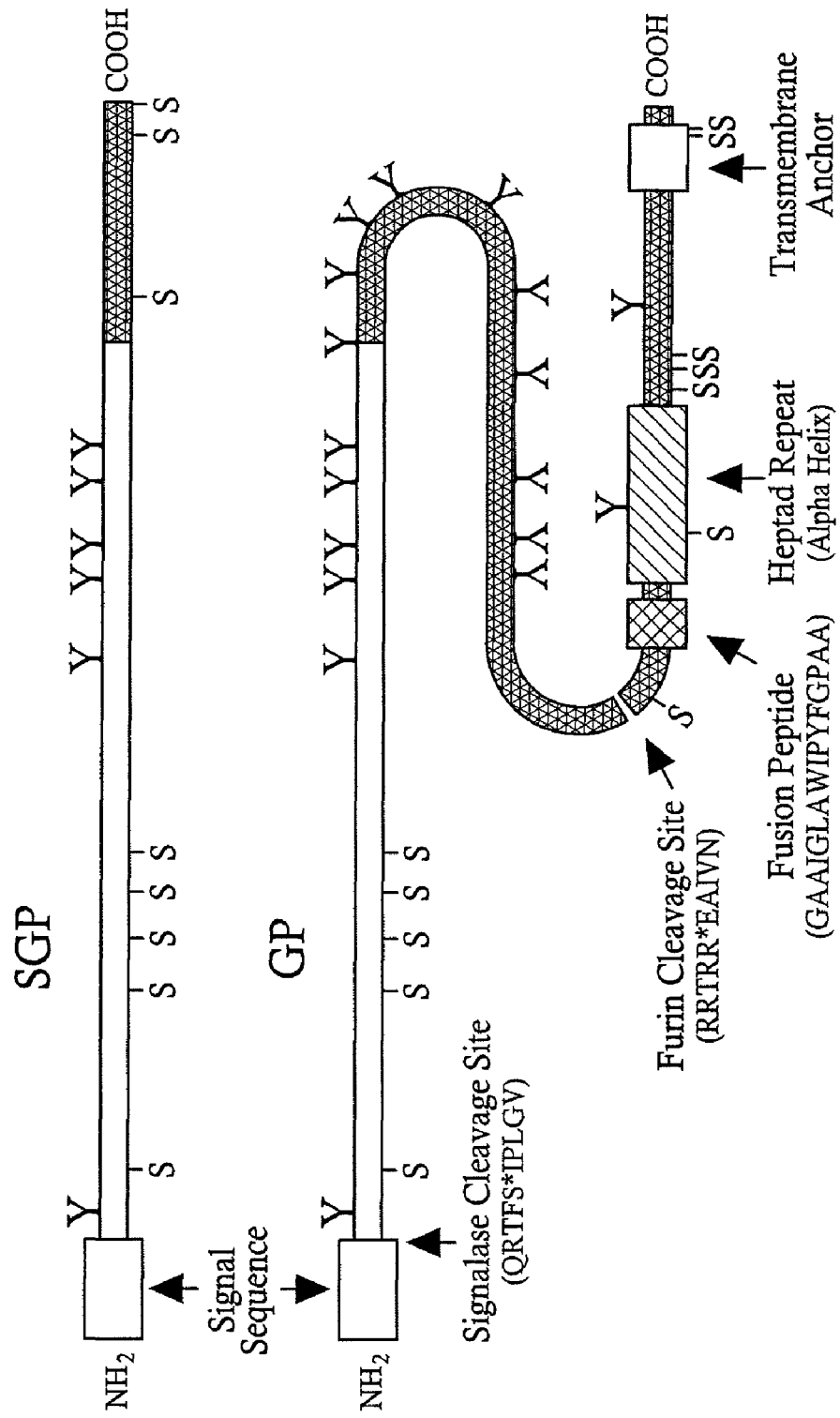
FIG. 44 is a diagrammatic representation of secreted glycoprotein (SGP) and glycoprotein (GP) molecules of Ebola virus (Zaire species isolated in 1976) showing important structural features. The white N-terminal regions of SGP and GP correspond to identical (shared) sequences, while the black C termini identify sequences unique to GP or SGP molecules. The common signalase cleavage sites for both SGP and GP and the furin cleavage site for GP0 (uncleaved form of GP) (↓) were determined by N-terminal sequencing. Also shown are cysteine residues (S), predicted N-linked glycosylation sites (Y-shaped projections), a predicted fusion peptide, a heptad repeat sequence, and a transmembrane anchor sequence. In Ebola viruses, the positions of these structures are conserved and their sequences are very similar or, in the case of N-linked glycosylation sites, are at least concentrated in the central region of GP. Signalase cleavage site is SEQ ID NO: 48, Furin cleavage site is SEQ ID NO: 49, and Fusion peptide is SEQ ID NO: 50.

Referring to FIG. 44, for Zaire species of EBO virus, the N-terminal 295 residues (including signal sequence) of the SGP (364 total residues) and GP (676 total residues) are identical, but the length and composition of their C-terminal sequences are unique. The GP, a type 1 transmembrane protein, is found on the surface of the infectious virion and functions in attachment structure in the binding and entry of the virus into susceptible cells. Comparisons of GP predicted amino acid sequences for all species of EBO virus show a general conservation in the N-terminal and C-terminal regions (each approximately one-third of the total sequence) and are separated by a highly variable middle section. This protein is highly glycosylated, containing large amounts of N- and O-linked glycans, and for Marburg (MBG) virus (another type of filovirus) has been shown to form trimers. Just N terminal to the transmembrane anchor sequence of the GP (residues 650 to 672) is a motif (residues 585 to 609) that is highly conserved in filoviruses. This sequence also has a high degree of homology with a motif in the glycoproteins of oncogenic retroviruses that has been shown to be immunosuppressive in vitro. Partially overlapping this motif is a heptad repeat sequence (53 residues; positions 541 to 593) that is thought to function in the formation of intermolecular coiled coils in the assembly of trimers, similar to structures predicted for the surface glycoproteins of other viruses. Immediately N terminal to this sequence is a predicted fusion peptide followed closely by a putative multibasic cleavage site for a subtilisin/kexin-like convertase, furin. Cleavage by furin has been indirectly demonstrated by use of specific inhibitors and is predicted to occur at the last arginine in the sequence RRTRR↓ (position 501 from the beginning of the open reading frame [ORF]). Although the role of the SGP is less defined, recent studies have shown that SGP can bind to neutrophils, while GP binds to endothelial cells. The different binding patterns of SGP and GP suggest that despite having identical N-terminal amino acid sequences (~280 residues), these glycoproteins are structurally very distinct from one another.

Figure 45:
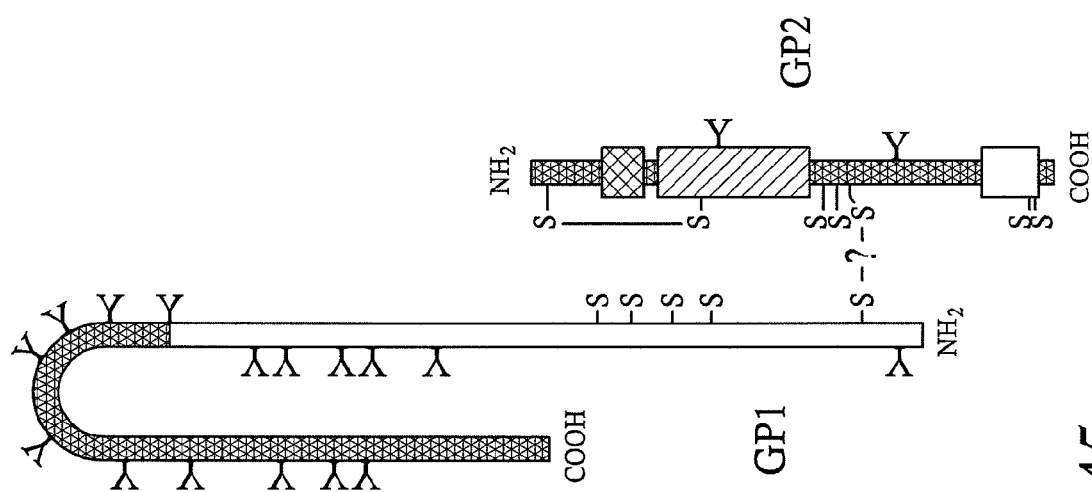
FIG. 45 is a diagrammatic representation of the structural GP. Shown is the predicted orientation of the GP1-GP2 heterodimer linked by undetermined disulfide bonding (indicated by the question mark). Intramolecular disulfide bonds that are shown come from prior predictions based on similarities to retrovirus glycoprotein structures. See FIG. 44 for other features of the amino acid sequence.

Referring to FIG. 45, the glycoproteins expressed by a Zaire species of Ebola virus were analyzed for cleavage, oligomerization, and other structural properties to better define their functions. The 50- to 70-kDa secreted and 150-kDa virion/structural glycoproteins (SGP and GP, respectively), which share the 295 N-terminal residues, are cleaved near the N terminus by signalase. A second cleavage event, occurring in GP at a multibasic site (RRTRR↓) (SEQ ID NO: 51) that is likely mediated by furin, results in two glycoproteins (GP1 and GP2) linked by disulfide bonding. This furin cleavage site is present in the same position in the GPs of all Ebola viruses (R[R/K]X[R/K]R↓), and one is predicted for Marburg viruses (R[R/K]KR↓), although in a different location. Based on the results of cross-linking studies, investigators were able to determine that Ebola virion peplomers are composed of trimers of GP1-GP2 heterodimers and that aspects of their structure are similar to those of retroviruses (including lentiviruses like HIV-1 and HIV-2), paramyxoviruses, and influenza viruses. Investigators also determined that SGP is secreted from infected cells almost exclusively in the form of a homodimer that is joined by disulfide bonding.

Figure 46:
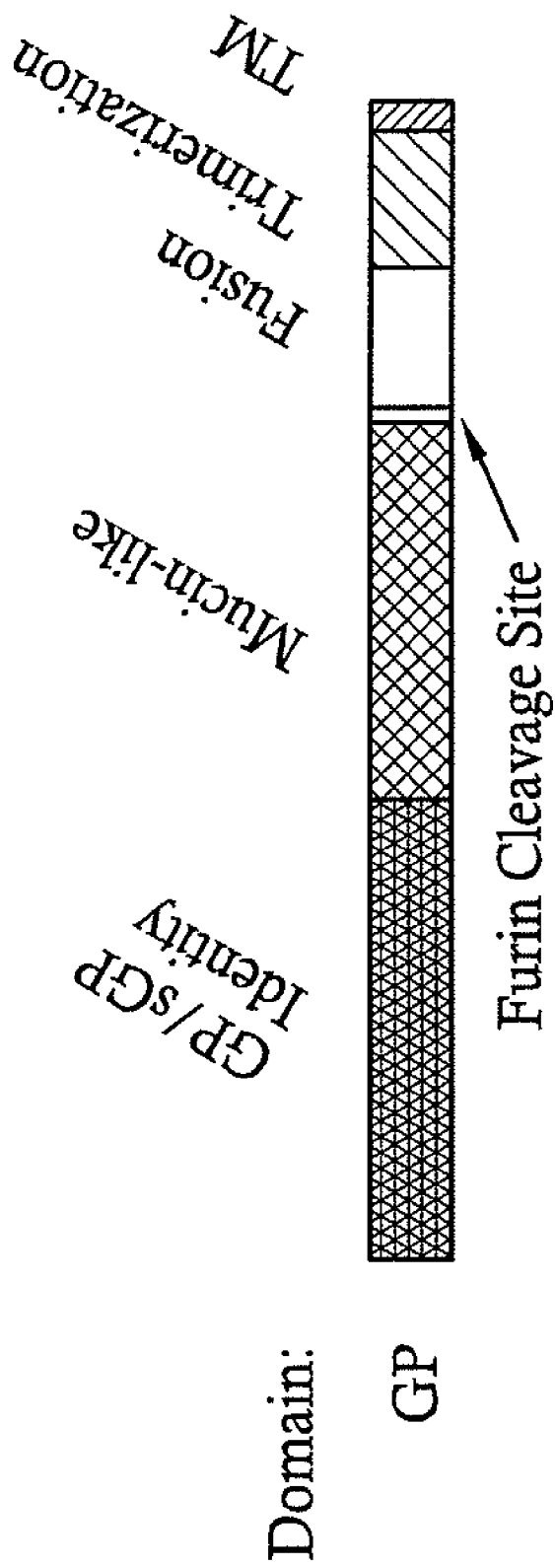
FIG. 46 shows induction of the cytopathic effects by Ebola virus glycoproteins and mapping of the molecular determinants of cytopathicity.

Referring to FIG. 46, investigators defined the main viral determinant of Ebola virus pathogenicity; synthesis of the virion glycoprotein (GP) of Ebola virus Zaire induced cytotoxic effects in human endothelial cells in vitro and in vivo. This effect mapped to a serine-threonine-rich, mucin-like domain of this type I transmembrane glycoprotein, one of seven gene products of the virus. Gene transfer of GP into explanted human or porcine blood vessels caused massive endothelial cell loss within 48 hours that led to a substantial increase in vascular permeability. Deletion of the mucin-like region of GP abolished these effects without affecting protein expression or function. GP derived from the Reston strain of virus, which causes disease in non-human primates but not in man, did not disrupt the vasculature of human blood vessels. In contrast, the Zaire GP induced endothelial cell disruption and cytotoxicity in both non-human primate and human blood vessels, and the mucin domain was required for this effect. These findings indicate that GP, through its mucin domain, is the viral determinant of Ebola pathogenicity and likely contributes to hemorrhage during infection.

Nucleic Acid Molecules

As indicated herein, nucleic acid molecules of the present invention may be in the form of RNA or in the form of DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a wild-type filovirus structural gene product; and DNA molecules which comprise a sequence substantially different from those described above but which, due to the degeneracy of the genetic code, still encode an ORF of a wild-type filovirus structural gene product. Of course, the genetic code is well known in the art.

The present invention is further directed to fragments of the nucleic acid molecules described herein. By a fragment of a nucleic acid molecule having the nucleotide sequence of an ORF encoding a wild-type filovirus structural gene product is intended fragments at least about 15 nt., and more preferably at least about 20 nt., still more preferably at least about 30 nt., and even more preferably, at least about 40 nt. in length. Of course, larger fragments 50, 100, 150, 200, 250, 300, 350, 400, 450, or 500 nt. in length are also intended according to the present invention as are fragments corresponding to most, if not all, of the nucleotide sequence of the ORF encoding a wild-type filovirus structural gene product. By a fragment at least 20 nt. in length, for example, is intended fragments which include 20 or more contiguous bases from the nucleotide sequence of the ORF of a wild-type filovirus structural gene product.

Preferred nucleic acid fragments of the present invention include nucleic acid molecules encoding epitope-bearing portions of the filovirus structural protein. In particular, such nucleic acid fragments of the present invention include nucleic acid molecules encoding epitope-bearing domains of a filovirus structural protein, where the domain is the GP/SGP identity domain, the mucin-like domain, the furin cleavage site, the fusion peptide domain, the heptad repeat domain, the transmembrane anchor domain, and the intracellular domain, and any combination thereof, for example, a filovirus glycoprotein having a truncation at the carboxy terminus to delete the transmembrane anchor and intracellular domain, a filovirus glycoprotein having a truncation at the carboxy terminus to delete the heptad repeat domain and transmembrane anchor and intracellular domain, a filovirus glycoprotein having a truncation at the carboxy terminus to delete the fusion peptide domain, heptad repeat domain, and transmembrane anchor and intracellular domain, a filovirus glycoprotein having a truncation at the carboxy terminus to delete the furin cleavage site, fusion peptide domain, heptad repeat domain, and transmembrane anchor and intracellular domain, a filovirus glycoprotein having a truncation at the carboxy terminus to delete the mucin-like domain, furin cleavage site, fusion peptide domain, heptad repeat domain, and transmembrane anchor and intracellular domain. Another example is a filovirus glycoprotein having an amino, internal, or carboxy deletion to delete the mucin-like domain, the furin cleavage site, the fusion peptide domain, the heptad repeat domain, the transmembrane anchor domain, or the intracellular domain.

In another aspect, the invention provides a nucleic acid molecule comprising a polynucleotide which hybridizes under stringent hybridization conditions to a portion of the polynucleotide in a nucleic acid molecule of the invention described above. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt.), and more preferably at least about 20 nt., still more preferably at least about 30 nt., and even more preferably about 30-70 nt. of the reference polynucleotide.

By a portion of a polynucleotide of "at least 20 nt. in length," for example, is intended 20 or more contiguous nucleotides from the nucleotide sequence of the reference polynucleotide. Of course, a polynucleotide which hybridizes only to a poly A sequence or a complementary stretch of T (or U) residues, would not be included in a polynucleotide of the invention used to hybridize to a portion of a nucleic acid of the invention, since such a polynucleotide would hybridize to any nucleic acid molecule containing a poly A stretch or the complement thereof (e.g., practically any double-stranded cDNA clone).

As indicated herein, nucleic acid molecules of the present invention which encode a filovirus structural gene product may include, but are not limited to those encoding the amino acid sequence of the full-length polypeptide, by itself, the coding sequence for the full-length polypeptide and additional sequences, such as those encoding a leader or secretory sequence, such as a pre-, or pro- or prepro-protein sequence, the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; and additional coding sequence which codes for additional amino acids, such as those which provide additional functionalities.

The present invention further relates to variants of the nucleic acid molecules of the present invention, which encode portions, analogs or derivatives of the filovirus structural gene product. Variants may occur naturally, such as a natural allelic variant. By an "allelic variant" is intended one of several alternate forms of a gene occupying a given locus on a genome of an organism. (*Genes II*, Lewin, B., ed., John Wiley & Sons, 1985 New York). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the filovirus structural gene product or portions thereof. Also especially preferred in this regard are conservative substitutions.

Further embodiments of the invention include nucleic acid molecules comprising a polynucleotide having a nucleotide sequence at least 95% identical, and more preferably at least 96%, 97%, 98% or 99% identical to a nucleotide sequence encoding a polypeptide having the amino acid sequence of a wild-type filovirus structural gene product or fragment thereof or a nucleotide sequence complementary thereto.

By a polynucleotide having a nucleotide sequence at least, for example, 95% "identical" to a reference nucleotide sequence encoding a filovirus structural gene product is intended that the nucleotide sequence of the polynucleotide is identical to the reference sequence except that the polynucleotide sequence may include up to five point mutations per each 100 nucleotides of the reference nucleotide sequence encoding the Ebola virus structural gene product. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to the reference nucleotide sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, 1981 *Advances in Applied Mathematics* 2:482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequences shown herein in the Sequence Listing which encode a polypeptide having Ebola, Marburg, or Lassa virus polypeptide activity. By "a polypeptide having Ebola, Marburg, or Lassa virus polypeptide activity" is intended polypeptides exhibiting Ebola, Marburg, or Lassa virus polypeptide activity in a particular biological assay. For example, GP, SGP or NP protein activity can be measured for changes in immunological character by an appropriate immunological assay.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence shown herein in the Sequence Listing will encode a polypeptide "having Ebola, Marburg, or Lassa virus polypeptide activity". In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Ebola, Marburg, or Lassa virus polypeptide activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al. 1990 *Science* 247:1306-1310, wherein the authors indicate that proteins are surprisingly tolerant of amino acid substitutions.

Polypeptides and Fragments

The invention further provides a filovirus polypeptide having the amino acid sequence encoded by an open reading frame (ORF) of a wild-type filovirus structural gene, or a peptide or polypeptide comprising a portion thereof (e.g., SGP).

It will be recognized in the art that some amino acid sequences of the filovirus polypeptides can be varied without significant effect of the structure or function of the protein. If such differences in sequence are contemplated, it should be remembered that there will be critical areas on the protein which determine activity.

Thus, the invention further includes variations of the filovirus polypeptide which show substantial filovirus polypeptide activity or which include regions of filovirus protein such as the protein portions discussed below. Such mutants include deletions, insertions, inversions, repeats, and type substitutions. As indicated, guidance concerning which amino acid changes are likely to be phenotypically silent can be found in Bowie, J. U. et al. 1990 *Science* 247:1306-1310.

Thus, the fragment, derivative or analog of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein (see Table A).

TABLE A

Conservative Amino Acid Substitutions

| | |
|---|---|
| Aromatic | Phenylalanine |
| | Tryptophan |
| | Tyrosine |
| Ionizable: Acidic | Aspartic Acid |
| | Glutamic Acid |
| Ionizable: Basic | Arginine |
| | Histidine |
| | Lysine |
| Nonionizable Polar | Asparagine |
| | Glutamine |
| | Selenocystine |
| | Serine |
| | Threonine |
| Nonpolar (Hydrophobic) | Alanine |
| | Glycine |
| | Isoleucine |
| | Leucine |
| | Proline |
| | Valine |
| Sulfur Containing | Cysteine |
| | Methionine |

Of course, the number of amino acid substitutions a skilled artisan would make depends on many factors, including those described above. Generally speaking, the number of amino acid substitutions for any given filovirus polypeptide will not be more than 50, 40, 30, 20, 10, 5 or 3.

Amino acids in the filovirus polypeptides of the present invention that are essential for function can be identified by methods known in the art, such as site-directed mutagenesis or alanine-scanning mutagenesis (Cunningham & Wells 1989 *Science* 244:1081-1085). The latter procedure introduces single alanine mutations at every residue in the molecule. The resulting mutant molecules are then tested for biological activity such as changes in immunological character.

The polypeptides of the present invention are conveniently provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the filovirus polypeptide can be substantially purified by the one-step method described in Smith and Johnson 1988 *Gene* 67:31-40.

The polypeptides of the present invention include a polypeptide comprising a polypeptide having the amino acid sequence of a wild-type filovirus structural gene product or portion thereof or encoded by a nucleic acid sequence shown herein in the Sequence Listing; as well as polypeptides which are at least 95% identical, and more preferably at least 96%, 97%, 98%, or 99% identical to those described above.

By a polypeptide having an amino acid sequence at least, for example, 95% "identical" to a reference amino acid sequence of an filovirus polypeptide is intended that the amino acid sequence of the polypeptide is identical to the reference sequence except that the polypeptide sequence may include up to five amino acid alterations per each 100 amino acids of the reference amino acid of the filovirus polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98%, or 99% identical to a reference amino acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another aspect, the invention provides portions of the polypeptides described herein with at least 30 amino acids and more preferably at least 50 amino acids. Preferred portions of the present invention include polypeptides comprising an epitope-bearing portion of a filovirus structural protein. In particular, preferred portions of the present invention include polypeptides comprising an epitope-bearing domain of a filovirus structural protein, where the domain is the GP/SGP identity domain, the mucin-like domain, the furin cleavage site, the fusion peptide domain, the heptad repeat domain, the transmembrane anchor domain, and the intracellular domain, and any combination thereof, for example, a filovirus glycoprotein having a truncation at the carboxy terminus to delete the transmembrane anchor and intracellular domain, a filovirus glycoprotein having a truncation at the carboxy terminus to delete the heptad repeat domain and transmembrane anchor and intracellular domain, a filovirus glycoprotein having a truncation at the carboxy terminus to delete the fusion peptide domain, heptad repeat domain, and transmembrane anchor and intracellular domain, a filovirus glycoprotein having a truncation at the carboxy terminus to delete the furin cleavage site, fusion peptide domain, heptad repeat domain, and transmembrane anchor and intracellular domain, and a filovirus glycoprotein having a truncation at the carboxy terminus to delete the mucin-like domain, furin cleavage site, fusion peptide domain, heptad repeat domain, and transmembrane anchor and intracellular domain. Another example is a filovirus glycoprotein having an amino, internal, or carboxy deletion to delete the mucin-like domain, the furin cleavage site, the fusion peptide domain, the heptad repeat domain, the transmembrane anchor domain, or the intracellular domain.

The polypeptides of the invention may be produced by any conventional means (Houghten, R. A. 1985 *PNAS USA*

82:5131-5135). The "Simultaneous Multiple Peptide Synthesis (SMPS)" process is described in U.S. Pat. No. 4,631,211 to Houghten et al. (1986).

The present invention also relates to vectors which include the nucleic acid molecules of the present invention, host cells which are genetically engineered with the recombinant vectors, and the production of filovirus polypeptides or fragments thereof by recombinant techniques.

The present invention relates to "prime and boost" immunization regimes in which the immune response induced by administration of a priming composition is boosted by administration of a boosting composition. The present invention is based on the inventors' experimental demonstration that effective boosting can be achieved using replication-defective adenovirus vectors, following priming with any of a variety of different types of priming compositions. The present invention employs replication-deficient adenovirus which, as the experiments described below show, has been found to be an effective means for providing a boost to an immune response primed to antigen using any of a variety of different priming compositions.

Replication-deficient adenovirus derived from human serotype 5 has been developed as a live viral vector by Graham and colleagues (Graham & Prevec 1995 *Mol Biotechnol* 3:207-20; Bett et al. 1994 *PNAS USA* 91:8802-6). Adenoviruses are non-enveloped viruses containing a linear double-stranded DNA genome of around 3600 bp. Recombinant viruses can be constructed by in vitro recombination between an adenovirus genome plasmid and a shuttle vector containing the gene of interest together with a strong eukaryotic promoter, in a permissive cell line which allows viral replication. High viral titres can be obtained from the permissive cell line, but the resulting viruses, although capable of infecting a wide range of cell types, do not replicate in any cells other than the permissive line, and are therefore a safe antigen delivery system. Recombinant adenoviruses have been shown to elicit protective immune responses against a number of antigens including tick-borne encephalitis virus NS1 protein (Jacobs et al. 1992 *J Virol* 66:2086-95) and measles virus nucleoprotein (Fooks et al. 1995 *Virology* 210:456-65).

Remarkably, the experimental work described below demonstrates that use of embodiments of the present invention allows for recombinant replication-defective adenovirus expressing an antigen to boost an immune response primed by a DNA vaccine. The replication-defective adenovirus was found to induce an immune response after intramuscular immunization. In prime/boost vaccination regimes the replication-defective adenovirus is also envisioned as being able to prime a response that can be boosted by a different recombinant virus or recombinantly produced antigen.

Non-human primates immunized with plasmid DNA and boosted with replication-defective adenovirus were protected against challenge. Both recombinant replication-deficient adenovirus and plasmid DNA are vaccines that are safe for use in humans. Advantageously, the inventors found that a vaccination regime used intramuscular immunization for both prime and boost can be employed, constituting a general immunization regime suitable for inducing an immune response, e.g., in humans.

The present invention in various aspects and embodiments employs a replication-deficient adenovirus vector encoding an antigen for boosting an immune response to the antigen primed by previous administration of the antigen or nucleic acid encoding the antigen.

A general aspect of the present invention provides for the use of a replication-deficient adenoviral vector for boosting an immune response to an antigen.

One aspect of the present invention provides a method of boosting an immune response to an antigen in an individual, the method including provision in the individual of a replication-deficient adenoviral vector including nucleic acid encoding the antigen operably linked to regulatory sequences for production of antigen in the individual by expression from the nucleic acid, whereby an immune response to the antigen previously primed in the individual is boosted.

An immune response to an antigen may be primed by genetic immunization, by infection with an infectious agent, or by recombinantly produced antigen.

A further aspect of the invention provides a method of inducing an immune response to an antigen in an individual, the method comprising administering to the individual a priming composition comprising the antigen or nucleic acid encoding the antigen and then administering a boosting composition which comprises a replication-deficient adenoviral vector including nucleic acid encoding the antigen operably linked to regulatory sequences for production of antigen in the individual by expression from the nucleic acid.

A further aspect provides for use of a replication-deficient adenoviral vector, as disclosed, in the manufacture of a medicament for administration to a mammal to boost an immune response to an antigen. Such a medicament is generally for administration following prior administration of a priming composition comprising the antigen.

The priming composition may comprise any viral vector, including adenoviral, or other than adenoviral, such as a vaccinia virus vector such as a replication-deficient strain such as modified virus Ankara (MVA) (Mayr et al. 1978 *Zentralbl Bakteriol* 167:375-90; Sutter and Moss 1992 *PNAS USA* 89:10847-51; Sutter et al. 1994 *Vaccine* 12:1032-40) or NYVAC (Tartaglia et al. 1992 *Virology* 118:217-32), an avipox vector such as fowlpox or canarypox, e.g., the strain known as ALVAC (Kanapox, Paoletti et al. 1994 *Dev Biol Stand* 1994 82:65-9), or a herpes virus vector.

The priming composition may comprise DNA encoding the antigen, such DNA preferably being in the form of a circular plasmid that is not capable of replicating in mammalian cells. Any selectable marker should not be resistant to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boosting with first and second boosting compositions, the first and second boosting compositions being the same or different from one another, e.g., as exemplified below. Still further boosting compositions may be employed without departing from the present invention. In one embodiment, a triple immunization regime employs DNA, then adenovirus (Ad) as a first boosting composition, and then MVA as a second boosting composition, optionally followed by a further (third) boosting composition or subsequent boosting administration of one or other or both of the same or different vectors. Another option is DNA then MVA then Ad, optionally followed by subsequent boosting administration of one or other or both of the same or different vectors.

The antigen to be included in respective priming and boosting compositions (however many boosting compositions are employed) need not be identical, but should share epitopes. The antigen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

Within the replication-deficient adenoviral vector, regulatory sequences for expression of the encoded antigen will include a promoter. By "promoter" is meant a sequence of nucleotides from which transportation may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, enhancer sequences, marker genes, internal ribosome entry site (IRES) and other sequences may be included as appropriate, in accordance with the knowledge and practice of the ordinary person skilled in the art: see, for example, *Molecular Cloning: a Laboratory Manual*, 2$^{nd}$ edition, Sambrook et al. 1989 Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Ausubel et al. eds., John Wiley & Sons, 1994.

Suitable promoters for use in aspects and embodiments of the present invention include the cytomegalovirus immediate early (CMV IE) promoter, with or without intron A, and any other promoter that is active in mammalian cells.

Either or both of the priming and boosting compositions may include an adjuvant or cytokine, such as alpha-interferon, gamma-interferon, platelet-derived growth factor (PDGF), granulocyte macrophage-colony stimulating factor (GM-CSF) granulocyte-colony stimulating factor (gCSF), tumor necrosis factor (TNF), epidermal growth factor (EGF), IL-1, IL-2, IL-4, IL-6, IL-8, IL-10 and IL-12, or encoding nucleic acid therefor.

Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks.

Preferably, administration of priming composition, boosting composition, or both priming and boosting compositions, is intramuscular immunization.

Intramuscular administration of adenovirus vaccines or plasmid DNA may be achieved by using a needle to inject a suspension of the virus or plasmid DNA. An alternative is the use of a needless injection device to administer a virus or plasmid DNA suspension (using, e.g., Biojector™) or a freeze-dried powder containing the vaccine (e.g., in accordance with techniques and products of Powderject), providing for manufacturing individually prepared doses that do not need cold storage. This would be a great advantage for a vaccine that is needed in rural areas of Africa.

Adenovirus is a virus with an excellent safety record in human immunizations. The generation of recombinant viruses can be accomplished simply, and they can be manufactured reproducibly in large quantities. Intramuscular administration of recombinant replication-deficient adenovirus is therefore highly suitable for prophylactic or therapeutic vaccination of humans against diseases which can be controlled by an immune response.

The individual may have a disease or disorder such that delivery of the antigen and generation of an immune response to the antigen is of benefit or has a therapeutically beneficial effect.

Most likely, administration will have prophylactic aim to generate an immune response against a pathogen or disease before infection or development of symptoms.

Diseases and disorders that may be treated or prevented in accordance with the present invention include those in which an immune response may play a protective or therapeutic role.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, intramucosal (e.g., gut), intranasal, intramuscular, or intraperitoneal routes.

As noted, administration is preferably intradermal, subcutaneous or intramuscular.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A slow-release formulation may be employed.

Following production of replication-deficient adenoviral particles and optional formulation of such particles into compositions, the particles may be administered to an individual, particularly human or other primate.

Administration may be to another mammal, e.g., rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences*, 16$^{th}$ edition, Osol, A. ed., 1980.

In one preferred regimen, DNA is administered (preferably intramuscularly) at a dose of 10 micrograms to 50 milligrams/injection, followed by adenovirus (preferably intramuscularly) at a dose of $5 \times 10^7$-$1 \times 10^{12}$ particles/injection.

The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g., protection against disease.

Further aspects and embodiments of the present invention will be apparent to those of ordinary skill in the art, in view of the above disclosure and following experimental exemplification, included by way of illustration and not limitation, and with reference to the attached figures.

Development of a Preventive Vaccine for Ebola Virus Infection in Primates

Genetic immunization has been shown to influence both humoral and cellular immune activation pathways and to protect against infection by human pathogens (Tang, D. C. et al. 1992 Nature 356:152-154; Ulmer, J. B. et al. 1993 Science 259:1745-1749; Wang, B. et al. 1993 PNAS USA 90:4156-4160; Sedegah, M. et al. 1994 PNAS USA 91:9866-9870). The effectiveness of plasmid vaccines is thought to result from host cell protein synthesis and endogenous presentation of the immunogen, and possibly to immunostimulatory effects of plasmid DNA itself (Krieg, A. M. et al. 1995 Nature 374:546-549; Sato, Y. et al. 1996 Science 273:352-354). DNA vaccines have been shown to elicit specific immune responses to Ebola virus antigens and to protect guinea pigs (Xu, L. et al. 1998 Nat Med 4:7-42) and mice (Vanderzanden, L. et al. 1998 Virology 246:134-144) against challenge with Ebola virus adapted to produce lethal infection in rodents (Connolly, B. M. et al. 1999 J Infect Dis 179:S203-S217; Bray, M. et al. 1998 J Infect Dis 178:651-661). Although both cell-mediated and humoral immune responses were elicited, antibody titer correlated with the degree of protection in animals immunized with plasmids encoding proteins from the Zaire subtype of Ebola virus.

A broadly effective vaccine would need to provide immunity to the multiple Ebola subtypes isolated in human infections (Zaire, Sudan and Ivory Coast), but a multivalent vaccine might dilute the specific immune response demonstrated for the single subtype vaccine. To address this concern, we analyzed the efficacy of the original Ebola Zaire DNA vaccine in comparison to its use in combination with DNA from Ebola subtypes Sudan and Ivory Coast. As in a previous study (Xu, L. et al. 1998 Nat Med 4:7-42), immunization with a single plasmid encoding Zaire subtype virion glycoprotein, GP(Z), generated a substantial virus-specific antibody response and conferred protective immunity in guinea pigs (Table I). Inclusion of a plasmid expressing Ebola nucleoprotein, NP, did not affect the antibody titer to Ebola GP(Z) or diminish its protective efficacy. Further broadening of the vaccine components to include NP and three subtypes of Ebola glycoprotein, Zaire, Ivory Coast and Sudan, GP(Z,IC,S)+NP, yielded a pre-challenge immune response comparable to the single-plasmid vaccine. Moreover, complete protection from infection with Ebola Zaire was achieved in guinea pigs that received the multivalent vaccine (Table I, subjects 13-16). Anamnestic antibody was not induced by the virus challenge, indicating that the vaccine itself provided an immune response sufficient to efficiently clear the virus.

These findings show that multivalent plasmid immunization did not substantially diminish glycoprotein (GP)-specific antibody production and its protective efficacy in a rodent model.

TABLE I

Multivalent genetic immunization in guinea pigs

| ID | Immunization | ELISA IgG | Survival |
|---|---|---|---|
| 1 | Plasmid | 0 | No |
| 2 | Plasmid | 0 | No |
| 3 | Plasmid | 0 | No |
| 4 | Plasmid | 0 | No |
| 5 | GP(Z) | 6400 | Yes |
| 6 | GP(Z) | 6400 | Yes |
| 7 | GP(Z) | 6400 | Yes |
| 8 | GP(Z) | 3200 | Yes |
| 9 | GP(Z) + NP | 6400 | Yes |
| 10 | GP(Z) + NP | 6400 | Yes |
| 11 | GP(Z) + NP | 6400 | Yes |
| 12 | GP(Z) + NP | 6400 | Yes |
| 13 | GP(Z, IC, S) + NP | 6400 | Yes |
| 14 | GP(Z, IC, S) + NP | 1600 | Yes |
| 15 | GP(Z, IC, S) + NP | 6400 | Yes |
| 16 | GP(Z, IC, S) + NP | 6400 | Yes |

Table I. Comparison of multivalent vs. monovalent genetic immunization in guinea pigs. Guinea pigs were immunized intramuscularly three times at two-week intervals with 100 µg of DNA (Plasmid, 100 µg p1012; GP(Z), 100 µg pGP(Z); GP(Z) + NP, 75 µg pGP(Z) and 25 µg pNP; GP(Z, IC, S) + NP, 25 µg each of pGP(Z), pGP(IC), pGP(S) and pNP). Serum was collected 6 weeks after the first injection and pre-challenge titers for antibody to Ebola GP (ELISA IgG) were measured by ELISA (Ksiazek, T. G. et al. 1992 J Clin Microbiol 30: 947-950) and are displayed as the reciprocal endpoint dilution. Three months after the final immunization the animals were challenged as described (Xu, L. et al. 1998 Nat Med 4: 37-42).

Figure 47:
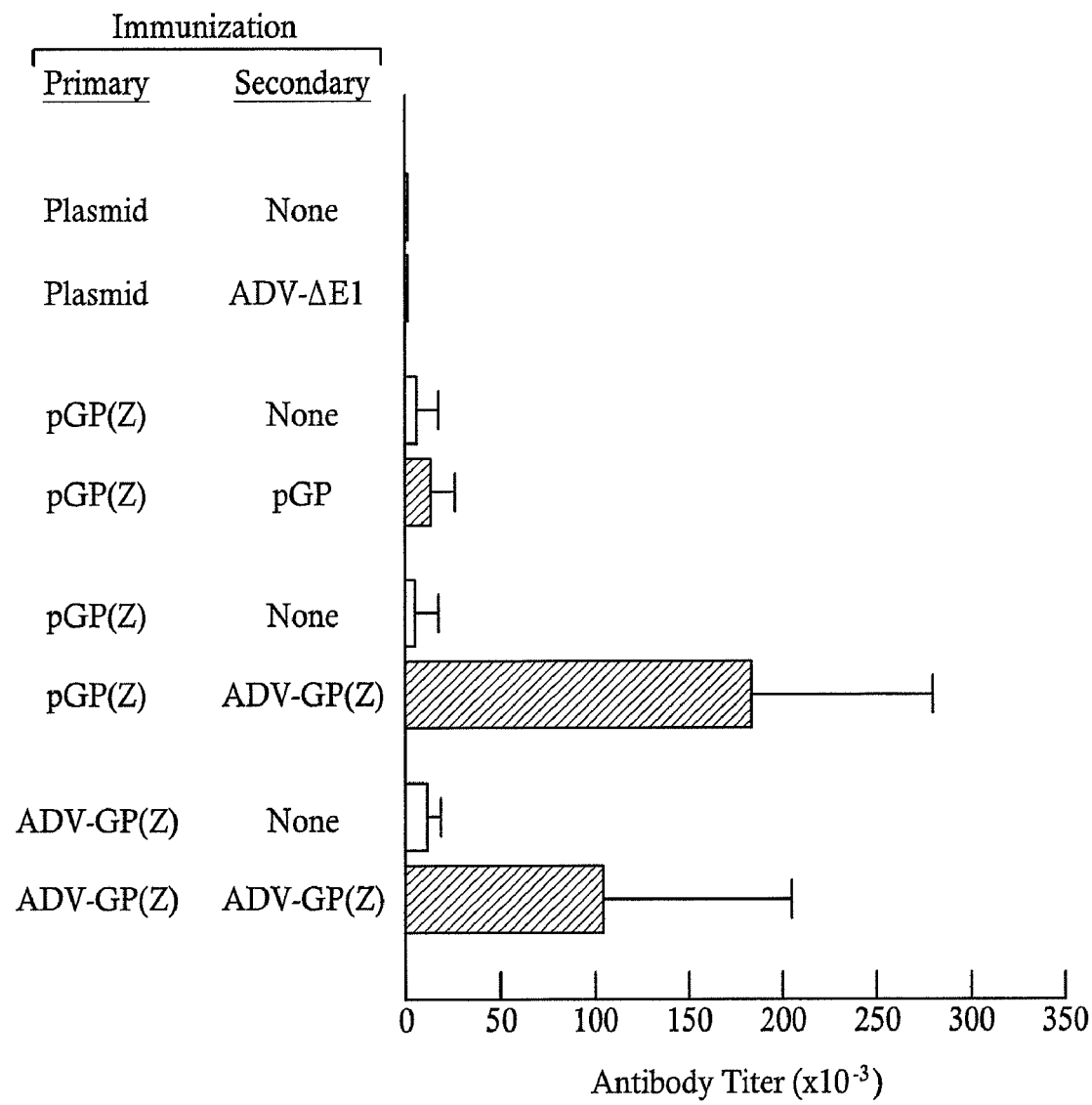
FIG. 47 shows Ebola-specific antibody responses generated by different DNA/adenovirus prime-boost combinations. Data are the means of the reciprocal endpoint dilution for each group of mice and error bars represent the standard deviation.

Because protection in the rodent model of Ebola virus infection correlated with antibody titers, and efficient humoral responses may influence clinical outcome in human disease (Baize, S. et al. 1999 Nat Med 5:423-426; Maruyama, T. et al. 1999 J Virol 73:6024-6030), we considered it important to elicit a strong humoral response for vaccines tested in primates, although cell-mediated immunity is coordinately induced and likely contributes to protection (Xu, L. et al. 1998 Nat Med 4:37-42). Recently, regimens of DNA priming followed by administration of viral vectors have demonstrated enhanced immune responses compared to vaccines using DNA alone (Sedegah, M. et al. 1998 PNAS USA 95:7648-7653; Hanke, T. et al. 1998 Vaccine 16:439-445; Robinson, H. L. et al. 1999 Nat Med 5:526-534; Schneider, J. et al. 1998 Nat Med 4:397-402). Recombinant, replication-deficient adenoviruses can be grown to high titer, infect antigen-presenting cells, and induce potent immune responses (Davis, A. R. et al. 1985 PNAS USA 82:7560-7564; Natuk, R. J. et al. 1992 PNAS USA 89:7777-7781; Xiang, Z. Q. et al. 1996 Virology 219: 220-227). Adenoviruses have shown a boosting effect in mice (Xiang, Z. Q. et al. 1999 J Immunol 162:6716-6723), but the combination of DNA and adenovirus has not been tested for efficacy in an infectious challenge model, and the success of this approach in primates is yet unknown. We therefore developed a recombinant adenoviral vector that directs high level GP expression ADV-GP(Z) and used this vector to test whether a modified prime-boost strategy would augment the antibody response to Ebola virus obtained with naked DNA alone. Mice were injected with DNA and adenovirus vectors either singly or in combinations, and cell-mediated and humoral immune responses were assessed. A 10- to 100-fold increase in antibody titer was found in mice injected with DNA followed by an adenovirus boost, compared to DNA immunization alone (FIG. 47). An increase in cytotoxic T cell responses was also observed with this combination. Immunization with ADV-GP(Z) alone yielded antibody titers that were not significantly different from those obtained with the DNA prime, adenovirus boost immunization. These data suggest that immunogenicity of the Ebola GP DNA vaccine in mice is improved by boosting with recombinant adenovirus and that this strategy might represent a useful approach to enhance immune responses in non-human primates.

Figure 48:
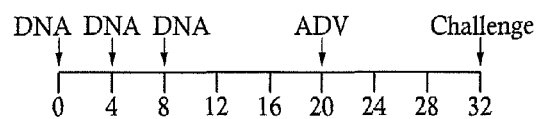
FIG. 48 (A-D) shows DNA-Adenovirus immunization of cynomolgus macaques. A) Immunization schedule for DNA and/or adenovirus injections, and challenge with the wild-type Mayinga strain of the Zaire subtype of Ebola virus. B) Elisa titers of Ebola-specific antibodies in serum. Serum was collected at week 12 (open bar) and 2 days before the immunization at week 24 (closed bar). C) Lymphoproliferative responses to Ebola-secreted glycoprotein (SGP) following immunization. Bars represent the average fold-proliferation of all four blood samples for each subject. The standard deviation is not shown because the baseline level of induction varied between experiments. However, PBMC from all 8 animals were assayed within the same experiment for each time point, and the averages displayed in the figure are representative of the results obtained for any single time point. D) Lymphoproliferative responses to Ebola SGP in bulk PBMC following depletion of lymphocyte subsets. PBMC from week 24 were treated with Dynal magnetic beads coated with the indicated antibody to deplete CD4+ or CD8+ cell subsets. Cells remaining after depletion were normalized for input cell number and stimulated as described in the Example. Results are shown for two control (Subjects 2 and 3) and two vaccinated (Subjects 6 and 7) monkeys.
Figure 48:
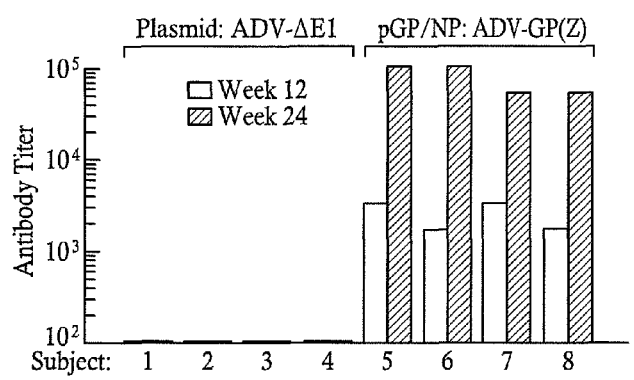
Figure 48:
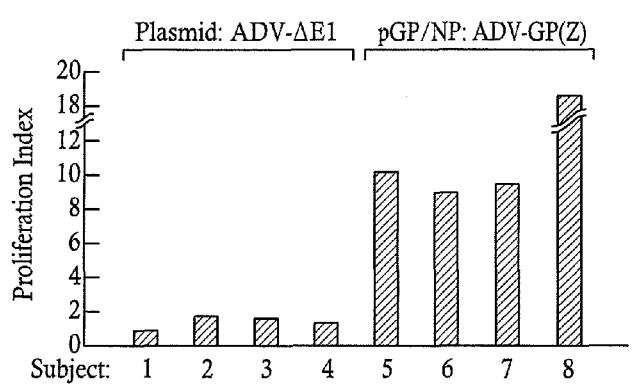
Figure 48:
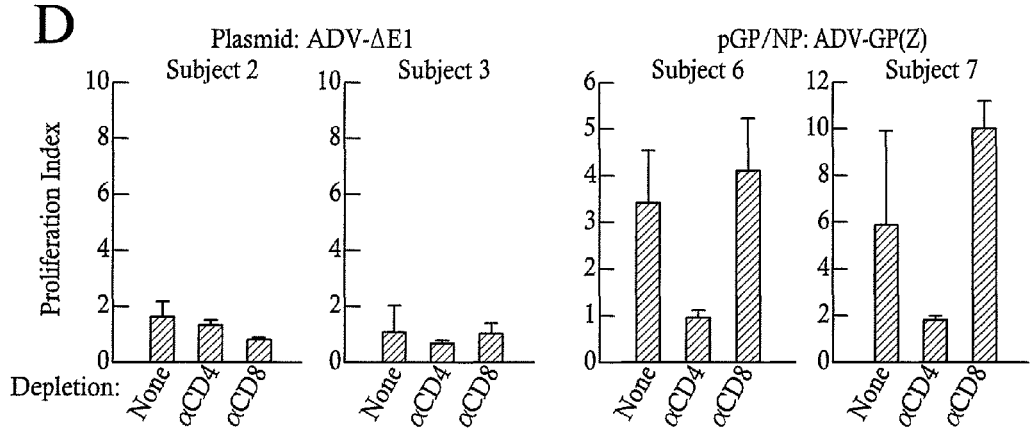

Whereas the rodent model has been useful in the development of a vaccine strategy, Ebola virus isolated directly from humans must first be adapted by multiple, sequential passage in rodents in order to produce a lethal infection in mice or guinea pigs (Connolly, B. M. et al. 1999 *J Infect Dis* 179: S203-S217; Bray, M. et al. 1998 *J Infect Dis* 178:651-661). Primate models of Ebola infection are thought to have a stronger predictive value for human disease and immune protection. We therefore conducted studies in non-human primates using a bimodal DNA/ADV vaccine and the multiple plasmid strategy that correlated with protection in guinea pigs. Cynomolgus macaques (*Macaca fascicularis*) received 3 injections of naked DNA vectors at 4-week intervals (FIG. 48A) and, after several months of rest which has been shown to boost immune responses (Letvin, N. L. et al. 1997 *PNAS USA* 94:9378-9383), were boosted with recombinant adenovirus expressing only the Zaire glycoprotein (FIG. 48A). Control animals received empty vectors (plasmid DNA and ADV-ΔE1 recombinant adenovirus), and vaccinated animals received the multicomponent DNA vaccine containing NP and three subtypes of Ebola GP (pGP/NP), followed by ADV-GP(Z). As expected, anti-Ebola serum antibodies could not be detected in control animals, but in animals receiving the Ebola vaccine, an antigen-specific antibody response was detected at week 12, one month after the third DNA injection (FIG. 48B). After boosting with recombinant adenovirus, antibody titers increased 10- to 20-fold over the levels obtained with DNA alone. Three months after the final immunization, antibody levels remained high, except for one animal (subject 8) whose titer dropped slightly from $5 \times 10^4$ to $1.3 \times 10^4$.

Primate cellular responses to Ebola antigens were next examined with an in vitro lymphocyte proliferation assay. In control monkeys, antigen-specific lymphocyte proliferation, measured by $^3$H-thymidine uptake, was equivalent to that in matched, unstimulated cells, resulting in a proliferation index near 1.0 for each animal (FIG. 48C). In contrast, peripheral blood mononuclear cells (PBMC) from animals immunized with the multivalent vaccine showed 9- to 20-fold increased stimulation, demonstrating a robust immune response to Ebola antigen at the cellular level. Depletion of CD4-positive lymphocytes reduced the antigen-stimulated proliferative response of PBMC from vaccinated monkeys to the level observed in control animals (FIG. 48D). Depletion of CD8-positive lymphocytes, however, did not affect Ebola antigen-specific lymphocyte proliferation. Therefore, the CD4-positive subset of lymphocytes, which provide the T cell help required for high antibody titers, contributes to the vaccine-induced cellular immune response.

Figure 49:
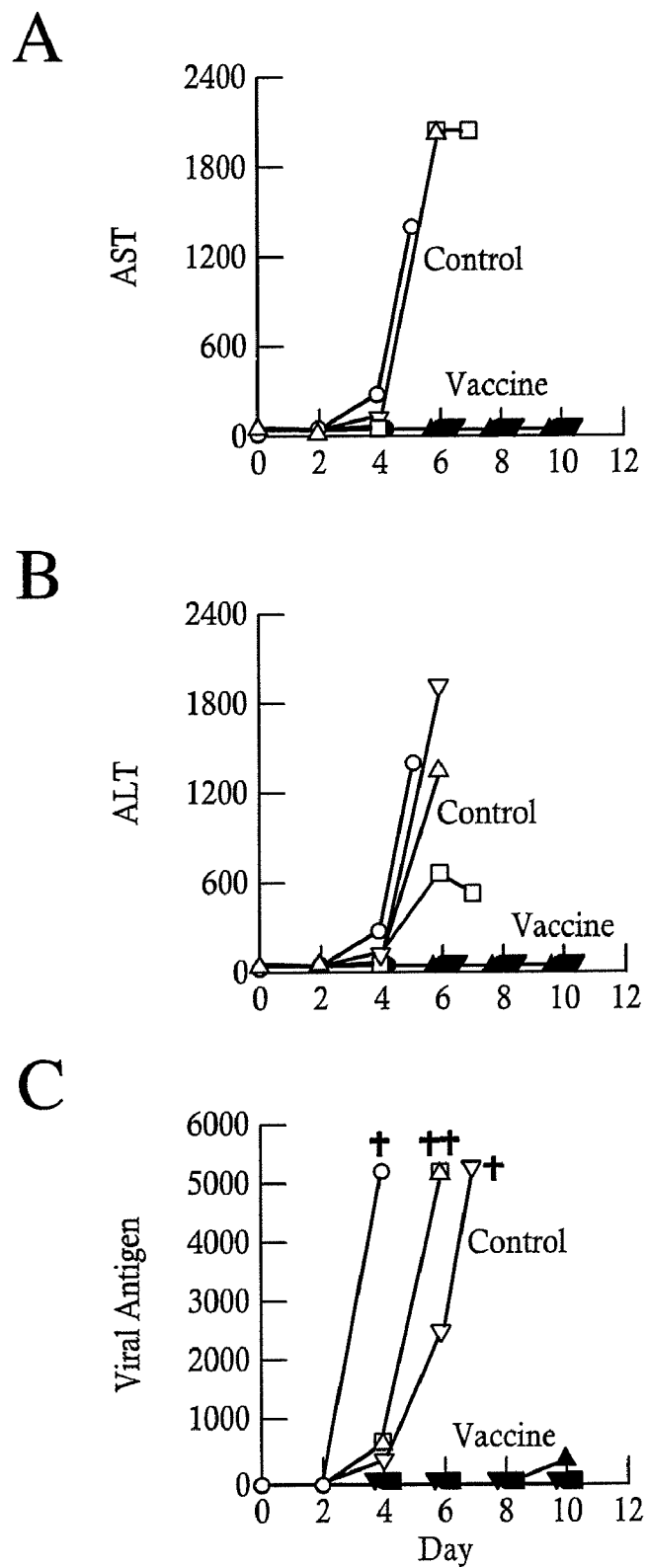
FIG. 49 (A-C) shows protection of cynomolgus macaques against lethal challenge with Ebola virus after DNA-adenovirus immunization. A, B) Hepatic enzyme levels in monkeys after challenge with Ebola virus. Liver enzymes [alanine aminotransferase (ALT) and aspartate aminotransferase (AST)] levels in the non-human primate sera were measured by standard recommended procedures using General chemistry 12 reagent disk for the Piccolo™ Analyzer (Abaxis, Inc., Sunnyvale, Calif.). Results are shown for four immunized (closed symbols) and four control (open symbols) monkeys. C) Plasma viraemia in monkeys following infection with Ebola virus. Crosses represent time of death in control animals [days 5 (subject 1) and 6 (subjects 2 and 4)]. One control animal, subject 3, was euthanized on day 7 when it was moribund. One vaccinated animal that was resistant to infection, subject 5, was euthanized on day 10 for histological examination of tissues. By day 17, none of the animals had detectable viraemia, and they remained aviraemic for the duration of the observation period (6 months). Data are the reciprocal endpoint dilution of serum for each monkey. Results are shown for four immunized (closed symbols) and four control (open symbols) monkeys.

To determine the protective efficacy of this vaccination regimen, monkeys were challenged with a lethal dose of the wild-type Mayinga strain from the Zaire subtype of Ebola virus. In the control monkeys, blood chemistry revealed an increase in hepatic enzymes (FIGS. 49A, B) that is characteristic for Ebola virus infection (Fisher-Hoch, S. P. et al. 1985 *J Infect Dis* 152:887-894). No such increase was observed in vaccinated subjects. The elevation of serum alanine aminotransferase (ALT) and aspartate aminotransferase (AST) was parallel to a dramatic increase in viraemia in all of the control animals (FIG. 49C). In contrast, no substantial increase in viral load was observed in vaccinated monkeys. The kinetics of disease progression was similar among the control animals, and the disease incidence was 100% in this group. Death occurred between days 5 and 6 for 3 animals, and the last monkey, moribund, was euthanized on day 7. In contrast, 4 out of 4 monkeys immunized with the combination DNA-adenovirus vaccine survived this lethal challenge of Ebola virus, and sterilizing immunity was achieved in 3 out of 4 subjects. The remaining animal showed a small transient rise in viral antigen; however, when followed long-term, all vaccinated animals showed no signs or symptoms of infection, and there was no detectable viraemia for more than 6 months after infection, as measured by ELISA detection of viral antigen (FIG. 49A) and end point titration analysis of cultured virus. The vaccine recipient (subject 8) that exhibited a transient low level of viraemia on day 10 returned to undetectable levels by day 17.

As the natural reservoir for Ebola virus is unknown, the potential for traditional public health measures to prevent future outbreaks is limited, thus increasing the urgency for the development of a vaccine and therapeutics in humans. The present findings demonstrate that primates can be immunized against the lethal effects of Ebola virus infection, and that sterilizing immunity can be achieved using a heterologous prime-boost strategy. A multicomponent genetic vaccine expressing Ebola virus structural proteins from diverse geographic isolates generated a strong antigen-specific immune response and resulted in the survival of immunized primates after challenge with a lethal dose of Ebola Zaire, the subtype of this virus associated with the highest number of deaths in human infections. The results of this study suggest that T-cell mediated and humoral immunity contribute to virus clearance in non-human primates, consistent with previous studies in rodents (Xu, L. et al. 1998 *Nat Med* 4:37-42; Wilson, J. et al. 2000 *Science* 287:1664-1666). Two immune parameters, antibody titer (1:75,000 vs.<1:100, P=0.001) and the cellular proliferative response (~12-fold vs. 1.4-fold, P=0.0014), provided highly significant immune correlates of protection. Studies investigating the correlates of immune protection from Ebola virus infection in humans are hampered by the aggressive nature of the virus and necessarily high level of biosafety containment. With the model of primate immunity presented here, it is envisioned as now being possible to elucidate the mechanisms of immune protection from Ebola virus infection, to advance immune-based anti-viral therapies, and to develop a human vaccine for this pathogen and even other infectious causes of hemorrhagic fever.

Descriptions of Ebola, Marburg, and Lassa Constructs

VRC6000 VRC6000 (pVR1012-GP(Z)).
  Backbone, pVR1012 (#450) expressing Ebola Glycoprotein of Zaire Subtype. Orientation is BamHI/EcoRI/EcoRV/EcoRI/BglII)
VRC6001 VRC6001 (pVR1012x/s-GP(Z)) No other description.
  This is the same as 6000, with the addition of an Sfi restriction site to the pVR1012 backbone.
VRC6002 VRC6002 (pVR1012-GP(Z) delta MUC).
  The mucin-like domain of GP(Z) was deleted. 530 bp in the backbone, pVR1012 GP(Z) were deleted from EarI (2844) to BfaI(3374). This mutant can bind to the Ebola receptor.
VRC6003 VRC6003 (pVR1012-GP(Z) delta MUC delta FUR).
  The mucin-like domain and furin-cleavage site of GP(Z) were deleted. 593 bp in the backbone, pVR1012 GP (Z)

were deleted, from EarI(2844) to EarI(3437). The protein has properties similar to pVR1012-GP(Z) delta MUC.

VRC6004 VRC6004 (pVR1012-GP(Z) delta GP2).
A majority of the GP2 region in GP(Z) was deleted. 430 bp from the backbone, pVR1012-GP (Z) were deleted from BclI(3414) to BspEI(3844). The TM (transmembrane) region was retained.

VRC6005 VRC6005 (pVR1012-GP(Z) delta GP2 delta C-term A).
This is a C-terminal deletion of GP2. 267 bp were deleted from the pVR1012-GP (Z) backbone, from MscI(3623) to BspMI(3890).

VRC6006 VRC6006 (pVR1012-GP(Z) delta GP2 delta C-term B).
This is a smaller deletion of GP2 C-terminal. 110 bp of backbone pVR1012-GP(Z) were deleted from BstXI (3780) to BspMI(3890).

VRC6007 VRC6007 (pVR1012-GP(Z) delta GP2 delta FUS).
The fusion peptide in GP2 of GP(Z) was deleted in this mutant, using PCR. 47 bp from the backbone, pVR1012-GP(Z), was deleted from (3508-3555).

VRC6008 VRC6008 (pVR1012-GP(Z) delta TM).
The TM region of GP(Z) was truncated in this mutant. A stop codon (TGA) was added downstream of the BspMI site(3889). This protein is secreted and doesn't form a trimer.

VRC6052 VRC 6052 (pVR1012-GP(Z) delta sGP).
The majority of the SGP/GP homology region was deleted. 687 bp from the backbone, pVR1012-GP(Z), were deleted from HincII(2083) to HincII(2270).

VRC6101 VRC6101 (pVR1012x/s Ebola GP(R) (dTM)).
The vector expresses Ebola glycoprotein (subtype Reston) without its transmembrane and intracellular domains. Using PCR, a stop codon was generated downstream of a.a. 650 of GP(R), followed by an XbaI site. This protein can be secreted and is termed GP(R)(dTM).

VRC6110 VRC6110 (pAdApt Ebola GP(R) (dTM)).
An adenoviral shuttle vector expressing Ebola virus glycoprotein (Reston subtype) without its transmembrane and intracellular domains. Using PCR, a stop codon was generated downstream of a.a. 651 of GP(Reston), followed by an XbaI site. The resulting recombinant adenovirus expresses a 651a.a. secreted glycoprotein termed GP(R)(dTM).

VRC6200 VRC6200 (pVR1012-GP(S)).
Backbone, pVR1012(#450), expressing Ebola Glycoprotein of the Sudan Subtype. Orientation is EcoRI/EcoRV/BamHI/BamHI/BamHI/XbaI.

VRC6201 VRC6201 (pVR1012x/s Ebola GP(S)).
No other description, but this is the same as 6200 with the addition of an Sfi site to the 1012 backbone.

VRC6202 VRC6202 (pVR1012-GP(S) delta TM).
The TM region of GP(S) was truncated in this mutant. A stop codon (TGA) was added downstream of the BspMI site(xxx). This protein is secreted and doesn't form a trimer.

VRC6300 VRC6300 (pVR1012-GP(IC)).
Backbone, pVR1012(#450), expressing Ebola Glycoprotein of the Ivory Coast Subtype. Orientation is EcoRI/EcoRV/BamHI/BamHI/BamHI/XbaI.

VRC6301 VRC6301 (pVR1012x/s-GP(IC)).
No other description, but this is the same as 6300 with the addition of an Sfi site to the 1012 backbone.

VRC6302 VRC6302 (pVR1012-GP(IC) delta TM).
The TM region of GP(IC) was truncated in this mutant. A stop codon (TGA) was added downstream of the BspMI site. This protein is secreted and doesn't form a trimer.

VRC6303 VRC 6303 (pVR1012x/s Ebola GP (IC) (dTM)).
A pVRC2000 based vector expressing Ebola glycoprotein (Ivory Coast subtype) without transmembrane and intracellular domains. Using PCR, a stop codon was generated downstream of a.a. 650, followed by a BglII site. The vector expresses a 650 a.a. secreted glycoprotein (a.a. 1-a.a. 650).

VRC6310 VRC6310 (pAdApt Ebola GP (IC) (dTM)).
An adenoviral shuttle vector expressing Ebola glycoprotein (subtype Ivory Coast) without its transmembrane and intracellular domains. Using PCR, a stop codon was generated downstream of a.a. 651 of GP(IC). The resulting recombinant adenovirus expresses a 651a.a secreted glycoprotein termed as GP(IC)(dTM).

VRC6351 VRC6351 (pVR1012x/s-sGP(IC)). No other description.

VRC6400 VRC6400 (pVR1012-NP).
Backbone, pVR1012(#450) expressing Ebola Nucleoprotein of the Ivory Coast Subtype.

VRC6401 VRC6401 (pVR1012x/s-NP).
No other description, but this is the same as 6400 with the addition of an Sfi site to the 1012 backbone.

VRC6500 VRC6500 (pVR1012-VP35).
The backbone is pVR1012(#450). The insert is VP35 from Ebola cloned from pGEM 3Zf(+)VP35(#1213).

VRC6600 VRC6600 (pAD/CMV-GP(dTM)(Z-CITE-S). No other description.

VRC6601 VRC6601 (pAdApt Ebola GP(S)). No other description.

VRC6602 VRC6602 (pAdApt Ebola GP(S)(dTM)).
An adenoviral shuttle vector expressing Ebola glycoprotein (Sudan subtype) without its transmembrane and intracellular domains. A stop codon was fused downstream of a.a. 650 of GP(S). The resulting recombinant adenovirus expresses a 654 a.a. secreted glycoprotein, termed as GP(S)(dTM).

VRC6603 VRC6603 (pAdApt Ebola GP(Z)). No other description.

VRC6604 VRC6604 (pAdApt Ebola GP(Z)(dTM)).
Adenoviral shuttle vector expressing Ebola glycoprotein (subtype Zaire) without its transmembrane and intracellular domains. A stop codon was fused downstream of a.a. 651 of GP(Z). The resulting recombinant adenovirus expresses a 655 a.a. secreted glycoprotein termed as GP(Z)(dTM).

VRC6701 VRC6701 (pVR1012-Marburg).
Marburg glycoprotein (GP) open reading frame, Musoke strain. Marburg was cloned into backbone #450(Bam (blunt)/XbaI) from VRC6700 (Xba/PvuII).

VRC6702 VRC6702 (pVR1012x/s Marburg GP (dTM)).
This vector expresses the Marburg virus glycoprotein without its transmembrane and intracellular domains. Using PCR, a stop codon was generated downstream of a.a. 650 of GP(Marburg), followed by a BglII site. This protein can be secreted and termed as GP(Marburg) (dTM).

VRC6710 VRC6710 (pAdApt Marburg GP (dTM)).
Adenoviral shuttle vector (pVRC1290) expressing Marburg virus glycoprotein without transmembrane and intracellular domains. Using PCR, a terminator codon was generated downstream of a.a. 650, followed by a BglII site. The resulting recombinant adenovirus expresses a 650 a.a. secreted protein (a.a. 1-a.a. 650).

VRC6800 VRC6800 (pVR1012x/s Lassa GP). No other description.
VRC6801 VRC6801 (pVR1012x/s Lassa GP (dTM). No other description.
VRC6810 VRC6810 (pAdApt Lassa GP). No other description.
VRC6811 VRC6811 (pAdApt Lassa GP (dTM)). No other description.

EXAMPLE 1

Vector construction. The construction of DNA vectors expressing Ebola Zaire glycoprotein (GP), secreted GP (SGP), and nucleoprotein (NP) has been described in Xu, L. et al. 1998 *Nat Med* 4:37-42. The GP Sudan and Ivory Coast expression vectors were constructed similarly. Briefly, GP open reading frames were generated from polymerase chain reaction after reverse transcription of RNA (RT-PCR) products of infected cell RNA using the following primers: 5' ATC TTC AGG ATC TCG CCA TGG A 3' (Sudan GP gene; NcoI>ATG; SEQ ID NO: 44), 5' GAT ATT CAA CAA AGC AGC TTG CAG 3' (Sudan GP gene; C-terminus GP stop; SEQ ID NO: 45), 5' CTA ATC ACA GTC ACC ATG GGA 3' (Ivory Coast GP gene; NcoI>ATG; SEQ ID NO: 46), 5' AAA GTA TGA TGC TAT ATT AGT TCA 3' (Ivory Coast GP gene; C-terminus GP stop; SEQ ID NO: 47) yielding the TA clones PCR2.1 Sudan and PCR2.1 Ivory Coast. The Sudan glycoprotein was digested from plasmid PCR2.1 with XbaI/HindIII, Klenow treated, and cloned into the XbaI site of p1012 (Xu, L. et al. 1998 *Nat Med* 4:37-42). Ivory Coast GP was digested from plasmid PCR2.1 with EcoRI, Klenow treated, and cloned into the XbaI site of p1012 (Xu, L. et al. 1998 *Nat Med* 4:37-42).

To make ADV-GP, the BamHI/EcoRI fragment of GP(Z) was digested from pGEM-3Zf(−)-GP, treated with Klenow, and inserted into HindIII/XbaI/Kle/CIP treated pRc/CMV plasmid. The resulting plasmid (PRC/CMV-GP(Z)) was digested by NruI/DraIII and treated with Klenow. The NruI/DraIII/Kle fragment containing the CMV enhancer, GP(Z) DNA and bovine growth hormone polyadenylation signal was inserted into the BglII site of the adenoviral shuttle plasmid pAdBglII (Ohno, T. et al. 1994 Science 265:781-784). The adenovirus, a first generation dl 309-based Ad5 vector, contained a deletion in E1 to render the vector replication-defective and a partial deletion/substitution in E3, which disrupts the coding sequences for the E3 proteins with a relative molecular mass of 14.7 kD, 14.5 kD and 10.4 kD, respectively. The recombinant adenovirus expressing Zaire GP, ADV-GP(Z), was made according to previously published methods (Aoki, K. et al. 1999 *Mol Med* 5:224-231). The dose of adenovirus administered, $10^{10}$ plaque-forming units (PFU) per animal (approximately $3 \times 10^9$ PFU/kg), is within the range used safely in human gene therapy trials.

Animal study and safety. Eight cynomolgus macaques (*Macaca fascicularis*), 3 years of age and weighing 2-3 kg, obtained from Covance (Princeton, N.J.), were used for the immunization and challenge experiment. To obtain blood specimens and administer vaccines, the monkeys were anesthetized with Ketamine. The animals were housed singly and received regular enrichment according to the Guide for the Care and Use of Laboratory Animals (DHEW No. NIH 86-23). Just before the Ebola virus challenge and up to the end of the experiment, the animals were maintained in the Maximum Containment Laboratory (BSL-4) and fed and checked daily. One animal was euthanized that appeared moribund and was subsequently necropsied for pathologic examination. In addition, a single asymptomatic vaccinated animal was euthanized for pathologic and virologic analysis.

Mouse immunization. DNA and adenovirus vectors expressing Ebola Zaire GP or NP were constructed as described previously (Xu, L. et al. 1998 *Nat Med* 4:37-42; Ohno, T. et al. 1994 *Science* 265:781-784), with gene expression under the control of the cytomegalovirus enhancer and promoter. Mice were immunized intramuscularly with 100 μg of DNA (pGP or a p1012 plasmid control) or $10^8$ PFU of adenovirus (ADV-GP or ADV-ΔE1 control virus) on days 0, 14, and 28 and blood was collected on day 28. On day 42, mice received an intramuscular boost with DNA or adenovirus and titers were re-measured on day 56. ELISA IgG titers were determined using 96-well plates coated with a preparation of Ebola virus antigen derived from purified virions and enriched for membrane-associated proteins (GP, VP40 and VP24) (Ksiazek, T. G. et al. 1992 *J Clin Microbiol* 30:947-950). Specific antigen binding was detected using a goat anti-human IgG(H+L)-horseradish peroxidase conjugate and ABTS/Peroxide (substrate/indicator).

Macaque immunization. For the DNA immunizations, animals received 1 mg each of DNA expressing GP(Zaire) [GP (Z)], GP(Ivory Coast) [pGP(IC)], GP(Sudan) [pGP(S)] and NP(Zaire) administered as a mixture [pGP/NP], or 4 mg empty [pGP(Z)] control plasmid bilaterally (2 mg per side) in the deltoid muscle. Immunization at weeks 0 and 4 were by IM injection, and at week 8 by Biojector. For the adenovirus boost, animals received $10^{10}$ PFU of ADV-GP (Zaire subtype) or ADV-ΔE1 (empty vector) divided into two doses administered bilaterally in the deltoid muscle. At week 32, all animals received an intraperitoneal injection of approximately 6 PFUs of Ebola virus (Zaire 1976 isolate; Mayinga strain) (Kiley, M. P. et al. 1980 *J Gen Virol* 49:333-341) in 1 ml Hanks' buffered salt solution. The virus was isolated directly from patient blood and used after a single passage in Vero cells.

ELISA IgG titers were determined as above for control (Plasmid: ADV-ΔE1) and immunized [pGP/NP: ADV-GP (Z)] monkeys. The reciprocal endpoint of dilution for each subject was at week 12 and week 24. Serum antibody levels were measured by ELISA as described (Ksiazek, T. G. et al. 1992 *J Clin Microbiol* 30:947-950).

Blood was collected from control (plasmid: ADV-ΔE1) or immunized [pGP/NP: ADV-GP(Z)] animals 1-3 days prior to the immunizations at weeks 4, 8 and 20, and at week 24. Blood was separated over a Percoll gradient to obtain the lymphocyte enriched population. Lymphocytes were stimulated as described (Xu, L. et al. 1998 *Nat Med* 4:37-42) for 5 days in vitro using supernatant from cells transfected with either Ebola secreted glycoprotein (SGP) or empty plasmid, and proliferation was measured by $^3$H-thymidine uptake. The proliferation index was calculated as the proliferation in wells receiving SGP divided by proliferation in wells receiving control supernatant.

Viral detection in macaques. The presence of circulating Ebola virus antigen was detected as described (Ksiazek, T. G. et al. 1992 *J Clin Microbiol* 30:947-950) by capturing VP40 protein from serial dilutions of monkey plasma. 96-well plates coated with antiVP40 mAb were used to capture antigen, and detection was with a rabbit anti-Ebola virus serum.

EXAMPLE 2

The amino acid sequences of Ebola GP(Zaire) and NP (Zaire) were obtained from Genbank: GP(Zaire), Genbank accession no. P87666; NP(Zaire), Genbank accession no. NC_002549; while GP(Sudan/Gulu) was obtained from the CDC. The amino acid sequences were then back-translated to DNA sequences using mammalian preferred codons. Serial 75 bp oligos with 25 bp overlapping were prepared to cover the entire gene. The oligos were then assembled into intact mammalian genes containing preferred codons using PCR. In the design, a stop codon was introduced in front of the predicted transmembrane domains of GP(Zaire) (a.a. 648-676) and GP (Sudan/Gulu) (a.a. 648-676) so that this region was excluded from these synthetically created genes. The deletions also led to the loss of a 4 a.a. cytoplasmic region in both constructs. Final sequencing of the Ebola GP (Zaire) sequence revealed 10 divergent amino acids from the laboratory GP sequence, which was used in our animal studies and these were corrected by site-directed mutagenesis. These inserts were cloned into p1012 x/s by XbaI/Sa/I.

Construction of CMV/R-GP(S/G)(ΔTM)/h

The codon-modified, transmembrane domain deleted form of the Ebola GP (Sudan/Gulu) gene was excised from p1012 (x/s)-GP(S/G)(ΔTM)/h using Sa/I/KpnI, and inserted into the Sa/I/KpnI digested CMV/R/MCS plasmid.

Construction of CMV/R GP(Z) (ΔTM)/h

The codon-modified, transmembrane domain deleted form of the Ebola GP (Zaire) gene was excised from p1012 x/s-GP (Z)(dTM)/h Sa/I/BglII sites and cloned into the Sa/I/BglII sites of the CMV/R plasmid.

Construction of CMV/R Ebola NP

The NotI-KpnI fragment from VRC6400 (pVR1012-NP) expressing Ebola nucleoprotein of Zaire Subtype was excised and cloned into the NotI/KpnI sites of the CMV/R plasmid.

EXAMPLE 3

Improved Non-Viral Mammalian Expression Vector

This invention provides an improved mammalian expression vector which generates a higher level of protein expression than vectors currently in use.

Initially, 3 new vectors, each containing a different enhancer, were developed and tested. The RSV enhancer, the mouse ubiquitin enhancer (mUBB), and the CMV enhancer (Xu et al. 1998 *Nature Med.* 4:37-42) were each combined with the HTLV-1 R region (Takebe et al. 1988 *Mol Cell Biol* 8:466-472) to create separate vectors. When these 3 vectors were compared to the backbone containing the CMV enhancer in combination with the CMV translational enhancer and intron (CMVint), which is currently the most effective vector, in vitro data showed that expression with the vector containing the CMV/R was increased 5-10 fold compared to CMV/int, and immunological studies showed induction of significantly higher CD4 and CD8 T cell responses compared to CMVint. Both in vivo and in vitro responses were markedly higher with this new vector. Neither of the other two vectors produced comparable results.

The expression vector is unique in that it uses a specific translational enhancer in combination with specific enhancer/promoters to yield high levels of expression and enhanced immunogenicity for DNA vaccines. This is particularly important because the potency of these vaccines in humans is marginal and generic improvements can serve as important platforms to make the technology practical for human use. The expression vector cassettes can be used in other gene based vaccines as well, or for production of recombinant proteins from eukaryotic expression vectors. The invention is useful in the production of genetic vaccines and gene therapies for a wide variety of diseases, including HIV and other viral diseases and cancer.

Figure 50:
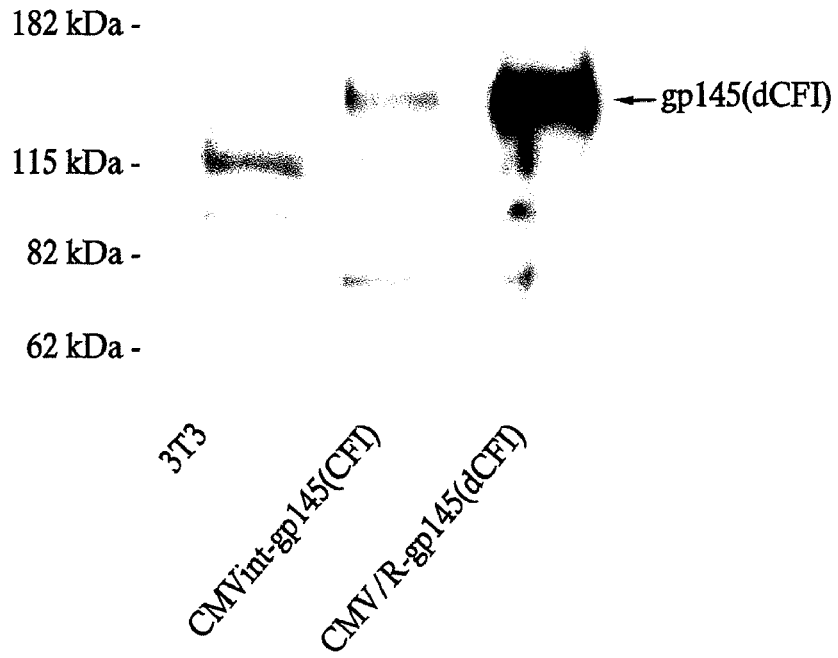
FIG. 50 (A-B) shows enhanced expression of modified CMV expression vector, CMV/R.
Figure 50:
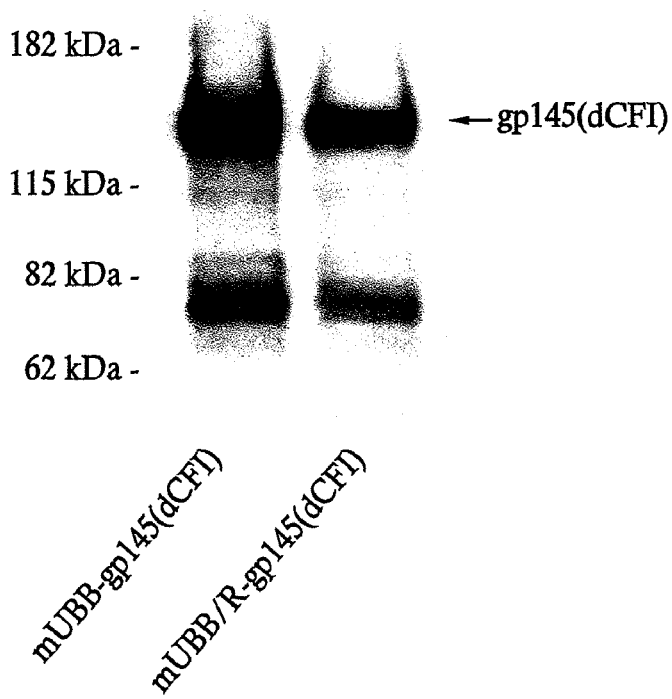

FIG. 50. Enhanced Expression of Modified CMV Expression Vector, CMV/R.

Mouse fibroblast 3T3 cells were transfected with (A) vector alone (lane 1), CMVint-gp-145(dCFI) (lane 2), CMV/R-gp145(dCFI) (lane 3) or (B) mUBB-gp145(dCFI) (lane 4), mUBB/R-gp145(dCFI) (lane 5) in 6-well tissue culture dishes with 0.5 ug of the corresponding plasmids using calcium phosphate. 24 hours after transfection, cells were harvested and lysed in lysis buffer (50 mM HEPES, 150 mM NaCl, 1% NP-40, Mini Complete protease inhibitor cocktail (Roche)). 10 μg of total protein of each sample were separated on a 4-15% gradient gel using SDS-PAGE, followed by protein transfer and Western blot analysis. Human HIV-IgG (1:5000) was used as the primary antibody, and HRP-conjugated goat anti-human IgG (1:5000) as the secondary antibody. The membrane was developed using the ECL Western blot developing system. The arrow indicates the specific band for the HIV Env gp145(ΔCFI) polyprotein.

Figure 51:
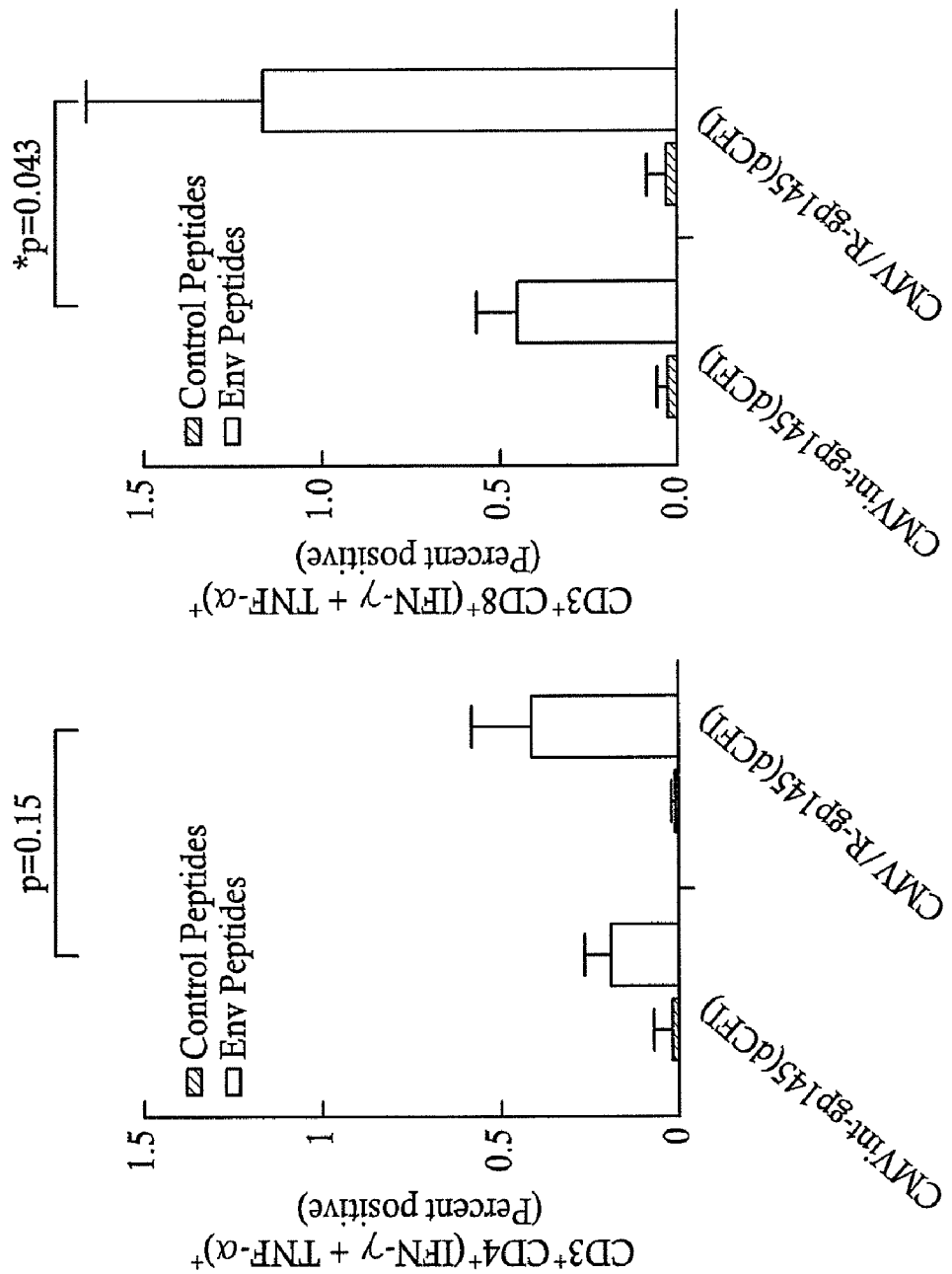
FIG. 51 shows enhanced immunogenicity of modified CMV expression vector, CMV/R, in mice.

FIG. 51. Enhanced Immunogenicity of Modified CMV Expression Vector, CMV/R, in Mice.

Five mice in each group were immunized with 50 μg of the indicated plasmid DNA at weeks 0, 2, and 6. 10 days after the last injection, splenocytes from each mouse were harvested and stimulated using a pool of control peptides (15 mer), or a pool of HIV Env peptides (15 mer) for 6 hours. The stimulated splenocytes were stained using a cocktail of antibodies containing PE-anti-mouse CD3, PerCP-anti-mouse CD4, APC-anti-mouse CD8, FITC-anti-mouse IFN-γ and FITC-anti-mouse TNF-α. The samples were analyzed by flow cytometry. CD3/CD4/IFN-γ/TNF-α and CD3/CD8/IFN-γ/TNF-α positive cell numbers were measured using FloJo software (Treestar).

The CMV Enhancer/Promoter, R Region (HTVL-1), CMV IE Splicing Acceptor Sequence (SEQ ID NO: 52):
CCATTGCATACGTTGTATCCATATCATAATATGTACATTTATATTGGCT

CATGTCCAACATTACCGCCATGTTGACATTGATTATTGACTAGTTATTA

ATAGTAATCAATTACGGGGTCATTAGTTCATAGCCCATATATGGAGTTC

CGCGTTACATAACTTACGGTAAATGGCCCGCCTGGCTGACCGCCCAACG

ACCCCCGCCCATTGACGTCAATAATGACGTATGTTCCCATAGTAACGCC

AATAGGGACTTTCCATTGACGTCAATGGGTGGAGTATTTACGGTAAACT

GCCCACTTGGCAGTACATCAAGTGTATCATATGCCAAGTACGCCCCCTA

TTGACGTCAATGACGGTAAATGGCCCGCCTGGCATTATGCCCAGTACAT

GACCTTATGGGACTTTCCTACTTGGCAGTACATCTACGTATTAGTCATC

GCTATTACCATGGTGATGCGGTTTTGGCAGTACATCAATGGGCGTGGAT

AGCGGTTTGACTCACGGGGATTTCCAAGTCTCCACCCCATTGACGTCAA

TGGGAGTTTGTTTTGGCACCAAAATCAACGGGACTTTCCAAAATGTCGT

AACAACTCCGCCCCATTGACGCAAATGGGCGGTAGGCGTGTACGGTGGG

AGGTCTATATAAGCAGAGCTCGTTTAGTGAACCGTCAGATCGCCTGGAG

ACGCCATCCACGCTGTTTTGACCTCCATAGAAGACACCGGGACCGATCC

AGCCTCCATCGGCTCGCATCTCTCCTTCACGCGCCCGCCGCCTTACCTG

-continued

```
AGGCCGCCATCCACGCCGGTTGAGTCGCGTTCTGCCGCCTCCCGCCTGT

GGTGCCTCCTGAACTACGTCCGCCGTCTAGGTAAGTTTAGAGCTCAGGT

CGAGACCGGGCCTTTGTCCGGCGCTCCCTTGGAGCCTACCTAGACTCAG

CCGGCTCTCCACGCTTTGCCTGACCCTGCTTGCTCAACTCTAGTTAACG

GTGGAGGGCAGTGTAGTCTGAGCAGTACTCGTTGCTGCCGCGCGCGCCA

CCAGACATAATAGCTGACAGACTAACAGACTGTTCCTTTCCATGGGTCT
TTTCTGCAG
```

1-741: CMV Enhancer/Promoter 742-972: HTLV-1 R region 973-1095: CMV/IE Splicing Acceptor While the present invention has been described in some detail for purposes of clarity and understanding, one skilled in the art will appreciate that various changes in form and detail can be made without departing from the true scope of the invention. All figures, tables, and appendices, as well as patents, applications and publications referred to above are hereby incorporated by reference.

What is claimed is:

1. A vaccine comprising an adenoviral vector comprising a sequence encoding Marburg virus glycoprotein being at least 95% identical to Marburg virus glycoprotein that is encoded in the construct VRC6701 (SEQ ID NO:30).

2. The vaccine of claim 1, wherein the sequence encoding Marburg virus glycoprotein is the sequence as present in the construct VRC6701 (SEQ ID NO:30).

3. A composition for boosting an immune response to a viral antigen in an individual, comprising an adenoviral vector comprising a sequence encoding Marburg virus glycoprotein being at least 95% identical to Marburg virus glycoprotein that is encoded in the construct VRC6701 (SEQ ID NO:30).

4. The composition of claim 3, wherein the sequence encoding Marburg virus glycoprotein is the sequence as present in construct VRC6701 (SEQ ID NO:30).

5. A method for boosting an immune response to a viral antigen in an individual, comprising administering to the individual a composition comprising an adenoviral vector comprising a sequence encoding Marburg virus glycoprotein being at least 95% identical to Marburg virus glycoprotein that is encoded in the construct VRC6701 (SEQ ID NO:30).

6. The method of claim 5, wherein the sequence encoding Marburg virus glycoprotein is the sequence as present in VRC6701 (SEQ ID NO:30).

7. The method of claim 5, wherein the viral antigen is a Marburg virus antigen.

8. The method of claim 5, wherein the administering is performed by injection.

9. The method of claim 8, wherein the administering is performed at a dose of $5 \times 10^7$ to $1 \times 10^{12}$ particles per injection.

* * * * *

SEQUENCE LISTING

```
<160> NUMBER OF SEQ ID NOS: 52

<210> SEQ ID NO 1
<211> LENGTH: 7154
<212> TYPE: DNA
<213> ORGANISM: Artificial Sequence
<220> FEATURE:
<223> OTHER INFORMATION: Synthetic Construct pVR1012 -GP(Z)

<400> SEQUENCE: 1
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccctttggc    1080 tcttatgcat gctatactgt ttttggcttg ggcctatac acccccgctt ccttatgcta    1140
taggtgatgg tatagcttag cctataggtg tgggttattg accattattg accactcccc    1200
tattggtgac gatactttcc attactaatc cataacatg ctctttgcca caactatctc    1260
tattggctat atgccaatac tctgtccttc agagactgac acggactctg tattttaca    1320 ggatggggtc ccatttatta tttacaaatt cacatataca acaacgccgt cccccgtgcc    1380
cgcagttttt attaaacata gcgtgggatc tccacgcgaa tctcgggtac gtgttccgga   1440
catgggctct tctccggtag cggcggagct tccacatccg agccctggtc ccatgcctcc    1500
```

```
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttcccccgg    2340
tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg atactgcccc aagctaagaa ggacttcttc    2520
agctcacacc ccttgagaga gccggtcaat gcaacgagg acccgtctag tggctactat    2580
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gaccccaaa agcagagaac    3240
accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg gataccatat    3540
ttcgggccag cagccgaggg aatttacata gaggggctaa tgcacaatca agatggttta    3600
atctgtgggt tgagacagct ggccaacgag acgactcaag ctcttcaact gttcctgaga    3660
gccacaactg agctacgcac cttttcaatc ctcaaccgta aggcaattga tttcttgctg    3720
cagcgatggg gcggcacatg ccacattctg ggaccggact gctgtatcga accacatgat    3780
tggaccaaga acataacaga caaaattgat cagattattc atgattttgt tgataaaacc    3840
cttccggacc agggggacaa tgacaattgg tggacaggat ggagacaatg gataccggca    3900
```

```
ggtattggag ttacaggcgt tgtaattgca gttatcgctt tattctgtat atgcaaattt   3960
gtcttttagt ttttcttcag attgcttcat ggaaaagctc agcctcaaat caatgaaacc   4020
aggatttaat tatatggatt acttgaatct aagattactt gacaaatgat aatataatac   4080
actggagctt taaacatagc caatgtgatt ctaactcctt taaactcaca gttaatcata   4140
aacaaggttt gaggtaccga gctcgaattg atctgctgtg ccttctagtt gccagccatc   4200
tgttgtttgc ccctcccccg tgccttcctt gaccctggaa ggtgccactc ccactgtcct   4260
ttcctaataa aatgaggaaa ttgcatcgca ttgtctgagt aggtgtcatt ctattctggg   4320
gggtggggtg gggcaggaca gcaaggggga ggattgggaa gacaatagca ggcatgctgg   4380
ggatgcggtg ggctctatgg gtacccaggt gctgaagaat tgacccggtt cctcctgggc   4440 cagaagaag caggcacatc cccttctctg tgacacaccc tgtccacgcc cctggttctt    4500
agttccagcc ccactcatag gacactcata gctcaggagg ctccgcctt caatcccacc    4560 cgctaaagta cttggagcgg tctctccctc cctcatcagc ccaccaaacc aaacctagcc   4620
tccaagagtg ggaagaaatt aaagcaagat aggctattaa gtgcagaggg agagaaaatg   4680
cctccaacat gtgaggaagt aatgagagaa atcatagaat ttcttccgct tcctcgctca   4740
ctgactcgct gcgctcggtc gttcggctgc ggcgagcggt atcagctcac tcaaaggcgg   4800
taatacggtt atccacagaa tcaggggata acgcaggaaa gaacatgtga gcaaaaggcc   4860
agcaaaaggc caggaaccgt aaaaaggccg cgttgctggc gttttccat aggctccgcc    4920 cccctgacga gcatcacaaa aatcgacgct caagtcagag gtggcgaaac ccgacaggac   4980
tataaagata ccaggcgttt ccccctggaa gctccctcgt gcgctctcct gttccgaccc   5040
tgccgcttac cggatacctg tccgcctttc tcccttcggg aagcgtggcg ctttctcata   5100
gctcacgctg taggtatctc agttcggtgt aggtcgttcg ctccaagctg ggctgtgtgc   5160
acgaaccccc cgttcagccc gaccgctgcg ccttatccgg taactatcgt cttgagtcca   5220
acccggtaag acacgactta tcgccactgg cagcagccac tggtaacagg attagcagag   5280
cgaggtatgt aggcggtgct acagagttct tgaagtggtg cctaactac ggctacacta    5340 gaagaacagt atttggtatc tgcgctctgc tgaagccagt taccttcgga aaaagagttg   5400
gtagctcttg atccggcaaa caaaccaccg ctggtagcgg tggtttttt gtttgcaagc    5460 agcagattac gcgcagaaaa aaggatctca agaagatcc tttgatcttt tctacggggt    5520
ctgacgctca gtggaacgaa aactcacgtt aagggatttt ggtcatgaga ttatcaaaaa   5580
ggatcttcac ctagatcctt ttaaattaaa aatgaagttt taaatcaatc taagtatat    5640 atgagtaaac ttggtctgac agttaccaat gcttaatcag tgaggcacct atctcagcga   5700
tctgtctatt tcgttcatcc atagttgcct gactcggggg ggggggcgc tgaggtctgc    5760 ctcgtgaaga aggtgttgct gactcatacc aggcctgaat cgccccatca tccagccaga   5820
aagtgaggga gccacggttg atgagagctt tgttgtaggt ggaccagttg gtgatttga    5880 acttttgctt tgccacgaaa cggtctgcgt tgtcggaag atgcgtgatc tgatccttca    5940
actcagcaaa agttcgattt attcaacaaa gccgccgtcc cgtcaagtca gcgtaatgct   6000
ctgccagtgt tacaaccaat taaccaattc tgattagaaa aactcatcga gcatcaaatg   6060
aaactgcaat ttattcatat caggattatc aataccatat tttgaaaaa gccgtttctg    6120 taatgaagga gaaaactcac cgaggcagtt ccataggatg caagatcct ggtatcggtc    6180 tgcgattccg actcgtccaa catcaataca acctattaat ttcccctcgt caaaataag    6240 gttatcaagt gagaaatcac catgagtgac gactgaatcc ggtgagaatg gcaaaagctt   6300
```

```
atgcatttct ttccagactt gttcaacagg ccagccatta cgctcgtcat caaaatcact    6360
cgcatcaacc aaaccgttat tcattcgtga ttgcgcctga gcgagacgaa atacgcgatc    6420
gctgttaaaa ggacaattac aaacaggaat cgaatgcaac cggcgcagga acactgccag    6480
cgcatcaaca atattttcac ctgaatcagg atattcttct aatacctgga atgctgtttt    6540
cccggggatc gcagtggtga gtaaccatgc atcatcagga gtacggataa aatgcttgat    6600
ggtcggaaga ggcataaatt ccgtcagcca gtttagtctg accatctcat ctgtaacatc    6660
attggcaacg ctacctttgc catgtttcag aaacaactct ggcgcatcgg gcttcccata    6720
caatcgatag attgtcgcac ctgattgccc gacattatcg cgagcccatt tatacccata    6780
taaatcagca tccatgttgg aatttaatcg cggcctcgag caagacgttt cccgttgaat    6840
atggctcata cacccccttg tattactgtt tatgtaagca gacagtttta ttgttcatga    6900
tgatatattt ttatcttgtg caatgtaaca tcagagattt tgagacacaa cgtggctttc    6960
cccccccccc cattattgaa gcatttatca gggttattgt ctcatgagcg gatacatatt    7020
tgaatgtatt tagaaaaata aacaaatagg ggttccgcgc acatttcccc gaaaagtgcc    7080
acctgacgtc taagaaacca ttattatcat gacattaacc tataaaaata ggcgtatcac    7140
gaggcccttt cgtc                                                      7154
```

<210> SEQ ID NO 2
<211> LENGTH: 7188
<212> TYPE: DNA
<213> ORGANISM: Artificial Sequence
<220> FEATURE:
<223> OTHER INFORMATION: Synthetic Construct pVR1012x/s Ebola GP(Z)

<400> SEQUENCE: 2

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
```

```
tattggtgac gatactttcc attactaatc cataacatgg ctctttgcca caactatctc    1260
tattggctat atgccaatac tctgtccttc agagactgac acggactctg tattttaca    1320 ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg gctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaaact gctacaatct tgaaatcaaa    2280
aaacctgacg ggagtgagtg tctaccagca gcgccagacg ggattcgggg cttcccccgg    2340
tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg tatactgcccc aagctaagaa ggacttcttc    2520
agctcacacc ccttgagaga gccggtcaat gcaacggagg acccgtctag tggctactat    2580
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gacccccaaa agcagagaac    3240
accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caacccctaat    3480 ttacattact ggactactca ggatgaaggt gctgcaatcg gactggcctg gataccatat    3540
ttcgggccag cagccgaggg aatttacata gaggggctaa tgcacaatca agatggtttta   3600
```

```
atctgtgggt tgagacagct ggccaacgag acgactcaag ctcttcaact gttcctgaga    3660
gccacaactg agctacgcac cttttcaatc ctcaaccgta aggcaattga tttcttgctg    3720
cagcgatggg gcggcacatg ccacattctg ggaccggact gctgtatcga accacatgat    3780
tggaccaaga acataacaga caaaattgat cagattattc atgattttgt tgataaaacc    3840
cttccggacc aggggacaa tgacaattgg tggacaggat ggagacaatg gataccggca     3900
ggtattggag ttacaggcgt tgtaattgca gttatcgctt tattctgtat atgcaaattt    3960
gtcttttagt ttttcttcag attgcttcat ggaaaagctc agcctcaaat caatgaaacc    4020
aggatttaat tatatggatt acttgaatct aagattactt gacaaatgat aatataatac    4080
actggagctt taaacatagc caatgtgatt ctaactcctt taaactcaca gttaatcata    4140
aacaaggttt gaggtaccga gctcgaattg atctgctgtg ccttctagtt gccagccatc    4200
tgttgtttgc ccctccccg tgccttcctt gaccctggaa ggtgccactc ccactgtcct     4260
ttcctaataa aatgaggaaa ttgcatcgca ttgtctgagt aggtgtcatt ctattctggg    4320
gggtggggtg gggcaggaca gcaaggggga ggattgggaa gacaatagca ggcatgctgg    4380
ggatgcggtg ggctctatgg gtacccaggt gctgaagaat tgacccggtt cctcctgggc    4440
cagaaagaag caggcacatc cccttctctg tgacacaccc tgtccacgcc cctggttctt    4500
agttccagcc ccactcatag gacactcata gctcaggagg gctccgcctt caatcccacc    4560
cgctaaagta cttggagcgg tctctccctc cctcatcagc ccaccaaacc aaacctagcc    4620
tccaagagtg gaagaaatt aaagcaagat aggctattaa gtgcagaggg agagaaaatg     4680
cctccaacat gtgaggaagt aatgagagaa atcatagaat tttaaggcca tgatttaagg    4740
ccatcatggc cttaatcttc cgcttcctcg ctcactgact cgctgcgctc ggtcgttcgg    4800
ctgcggcgag cggtatcagc tcactcaaag gcggtaatac ggttatccac agaatcaggg    4860
gataacgcag gaaagaacat gtgagcaaaa ggccagcaaa aggccaggaa ccgtaaaaag    4920
gccgcgttgc tggcgttttt ccataggctc cgcccccctg acgagcatca caaaaatcga    4980
cgctcaagtc agaggtggcg aaacccgaca ggactataaa gataccaggc gtttccccct    5040
ggaagctccc tcgtgcgctc tcctgttccg accctgccgc ttaccggata cctgtccgcc    5100
tttctccctt cgggaagcgt ggcgctttct catagctcac gctgtaggta tctcagttcg    5160
gtgtaggtcg ttcgctccaa gctgggctgt gtgcacgaac cccccgttca gcccgaccgc    5220
tgcgccttat ccggtaacta tcgtcttgag tccaacccgg taagacacga cttatcgcca    5280
ctggcagcag ccactggtaa caggattagc agagcgaggt atgtaggcgg tgctacagag    5340
ttcttgaagt ggtggcctaa ctacggctac actagaagaa cagtatttgg tatctgcgct    5400
ctgctgaagc cagttacctt cggaaaaaga gttggtagct cttgatccgg caaacaaacc    5460
accgctggta gcggtggttt ttttgtttgc aagcagcaga ttacgcgcag aaaaaaagga    5520
tctcaagaag atcctttgat cttttctacg gggtctgacg ctcagtggaa cgaaaactca    5580
cgttaaggga ttttggtcat gagattatca aaaaggatct tcacctagat ccttttaaat    5640
taaaaatgaa gttttaaatc aatctaaagt atatatgagt aaacttggtc tgacagttac    5700
caatgcttaa tcagtgaggc acctatctca gcgatctgtc tatttcgttc atccatagtt    5760
gcctgactcg ggggggggg gcgctgaggt ctgcctcgtg aagaaggtgt tgctgactca     5820
taccaggcct gaatcgcccc atcatccagc cagaaagtga gggagccacg ttgatgaga    5880 gctttgttgt aggtggacca gttggtgatt ttgaactttt gctttgccac ggaacggtct    5940
gcgttgtcgg gaagatgcgt gatctgatcc ttcaactcag caaaagttcg atttattcaa    6000
```

```
caaagccgcc gtcccgtcaa gtcagcgtaa tgctctgcca gtgttacaac caattaacca    6060
attctgatta gaaaaactca tcgagcatca aatgaaactg caatttattc atatcaggat    6120
tatcaatacc atattttga aaaagccgtt tctgtaatga aggagaaaac tcaccgaggc    6180
agttccatag gatggcaaga tcctggtatc ggtctgcgat tccgactcgt ccaacatcaa    6240
tacaacctat taatttcccc tcgtcaaaaa taaggttatc aagtgagaaa tcaccatgag    6300
tgacgactga atccggtgag aatggcaaaa gcttatgcat ttctttccag acttgttcaa    6360
caggccagcc attacgctcg tcatcaaaat cactcgcatc aaccaaaccg ttattcattc    6420
gtgattgcgc ctgagcgaga cgaaatacgc gatcgctgtt aaaaggacaa ttacaaacag    6480
gaatcgaatg caaccggcgc aggaacactg ccagcgcatc aacaatattt tcacctgaat    6540
caggatattc ttctaatacc tggaatgctg ttttcccggg gatcgcagtg gtgagtaacc    6600
atgcatcatc aggagtacgg ataaaatgct tgatggtcgg aagaggcata aattccgtca    6660
gccagtttag tctgaccatc tcatctgtaa catcattggc aacgctacct tgccatgttt    6720
tcagaaacaa ctctggcgca tcgggcttcc catacaatcg atagattgtc gcacctgatt    6780
gcccgacatt atcgcgagcc catttatacc catataaatc agcatccatg ttggaattta    6840
atcgcggcct cgagcaagac gtttcccgtt gaatatggct cataacaccc cttgtattac    6900
tgtttatgta agcagacagt tttattgttc atgatgatat ttttatct tgtgcaatgt     6960 aacatcagag attttgagac acaacgtggc tttccccccc ccccattat tgaagcattt    7020 atcagggtta ttgtctcatg agcggataca tatttgaatg tatttagaaa aataaacaaa    7080
taggggttcc gcgcacattt ccccgaaaag tgccacctga cgtctaagaa accattatta    7140
tcatgacatt aacctataaa aataggcgta tcacgaggcc ctttcgtc                7188

<210> SEQ ID NO 3
<211> LENGTH: 6624
<212> TYPE: DNA
<213> ORGANISM: Artificial Sequence
<220> FEATURE:
<223> OTHER INFORMATION: Synthetic Construct pVR1012-GP(Z) delta MUC

<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggga ctttccattg acgtcaatgg gtggagtatt tacggtaaac    540
tgcccacttg gcagtacatc aagtgtatca tatgccaagt acgccccta ttgacgtcaa      600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag    900
```

```
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccccttggc    1080
tcttatgcat gctatactgt ttttggcttg gggcctatac accccgctt ccttatgcta    1140
taggtgatgg tatagcttag cctataggtg tgggttattg accattattg accactcccc   1200
tattggtgac gatactttcc attactaatc cataacatgg ctcttgcca caactatctc    1260
tattggctat atgccaatac tctgtccttc agagactgac acggactctg tattttaca    1320
ggatggggtc ccatttatta tttacaaatt cacatataca acaacgccgt ccccgtgcc    1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttc ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatgggct tcaggtccgg tgtcccacca    2220
aaggtggtca attatgaagc tggtgaatgg gctgaaaact gctacaatct tgaaatcaaa   2280
aaacctgacg ggagtgagtg tctaccagca gcgccagacg ggattcgggg cttccccgg    2340
tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca cccccgaaat tgatacaaca atcggggagt gggccttctg ggaaactaaa   2820
aaaaacctca ctagaaaaat tcgtaggctt aattaccaat actattgctg gagtcgcagg   2880
actgatcaca ggcgggagaa gaactcgaag agaagcaatt gtcaatgctc aacccaaatg   2940
caaccctaat ttacattact ggactactca ggatgaaggt gctgcaatcg gactggcctg   3000
gataccatat ttcgggccag cagccgaggg aatttacata gaggggctaa tgcacaatca   3060
agatggttta atctgtgggt tgagacagct ggccaacaga acgactcaag ctcttcaact   3120
gttcctgaga gccacaactg agctacgcac cttttcaatc ctcaaccgta aggcaattga   3180
tttcttgctg cagcgatggg gcggcacatg ccacattctg ggaccggact gctgtatcga   3240
accacatgat tggaccaaga acataacaga caaaattgat cagattattc atgattttgt   3300
```

```
tgataaaacc cttccggacc aggggggacaa tgacaattgg tggacaggat ggagacaatg  3360
gataccggca ggtattggag ttacaggcgt tgtaattgca gttatcgctt tattctgtat  3420
atgcaaattt gtcttttagt ttttcttcag attgcttcat ggaaaagctc agcctcaaat  3480
caatgaaacc aggatttaat tatatggatt acttgaatct aagattactt gacaaatgat  3540
aatataatac actggagctt taaacatagc caatgtgatt ctaactcctt taaactcaca  3600
gttaatcata aacaaggttt gaggtaccga gctcgaattg atctgctgtg ccttctagtt  3660
gccagccatc tgttgtttgc ccctcccccg tgccttcctt gaccctggaa ggtgccactc  3720
ccactgtcct ttcctaataa aatgaggaaa ttgcatcgca ttgtctgagt aggtgtcatt  3780
ctattctggg gggtggggtg gggcaggaca gcaagggga ggattgggaa gacaatagca  3840
ggcatgctgg ggatgcggtg ggctctatgg gtacccaggt gctgaagaat tgacccggtt  3900
cctcctgggc cagaaagaag caggcacatc cccttctctg tgacacaccc tgtccacgcc  3960
cctggttctt agttccagcc ccactcatag gacactcata gctcaggagg ctccgcctt   4020 caatcccacc cgctaaagta cttggagcgg tctctcccctc cctcatcagc ccaccaaacc  4080
aaacctagcc tccaagagtg ggaagaaatt aaagcaagat aggctattaa gtgcagaggg  4140
agagaaaatg cctccaacat gtgaggaagt aatgagagaa atcatagaat ttcttccgct  4200
tcctcgctca ctgactcgct gcgctcggtc gttcggctgc ggcgagcggt atcagctcac  4260
tcaaaggcgg taatacggtt atccacagaa tcaggggata acgcaggaaa gaacatgtga  4320
gcaaaaggcc agcaaaaggc caggaaccgt aaaaaggccg cgttgctggc gtttttccat  4380
aggctccgcc cccctgacga gcatcacaaa aatcgacgct caagtcagag gtggcgaaac  4440
ccgacaggac tataaagata ccaggcgttt ccccctggaa gctccctcgt gcgctctcct  4500
gttccgaccc tgccgcttac cggatacctg tccgcctttc tcccttcggg aagcgtggcg  4560
ctttctcata gctcacgctg taggtatctc agttcggtgt aggtcgttcg ctccaagctg  4620
ggctgtgtgc acgaaccccc cgttcagccc gaccgctgcg ccttatccgg taactatcgt  4680
cttgagtcca acccggtaag acacgactta tcgccactgg cagcagccac tggtaacagg  4740
attagcagag cgaggtatgt aggcggtgct acagagttct tgaagtggtg gcctaactac  4800
ggctacacta agaacagt attttggtatc tgcgctctgc tgaagccagt taccttcgga  4860
aaaagagttg gtagctcttg atccggcaaa caaaccaccg ctggtagcgg tggtttttt   4920 gtttgcaagc agcagattac gcgcagaaaa aaaggatctc aagaagatcc tttgatcttt  4980
tctacggggt ctgacgctca gtggaacgaa aactcacgtt aagggatttt ggtcatgaga  5040
ttatcaaaaa ggatcttcac ctagatcctt ttaaattaaa aatgaagttt taaatcaatc  5100
taaagtatat atgagtaaac ttggtctgac agttaccaat gcttaatcag tgaggcacct  5160
atctcagcga tctgtctatt tcgttcatcc atagttgcct gactcggggg gggggggcgc  5220
tgaggtctgc ctcgtgaaga aggtgttgct gactcatacc aggcctgaat cgccccatca  5280
tccagccaga aagtgaggga gccacggttg atgagagctt tgttgtaggt ggaccagttg  5340
gtgattttga acttttgctt tgccacgaa cggtctgcgt tgtcgggaag atgcgtgatc  5400
tgatccttca actcagcaaa agttcgattt attcaacaaa gccgccgtcc cgtcaagtca  5460
gcgtaatgct ctgccagtgt tacaaccaat taaccaattc tgattagaaa aactcatcga  5520
gcatcaaatg aaactgcaat ttattcatat caggattatc aataccatat ttttgaaaaa  5580
gccgtttctg taatgaagga gaaaactcac cgaggcagtt ccataggatg caagatcct   5640 ggtatcggtc tgcgattccg actcgtccaa catcaataca acctattaat ttcccctcgt  5700
```

```
caaaaataag gttatcaagt gagaaatcac catgagtgac gactgaatcc ggtgagaatg    5760
gcaaaagctt atgcatttct ttccagactt gttcaacagg ccagccatta cgctcgtcat    5820
caaaatcact cgcatcaacc aaaccgttat tcattcgtga ttgcgcctga gcagacgaa     5880 atacgcgatc gctgttaaaa ggacaattac aaacaggaat cgaatgcaac cggcgcagga    5940
acactgccag cgcatcaaca atattttcac ctgaatcagg atattcttct aatacctgga    6000
atgctgtttt cccggggatc gcagtggtga gtaaccatgc atcatcagga gtacggataa    6060
aatgcttgat ggtcggaaga ggcataaaat ccgtcagcca gtttagtctg accatctcat    6120
ctgtaacatc attggcaacg ctacctttgc catgtttcag aaacaactct ggcgcatcgg    6180
gcttcccata caatcgatag attgtcgcac ctgattgccc gacattatcg cgagcccatt    6240
tatacccata taaatcagca tccatgttgg aatttaatcg cggcctcgag caagacgttt    6300
cccgttgaat atggctcata caccccttg tattactgtt tatgtaagca gacagtttta    6360
ttgttcatga tgatatattt ttatcttgtg caatgtaaca tcagagattt tgagacacaa    6420
cgtggctttc ccccccccc cattattgaa gcatttatca gggttattgt ctcatgagcg    6480
gatacatatt tgaatgtatt tagaaaaata acaaataggg gttccgcgc acatttcccc    6540 gaaaagtgcc acctgacgtc taagaaacca ttattatcat gacattaacc tataaaaata    6600
ggcgtatcac gaggccctttt cgtc                                          6624

<210> SEQ ID NO 4
<211> LENGTH: 6561
<212> TYPE: DNA
<213> ORGANISM: Artificial Sequence
<220> FEATURE:
<223> OTHER INFORMATION: Synthetic Construct pVR1012-GP(Z) deltaMUC
      delta FUR

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccctttggc     1080
```

```
tcttatgcat gctatactgt ttttggcttg gggcctatac accccgcttc cttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca caacgccgt cccccgtgcc     1380 cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaaact gctacaatct tgaaatcaaa    2280
aaacctgacg ggagtgagtg tctaccagca gcgccagacg ggattcgggg cttcccccgg    2340
tgccggtatg tgcacaaagt atcaggaacg ggaccgtgtg ccggagactt tgccttccat    2400
aaagagggtg cttcttcct gtatgatcga cttgcttcca cagttatcta ccgaggaacg     2460
actttcgctg aaggtgtcgt tgcatttctg atactgcccc aagctaagaa ggacttcttc    2520
agctcacacc ccttgagaga gccggtcaat gcaacgagg acccgtctag tggctactat     2580
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcggaagaga agcaattgtc aatgctcaac ccaaatgcaa    2880
ccctaattta cattactgga ctactcagga tgaaggtgct gcaatcggac tggcctggat    2940
accatatttc gggccagcag ccgagggaat ttacatagag gggctaatgc acaatcaaga    3000
tggtttaatc tgtgggttga gacagctggc caacgagacg actcaagctc ttcaactgtt    3060
cctgagagcc acaactgagc tacgcacctt ttcaatcctc aaccgtaagg caattgattt    3120
cttgctgcag cgatggggcg gcacatgcca cattctggga ccggactgct gtatcgaacc    3180
acatgattgg accaagaaca taacagacaa aattgatcag attattcatg attttgttga    3240
taaaaccctt ccggaccagg ggacaatga caattggtgg acaggatgga gacaatggat    3300
accggcaggt attggagtta caggcgttgt aattgcagtt atcgctttat tctgtatatg    3360
caaatttgtc ttttagtttt tcttcagatt gcttcatgga aaagctcagc tcaaatcaa    3420 tgaaaccagg atttaattat atggattact tgaatctaag attacttgac aaatgataat    3480
```

```
ataatacact ggagctttaa acatagccaa tgtgattcta actcctttaa actcacagtt   3540
aatcataaac aaggtttgag gtaccgagct cgaattgatc tgctgtgcct tctagttgcc   3600
agccatctgt tgtttgcccc tccccgtgc cttccttgac cctggaaggt gccactccca    3660
ctgtcctttc ctaataaaat gaggaaattg catcgcattg tctgagtagg tgtcattcta   3720
ttctgggggg tggggtgggg caggacagca aggggagga ttgggaagac aatagcaggc    3780
atgctgggga tgcggtgggc tctatgggta cccaggtgct gaagaattga cccgttcct    3840
cctgggccag aaagaagcag gcacatcccc ttctctgtga cacaccctgt ccacgcccct   3900
ggttcttagt tccagcccca ctcataggac actcatagct caggagggct ccgccttcaa   3960
tcccacccgc taaagtactt ggagcggtct ctccctccct catcagccca ccaaaccaaa   4020
cctagcctcc aagagtggga agaaattaaa gcaagatagg ctattaagtg cagagggaga   4080
gaaaatgcct ccaacatgtg aggaagtaat gagagaaatc atagaatttc ttccgcttcc   4140
tcgctcactg actcgctgcg ctcggtcgtt cggctgcggc gagcggtatc agctcactca   4200
aaggcggtaa tacggttatc cacagaatca ggggataacg caggaaagaa catgtgagca   4260
aaaggccagc aaaaggccag gaaccgtaaa aaggccgcgt tgctggcgtt tttccatagg   4320
ctccgccccc ctgacgagca tcacaaaaat cgacgctcaa gtcagaggtg gcgaaacccg   4380
acaggactat aaagatacca ggcgtttccc cctggaagct ccctcgtgcg ctctcctgtt   4440
ccgaccctgc cgcttaccgg atacctgtcc gcctttctcc cttcgggaag cgtggcgctt   4500
tctcatagct cacgctgtag gtatctcagt tcggtgtagg tcgttcgctc caagctgggc   4560
tgtgtgcacg aaccccccgt tcagcccgac cgctgcgcct tatccggtaa ctatcgtctt   4620
gagtccaacc cggtaagaca cgacttatcg ccactggcag cagccactgg taacaggatt   4680
agcagagcga ggtatgtagg cggtgctaca gagttcttga agtggtggcc taactacggc   4740
tacactagaa gaacagtatt tggtatctgc gctctgctga gccagttac cttcggaaaa    4800
agagttggta gctcttgatc cggcaaacaa accaccgctg gtagcggtgg ttttttttgtt   4860
tgcaagcagc agattacgcg cagaaaaaaa ggatctcaag aagatccttt gatcttttct    4920
acggggtctg acgctcagtg gaacgaaaac tcacgttaag ggattttggt catgagatta    4980
tcaaaaagga tcttcaccta gatcctttta aattaaaaat gaagttttaa atcaatctaa    5040
agtatatatg agtaaacttg gtctgacagt taccaatgct taatcagtga ggcacctatc    5100
tcagcgatct gtctatttcg ttcatccata gttgcctgac tcgggggggg gggcgctga    5160
ggtctgcctc gtgaagaagg tgttgctgac tcataccagg cctgaatcgc ccatcatcc    5220
agccagaaag tgagggagcc acggttgatg agagctttgt tgtaggtgga ccagttggtg   5280
attttgaact tttgctttgc cacggaacgg tctgcgttgt cgggaagatg cgtgatctga   5340
tccttcaact cagcaaaagt tcgatttatt caacaaagcc gccgtcccgt caagtcagcg    5400
taatgctctg ccagtgttac aaccaattaa ccaattctga ttagaaaaac tcatcgagca   5460
tcaaatgaaa ctgcaatttta ttcatatcag gattatcaat accatatttt tgaaaaagcc   5520
gtttctgtaa tgaaggagaa aactcaccga ggcagttcca taggatgca agatcctggt    5580
atcggtctgc gattccgact cgtccaacat caatacaacc tattaatttc cctcgtcaa    5640
aaataaggtt atcaagtgag aaatcaccat gagtgacgac tgaatccggt gagaatggca   5700
aaagcttatg catttctttc cagacttgtt caacaggcca gccattacgc tcgtcatcaa    5760
aatcactcgc atcaaccaaa ccgttattca ttcgtgattg cgcctgagcg agacgaaata   5820
cgcgatcgct gttaaaagga caattacaaa caggaatcga atgcaaccgg cgcaggaaca   5880
```

-continued

| | |
|---|---|
| ctgccagcgc atcaacaata ttttcacctg aatcaggata ttcttctaat acctggaatg | 5940 |
| ctgttttccc ggggatcgca gtggtgagta accatgcatc atcaggagta cggataaaat | 6000 |
| gcttgatggt cggaagaggc ataaattccg tcagccagtt tagtctgacc atctcatctg | 6060 |
| taacatcatt ggcaacgcta cctttgccat gtttcagaaa caactctggc gcatcgggct | 6120 |
| tcccatacaa tcgatagatt gtcgcacctg attgcccgac attatcgcga gcccatttat | 6180 |
| acccatataa atcagcatcc atgttggaat ttaatcgcgg cctcgagcaa gacgtttccc | 6240 |
| gttgaatatg gctcataaca ccccttgtat tactgtttat gtaagcagac agttttattg | 6300 |
| ttcatgatga tatatttta tcttgtgcaa tgtaacatca gagattttga gacacaacgt | 6360 |
| ggctttcccc cccccccat tattgaagca tttatcaggg ttattgtctc atgagcggat | 6420 |
| acatatttga atgtatttag aaaaataaac aaataggggt tccgcgcaca tttccccgaa | 6480 |
| aagtgccacc tgacgtctaa gaaaccatta ttatcatgac attaacctat aaaaataggc | 6540 |
| gtatcacgag gccctttcgt c | 6561 |

<210> SEQ ID NO 5
<211> LENGTH: 6724
<212> TYPE: DNA
<213> ORGANISM: Artificial Sequence
<220> FEATURE:
<223> OTHER INFORMATION: Synthetic Construct pVR1012-GP(Z) delta GP2

<400> SEQUENCE: 5

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccctttggc | 1080 |
| tcttatgcat gctatactgt ttttggcttg gggcctatac accccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tattttaca | 1320 |
| ggatggggtc ccatttatta tttacaaatt cacatataca acaacgccgt cccccgtgcc | 1380 |

```
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg gctcgcacg gctgacgcag atggaagact taaggcagcg     1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttccccgg    2340 tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg atactgcccc aagctaagaa ggacttcttc    2520
agctcacacc ccttgagaga gccggtcaat gcaacggagg accgtctag tggctactat     2580 tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg acccccaaa agcagagaac     3240 accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actccggacc    3420 aggggggacaa tgacaattgg tggacaggat ggagacaatg gataccggca ggtattggag    3480
ttacaggcgt tgtaattgca gttatcgctt tattctgtat atgcaaattt gtcttttagt    3540
ttttcttcag attgcttcat ggaaaagctc agcctcaaat caatgaaacc aggatttaat    3600
tatatggatt acttgaatct aagattactt gacaaatgat aatataatac actggagctt    3660
taaacatagc caatgtgatt ctaactcctt taaactcaca gttaatcata acaaggtttt    3720
gaggtaccga gctcgaattg atctgctgtg ccttctagtt gccagccatc tgttgtttgc    3780
```

-continued

```
ccctcccccg tgccttcctt gaccctggaa ggtgccactc ccactgtcct ttcctaataa   3840
aatgaggaaa ttgcatcgca ttgtctgagt aggtgtcatt ctattctggg gggtggggtg   3900
gggcaggaca gcaaggggga ggattgggaa gacaatagca ggcatgctgg ggatgcggtg   3960
ggctctatgg gtacccaggt gctgaagaat tgacccggtt cctcctgggc cagaaagaag   4020
caggcacatc cccttctctg tgacacaccc tgtccacgcc cctggttctt agttccagcc   4080
ccactcatag gacactcata gctcaggagg gctccgcctt caatcccacc cgctaaagta   4140
cttggagcgg tctctcccctc cctcatcagc ccaccaaacc aaacctagcc tccaagagtg   4200
ggaagaaatt aaagcaagat aggctattaa gtgcagaggg agagaaaatg cctccaacat   4260
gtgaggaagt aatgagagaa atcatagaat ttcttccgct tcctcgctca ctgactcgct   4320
gcgctcggtc gttcggctgc ggcgagcggt atcagctcac tcaaaggcgg taatacggtt   4380
atccacagaa tcaggggata acgcaggaaa gaacatgtga gcaaaaggcc agcaaaaggc   4440
caggaaccgt aaaaaggccg cgttgctggc gttttttccat aggctccgcc cccctgacga   4500
gcatcacaaa aatcgacgct caagtcagag gtggcgaaac ccgacaggac tataaagata   4560
ccaggcgttt cccctggaa gctccctcgt gcgctctcct gttccgaccc tgccgcttac   4620
cggatacctg tccgccttc tcccttcggg aagcgtggcg ctttctcata gctcacgctg   4680
taggtatctc agttcggtgt aggtcgttcg ctccaagctg ggctgtgtgc acgaaccccc   4740
cgttcagccc gaccgctgcg ccttatccgg taactatcgt cttgagtcca acccggtaag   4800
acacgactta tcgccactgg cagcagccac tggtaacagg attagcagag cgaggtatgt   4860
aggcggtgct acagagttct tgaagtggtg gcctaactac ggctacacta agaacagt    4920 atttggtatc tgcgctctgc tgaagccagt taccttcgga aaagagttg gtagctcttg   4980 atccggcaaa caaaccaccg ctggtagcgg tggtttttt gtttgcaagc agcagattac   5040
gcgcagaaaa aaaggatctc aagaagatcc tttgatcttt tctacggggt ctgacgctca   5100
gtggaacgaa aactcacgtt aagggatttt ggtcatgaga ttatcaaaaa ggatcttcac   5160
ctagatcctt ttaaattaaa aatgaagttt taaatcaatc taaagtatat atgagtaaac   5220
ttggtctgac agttaccaat gcttaatcag tgaggcacct atctcagcga tctgtctatt   5280
tcgttcatcc atagttgcct gactcggggg ggggggcgc tgaggtctgc ctcgtgaaga   5340
aggtgttgct gactcatacc aggcctgaat cgccccatca tccagccaga agtgagggaa   5400
gccacggttg atgagagctt tgttgtaggt ggaccagttg gtgattttga acttttgctt   5460
tgccacggaa cggtctgcgt tgtcgggaag atgcgtgatc tgatccttca actcagcaaa   5520
agttcgattt attcaacaaa gccgccgtcc cgtcaagtca gcgtaatgct ctgccagtgt   5580
tacaaccaat taaccaattc tgattagaaa aactcatcga gcatcaaatg aaactgcaat   5640
ttattcatat caggattatc aataccatat ttttgaaaaa gccgtttctg taatgaagga   5700
gaaaactcac cgaggcagtt ccataggatg gcaagatcct ggtatcggtc tgcgattccg   5760
actcgtccaa catcaataca acctattaat ttcccctcgt caaaaataag gttatcaagt   5820
gagaaatcac catgagtgac gactgaatcc ggtgagaatg gcaaaagctt atgcatttct   5880
ttccagactt gttcaacagg ccagccatta cgctcgtcat caaaatcact cgcatcaacc   5940
aaaccgttat tcattcgtga ttgcgcctga gcgagacgaa atacgcgatc gctgttaaaa   6000
ggacaattac aaacaggaat cgaatgcaac cggcgcagga acactgccag cgcatcaaca   6060
atattttcac ctgaatcagg atattcttct aatacctgga atgctgtttt cccggggatc   6120
gcagtggtga gtaaccatgc atcatcagga gtacggataa aatgcttgat ggtcggaaga   6180
```

-continued

```
ggcataaaatt ccgtcagcca gtttagtctg accatctcat ctgtaacatc attggcaacg      6240
ctacctttgc catgtttcag aaacaactct ggcgcatcgg gcttcccata caatcgatag      6300
attgtcgcac ctgattgccc gacattatcg cgagcccatt tatacccata taaatcagca      6360
tccatgttgg aatttaatcg cggcctcgag caagacgttt cccgttgaat atggctcata      6420
acaccccttg tattactgtt tatgtaagca gacagtttta ttgttcatga tgatatattt      6480
ttatcttgtg caatgtaaca tcagagattt tgagacacaa cgtggctttc ccccccccc       6540 cattattgaa gcatttatca gggttattgt ctcatgagcg gatacatatt tgaatgtatt      6600
tagaaaaata aacaaatagg ggttccgcgc acatttcccc gaaaagtgcc acctgacgtc      6660
taagaaacca ttattatcat gacattaacc tataaaaata ggcgtatcac gaggccctt       6720 cgtc                                                                    6724

<210> SEQ ID NO 6
<211> LENGTH: 6887
<212> TYPE: DNA
<213> ORGANISM: Artificial Sequence
<220> FEATURE:
<223> OTHER INFORMATION: Synthetic Construct pVR1012-GP(Z) delta GP2
      delta C-term A

<400> SEQUENCE: 6
tcgcgcgttt cggtgatgac ggtgaaaacc tctgacacat gcagctcccg gagacggtca        60
cagcttgtct gtaagcggat gccggagcag acaagcccg tcagggcgcg tcagcgggtg       120
ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca acgacccccg cccattgacg tcaataatga cgtatgttcc      480
catagtaacg ccaatagggga cttcccattg acgtcaatgg gtggagtatt tacggtaaac      540
tgcccacttg gcagtacatc aagtgtatca tatgccaagt acgccccta ttgacgtcaa       600 tgacggtaaa tggcccgcct ggcattatgc ccagtacatg accttatggg acttcctac       660 ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt tgacctcca       960 tagaagacac cgggaccgat ccagcctccg cggccgggaa cggtgcattg gaacgcggat     1020
tccccgtgcc aagagtgacg taagtaccgc ctatagactc tataggcaca ccctttggc      1080 tcttatgcat gctatactgt ttttggcttg gggcctatac accccgctt ccttatgcta      1140 taggtgatgg tatagcttag cctataggtg tgggttattg accattattg accactcccc      1200
tattggtgac gatactttcc attactaatc cataacatgg ctctttgcca caactatctc      1260
tattggctat atgccaatac tctgtccttc agagactgac acggactctg tatttttaca      1320
ggatggggtc ccatttatta tttacaaatt cacatataca acaacgccgt ccccgtgcc      1380 cgcagttttt attaaacata gcgtgggatc tccacgcgaa tctcgggtac gtgttccgga     1440
catgggctct tctccggtag cggcggagct tccacatccg agccctggtc ccatgcctcc     1500
```

```
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttcccccgg    2340
tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg atactgcccc aagctaagaa ggacttcttc    2520
agctcacacc ccttgagaga gccggtcaat gcaacgaagg acccgtctag tggctactat    2580
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gacccccaaa agcagagaac    3240
accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg ataccatat    3540 ttcgggccag cagccgaggg aatttacata gaggggctaa tgcacaatca agatggttta    3600
atctgtgggt tgagacagct ggggataccg gcaggtattg gagttacagg cgttgtaatt    3660
gcagttatcg ctttattctg tatatgcaaa tttgtctttt agttttctt cagattgctt    3720 catggaaaag ctcagcctca aatcaatgaa accaggattt aattatatgg attacttgaa    3780
tctaagatta cttgacaaat gataaatata tacactggag cttttaaacat agccaatgtg    3840 attctaactc ctttaaactc acagttaatc ataaacaagg tttgaggtac cgagctcgaa    3900
```

```
ttgatctgct gtgccttcta gttgccagcc atctgttgtt tgcccctccc ccgtgccttc    3960
cttgaccctg gaaggtgcca ctcccactgt cctttcctaa taaaatgagg aaattgcatc    4020
gcattgtctg agtaggtgtc attctattct gggggggtggg gtggggcagg acagcaaggg    4080
ggaggattgg gaagacaata gcaggcatgc tggggatgcg gtgggctcta tgggtaccca    4140
ggtgctgaag aattgacccg gttcctcctg ggccagaaag aagcaggcac atccccttct    4200
ctgtgacaca ccctgtccac gccctggtt cttagttcca gccccactca taggacactc     4260
atagctcagg agggctccgc cttcaatccc acccgctaaa gtacttggag cggtctctcc    4320
ctccctcatc agcccaccaa accaaaccta gcctccaaga gtgggaagaa attaaagcaa    4380
gataggctat taagtgcaga gggagagaaa atgcctccaa catgtgagga agtaatgaga    4440
gaaatcatag aatttcttcc gcttcctcgc tcactgactc gctgcgctcg gtcgttcggc    4500
tgcggcgagc ggtatcagct cactcaaagg cggtaatacg gttatccaca gaatcagggg    4560
ataacgcagg aaagaacatg tgagcaaaag gccagcaaaa ggccaggaac cgtaaaaagg    4620
ccgcgttgct ggcgttttc cataggctcc gccccctga cgagcatcac aaaaatcgac       4680
gctcaagtca gaggtggcga aacccgacag gactataaag ataccaggcg tttccccctg    4740
gaagctccct cgtgcgctct cctgttccga ccctgccgct taccggatac ctgtccgcct    4800
ttctcccttc gggaagcgtg cgctttctc atagctcacg ctgtaggtat ctcagttcgg     4860
tgtaggtcgt tcgctccaag ctgggctgtg tgcacgaacc ccccgttcag cccgaccgct    4920
gcgccttatc cggtaactat cgtcttgagt ccaacccgt aagacacgac ttatcgccac     4980
tggcagcagc cactggtaac aggattagca gagcgaggta tgtaggcggt gctacagagt    5040
tcttgaagtg gtggcctaac tacggctaca ctagaagaac agtatttggt atctgcgctc    5100
tgctgaagcc agttaccttc ggaaaaagag ttggtagctc ttgatccggc aaacaaacca    5160
ccgctggtag cggtggtttt tttgtttgca agcagcagat tacgcgcaga aaaaaaggat    5220
ctcaagaaga tcctttgatc ttttctacgg ggtctgacgc tcagtggaac gaaaactcac    5280
gttaagggat tttggtcatg agattatcaa aaaggatctt cacctagatc ctttaaatt     5340 aaaaatgaag ttttaaatca atctaaagta tatatgagta aacttggtct gacagttacc    5400
aatgcttaat cagtgaggca cctatctcag cgatctgtct atttcgttca tccatagttg    5460
cctgactcgg ggggggggg cgctgaggtc tgcctcgtga agaaggtgtt gctgactcat       5520
accaggcctg aatcgcccca tcatccagcc agaaagtgag ggagccacgg ttgatgagag    5580 cttttgttgta ggtggaccag ttggtgattt tgaacttttg ctttgccacg gaacggtctg    5640
cgttgtcggg aagatgcgtg atctgatcct tcaactcagc aaaagttcga tttattcaac    5700
aaagccgccg tcccgtcaag tcagcgtaat gctctgccag tgttacaacc aattaaccaa    5760
ttctgattag aaaaactcat cgagcatcaa atgaaactgc aatttattca tatcaggatt    5820
atcaatacca tatttttgaa aaagccgttt ctgtaatgaa ggagaaaact caccgaggca    5880
gttccatagg atggcaagat cctggtatcg gtctgcgatt ccgactcgtc aacatcaat     5940 acaacctatt aatttccct cgtcaaaaat aaggttatca agtgagaaat caccatgagt     6000
gacgactgaa tccggtgaga atggcaaaag ctttatgcatt tctttccaga cttgttcaac    6060
aggccagcca ttacgctcgt catcaaaatc actcgcatca accaaccgt tattcattcg      6120 tgattgcgcc tgagcgagac gaaatacgcg atcgctgtta aaaggacaat acaaacagg     6180 aatcgaatgc aaccggcgca ggaacactgc cagcgcatca acaatatttt cacctgaatc    6240
aggatattct tctaatacct ggaatgctgt tttcccgggg atcgcagtgg tgagtaacca    6300
```

| | | | |
|---|---|---|---|
| tgcatcatca | ggagtacgga | taaaatgctt gatggtcgga agaggcataa attccgtcag | 6360 |
| ccagtttagt | ctgaccatct | catctgtaac atcattggca acgctacctt tgccatgttt | 6420 |
| cagaaacaac | tctggcgcat | cgggcttccc atacaatcga tagattgtcg cacctgattg | 6480 |
| cccgacatta | tcgcgagccc | atttataccc atataaatca gcatccatgt tggaatttaa | 6540 |
| tcgcggcctc | gagcaagacg | tttcccgttg aatatggctc ataacacccc ttgtattact | 6600 |
| gtttatgtaa | gcagacagtt | ttattgttca tgatgatata tttttatctt gtgcaatgta | 6660 |
| acatcagaga | ttttgagaca | caacgtggct ttcccccccc ccccattatt gaagcattta | 6720 |
| tcagggttat | tgtctcatga | gcggatacat atttgaatgt atttagaaaa ataaacaaat | 6780 |
| aggggttccg | cgcacatttc | cccgaaaagt gccacctgac gtctaagaaa ccattattat | 6840 |
| catgacatta | acctataaaa | ataggcgtat cacgaggccc tttcgtc | 6887 |

<210> SEQ ID NO 7
<211> LENGTH: 7044
<212> TYPE: DNA
<213> ORGANISM: Artificial Sequence
<220> FEATURE:
<223> OTHER INFORMATION: Synthetic Construct pVR1012-GP(Z) delta GP2
    Delta C-term B

<400> SEQUENCE: 7

| | | | |
|---|---|---|---|
| tcgcgcgttt | cggtgatgac | ggtgaaaacc tctgacacat gcagctcccg gagacggtca | 60 |
| cagcttgtct | gtaagcggat | gccgggagca gacaagcccg tcaggcgcg tcagcgggtg | 120 |
| ttggcgggtg | tcgggctgg | cttaactatg cggcatcaga gcagattgta ctgagagtgc | 180 |
| accatatgcg | gtgtgaaata | ccgcacagat gcgtaaggag aaaataccgc atcagattgg | 240 |
| ctattggcca | ttgcatacgt | tgtatccata tcataatatg tacatttata ttggctcatg | 300 |
| tccaacatta | ccgccatgtt | gacattgatt attgactagt tattaatagt aatcaattac | 360 |
| ggggtcatta | gttcatagcc | catatatgga gttccgcgtt acataactta cggtaaatgg | 420 |
| cccgcctgc | tgaccgccca | acgacccccg cccattgacg tcaataatga cgtatgttcc | 480 |
| catagtaacg | ccaataggga | cttccattg acgtcaatgg gtggagtatt tacggtaaac | 540 |
| tgcccacttg | gcagtacatc | aagtgtatca tatgccaagt acgccccta ttgacgtcaa | 600 |
| tgacggtaaa | tggcccgcct | ggcattatgc ccagtacatg accttatggg actttcctac | 660 |
| ttggcagtac | atctacgtat | tagtcatcgc tattaccatg gtgatgcggt tttggcagta | 720 |
| catcaatggg | cgtggatagc | ggtttgactc acggggattt ccaagtctcc accccattga | 780 |
| cgtcaatggg | agtttgtttt | ggcaccaaaa tcaacgggac tttccaaaat gtcgtaacaa | 840 |
| ctccgcccca | ttgacgcaaa | tgggcggtag gcgtgtacgg tggaggtct atataagcag | 900 |
| agctcgttta | gtgaaccgtc | agatcgcctg gagacgccat ccacgctgtt tgacctcca | 960 |
| tagaagacac | cgggaccgat | ccagcctccg cggccgggaa cggtgcattg gaacgcggat | 1020 |
| tccccgtgcc | aagagtgacg | taagtaccgc ctatagactc tataggcaca cccctttggc | 1080 |
| tcttatgcat | gctatactgt | ttttggcttg gggcctatac accccgctt ccttatgcta | 1140 |
| taggtgatgg | tatagcttag | cctataggtg tgggttattg accattattg accactcccc | 1200 |
| tattggtgac | gatactttcc | attactaatc cataacatgg ctctttgcca caactatctc | 1260 |
| tattggctat | atgccaatac | tctgtccttc agagactgac acggactctg tattttaca | 1320 |
| ggatggggtc | ccatttatta | tttacaaatt cacatataca acaacgccgt ccccgtgcc | 1380 |
| cgcagttttt | attaaacata | gcgtgggatc tccacgcgaa tctcgggtac gtgttccgga | 1440 |

```
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaaact gctacaatct tgaaatcaaa    2280
aaacctgacg ggagtgagtg tctaccagca gcgccagacg ggattcgggg cttcccccgg    2340
tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg tatactgcccc aagctaagaa ggacttcttc    2520
agctcacacc ccttgagaga gccggtcaat gcaacggagg accgtctag tggctactat     2580 tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata caagtgggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gaccccaaaa agcagagaac    3240
accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg gataccatat    3540
ttcgggccag cagccgaggg aatttacata gaggggctaa tgcacaatca agatggttta    3600
atctgtgggt tgagacagct ggccaacgag acgactcaag ctcttcaact gttcctgaga    3660
gccacaactg agctacgcac cttttcaatc ctcaaccgta aggcaattga tttcttgctg    3720
cagcgatggg gcggcacatg ccacattctg ggaccggact gctgtatcga accacatgag    3780
gataccggca ggtattggag ttacaggcgt tgtaattgca gttatcgctt tattctgtat    3840
```

```
atgcaaattt gtcttttagt ttttcttcag attgcttcat ggaaaagctc agcctcaaat    3900
caatgaaacc aggatttaat tatatggatt acttgaatct aagattactt gacaaatgat    3960
aatataatac actggagctt taaacatagc caatgtgatt ctaactcctt taaactcaca    4020
gttaatcata aacaaggttt gaggtaccga gctcgaattg atctgctgtg ccttctagtt    4080
gccagccatc tgttgtttgc ccctcccccg tgccttcctt gaccctggaa ggtgccactc    4140
ccactgtcct ttcctaataa aatgaggaaa ttgcatcgca ttgtctgagt aggtgtcatt    4200
ctattctggg gggtggggtg gggcaggaca gcaaggggga ggattgggaa gacaatagca    4260
ggcatgctgg ggatgcggtg ggctctatgg gtacccaggt gctgaagaat tgacccggtt    4320
cctcctgggc cagaaagaag caggcacatc cccttctctg tgacacaccc tgtccacgcc    4380
cctggttctt agttccagcc ccactcatag gacactcata gctcaggagg ctccgcctt    4440 caatcccacc cgctaaagta cttggagcgg tctctccctc cctcatcagc ccaccaaacc    4500
aaacctagcc tccaagagtg ggaagaaatt aaagcaagat aggctattaa gtgcagaggg    4560
agagaaaatg cctccaacat gtgaggaagt aatgagagaa atcatagaat tcttccgct    4620 tcctcgctca ctgactcgct cgctcggtc gttcggctgc ggcgagcggt atcagctcac    4680
tcaaaggcgg taatacggtt atccacagaa tcagggata acgcaggaaa gaacatgtga    4740
gcaaaaggcc agcaaaaggc caggaaccgt aaaaaggccg cgttgctggc gtttttccat    4800
aggctccgcc cccctgacga gcatcacaaa aatcgacgct caagtcagag gtggcgaaac    4860
ccgacaggac tataaagata ccaggcgttt cccctggaa gctccctcgt gcgctctcct    4920
gttccgaccc tgccgcttac cggatacctg tccgccttc tcccttcggg aagcgtggcg    4980
ctttctcata gctcacgctg taggtatctc agttcggtgt aggtcgttcg ctccaagctg    5040
ggctgtgtgc acgaaccccc cgttcagccc gaccgctgcg ccttatccgg taactatcgt    5100
cttgagtcca acccggtaag acacgactta tcgccactgg cagcagccac tggtaacagg    5160
attagcagag cgaggtatgt aggcggtgct acagagttct tgaagtggtg gcctaactac    5220
ggctacacta aagaacagt atttggtatc tgcgctctgc tgaagccagt taccttcgga    5280
aaaagagttg gtagctcttg atccggcaaa caaaccaccg ctggtagcgg tggtttttt    5340 gtttgcaagc agcagattac gcgcagaaaa aaggatctc aagaagatcc tttgatcttt    5400
tctacggggt ctgacgctca gtggaacgaa aactcacgtt aagggatttt ggtcatgaga    5460
ttatcaaaaa ggatcttcac ctagatcctt ttaaattaaa aatgaagttt taaatcaatc    5520
taaagtatat atgagtaaac ttggtctgac agttaccaat gcttaatcag tgaggcacct    5580
atctcagcga tctgtctatt tcgttcatcc atagttgcct gactcggggg gggggggcgc    5640
tgaggtctgc ctcgtgaaga aggtgttgct gactcatacc aggcctgaat cgccccatca    5700
tccagccaga aagtgaggga gccacggttg atgagagctt tgttgtaggt ggaccagttg    5760
gtgattttga acttttgctt tgccacggaa cggtctgcgt tgtcgggaag atgcgtgatc    5820
tgatccttca actcagcaaa agttcgattt attcaacaaa gccgccgtcc cgtcaagtca    5880
gcgtaatgct ctgccagtgt tacaaccaat taaccaattc tgattagaaa aactcatcga    5940
gcatcaaatg aaactgcaat ttattcatat caggattatc aataccatat ttttgaaaaa    6000
gccgtttctg taatgaagga gaaaactcac cgaggcagtt ccataggatg caagatcct    6060 ggtatcggtc tgcgattccg actcgtccaa catcaataca acctattaat ttcccctcgt    6120
caaaaataag gttatcaagt gagaaatcac catgagtgac gactgaatcc ggtgagaatg    6180
gcaaaagctt atgcatttct ttccagactt gttcaacagg ccagccatta cgctcgtcat    6240
```

```
caaaatcact cgcatcaacc aaaccgttat tcattcgtga ttgcgcctga gcgagacgaa      6300
atacgcgatc gctgttaaaa ggacaattac aaacaggaat cgaatgcaac cggcgcagga      6360
acactgccag cgcatcaaca atattttcac ctgaatcagg atattcttct aatacctgga      6420
atgctgtttt cccggggatc gcagtggtga gtaaccatgc atcatcagga gtacggataa      6480
aatgcttgat ggtcggaaga ggcataaatt ccgtcagcca gtttagtctg accatctcat      6540
ctgtaacatc attggcaacg ctacctttgc catgtttcag aaacaactct ggcgcatcgg      6600
gcttcccata caatcgatag attgtcgcac ctgattgccc gacattatcg cgagcccatt      6660
tatacccata taaatcagca tccatgttgg aatttaatcg cggcctcgag caagacgttt      6720
cccgttgaat atggctcata caccccttg tattactgtt tatgtaagca gacagtttta      6780
ttgttcatga tgatatattt ttatcttgtg caatgtaaca tcagagattt tgagacacaa      6840
cgtggctttc cccccccccc cattattgaa gcatttatca gggttattgt ctcatgagcg      6900
gatacatatt tgaatgtatt tagaaaaata aacaaatagg ggttccgcgc acatttcccc      6960
gaaaagtgcc acctgacgtc taagaaacca ttattatcat gacattaacc tataaaaata      7020
ggcgtatcac gaggcccttt cgtc                                              7044

<210> SEQ ID NO 8
<211> LENGTH: 7106
<212> TYPE: DNA
<213> ORGANISM: Artificial Sequence
<220> FEATURE:
<223> OTHER INFORMATION: Synthetic Construct pVR1012-GP(Z) delta GP2
      delta FUS

<400> SEQUENCE: 8
tcgcgcgttt cggtgatgac ggtgaaaacc tctgacacat gcagctcccg gagacggtca       60
cagcttgtct gtaagcggat gccggagca gacaagcccg tcagggcgcg tcagcgggtg      120
ttggcgggtg tcgggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca acgacccccg cccattgacg tcaataatga cgtatgttcc      480
catagtaacg ccaataggga ctttccattg acgtcaatgg gtggagtatt tacggtaaac      540
tgcccacttg gcagtacatc aagtgtatca tatgccaagt acgccccta ttgacgtcaa      600 tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag cgtgtacgg tgggaggtct atataagcag      900
agctcgttta gtgaaccgtc agatcgcctg gagacgccat ccacgctgtt ttgacctcca      960
tagaagacac cgggaccgat ccagcctccg cggccgggaa cggtgcattg gaacgcggat     1020
tccccgtgcc aagagtgacg taagtaccgc ctatagactc tataggcaca ccctttggc     1080 tcttatgcat gctatactgt ttttggcttg gggcctatac ccccgcttc cttatgcta     1140 taggtgatgt tatagcttag cctataggtg tgggttattg accattattg accactcccc     1200
tattggtgac gatactttcc attactaatc cataacatgg ctctttgcca caactatctc     1260
```

```
tattggctat atgccaatac tctgtccttc agagactgac acggactctg tattttaca    1320
ggatggggtc ccatttatta tttacaaatt cacatataca acaacgccgt ccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttccccgg    2340
tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg atactgcccc aagctaagaa ggacttcttc    2520
agctcacacc ccttgagaga gccggtcaat gcaacggagg acccgtctag tggctactat    2580
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gaccccaaa agcagagaac    3240
accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caacccctaat    3480
ttacattact ggactactca ggatgaagag ggaattttaca tagaggggct aatgcacaat    3540
caagatggtt taatctgtgg gttgagacag ctggccaacg agacgactca agctcttcaa    3600
ctgttcctga gagccacaac tgagctacgc accttttcaa tcctcaaccg taaggcaatt    3660
```

```
gatttcttgc tgcagcgatg gggcggcaca tgccacattc tgggaccgga ctgctgtatc   3720
gaaccacatg attggaccaa gaacataaca gacaaaattg atcagattat tcatgatttt   3780
gttgataaaa cccttccgga ccaggggac aatgacaatt ggtggacagg atggagacaa    3840
tggataccgg caggtattgg agttacaggc gttgtaattg cagttatcgc tttattctgt   3900
atatgcaaat ttgtcttta gttttcttc agattgcttc atggaaaagc tcagcctcaa     3960
atcaatgaaa ccaggattta attatatgga ttacttgaat ctaagattac ttgacaaatg   4020
ataatataat acactggagc tttaaacata gccaatgtga ttctaactcc tttaaactca   4080
cagttaatca taaacaaggt ttgaggtacc gagctcgaat tgatctgctg tgccttctag   4140
ttgccagcca tctgttgttt gcccctcccc cgtgccttcc ttgaccctgg aaggtgccac   4200
tcccactgtc ctttcctaat aaaatgagga aattgcatcg cattgtctga gtaggtgtca   4260
ttctattctg gggggtgggg tgggcagga cagcaagggg gaggattggg aagacaatag    4320
caggcatgct ggggatgcgg tgggctctat gggtacccag gtgctgaaga attgacccgg   4380
ttcctcctgg gccagaaaga agcaggcaca tccccttctc tgtgacacac cctgtccacg   4440
cccctggttc ttagttccag ccccactcat aggacactca tagctcagga gggctccgcc   4500
ttcaatccca cccgctaaag tacttggagc ggtctctccc tccctcatca gcccaccaaa   4560
ccaaacctag cctccaagag tgggaagaaa ttaaagcaag ataggctatt aagtgcagag   4620
ggagagaaaa tgcctccaac atgtgaggaa gtaatgagag aaatcataga atttcttccg   4680
cttcctcgct cactgactcg ctgcgctcgg tcgttcggct gcggcgagcg gtatcagctc   4740
actcaaaggc ggtaatacgg ttatccacag aatcaggga taacgcagga agaacatgt    4800 gagcaaaagg ccagcaaaag gccaggaacc gtaaaaaggc cgcgttgctg cgttttttcc   4860
ataggctccg ccccctgac gagcatcaca aaaatcgacg ctcaagtcag aggtggcgaa    4920
acccgacagg actataaaga taccaggcgt ttccccctgg aagctccctc gtgcgctctc   4980
ctgttccgac cctgccgctt accggatacc tgtccgcctt tctcccttcg ggaagcgtgg   5040
cgctttctca tagctcacgc tgtaggtatc tcagttcggt gtaggtcgtt cgctccaagc   5100
tgggctgtgt gcacgaaccc cccgttcagc ccgaccgctg cgccttatcc ggtaactatc   5160
gtcttgagtc caacccggta agacacgact tatcgccact ggcagcagcc actggtaaca   5220
ggattagcag agcgaggtat gtaggcggtg ctacagagtt cttgaagtgg tggcctaact   5280
acggctacac tagaagaaca gtatttggta tctgcgctct gctgaagcca gttaccttcg   5340
gaaaaagagt tggtagctct tgatccggca acaaaccac cgctggtagc ggtggttttt    5400
ttgtttgcaa gcagcagatt acgcgcagaa aaaaaggatc tcaagaagat cctttgatct   5460
tttctacggg gtctgacgct cagtggaacg aaaactcacg ttaagggatt ttggtcatga   5520
gattatcaaa aaggatcttc acctagatcc ttttaaatta aaaatgaagt tttaaatcaa   5580
tctaaagtat atatgagtaa acttggtctg acagttacca atgcttaatc agtgaggcac   5640
ctatctcagc gatctgtcta tttcgttcat ccatagttgc ctgactcggg gggggggc     5700 gctgaggtct gcctcgtgaa gaaggtgttg ctgactcata ccaggcctga atcgccccat   5760
catccagcca gaaagtgagg gagccacggt tgatgagagc tttgttgtag gtggaccagt   5820
tggtgatttt gaacttttgc tttgccacgg aacggtctgc gttgtcggga agatgcgtga   5880
tctgatcctt caactcagca aaagttcgat ttattcaaca agccgccgt cccgtcaagt    5940 cagcgtaatg ctctgccagt gttacaacca attaaccaat tctgattaga aaactcatc    6000 gagcatcaaa tgaaactgca atttattcat atcaggatta tcaataccat atttttgaaa   6060
```

```
aagccgtttc tgtaatgaag gagaaaactc accgaggcag ttccatagga tggcaagatc   6120
ctggtatcgg tctgcgattc cgactcgtcc aacatcaata caacctatta atttccccctc  6180 gtcaaaaata aggttatcaa gtgagaaatc accatgagtg acgactgaat ccggtgagaa   6240
tggcaaaagc ttatgcattt cttccagac ttgttcaaca ggccagccat tacgctcgtc    6300
atcaaaatca ctcgcatcaa ccaaaccgtt attcattcgt gattgcgcct gagcgagacg   6360
aaatacgcga tcgctgttaa aaggacaatt acaaacagga tcgaatgca accggcgcag    6420 gaacactgcc agcgcatcaa caatattttc acctgaatca ggatattctt ctaatacctg   6480
gaatgctgtt ttcccgggga tcgcagtggt gagtaaccat gcatcatcag gagtacggat   6540
aaaatgcttg atggtcggaa gaggcataaa ttccgtcagc cagtttagtc tgaccatctc    6600
atctgtaaca tcattggcaa cgctaccttt gccatgtttc agaaacaact ctggcgcatc    6660
gggcttccca tacaatcgat agattgtcgc acctgattgc ccgacattat cgcgagccca    6720
tttataccca tataaatcag catccatgtt ggaatttaat cgcggcctcg agcaagacgt   6780
ttcccgttga atatggctca taacacccct tgtattactg tttatgtaag cagacagttt   6840
tattgttcat gatgatatat ttttatcttg tgcaatgtaa catcagagat tttgagacac   6900
aacgtggctt tccccccccc cccattattg aagcatttat cagggttatt gtctcatgag   6960
cggatacata tttgaatgta tttagaaaaa taaacaaata ggggttccgc gcacatttcc    7020
ccgaaaagtg ccacctgacg tctaagaaac cattattatc atgacattaa cctataaaaa   7080
taggcgtatc acgaggccct ttcgtc                                        7106

<210> SEQ ID NO 9
<211> LENGTH: 6914
<212> TYPE: DNA
<213> ORGANISM: Artificial Sequence
<220> FEATURE:
<223> OTHER INFORMATION: Synthetic Construct pVR1012-GP(Z) delta TM

<400> SEQUENCE: 9
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggga ctttccattg acgtcaatgg gtggagtatt tacggtaaac   540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa    840
ctccgcccca ttgacgcaaa tgggcggtag cgtgtacggt gggaggtct atataagcag    900 agctcgtttt gtgaaccgtc agatcgcctg gagacgccat ccacgctgtt ttgacctcca    960
tagaagacac cgggaccgat ccagcctccg cggccgggaa cggtgcattg gaacgcggat   1020
```

```
tccccgtgcc aagagtgacg taagtaccgc ctatagactc tataggcaca cccctttggc   1080
tcttatgcat gctatactgt ttttggcttg gggcctatac accccgctt ccttatgcta    1140 taggtgatgg tatagcttag cctataggtg tgggttattg accattattg accactcccc   1200
tattggtgac gatactttcc attactaatc cataacatgg ctcttgcca caactatctc    1260 tattggctat atgccaatac tctgtccttc agagactgac acggactctg tattttaca    1320 ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttccccgg    2340 tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcgcagtgaa gagttgtctt tcacagttgt atcaaacgga   2880
gccaaaaaca tcagtggtca gagtccggcg cgaacttctt ccgacccagg accaacaca    2940 acaactgaag accacaaaat catggcttca gaaaattcct ctgcaatggt tcaagtgcac   3000
agtcaaggaa gggaagctgc agtgtcgcat ctaacaaccc ttgccacaat ctccacgagt   3060
ccccaatccc tcacaaccaa accaggtccg gacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg accccccaaa agcagagaac   3240
accaacacga gcaagagcac tgacttcctg gaccccgcca ccacaacaag tccccaaaac   3300
cacagcgaga ccgctggcaa caacaacact catcaccaag ataccggaga agagagtgcc   3360
agcagcggga agctaggctt aattaccaat actattgctg gagtcgcagg actgatcaca   3420
```

```
ggcgggagaa gaactcgaag agaagcaatt gtcaatgctc aacccaaatg caaccctaat   3480
ttacattact ggactactca ggatgaaggt gctgcaatcg gactggcctg gataccatat   3540
ttcgggccag cagccgaggg aatttacata gaggggctaa tgcacaatca agatggttta   3600
atctgtgggt tgagacagct ggccaacgag acgactcaag ctcttcaact gttcctgaga   3660
gccacaactg agctacgcac cttttcaatc ctcaaccgta aggcaattga tttcttgctg   3720
cagcgatggg gcggcacatg ccacattctg ggaccggact gctgtatcga accacatgat   3780
tggaccaaga acataacaga caaaattgat cagattattc atgattttgt tgataaaacc   3840
cttccggacc aggggacaa tgacaattgg tggacaggat ggagacaatg gatggccgca   3900
tcgtgactga ctgacgatct gcctcgcgag atctgctgtg ccttctagtt gccagccatc   3960
tgttgtttgc ccctccccg tgccttcctt gaccctggaa ggtgccactc ccactgtcct   4020
ttcctaataa aatgaggaaa ttgcatcgca ttgtctgagt aggtgtcatt ctattctggg   4080
gggtggggtg gggcaggaca gcaaggggga ggattgggaa gacaatagca ggcatgctgg   4140
ggatgcggtg ggctctatgg gtacccaggt gctgaagaat tgacccggtt cctcctgggc   4200
cagaaagaag caggcacatc cccttctctg tgacacaccc tgtccacgcc cctggttctt   4260
agttccagcc ccactcatag gacactcata gctcaggagg gctccgcctt caatcccacc   4320
cgctaaagta cttggagcgg tctctccctc cctcatcagc ccaccaaacc aaacctagcc   4380
tccaagagtg ggaagaaatt aaagcaagat aggctattaa gtgcagaggg agagaaaatg   4440
cctccaacat gtgaggaagt aatgagagaa atcatagaat tcttccgct tcctcgctca   4500 ctgactcgct gcgctcggtc gttcggctgc ggcgagcggt atcagctcac tcaaaggcgg   4560
taatacggtt atccacagaa tcaggggata acgcaggaaa gaacatgtga gcaaaaggcc   4620
agcaaaaggc caggaaccgt aaaaaggccg cgttgctggc gttttttccat aggctccgcc   4680 cccctgacga gcatcacaaa aatcgacgct caagtcagag gtggcgaaac ccgacaggac   4740
tataaagata ccaggcgttt ccccctggaa gctccctcgt gcgctctcct gttccgaccc   4800
tgccgcttac cggatacctg tccgcctttc tcccttcggg aagcgtggcg ctttctcata   4860
gctcacgctg taggtatctc agttcggtgt aggtcgttcg ctccaagctg ggctgtgtgc   4920
acgaaccccc cgttcagccc gaccgctgcg ccttatccgg taactatcgt cttgagtcca   4980
acccggtaag acacgactta tcgccactgg cagcagccac tggtaacagg attagcagag   5040
cgaggtatgt aggcggtgct acagagttct tgaagtggtg gcctaactac ggctacacta   5100
gaagaacagt atttggtatc tgcgctctgc tgaagccagt taccttcgga aaaagagttg   5160
gtagctcttg atccggcaaa caaaccaccg ctggtagcgg tggttttttt gtttgcaagc   5220
agcagattac gcgcagaaaa aaaggatctc aagaagatcc tttgatcttt tctacggggt   5280
ctgacgctca gtggaacgaa aactcacgtt aagggatttt ggtcatgaga ttatcaaaaa   5340
ggatcttcac ctagatcctt ttaaattaaa aatgaagttt taaatcaatc taaagtatat   5400
atgagtaaac ttggtctgac agttaccaat gcttaatcag tgaggcacct atctcagcga   5460
tctgtctatt tcgttcatcc atagttgcct gactcggggg ggggggcgc tgaggtctgc   5520 ctcgtgaaga aggtgttgct gactcatacc aggcctgaat cgccccatca tccagccaga   5580
aagtgaggga gccacggttg atgagagctt tgttgtaggt ggaccagttg gtgatttga   5640 acttttgctt tgccacggaa cggtctgcgt tgtcgggaag atgcgtgatc tgatccttca   5700
actcagcaaa agttcgattt attcaacaaa gccgccgtcc cgtcaagtca gcgtaatgct   5760
ctgccagtgt tacaaccaat taaccaattc tgattagaaa aactcatcga gcatcaaatg   5820
```

```
aaactgcaat ttattcatat caggattatc aataccatat ttttgaaaaa gccgtttctg    5880
taatgaagga gaaaactcac cgaggcagtt ccataggatg gcaagatcct ggtatcggtc    5940
tgcgattccg actcgtccaa catcaataca acctattaat ttcccctcgt caaaataag     6000 gttatcaagt gagaaatcac catgagtgac gactgaatcc ggtgagaatg gcaaaagctt    6060
atgcatttct ttccagactt gttcaacagg ccagccatta cgctcgtcat caaaatcact    6120
cgcatcaacc aaaccgttat tcattcgtga ttgcgcctga gcgagacgaa atacgcgatc    6180
gctgttaaaa ggacaattac aaacaggaat cgaatgcaac cggcgcagga acactgccag    6240
cgcatcaaca atattttcac ctgaatcagg atattcttct aatacctgga atgctgtttt    6300
cccggggatc gcagtggtga gtaaccatgc atcatcagga gtacggataa aatgcttgat    6360
ggtcggaaga ggcataaatt ccgtcagcca gtttagtctg accatctcat ctgtaacatc    6420
attggcaacg ctacctttgc catgtttcag aaacaactct ggcgcatcgg gcttcccata    6480
caatcgatag attgtcgcac ctgattgccc gacattatcg cgagcccatt tatacccata    6540
taaatcagca tccatgttgg aatttaatcg cggcctcgag caagacgttt cccgttgaat    6600
atggctcata caccccttg tattactgtt tatgtaagca gacagtttta ttgttcatga    6660
tgatatattt ttatcttgtg caatgtaaca tcagagattt tgagacacaa cgtggctttc    6720 ccccccccc cattattgaa gcatttatca gggttattgt ctcatgagcg gatacatatt    6780
tgaatgtatt tagaaaaata aacaaatagg ggttccgcgc acatttcccc gaaaagtgcc    6840
acctgacgtc taagaaacca ttattatcat gacattaacc tataaaaata ggcgtatcac    6900
gaggcccttt cgtc                                                       6914
```

<210> SEQ ID NO 10
<211> LENGTH: 6467
<212> TYPE: DNA
<213> ORGANISM: Artificial Sequence
<220> FEATURE:
<223> OTHER INFORMATION: Synthetic Construct pVR1012-GP(Z) delta SGP

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga cttttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tggaggtct atataagcag    900 agctcgttta gtgaaccgtc agatcgcctg gagacgccat ccacgctgtt tgacctcca    960
```

```
tagaagacac cgggaccgat ccagcctccg cggccgggaa cggtgcattg gaacgcggat    1020
tccccgtgcc aagagtgacg taagtaccgc ctatagactc tataggcaca cccctttggc    1080
tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca    1320 ggatggggtc ccatttatta tttacaaatt cacatataca acaacgccgt ccccgtgcc    1380 cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tccttccat gggtcttttc    1860 tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcaaccccga aattgataca    2100
acaatcgggg agtgggcctt ctgggaaact aaaaaaaacc tcactagaaa aattcgcagt    2160
gaagagttgt ctttcacagt tgtatcaaac ggagccaaaa acatcagtgg tcagagtccg    2220
gcgcgaactt cttccgaccc agggaccaac acaacaactg aagaccacaa aatcatggct    2280
tcagaaaatt cctctgcaat ggttcaagtg cacagtcaag gaagggaagc tgcagtgtcg    2340
catctaacaa cccttgccac aatctccacg agtccccaat ccctcacaac caaaccaggt    2400
ccggacaaca gcacccataa tacacccgtg tataaacttg acatctctga ggcaactcaa    2460
gttgaacaac atcaccgcag aacagacaac gacagcacag cctccgacac tccctctgcc    2520
acgaccgcag ccggacccc aaaagcagag aacaccaaca cgagcaagag cactgacttc    2580
ctggaccccg ccaccacaac aagtcccccaa accacagcg agaccgctgg caacaacaac    2640
actcatcacc aagataccgg agaagagagt gccagcagcg ggaagctagg cttaattacc    2700
aatactattg ctggagtcgc aggactgatc acaggcggga gaagaactcg aagagaagca    2760
attgtcaatg ctcaacccaa atgcaaccct aatttacatt actggactac tcaggatgaa    2820
ggtgctgcaa tcggactggc ctggatacca tatttcgggc cagcagccga gggaattac    2880 atagagggc taatgcacaa tcaagatggt ttaatctgtg ggttgagaca gctggccaac    2940
gagacgactc aagctcttca actgttcctg agagccacaa ctgagctacg caccttttca    3000
atcctcaacc gtaaggcaat tgatttcttg ctgcagcgat ggggcggcac atgccacatt    3060
ctggaccggg actgctgtat cgaaccacat gattggacca agaacataac agacaaaatt    3120
gatcagatta ttcatgattt tgttgataaa acccttccgg accaggggga caatgacaat    3180
tggtggacag gatggagaca atggataccg gcaggtattg gagttacagg cgttgtaatt    3240
gcagttatcg ctttattctg tatatgcaaa tttgtctttt agttttttctt cagattgctt    3300 catggaaaag ctcagcctca aatcaatgaa accaggattt aattatatgg attacttgaa    3360
```

```
tctaagatta cttgacaaat gataatataa tacactggag ctttaaacat agccaatgtg    3420
attctaactc ctttaaactc acagttaatc ataaacaagg tttgaggtac cgagctcgaa    3480
ttgatctgct gtgccttcta gttgccagcc atctgttgtt tgcccctccc ccgtgccttc    3540
cttgaccctg gaaggtgcca ctcccactgt cctttcctaa taaaatgagg aaattgcatc    3600
gcattgtctg agtaggtgtc attctattct ggggggtggg gtggggcagg acagcaaggg    3660
ggaggattgg gaagacaata gcaggcatgc tggggatgcg gtgggctcta tgggtaccca    3720
ggtgctgaag aattgacccg gttcctcctg ggccagaaag aagcaggcac atccccttct    3780
ctgtgacaca ccctgtccac gcccctggtt cttagttcca gccccactca taggacactc    3840
atagctcagg agggctccgc cttcaatccc acccgctaaa gtacttggag cggtctctcc    3900
ctccctcatc agcccaccaa accaaaccta gcctccaaga gtgggaagaa attaaagcaa    3960
gataggctat taagtgcaga gggagagaaa atgcctccaa catgtgagga agtaatgaga    4020
gaaatcatag aatttcttcc gcttcctcgc tcactgactc gctgcgctcg gtcgttcggc    4080
tgcggcgagc ggtatcagct cactcaaagg cggtaatacg gttatccaca gaatcagggg    4140
ataacgcagg aaagaacatg tgagcaaaag gccagcaaaa ggccaggaac cgtaaaaagg    4200
ccgcgttgct ggcgtttttc cataggctcc gcccccctga cgagcatcac aaaaatcgac    4260
gctcaagtca gaggtggcga aacccgacag gactataaag ataccaggcg tttccccctg    4320
gaagctccct cgtgcgctct cctgttccga ccctgccgct taccggatac ctgtccgcct    4380
ttctcccttc gggaagcgtg gcgctttctc atagctcacg ctgtaggtat ctcagttcgg    4440
tgtaggtcgt tcgctccaag ctgggctgtg tgcacgaacc ccccgttcag cccgaccgct    4500
gcgccttatc cggtaactat cgtcttgagt ccaacccggt aagacacgac ttatcgccac    4560
tggcagcagc cactggtaac aggattagca gagcgaggta tgtaggcggt gctacagagt    4620
tcttgaagtg gtggcctaac tacggctaca ctagaagaac agtatttggt atctgcgctc    4680
tgctgaagcc agttaccttc ggaaaaagag ttggtagctc ttgatccggc aaacaaacca    4740
ccgctggtag cggtggtttt tttgtttgca agcagcagat tacgcgcaga aaaaaaggat    4800
ctcaagaaga tcctttgatc ttttctacgg ggtctgacgc tcagtggaac gaaaactcac    4860
gttaagggat tttggtcatg agattatcaa aaaggatctt cacctagatc cttttaaatt    4920
aaaaatgaag ttttaaatca atctaaagta tatatgagta aacttggtct gacagttacc    4980
aatgcttaat cagtgaggca cctatctcag cgatctgtct atttcgttca tccatagttg    5040
cctgactcgg ggggggggg cgctgaggtc tgcctcgtga agaaggtgtt gctgactcat    5100
accaggcctg aatcgcccca tcatccagcc agaaagtgag ggagccacgg ttgatgagag    5160
ctttgttgta ggtggaccag ttggtgattt tgaacttttg ctttgccacg gaacggtctg    5220
cgttgtcggg aagatgcgtg atctgatcct tcaactcagc aaaagttcga tttattcaac    5280
aaagccgccg tcccgtcaag tcagcgtaat gctctgccag tgttacaacc aattaaccaa    5340
ttctgattag aaaaactcat cgagcatcaa atgaaactgc aatttattca tatcaggatt    5400
atcaatacca tatttttgaa aaagccgttt ctgtaatgaa ggagaaaact caccgaggca    5460
gttccatagg atggcaagat cctggtatcg gtctgcgatt ccgactcgtc aacatcaat    5520 acaacctatt aatttcccct cgtcaaaaat aaggttatca agtgagaaat caccatgagt    5580
gacgactgaa tccggtgaga atggcaaaag cttatgcatt tctttccaga cttgttcaac    5640
aggccagcca ttacgctcgt catcaaaatc actcgcatca accaaaccgt tattcattcg    5700
tgattgcgcc tgagcgagac gaaatacgcg atcgctgtta aaaggacaat acaaacagg    5760
```

```
aatcgaatgc aaccggcgca ggaacactgc cagcgcatca acaatatttt cacctgaatc    5820
aggatattct tctaatacct ggaatgctgt tttcccgggg atcgcagtgg tgagtaacca    5880
tgcatcatca ggagtacgga taaaatgctt gatggtcgga agaggcataa attccgtcag    5940
ccagtttagt ctgaccatct catctgtaac atcattggca acgctacctt tgccatgttt    6000
cagaaacaac tctggcgcat cgggcttccc atacaatcga tagattgtcg cacctgattg    6060
cccgacatta tcgcgagccc atttataccc atataaatca gcatccatgt tggaatttaa    6120
tcgcggcctc gagcaagacg tttcccgttg aatatggctc ataacacccc ttgtattact    6180
gtttatgtaa gcagacagtt ttattgttca tgatgatata tttttatctt gtgcaatgta    6240
acatcagaga ttttgagaca aacgtggct tccccccccc cccattatt gaagcattta    6300 tcagggttat tgtctcatga gcggatacat atttgaatgt atttagaaaa ataaacaaat    6360
aggggttccg cgcacatttc cccgaaaagt gccacctgac gtctaagaaa ccattattat    6420
catgacatta acctataaaa ataggcgtat cacgaggccc tttcgtc                  6467

<210> SEQ ID NO 11
<211> LENGTH: 6913
<212> TYPE: DNA
<213> ORGANISM: Artificial Sequence
<220> FEATURE:
<223> OTHER INFORMATION: Synthetic Construct pVR1012x/s Ebola GP(R)
      (dTM)

<400> SEQUENCE: 11
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca     960 tagaagacac cgggaccgat ccagcctccg cggccgggaa cggtgcattg gaacgcggat    1020
tccccgtgcc aagagtgacg taagtaccgc ctatagactc tataggcaca ccctttggc    1080 tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca    1320
```

```
ggatggggtc ccatttatta tttacaaatt cacatataca acaacgccgt ccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatccccaaa ttacctatac aacatggggt    1920
caggatatca acttctccaa ttgcctcggg aacgttttcg taaaacttcg ttcttagtat    1980
gggtaatcat cctcttccag cgagcaatct ccatgccgct tggtatagtg acaaatagca    2040
ctctcaaagc aacagaaatt gatcaattgg tttgtcggga caaactgtca tcaaccagtc    2100
agctcaagtc tgtggggctg aatctggaag gaaatggaat tgcaaccgat gtcccatcag    2160
caacaaaacg ctggggattt cgttcaggtg tgcctcccaa ggtggtcagc tatgaagccg    2220
gagaatgggc agaaaattgc tacaatctgg agatcaaaaa gtcagacgga agtgaatgcc    2280
tccctctccc tcccgacggt gtacgaggat tccctagatg tcgctatgtc cacaaagttc    2340
aaggaacagg tccttgtccc ggtgacttag cttttccataa aaatgggggct ttttcttgt    2400
atgatagatt ggcctcaact gtcatctacc gagggacaac ttttgctgaa ggtgtcgtag    2460
cttttttaat tctgtcagag cccaagaagc attttggaa ggctacacca gctcatgaac    2520
cggtgaacac aacagatgat tccacaagct actacatgac cctgacactc agctacgaga    2580
tgtcaaattt tgggggcaat gaaagtaaca cccttttaa ggtagacaac cacacatatg    2640
tgcaactaga tcgtccacac actccgcagt tccttgttca gctcaatgaa acacttcgaa    2700
gaaataatcg ccttagcaac agtacaggga gattgacttg gacattggat cctaaaattg    2760
aaccagatgt tggtgagtgg gccttctggg aaactaaaaa aacttttccc aacaacttca    2820
tggagaaaac ttgcatttcc aaattctatc aacccacacc aacaactcct cagatcagag    2880
cccggcggga actgtccaag gaaaaattag ctaccaccca cccgccaaca actccgagct    2940
ggttccaacg gattcccctc cagtggtttc agtgctcact gcaggacgga cagaggaaat    3000
gtcgacccaa ggtctaacca acggagagac aatcacaggt ttcaccgcga acccaatgac    3060
aaccaccatt gccccaagtc caaccatgac aagcgaggtt gataacaatg taccaagtga    3120
acaaccgaac aacacagcat ccattgaaga ctcccccccca tcggcaagca acgagacaat    3180
ttaccactcc gagatggatc cgatccaagg ctcgaacaac tccgcccaga gcccacagac    3240
caagaccacg ccagcaccca acatccccc gatgacccag acccgcaag agacggccaa    3300
cagcagcaaa ccaggaacca gcccaggaag cgcagccgga ccaagtcagc ccggactcac    3360
tataaataca gtaagtaagg tagctgattc actgagtccc accaggaaac aaaagcgatc    3420
ggttcgacaa acaccgctaa taaatgtaa cccagatctt tactattgga cagctgttga    3480
tgagggggca gcagtaggat tggcatggat tccatatttc ggacctgcag cagaaggcat    3540
ctacattgag ggtgtaatgc ataatcagaa tgggcttatt tgcgggctac gtcagctagc    3600
caatgaaact acccaggctc ttcaattatt tctgcgggcc acaacagaac tgaggactta    3660
ctcacttctt aacagaaaag ctattgattt tcttcttcaa cgatggggag gtacctgtcg    3720
```

```
aatcctagga ccatcttgtt gcattgagcc acatgattgg acaaaaaata ttactgatga   3780
aattaaccaa attaaacatg actttattga caatccccta ccagaccacg agatgatct    3840
taatctatgg acaggttgga gacaatggtg aatctagacc aggccctgga tccagatctg   3900
ctgtgccttc tagttgccag ccatctgttg tttgccccte cccgtgcct tccttgaccc    3960
tggaaggtgc cactcccact gtcctttcct aataaaatga ggaaattgca tcgcattgtc   4020
tgagtaggtg tcattctatt ctgggggtg gggtggggca ggacagcaag ggggaggatt    4080
gggaagacaa tagcaggcat gctggggatg cggtgggctc tatgggtacc caggtgctga   4140
agaattgacc cggttcctcc tgggccagaa agaagcaggc catcccctt ctctgtgaca    4200
caccctgtcc acgcccctgg ttcttagttc cagccccact cataggacac tcatagctca   4260
ggagggctcc gccttcaatc ccacccgcta aagtacttgg agcggtctct ccctccctca   4320
tcagcccacc aaaccaaacc tagcctccaa gagtgggaag aaattaaagc aagataggct   4380
attaagtgca gagggagaga aaatgcctcc aacatgtgag gaagtaatga gagaaatcat   4440
agaattttaa ggccatgatt taaggccatc atggccttaa tcttccgctt cctcgctcac   4500
tgactcgctg cgctcggtcg ttcggctgcg gcgagcggta tcagctcact caaaggcggt   4560
aatacggtta tccacagaat caggggataa cgcaggaaag aacatgtgag caaaaggcca   4620
gcaaaaggcc aggaaccgta aaaaggccgc gttgctggcg ttttccata ggctccgccc    4680
ccctgacgag catcacaaaa atcgacgctc aagtcagagg tggcgaaacc cgacaggact   4740
ataaagatac caggcgtttc ccctggaag ctccctcgtg cgctctcctg ttccgaccct    4800
gccgcttacc ggatacctgt ccgcctttct cccttcggga agcgtggcgc tttctcatag   4860
ctcacgctgt aggtatctca gttcggtgta ggtcgttcgc tccaagctgg gctgtgtgca   4920
cgaaccccc gttcagcccg accgctgcgc cttatccggt aactatcgtc ttgagtccaa    4980
cccggtaaga cacgacttat cgccactggc agcagccact ggtaacagga ttagcagagc   5040
gaggtatgta ggcggtgcta cagagttctt gaagtggtgg cctaactacg gctacactag   5100
aagaacagta tttggtatct gcgctctgct gaagccagtt accttcggaa aaagagttgg   5160
tagctcttga tccggcaaac aaaccaccgc tggtagcggt ggtttttttg tttgcaagca   5220
gcagattacg cgcagaaaaa aaggatctca agaagatcct ttgatctttt ctacggggtc   5280
tgacgctcag tggaacgaaa actcacgtta agggattttg gtcatgagat tatcaaaaag   5340
gatcttcacc tagatccttt taaattaaaa atgaagtttt aaatcaatct aaagtatata   5400
tgagtaaact tggtctgaca gttaccaatg cttaatcagt gaggcaccta tctcagcgat   5460
ctgtctattt cgttcatcca tagttgcctg actcggggg ggggggcgct gaggtctgcc    5520
tcgtgaagaa ggtgttgctg actcatacca ggcctgaatc gccccatcat ccagccagaa   5580
agtgagggag ccacggttga tgagagcttt gttgtaggtg gaccagttgg tgattttgaa   5640
cttttgcttt gccacggaac ggtctgcgtt gtcgggaaga tgcgtgatct gatccttcaa   5700
ctcagcaaaa gttcgattta ttcaacaaag ccgccgtccc gtcaagtcag cgtaatgctc   5760
tgccagtgtt acaaccaatt aaccaattct gattagaaaa actcatcgag catcaaatga   5820
aactgcaatt tattcatatc aggattatca ataccatatt tttgaaaaag ccgtttctgt   5880
aatgaaggag aaaactcacc gaggcagttc cataggatgg caagatcctg gtatcggtct   5940
gcgattccga ctcgtccaac atcaatacaa cctattaatt tcccctcgtc aaaaataagg   6000
ttatcaagtg agaaatcacc atgagtgacg actgaatccg gtgagaatgg caaaagctta   6060
tgcatttctt tccagacttg ttcaacaggc cagccattac gctcgtcatc aaaatcactc   6120
```

```
gcatcaacca aaccgttatt cattcgtgat tgcgcctgag cgagacgaaa tacgcgatcg   6180
ctgttaaaag gacaattaca aacaggaatc gaatgcaacc ggcgcaggaa cactgccagc   6240
gcatcaacaa tattttcacc tgaatcagga tattcttcta atacctggaa tgctgttttc   6300
ccggggatcg cagtggtgag taaccatgca tcatcaggag tacggataaa atgcttgatg   6360
gtcggaagag gcataaattc cgtcagccag tttagtctga ccatctcatc tgtaacatca   6420
ttggcaacgc tacctttgcc atgtttcaga aacaactctg gcgcatcggg cttcccatac   6480
aatcgataga ttgtcgcacc tgattgcccg acattatcgc gagcccattt atacccatat   6540
aaatcagcat ccatgttgga atttaatcgc ggcctcgagc aagacgtttc ccgttgaata   6600
tggctcataa cacccctttgt attactgttt atgtaagcag acagttttat tgttcatgat   6660
gatatatttt tatcttgtgc aatgtaacat cagagatttt gagacacaac gtggctttcc   6720
cccccccccc attattgaag catttatcag ggttattgtc tcatgagcgg atacatattt   6780 gaatgtatt agaaaaataa acaaataggg gttccgcgca catttccccg aaaagtgcca   6840
cctgacgtct aagaaaccat tattatcatg acattaacct ataaaaatag gcgtatcacg   6900
aggccctttc gtc                                                     6913

<210> SEQ ID NO 12
<211> LENGTH: 8131
<212> TYPE: DNA
<213> ORGANISM: Artificial Sequence
<220> FEATURE:
<223> OTHER INFORMATION: Synthetic Construct pAdApt Ebola GP(R)(dTM)

<400> SEQUENCE: 12
ttaattaacc gcaattctca tgtttgacag cttatcatca tcaataatat accttatttt     60
ggattgaagc caatatgata atgaggggt ggagtttgtg acgtggcgcg gggcgtggga    120
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga atctgaata attttgtgtt    360 actcatagcg cgtaatattt gtctagggcc gcggggactt tgaccgttta cgtggagact    420
cgcccaggtg ttttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacaaact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020 tcacgggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
```

```
cgtcaccgtc gtcgacacgt gtgatcagat atcaacttct ccaattgcct cgggaacgtt    1320
ttcgtaaaac ttcgttctta gtatgggtaa tcatcctctt ccagcgagca atctccatgc    1380
cgcttggtat agtgacaaat agcactctca aagcaacaga aattgatcaa ttggtttgtc    1440
gggacaaact gtcatcaacc agtcagctca agtctgtggg gctgaatctg gaaggaaatg    1500
gaattgcaac cgatgtccca tcagcaacaa aacgctgggg atttcgttca ggtgtgcctc    1560
ccaaggtggt cagctatgaa gccggagaat gggcagaaaa ttgctacaat ctggagatca    1620
aaaagtcaga cggaagtgaa tgcctccctc tccctcccga cggtgtacga ggattcccta    1680
gatgtcgcta tgtccacaaa gttcaaggaa caggtccttg tcccggtgac ttagcttttcc   1740 ataaaaatgg ggcttttttc ttgtatgata gattggcctc aactgtcatc taccgaggga    1800
caacttttgc tgaaggtgtc gtagctttt taattctgtc agagcccaag aagcattttt     1860
ggaaggctac accagctcat gaaccggtga acacaacaga tgattccaca agctactaca    1920
tgaccctgac actcagctac gagatgtcaa attttgggg caatgaaagt aacacccttt     1980
ttaaggtaga caaccacaca tatgtgcaac tagatcgtcc acacactccg cagttccttg    2040
ttcagctcaa tgaaacactt cgaagaaata atcgccttag caacagtaca gggagattga    2100
cttggacatt ggatcctaaa attgaaccag atgttggtga gtgggccttc tgggaaacta    2160
aaaaaacttt tcccaacaac ttcatggaga aaacttgcat ttccaaattc tatcaaccca    2220
caccaacaac tcctcagatc agagcccggc gggaactgtc caaggaaaaa ttagctacca    2280 cccaccccgcc aacaactccg agctggttcc aacggattcc cctccagtgg tttcagtgct   2340
cactgcagga cggacagagg aaatgtcgac ccaaggtcta accaacggag agacaatcac    2400
aggtttcacc gcgaacccaa tgacaaccac cattgcccca gtccaaccca tgacaagcga    2460
ggttgataac aatgtaccaa gtgaacaacc gaacaacaca gcatccattg aagactcccc    2520
cccatcggca gcaacgaga caatttacca ctccgagatg gatccgatcc aaggctcgaa     2580
caactccgcc cagagcccac agaccaagac cacgccagca cccacaacat ccccgatgac    2640
ccaggacccg caagacggg ccaacagcag caaaccagga accagccag gaagcgcagc      2700 cggaccaagt cagcccggac tcactataaa tacagtaagt aaggtagctg attcactgag    2760
tcccaccagg aaacaaaagc gatcggttcg acaaaacacc gctaataaat gtaacccaga    2820
tctttactat tggacagctg ttgatgaggg ggcagcagta ggattggcat ggattccata    2880
tttcggacct gcagcagaag gcatctacat tgagggtgta atgcataatc agaatgggct    2940
tatttgcggg ctacgtcagc tagccaatga aactacccag gctcttcaat tatttctgcg    3000
ggccacaaca gaactgagga cttactcact tcttaacaga aaagctattg attttcttct    3060
tcaacgatgg ggaggtacct gtcgaatcct aggaccatct tgttgcattg agccacatga    3120
ttggacaaaa aatattactg atgaaattaa ccaaattaaa catgacttta ttgacaatcc    3180
cctaccagac cacggagatg atcttaatct atggacaggt tggagacaat ggtgaatcta    3240
gaccaggccc tggatccaga tctgctgtgc cttctagttg ccagccatct gttgtttgcc    3300
cctcccccgt gccttccttg accctggaag gtgccactcc cactgtcctt tcctaataaa    3360
atgaggaaat tgcatcgcat tgtctgagta ggtgtcattc tattctgggg gtgggtgg     3420 ggcagcacag caaggggag gattgggaag acaatagcag gcatgctggg gatgcggtgg    3480
gctctatggg tacccagggc cgcataactt cgtataatgt atgctatacg aagttataag    3540
atctgtactg aaatgtgtgg gcgtggctta agggtgggaa agaatatata aggtgggggt    3600
cttatgtagt tttgtatctg ttttgcagca gccgccgccg ccatgagcac caactcgttt    3660
```

-continued

```
gatggaagca ttgtgagctc atatttgaca acgcgcatgc ccccatgggc cggggtgcgt    3720
cagaatgtga tgggctccag cattgatggt cgccccgtcc tgcccgcaaa ctctactacc    3780
ttgacctacg agaccgtgtc tggaacgccg ttggagactg cagcctccgc cgccgcttca    3840
gccgctgcag ccaccgcccg cgggattgtg actgactttg cttcctgag cccgcttgca     3900
agcagtgcag cttcccgttc atccgcccgc gatgacaagt tgacggctct tttggcacaa    3960
ttggattctt tgacccggga acttaatgtc gtttctcagc agctgttgga tctgcgccag    4020
caggtttctg ccctgaaggc ttcctcccct cccaatgcgg tttaaaacat aaataaaaaa    4080
ccagactctg tttggatttg gatcaagcaa gtgtcttgct gtctttattt aggggttttg    4140
cgcgcgcggt aggcccggga ccagcggtct cggtcgttga gggtcctgtg tattttttcc    4200
aggacgtggt aaaggtgact ctggatgttc agatacatgg gcataagccc gtctctgggg    4260
tggaggtagc accactgcag agcttcatgc tgcggggtgg tgttgtagat gatccagtcg    4320
tagcaggagc gctgggcgtg gtgcctaaaa atgtctttca gtagcaagct gattgccagg    4380
ggcaggccct tggtgtaagt gtttacaaag cggttaagct gggatgggtg catacgtggg    4440
gatatgagat gcatcttgga ctgtattttt aggttggcta tgttcccagc catatccctc    4500
cggggattca tgttgtgcag aaccaccagc acagtgtatc cggtgcactt gggaaatttg    4560
tcatgtagct tagaaggaaa tgcgtggaag aacttggaga cgcccttgtg acctccaaga    4620
ttttccatgc attcgtccat aatgatggca atgggcccac gggcggcggc ctgggcgaag    4680
atatttctgg gatcactaac gtcatagttg tgttccagga tgagatcgtc ataggccatt    4740
tttacaaagc gcgggcggag ggtgccagac tgcggtataa tggttccatc cggcccaggg    4800
gcgtagttac cctcacagat ttgcattttcc cacgctttga gttcagatgg ggggatcatg   4860
tctacctgcg gggcgatgaa gaaaacggtt ccggggtag gggagatcag ctgggaagaa    4920
agcaggttcc tgagcagctg cgacttaccg cagccgtgg gcccgtaaat cacacctatt     4980
accggctgca actggtagtt aagagagctg cagctgccgt catccctgag cagggggggcc   5040
acttcgttaa gcatgtccct gactcgcatg ttttccctga ccaaatccgc cagaaggcgc    5100
tcgccgccca gcgatagcag ttcttgcaag gaagcaaagt ttttcaacgg tttgagaccg    5160
tccgccgtag gcatgctttt gagcgtttga ccaagcagtt ccaggcggtc ccacagctcg    5220
gtcacctgct ctacggcatc tcgatccagc atatctcctc gtttcgcggg ttggggcggc    5280
tttcgctgta cggcagtagt cggtgctcgt ccagacgggc cagggtcatg tctttccacg    5340
ggcgcagggt cctcgtcagc gtagtctggg tcacggtgaa ggggtgcgct ccgggctgcg    5400
cgctggccag ggtgcgcttg aggctggtcc tgctggtgct gaagcgctgc cggtcttcgc    5460
cctgcgcgtc ggccaggtag catttgacca tggtgtcata gtccagcccc tccgcggcgt    5520
ggcccttggc gcgcagcttg cccttggagg aggcgccgca cgaggggcag tgcagacttt    5580
tgagggcgta gagcttgggc gcgagaaata ccgattccgg ggagtaggca tccgcgccgc    5640
aggccccgca gacggtctcg cattccacga gccaggtgag ctctggccgt tcgggtcaa    5700
aaaccaggtt tcccccatgc ttttgatgc gtttcttacc tctggtttcc atgagccggt    5760
gtccacgctc ggtgacgaaa aggctgtccg tgtccccgta tacagacttg agaggcctgt    5820
cctcgagcgt tgttccgcgg tcctcctcgt atagaaactc ggaccactct gagacaaagg    5880
ctcgcgtcca ggccagcacg aaggaggcta agtgggaggg gtagcggtcg ttgtccacta    5940
gggggtccac tcgctccagg gtgtgaagac acatgtcgcc ctcttcggca tcaaggaagg    6000
tgattggttt gtaggtgtag gccacgtgac cgggtgttcc tgaaggggg ctataaaagg     6060
```

```
gggtggggc gcgttcgtcc tcactctctt ccgcatcgct gtctgcgagg ccagctgtt    6120 ggggtgagtc gacgcgaggc tggatggcct tccccattat gattcttctc gcttccggcg   6180
gcatcgggat gcccgcgttg caggccatgc tgtccaggca ggtagatgac gaccatcagg   6240
gacagcttca aggccagcaa aaggccagga accgtaaaaa ggccgcgttg ctggcgtttt   6300
tccataggct ccgcccccct gacgagcatc acaaaaatcg acgctcaagt cagaggtggc   6360
gaaacccgac aggactataa agataccagg cgtttccccc tggaagctcc ctcgtgcgct   6420
ctcctgttcc gaccctgccg cttaccggat acctgtccgc ctttctccct cgggaagcg   6480 tggcgctttc tcatagctca cgctgtaggt atctcagttc ggtgtaggtc gttcgctcca   6540
agctgggctg tgtgcacgaa ccccccgttc agcccgaccg ctgcgcctta ccggtaact   6600 atcgtcttga gtccaacccg gtaagacacg acttatcgcc actggcagca gccactggta   6660
acaggattag cagagcgagg tatgtaggcg gtgctacaga gttcttgaag tggtggccta   6720
actacggcta cactagaagg acagtatttg gtatctgcgc tctgctgaag ccagttacct   6780
tcggaaaaag agttggtagc tcttgatccg gcaaacaaac caccgctggt agcggtggtt   6840
tttttgtttg caagcagcag attacgcgca gaaaaaagg atctcaagaa gatcctttga   6900
tcttttctac ggggtctgac gctcagtgga acgaaaactc acgttaaggg attttggtca   6960
tgagattatc aaaaaggatc ttcacctaga tccttttaaa ttaaaatga gttttaaat   7020 caatctaaag tatatatgag taaacttggt ctgacagtta ccaatgctta atcagtgagg   7080
cacctatctc agcgatctgt ctatttcgtt catccatagt tgcctgactc cccgtcgtgt   7140
agataactac gatacgggag ggcttaccat ctggccccag tgctgcaatg ataccgcgag   7200
acccacgctc accggctcca gatttatcag caataaacca gccagccgga agggccgagc   7260
gcagaagtgg tcctgcaact ttatccgcct ccatccagtc tattaattgt tgccgggaag   7320
ctagagtaag tagttcgcca gttaatagtt tgcgcaacgt tgttgccatt gctgcaggca   7380
tcgtggtgtc acgctcgtcg tttggtatgg cttcattcag ctccggttcc caacgatcaa   7440
ggcgagttac atgatccccc atgttgtgca aaaaagcggt tagctccttc ggtcctccga   7500
tcgttgtcag aagtaagttg gccgcagtgt tatcactcat ggttatggca gcactgcata   7560
attctcttac tgtcatgcca tccgtaagat gcttttctgt gactggtgag tactcaacca   7620
agtcattctg agaatagtgt atgcggcgac cgagttgctc ttgcccggcg tcaacacggg   7680
ataataccgc gccacatagc agaactttaa aagtgctcat cattggaaaa cgttcttcgg   7740
ggcgaaaact ctcaaggatc ttaccgctgt tgagatccag ttcgatgtaa cccactcgtg   7800
cacccaactg atcttcagca tcttttactt tcaccagcgt ttctgggtga gcaaaaacag   7860
gaaggcaaaa tgccgcaaaa aagggaataa gggcgacacg gaaatgttga atactcatac   7920
tcttcctttt tcaatattat tgaagcattt atcagggtta ttgtctcatg agcggataca   7980
tatttgaatg tatttagaaa aataaacaaa taggggttcc gcgcacattt ccccgaaaag   8040
tgccacctga cgtctaagaa accattatta tcatgacatt aacctataaa aataggcgta   8100
tcacgaggcc ctttcgtctt caagaattgt t                                 8131
```

<210> SEQ ID NO 13
<211> LENGTH: 7082
<212> TYPE: DNA
<213> ORGANISM: Artificial Sequence
<220> FEATURE:
<223> OTHER INFORMATION: Synthetic Construct pVR1012-GP(S)

<400> SEQUENCE: 13

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca cgacccccgc ccattgacg tcaataatga cgtatgttcc   480
catagtaacg ccaataggga ctttccattg acgtcaatgg gtggagtatt tacggtaaac   540
tgcccacttg gcagtacatc aagtgtatca tatgccaagt acgccccta ttgacgtcaa   600 tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctccg cggccgggaa cggtgcattg gaacgcggat  1020
tccccgtgcc aagagtgacg taagtaccgc ctatagactc tataggcaca ccctttggc   1080 tcttatgcat gctatactgt ttttggcttg gggcctatac accccgctt ccttatgcta   1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttaca   1320 ggatggggtc ccatttatta tttacaaatt cacatataca acaacgccgt cccccgtgcc   1380
cgcagttttt attaaacata gcgtgggatc tccacgcgaa tctcgggtac gtgttccgga  1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctagc tagatgcatg   1920
ctcgagcggc cgccagtgtg atggatatct gcagaattcg gcttatcttc aggatctcgc   1980
catggagggt cttagcctac tccaattgcc cagagataaa tttcgaaaaa gctctttctt   2040
tgtttgggtc atcatcttat ttcaaaaggc cttttccatg cctttgggtg ttgtgaccaa   2100 cagcactta gaagtaacag agattgacca gctagtctgc aaggatcatc ttgcatccac   2160
tgaccagctg aaatcagttg gtctcaacct cgaggggagc ggagtatcta ctgatatccc   2220
atctgcgaca aagcgttggg gcttcagatc tggtgtgcct cccaaggtgg tcagctatga   2280
agcaggagaa tgggctgaaa attgctacaa tcttgaaata aagaagccgg acgggagcga   2340
atgcttaccc ccaccgccgg atggtgtcag aggctttcca aggtgccgct atgttcacaa   2400
```

```
agcccaagga accgggccct gcccgggtga ctatgccttt cacaaggatg gagctttctt    2460
cctctatgac aggctggctt caactgtaat ttacagagga gtcaattttg ctagggggt    2520 aattgcattc ttgatattgg ctaaaccaaa ggaaacgttc cttcaatcac cccccattcg    2580
agaggcagta aactcactg aaaatacatc aagttactat gccacatcct acttggagta    2640
cgaaatcgaa aattttggtg ctcaacactc cacgacccct ttcaaaatta acaataatac    2700
ttttgttctt ctggacaggc cccacacgcc tcagttcctt ttccagctga atgataccat    2760
tcaccttcac caacagttga gcaacacaac tgggaaacta atttggacac tagatgctaa    2820
tatcaatgct gatattggtg aatgggcttt ttgggaaaat aaaaaaaatc tctccgaaca    2880
actacgtgga gaagagctgt ctttcgaaac tttatcgctc aacgagacag aagacgatga    2940
tgcgacatcg tcgagaacta caaagggaag aatctccgac cgggccacca ggaagtattc    3000
ggacctggtt ccaaaggatt cccctgggat ggtttcattg cacgtaccag aagggggaaac    3060 aacattgccg tctcagaatt cgacagaagg tcgaagagta gatgtgaata ctcaggaaac    3120
tatcacagag acaactgcaa caatcatagg cactaacggt aacaacatgc agatctccac    3180
catcgggaca ggactgagct ccagccaaat cctgagttcc tcaccgacca tggcaccaag    3240
ccctgagact cagacctcca caacctacac accaaaacta ccagtgatga ccaccgagga    3300
accaacaaca ccaccgagaa actctcctgg ctcaacaaca gaagcaccca ctctcaccac    3360
cccagagaat ataacaacag cggttaaaac tgttttgcca caagagtcca caagcaacgg    3420
tctaataact tcaacagtaa cagggattct tgggagcctt ggacttcgaa aacgcagcag    3480
aagacaagtt aacaccaggg ccacgggtaa atgcaatccc aacttacact actggactgc    3540
acaagaacaa cataatgctg ctgggattgc ctggatcccg tactttggac cgggtgcaga    3600
aggcatatac actgaaggcc ttatgcacaa ccaaaatgcc ttagtctgtg gactcagaca    3660
acttgcaaat gaaacaactc aagctctgca gcttttctta agggccacga cggagctgcg    3720
gacatatacc atactcaata ggaaggccat agatttcctt ctgcgacgat ggggcgggac    3780
atgtaggatc ctgggaccag attgttgcat tgagccacat gattggacca aaaacatcac    3840
tgataaaatc aaccaaatca tccatgattt catcgacaac cctttaccca atcaggataa    3900
tgatgataat tggtggacgg gctggagaca gtggatccct gcaggaatag gcattactgg    3960
aattattatt gcaatcattg ctcttctttg cgtctgcaag ctgctttgtt gaatatcaag    4020
ccgaattcca gcacactggc ggccgttact agtggatccg agctcggatc caagctctag    4080 accaggcccct ggatccagat ctgctgtgcc ttctagttgc cagccatctg ttgtttgccc    4140
ctcccccgtg ccttccttga ccctggaagg tgccactccc actgtccttt cctaataaaa    4200
tgaggaaatt gcatcgcatt gtctgagtag gtgtcattct attctggggg gtggggtggg    4260
gcaggacagc aagggggagg attgggaaga caatagcagg catgctgggg atgcggtggg    4320
ctctatgggt acccaggtgc tgaagaattg acccggttcc tcctgggcca gaaagaagca    4380
ggcacatccc cttctctgtg acacaccctg tccacgcccc tggttcttag ttccagcccc    4440
actcatagga cactcatagc tcaggagggc tccgccttca atcccacccg ctaaagtact    4500
tggagcggtc tctccctccc tcatcagccc accaaaccaa acctagcctc caagagtggg    4560
aagaaattaa agcaagatag gctattaagt gcagagggag agaaaatgcc tccaacatgt    4620
gaggaagtaa tgagagaaat catagaattt cttccgcttc ctcgctcact gactcgctgc    4680
gctcggtcgt tcggctgcgg cgagcggtat cagctcactc aaaggcggta atacggttat    4740
ccacagaatc aggggataac gcaggaaaga acatgtgagc aaaaggccag caaaaggcca    4800
```

```
ggaaccgtaa aaaggccgcg ttgctggcgt ttttccatag gctccgcccc cctgacgagc    4860
atcacaaaaa tcgacgctca agtcagaggt ggcgaaaccc gacaggacta taaagatacc    4920
aggcgtttcc ccctggaagc tccctcgtgc gctctcctgt tccgaccctg ccgcttaccg    4980
gatacctgtc cgccttttct ccttcgggaa gcgtggcgct ttctcatagc tcacgctgta    5040
ggtatctcag ttcggtgtag gtcgttcgct ccaagctggg ctgtgtgcac gaaccccccg    5100
ttcagcccga ccgctgcgcc ttatccggta actatcgtct tgagtccaac ccggtaagac    5160
acgacttatc gccactggca gcagccactg gtaacaggat tagcagagcg aggtatgtag    5220
gcggtgctac agagttcttg aagtggtggc ctaactacgg ctacactaga agaacagtat    5280
ttggtatctg cgctctgctg aagccagtta ccttcggaaa aagagttggt agctcttgat    5340
ccggcaaaca aaccaccgct ggtagcggtg gttttttgt ttgcaagcag cagattacgc    5400
gcagaaaaaa aggatctcaa gaagatcctt tgatctttc tacgggtct gacgctcagt    5460 ggaacgaaaa ctcacgttaa gggattttgg tcatgagatt atcaaaaagg atcttcacct    5520
agatcctttt aaattaaaaa tgaagtttta aatcaatcta agtatatat gagtaaactt    5580 ggtctgacag ttaccaatgc ttaatcagtg aggcacctat ctcagcgatc tgtctatttc    5640
gttcatccat agttgcctga ctcggggggg ggggcgctg aggtctgcct cgtgaagaag    5700
gtgttgctga ctcataccag gcctgaatcg ccccatcatc cagccagaaa gtgagggagc    5760
cacggttgat gagagctttg ttgtaggtgg accagttggt gattttgaac ttttgctttg    5820
ccacggaacg gtctgcgttg tcgggaagat gcgtgatctg atccttcaac tcagcaaaag    5880
ttcgatttat tcaacaaagc cgccgtcccg tcaagtcagc gtaatgctct gccagtgtta    5940
caaccaatta accaattctg attagaaaaa ctcatcgagc atcaaatgaa actgcaattt    6000
attcatatca ggattatcaa taccatattt ttgaaaaagc cgtttctgta atgaaggaga    6060
aaactcaccg aggcagttcc ataggatggc aagatcctgg tatcggtctg cgattccgac    6120
tcgtccaaca tcaatacaac ctattaattt cccctcgtca aaataaggt tatcaagtga    6180 gaaatcacca tgagtgacga ctgaatccgg tgagaatggc aaaagcttat gcatttcttt    6240
ccagacttgt tcaacaggcc agccattacg ctcgtcatca aaatcactcg catcaaccaa    6300
accgttattc attcgtgatt gcgcctgagc gagacgaaat acgcgatcgc tgttaaaagg    6360
acaattacaa acaggaatcg aatgcaaccg gcgcaggaac actgccagcg catcaacaat    6420
attttcacct gaatcaggat attcttctaa tacctggaat gctgttttcc cggggatcgc    6480
agtggtgagt aaccatgcat catcaggagt acgataaaa tgcttgatgg tcggaagagg    6540
cataaattcc gtcagccagt ttagtctgac catctcatct gtaacatcat tggcaacgct    6600
acctttgcca tgtttcagaa acaactctgg cgcatcgggc ttcccataca atcgatagat    6660
tgtcgcacct gattgcccga cattatcgcg agcccattta tacccatata atcagcatc    6720 catgttggaa tttaatcgcg gcctcgagca agacgtttcc cgttgaatat ggctcataac    6780
accccttgta ttactgttta tgtaagcaga cagttttatt gttcatgatg atatattttt    6840
atcttgtgca atgtaacatc agagattttg agacacaacg tggctttccc ccccccca    6900 ttattgaagc atttatcagg gttattgtct catgagcgga tacatatttg aatgtattta    6960
gaaaaataaa caaatagggg ttccgcgcac atttccccga aaagtgccac ctgacgtcta    7020
agaaaccatt attatcatga cattaaccta taaaaatagg cgtatcacga ggccctttcg    7080
tc                                                                    7082
```

<210> SEQ ID NO 14

-continued

```
<211> LENGTH: 7087
<212> TYPE: DNA
<213> ORGANISM: Artificial Sequence
<220> FEATURE:
<223> OTHER INFORMATION: Synthetic Construct pVR1012x/s Ebola GP(S)

<400> SEQUENCE: 14
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccccttggc    1080 tcttatgcat gctatactgt ttttggcttg ggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca     1320 ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgccagtgt gatggatatc    1920
tgcagaattc ggcttatctt caggatctcg ccatggaggg tcttagccta ctccaattgc    1980
ccagagataa atttcgaaaa agctctttct ttgtttgggt catcatctta tttcaaaagg    2040
ccttttccat gcctttgggt gttgtgacca acagcacttt agaagtaaca gagattgacc    2100
agctagtctg caaggatcat cttgcatcca ctgaccagct gaaatcagtt ggtctcaacc    2160
```

```
tcgagggag  cggagtatct  actgatatcc  catctgcgac  aaagcgttgg  ggcttcagat   2220
ctggtgtgcc  tcccaaggtg  gtcagctatg  aagcaggaga  atgggctgaa  aattgctaca   2280
atcttgaaat  aaagaagccg  gacgggagcg  aatgcttacc  cccaccgccg  gatggtgtca   2340
gaggctttcc  aaggtgccgc  tatgttcaca  agcccaagg   aaccgggccc  tgcccgggtg   2400
actatgcctt  tcacaaggat  ggagctttct  tcctctatga  caggctggct  tcaactgtaa   2460
tttacagagg  agtcaatttt  gctgagggg   taattgcatt  cttgatattg  gctaaaccaa   2520
aggaaacgtt  ccttcaatca  cccccattc   gagaggcagt  aaactacact  gaaaatacat   2580
caagttacta  tgccacatcc  tacttggagt  acgaaatcga  aaattttggt  gctcaacact   2640
ccacgaccct  tttcaaaatt  aacaataata  cttttgttct  tctggacagg  ccccacacgc   2700
ctcagttcct  tttccagctg  aatgatacca  ttcaccttca  ccaacagttg  agcaacacaa   2760
ctgggaaact  aatttggaca  ctagatgcta  atatcaatgc  tgatattggt  gaatgggctt   2820
tttgggaaaa  taaaaaaaat  ctctccgaac  aactacgtgg  agaagagctg  tctttcgaaa   2880
ctttatcgct  caacgagaca  gaagacgatg  atgcgacatc  gtcgagaact  acaaagggaa   2940
gaatctccga  ccgggccacc  aggaagtatt  cggacctggt  tccaaaggat  tcccctggga   3000
tggtttcatt  gcacgtacca  gaaggggaaa  caacattgcc  gtctcagaat  cgacagaaag   3060
gtcgaagagt  agatgtgaat  actcaggaaa  ctatcacaga  gacaactgca  acaatcatag   3120
gcactaacgg  taacaacatg  cagatctcca  ccatcgggac  aggactgagc  tccagccaaa   3180
tcctgagttc  ctcaccgacc  atggcaccaa  gccctgagac  tcagacctcc  acaacctaca   3240
caccaaaact  accagtgatg  accaccgagg  aatcaacaac  accaccgaga  aactctcctg   3300
gctcaacaac  agaagcaccc  actctcacca  cccagagaa   tataacaaca  gcggttaaaa   3360
ctgttttgcc  acaagagtcc  acaagcaacg  gtctaataac  ttcaacagta  acagggattc   3420
ttgggagcct  tggacttcga  aaacgcagca  gaagacaagt  taacaccagg  gccacgggta   3480
aatgcaatcc  caacttacac  tactggactg  cacaagaaca  acataatgct  gctgggattg   3540
cctggatccc  gtactttgga  ccgggtgcag  aaggcatata  cactgaaggc  cttatgcaca   3600
accaaaatgc  cttagtctgt  ggactcagac  aacttgcaaa  tgaaacaact  caagctctgc   3660
agcttttctt  aagggccacg  acggagctgc  ggacatatac  catactcaat  aggaaggcca   3720
tagatttcct  tctgcgacga  tggggcggga  catgtaggat  cctgggacca  gattgttgca   3780
ttgagccaca  tgattggacc  aaaaacatca  ctgataaaat  caaccaaatc  atccatgatt   3840
tcatcgacaa  ccctttaccc  aatcaggata  atgatgataa  ttggtggacg  ggctggagac   3900
agtggatccc  tgcaggaata  ggcattactg  gaattattat  tgcaatcatt  gctcttcttt   3960
gcgtctgcaa  gctgctttgt  tgaatatcaa  gccgaattcc  agcacactgg  cggccgttac   4020
tagtggatcc  gagctcggta  ccaagctcta  gaccaggccc  tggatccaga  tctgctgtgc   4080
cttctagttg  ccagccatct  gttgtttgcc  cctccccgt   gccttccttg  acctggaag   4140 gtgccactcc  cactgtcctt  tcctaataaa  atgaggaaat  tgcatcgcat  tgtctgagta   4200
ggtgtcattc  tattctgggg  ggtgggtgg   ggcaggacag  caaggggag   gattgggaag   4260 acaatagcag  gcatgctggg  gatgcggtgg  gctctatggg  tacccaggtg  ctgaagaatt   4320
gacccggttc  ctcctgggcc  agaaagaagc  aggcacatcc  ccttctctgt  gacacaccct   4380
gtccacgccc  ctggttctta  gttccagccc  cactcatagg  acactcatag  ctcaggaggg   4440
ctccgccttc  aatcccaccc  gctaaagtac  ttggagcggt  ctctccctcc  ctcatcagcc   4500
caccaaacca  aacctagcct  ccaagagtgg  gaagaaatta  aagcaagata  ggctattaag   4560
```

```
tgcagaggga gagaaaatgc ctccaacatg tgaggaagta atgagagaaa tcatagaatt   4620
ttaaggccat gatttaaggc catcatggcc ttaatcttcc gcttcctcgc tcactgactc   4680
gctgcgctcg gtcgttcggc tgcggcgagc ggtatcagct cactcaaagg cggtaatacg   4740
gttatccaca gaatcagggg ataacgcagg aaagaacatg tgagcaaaag ccagcaaaa    4800 ggccaggaac cgtaaaaagg ccgcgttgct ggcgtttttc cataggctcc gccccctga    4860 cgagcatcac aaaaatcgac gctcaagtca gaggtggcga acccgacag gactataaag    4920 ataccaggcg tttccccctg gaagctccct cgtgcgctct cctgttccga ccctgccgct   4980
taccggatac ctgtccgcct ttctcccttc gggaagcgtg gcgctttctc atagctcacg   5040
ctgtaggtat ctcagttcgg tgtaggtcgt tcgctccaag ctgggctgtg tgcacgaacc   5100
ccccgttcag cccgaccgct gcgccttatc cggtaactat cgtcttgagt ccaacccggt   5160
aagacacgac ttatcgccac tggcagcagc cactggtaac aggattagca gagcgaggta   5220
tgtaggcggt gctacagagt tcttgaagtg gtggcctaac tacggctaca ctagaagaac   5280
agtatttggt atctgcgctc tgctgaagcc agttaccttc ggaaaaagag ttggtagctc   5340
ttgatccggc aaacaaacca ccgctggtag cggtggtttt tttgtttgca agcagcagat   5400
tacgcgcaga aaaaaggat ctcaagaaga tcctttgatc ttttctacgg ggtctgacgc    5460
tcagtggaac gaaaactcac gttaagggat tttggtcatg agattatcaa aaaggatctt   5520
cacctagatc cttttaaatt aaaaatgaag ttttaaatca atctaaagta tatatgagta   5580
aacttggtct gacagttacc aatgcttaat cagtgaggca cctatctcag cgatctgtct   5640
atttcgttca tccatagttg cctgactcgg gggggggggg cgctgaggtc tgcctcgtga   5700
agaaggtgtt gctgactcat accaggcctg aatcgcccca tcatccagcc agaaagtgag   5760
ggagccacgg ttgatgagag ctttgttgta ggtggaccag ttggtgattt tgaacttttg   5820
ctttgccacg gaacggtctg cgttgtcggg aagatgcgtg atctgatcct caactcagc    5880 aaaagttcga tttattcaac aaagccgccg tcccgtcaag tcagcgtaat gctctgccag   5940
tgttacaacc aattaaccaa ttctgattag aaaaactcat cgagcatcaa atgaaactgc   6000
aatttattca tatcaggatt atcaatacca tatttttgaa aaagccgttt ctgtaatgaa   6060
ggagaaaact caccgaggca gttccatagg atggcaagat cctggtatcg gtctgcgatt   6120
ccgactcgtc caacatcaat acaacctatt aatttcccct cgtcaaaaat aaggttatca   6180
agtgagaaat caccatgagt gacgactgaa tccggtgaga atggcaaaag cttatgcatt   6240
tctttccaga cttgttcaac aggccagcca ttacgctcgt catcaaaatc actcgcatca   6300
accaaaccgt tattcattcg tgattgcgcc tgagcgagac gaaatacgcg atcgctgtta   6360
aaaggacaat tacaaacagg aatcgaatgc aaccggcgca ggaacactgc cagcgcatca   6420
acaatatttt cacctgaatc aggatattct tctaatacct ggaatgctgt tttcccgggg   6480
atcgcagtgg tgagtaacca tgcatcatca ggagtacgga taaatgctt gatggtcgga    6540 agaggcataa attccgtcag ccagtttagt ctgaccatct catctgtaac atcattggca   6600
acgctacctt tgccatgttt cagaaacaac tctggcgcat cgggcttccc atacaatcga   6660
tagattgtcg cacctgattg cccgacatta tcgcgagccc atttataccc atataaatca   6720
gcatccatgt tggaatttaa tcgcggcctc gagcaagacg tttcccgttg aatatggctc   6780
ataacacccc ttgtattact gtttatgtaa gcagacagtt ttattgttca tgatgatata   6840
tttttatctt gtgcaatgta acatcagaga ttttgagaca caacgtggct ttccccccc    6900 ccccattatt gaagcattta tcagggttat tgtctcatga gcggatacat atttgaatgt   6960
```

-continued

| | |
|---|---|
| atttagaaaa ataaacaaat aggggttccg cgcacatttc cccgaaaagt gccacctgac | 7020 |
| gtctaagaaa ccattattat catgacatta acctataaaa ataggcgtat cacgaggccc | 7080 |
| tttcgtc | 7087 |

<210> SEQ ID NO 15
<211> LENGTH: 6940
<212> TYPE: DNA
<213> ORGANISM: Artificial Sequence
<220> FEATURE:
<223> OTHER INFORMATION: Synthetic Construct pVR1012-GP(S) delta TM

<400> SEQUENCE: 15

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca cgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca cccctttggc | 1080 |
| tcttatgcat gctatactgt ttttggcttg gggcctatac accccgctt ccttatgcta | 1140 |
| taggtgatgg tatagcttag cctataggtg tgggttattg accattattg ccactcccc | 1200 |
| tattggtgac gatactttcc attactaatc cataacatgg ctctttgcca caactatctc | 1260 |
| tattggctat atgccaatac tctgtccttc agagactgac acggactctg tattttaca | 1320 |
| ggatggggtc ccatttatta tttacaaatt cacatataca acaacgccgt cccccgtgcc | 1380 |
| cgcagttttt attaaacata gcgtgggatc tccacgcgaa tctcgggtac gtgttccgga | 1440 |
| catgggctct tctccggtag cggcggagct tccacatccg agccctggtc ccatgcctcc | 1500 |
| agcggctcat ggtcgctcgg cagctccttg ctcctaacag tggaggccag acttaggcac | 1560 |
| agcacaatgc ccaccaccac cagtgtgccg cacaaggccg tggcggtagg gtatgtgtct | 1620 |
| gaaaatgagc gtggagattg ggctcgcacg gctgacgcag atggaagact taaggcagcg | 1680 |
| gcagaagaag atgcaggcag ctgagttgtt gtattctgat aagagtcaga ggtaactccc | 1740 |
| gttgcggtgc tgttaacggt ggagggcagt gtagtctgag cagtactcgt tgctgccgcg | 1800 |
| cgcgccacca gacataatag ctgacagact aacagactgt tcctttccat gggtcttttc | 1860 |
| tgcagtcacc gtcgtcgact ctagctagat gcatgctcga gcggccgcca gtgtgatgga | 1920 |

```
tatctgcaga attcggctta tcttcaggat ctcgccatgg agggtcttag cctactccaa    1980
ttgcccagag ataaatttcg aaaaagctct ttctttgttt gggtcatcat cttatttcaa    2040
aaggcctttt ccatgccttt gggtgttgtg accaacagca ctttagaagt aacagagatt    2100
gaccagctag tctgcaagga tcatcttgca tccactgacc agctgaaatc agttggtctc    2160
aacctcgagg ggagcggagt atctactgat atcccatctg cgacaaagcg ttggggcttc    2220
agatctggtg tgcctcccaa ggtggtcagc tatgaagcag gagaatgggc tgaaaattgc    2280
tacaatcttg aaataaagaa gccggacggg agcgaatgct accccccacc gccggatggt    2340
gtcagaggct ttccaaggtg ccgctatgtt cacaaagccc aaggaaccgg gccctgcccg    2400
ggtgactatg cctttcacaa ggatggagct ttcttcctct atgacaggct ggcttcaact    2460
gtaatttaca gaggagtcaa ttttgctgag ggggtaattg cattcttgat attggctaaa    2520
ccaaaggaaa cgttccttca atcaccccc attcgagagg cagtaaacta cactgaaaat    2580
acatcaagtt actatgccac atcctacttg gagtacgaaa tcgaaaattt tggtgctcaa    2640
cactccacga cccttttcaa aattaacaat aatacttttg ttcttctgga caggccccac    2700
acgcctcagt tccttttcca gctgaatgat accattcacc ttcaccaaca gttgagcaac    2760
acaactggga aactaatttg gacactagat gctaatatca atgctgatat tggtgaatgg    2820 gcttttggg aaaataaaaa aaatctctcc gaacaactac gtggagaaga gctgtctttc    2880
gaaactttat cgctcaacga gacagaagac gatgatgcga catcgtcgag aactacaaag    2940
ggaagaatct ccgaccgggc caccaggaag tattcggacc tggttccaaa ggattcccct    3000
gggatggttt cattgcacgt accagaaggg gaaacaacat gccgtctcca gaattcgaca    3060
gaaggtcgaa gagtagatgt gaatactcag gaaactatca cagagacaac tgcaacaatc    3120
ataggcacta acggtaacaa catgcagatc tccaccatcg ggacaggact gagctccagc    3180
caaatcctga gttcctcacc gaccatggca ccaagccctg agactcagac ctccacaacc    3240
tacacaccaa aactaccagt gatgaccacc gaggaaccaa caacaccacc gagaaactct    3300
cctggctcaa caacagaagc acccactctc accaccccag agaatataac aacagcggtt    3360
aaaactgttt tgccacaaga gtccacaagc aacggtctaa taacttcaac agtaacaggg    3420
attcttggga gccttggact tcgaaaacgc agcagaagac aagttaacac cagggccacg    3480
ggtaaatgca atcccaactt acactactgg actcacaag aacaacataa tgctgctggg    3540
attgcctgga tcccgtactt tggaccgggt gcagaaggca tatacactga aggccttatg    3600
cacaaccaaa atgccttagt ctgtggactc agacaacttg caaatgaaac aactcaagct    3660
ctgcagcttt tcttaagggc cacgacggag ctgcggacat ataccatact caataggaag    3720
gccatagatt tccttctgcg acgatggggc gggacatgta ggatcctggg accagattgt    3780
tgcattgagc acatgattg gaccaaaaac atcactgata aaatcaacca aatcatccat    3840
gatttcatcg acaacccttt acccaatcag gataatgatg ataattggtg gacgggctgg    3900
agacagtgga tcccggccgc atcgtgactg actgacgatc tgcctcgcgg atccagatct    3960
gctgtgcctt ctagttgcca gccatctgtt gtttgcccct ccccgtgcc ttccttgacc    4020 ctggaaggtg ccactcccac tgtcctttcc taataaaatg aggaaattgc atcgcattgt    4080
ctgagtaggt gtcattctat tctgggggt ggggtgggc aggacagcaa ggggaggat    4140 tgggaagaca atagcaggca tgctggggat gcggtgggct ctatgggtac ccaggtgctg    4200
aagaattgac ccggttcctc ctgggccaga aagaagcagg cacatcccct tctctgtgac    4260
acaccctgtc cacgcccctg gttcttagtt ccagccccac tcataggaca ctcatagctc    4320
```

```
aggagggctc cgccttcaat cccacccgct aaagtacttg gagcggtctc tccctccctc   4380
atcagcccac caaaccaaac ctagcctcca agagtgggaa gaaattaaag caagataggc   4440
tattaagtgc agagggagag aaaatgcctc caacatgtga ggaagtaatg agagaaatca   4500
tagaatttct tccgcttcct cgctcactga ctcgctgcgc tcggtcgttc ggctgcggcg   4560
agcggtatca gctcactcaa aggcggtaat acggttatcc acagaatcag gggataacgc   4620
aggaaagaac atgtgagcaa aaggccagca aaaggccagg aaccgtaaaa aggccgcgtt   4680
gctggcgttt ttccataggc tccgcccccc tgacgagcat cacaaaaatc gacgctcaag   4740
tcagaggtgg cgaaacccga caggactata aagataccag gcgtttcccc ctggaagctc   4800
cctcgtgcgc tctcctgttc cgaccctgcc gcttaccgga tacctgtccg cctttctccc   4860
ttcgggaagc gtggcgcttt ctcatagctc acgctgtagg tatctcagtt cggtgtaggt   4920
cgttcgctcc aagctgggct gtgtgcacga accccccgtt cagcccgacc gctgcgcctt   4980
atccggtaac tatcgtcttg agtccaaccc ggtaagacac gacttatcgc cactggcagc   5040
agccactggt aacaggatta gcagagcgag gtatgtaggc ggtgctacag agttcttgaa   5100
gtggtggcct aactacggct acactagaag aacagtattt ggtatctgcg ctctgctgaa   5160
gccagttacc ttcggaaaaa gagttggtag ctcttgatcc ggcaaacaaa ccaccgctgg   5220
tagcggtggt ttttttgttt gcaagcagca gattacgcgc agaaaaaaag gatctcaaga   5280
agatcctttg atcttttcta cggggtctga cgctcagtgg aacgaaaact cacgttaagg   5340
gattttggtc atgagattat caaaaaggat cttcacctag atccttttaa attaaaaatg   5400
aagttttaaa tcaatctaaa gtatatatga gtaaacttgg tctgacagtt accaatgctt   5460
aatcagtgag gcacctatct cagcgatctg tctatttcgt tcatccatag ttgcctgact   5520
cgggggggg gggcgctgag gtctgcctcg tgaagaaggt gttgctgact cataccaggc   5580
ctgaatcgcc ccatcatcca gccagaaagt gagggagcca cggttgatga gagctttgtt   5640
gtaggtggac cagttggtga ttttgaactt ttgctttgcc acggaacggt ctgcgttgtc   5700
gggaagatgc gtgatctgat ccttcaactc agcaaaagtt cgatttattc aacaaagccg   5760
ccgtcccgtc aagtcagcgt aatgctctgc cagtgttaca accaattaac caattctgat   5820
tagaaaaact catcgagcat caaatgaaac tgcaatttat tcatatcagg attatcaata   5880
ccatattttt gaaaaagccg tttctgtaat gaaggagaaa actcaccgag gcagttccat   5940
aggatggcaa gatcctggta tcggtctgcg attccgactc gtccaacatc aatacaacct   6000
attaatttcc cctcgtcaaa aataaggtta tcaagtgaga aatcaccatg agtgacgact   6060
gaatccggtg agaatggcaa aagcttatgc atttctttcc agacttgttc aacaggccag   6120
ccattacgct cgtcatcaaa atcactcgca tcaaccaaac cgttattcat tcgtgattgc   6180
gcctgagcga gacgaaatac gcgatcgctg ttaaaaggac aattacaaac aggaatcgaa   6240
tgcaaccggc gcaggaacac tgccagcgca tcaacaatat tttcacctga atcaggatat   6300
tcttctaata cctggaatgc tgttttcccg gggatcgcag tggtgagtaa ccatgcatca   6360
tcaggagtac ggataaaatg cttgatggtc ggaagaggca taaattccgt cagccagttt   6420
agtctgacca tctcatctgt aacatcattg gcaacgctac ctttgccatg tttcagaaac   6480
aactctggcg catcgggctt cccatacaat cgatagattg tcgcacctga ttgcccgaca   6540
ttatcgcgag cccatttata cccatataaa tcagcatcca tgttggaatt taatcgcggc   6600
ctcgagcaag acgtttcccg ttgaatatgg ctcataacac cccttgtatt actgtttatg   6660
taagcagaca gttttattgt tcatgatgat atatttttat cttgtgcaat gtaacatcag   6720
```

-continued

```
agattttgag acacaacgtg gctttccccc cccccccatt attgaagcat ttatcagggt      6780
tattgtctca tgagcggata catatttgaa tgtatttaga aaaataaaca aataggggtt      6840
ccgcgcacat ttccccgaaa agtgccacct gacgtctaag aaaccattat tatcatgaca      6900
ttaacctata aaaataggcg tatcacgagg ccctttcgtc                            6940
```

<210> SEQ ID NO 16
<211> LENGTH: 7002
<212> TYPE: DNA
<213> ORGANISM: Artificial Sequence
<220> FEATURE:
<223> OTHER INFORMATION: Synthetic Construct pVR1012-GP(IC)

<400> SEQUENCE: 16

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcagattgg       240
ctattggcca ttgcatacgt tgtatccata tcataatatg tacatttata ttggctcatg       300
tccaacatta ccgccatgtt gacattgatt attgactagt tattaatagt aatcaattac       360
ggggtcatta gttcatagcc catatatgga gttccgcgtt acataactta cggtaaatgg       420
cccgcctggc tgaccgccca acgacccccg cccattgacg tcaataatga cgtatgttcc       480
catagtaacg ccaatagggga ctttccattg acgtcaatgg gtggagtatt tacggtaaac      540
tgcccacttg gcagtacatc aagtgtatca tatgccaagt acgccccta ttgacgtcaa        600 tgacggtaaa tggcccgcct ggcattatgc ccagtacatg accttatggg actttcctac       660
ttggcagtac atctacgtat tagtcatcgc tattaccatg gtgatgcggt tttggcagta       720
catcaatggg cgtggatagc ggtttgactc acggggattt ccaagtctcc accccattga       780
cgtcaatggg agtttgtttt ggcaccaaaa tcaacgggac tttccaaaat gtcgtaacaa       840
ctccgcccca ttgacgcaaa tgggcggtag gcgtgtacgg tgggaggtct atataagcag       900
agctcgttta gtgaaccgtc agatcgcctg gagacgccat ccacgctgtt ttgacctcca       960
tagaagacac cgggaccgat ccagcctccg cggccgggaa cggtgcattg gaacgcggat      1020
tccccgtgcc aagagtgacg taagtaccgc ctatagactc tataggcaca ccctttggc       1080 tcttatgcat gctatactgt ttttggcttg gggcctatac accccgctt ccttatgcta       1140 taggtgatgg tatagcttag cctataggtg tgggttattg accattattg accactcccc       1200
tattggtgac gatactttcc attactaatc cataacatgg ctctttgcca caactatctc       1260
tattggctat atgccaatac tctgtccttc agagactgac acggactctg tattttttaca     1320 ggatggggtc ccatttatta tttacaaatt cacatataca acaacgccgt ccccgtgcc       1380 cgcagttttt attaaacata gcgtgggatc tccacgcgaa tctcgggtac gtgttccgga      1440
catgggctct tctccggtag cggcggagct tccacatccg agccctggtc ccatgcctcc      1500
agcggctcat ggtcgctcgg cagctccttg ctcctaacag tggaggccag acttaggcac      1560
agcacaatgc ccaccaccac cagtgtgccg cacaaggccg tggcggtagg gtatgtgtct      1620
gaaaatgagc gtggagattg ggctcgcacg gctgacgcag atggaagact taaggcagcg      1680
gcagaagaag atgcaggcag ctgagttgtt gtattctgat aagagtcaga ggtaactccc      1740
gttgcggtgc tgttaacggt ggagggcagt gtagtctgag cagtactcgt tgctgccgcg      1800
cgcgccacca gacataatag ctgacagact aacagactgt tcctttccat gggtcttttc      1860
```

```
tgcagtcacc gtcgtcgaca cgtgtgatca gatatcgcgg ccgctctaga attcggcttc    1920
taatcacagt caccatggga gcgtcaggga ttctgcaatt gccccgtgag cgcttcagga    1980
aaacatcttt ctttgtttgg gtaataatcc tattccataa agtcttttca atcccgttgg    2040
gggttgtaca caacaatacc ctacaagtga gtgatattga caagtttgtg tgccgagaca    2100
aactctcttc aactagccaa ttgaagtcag tcggttgaa cttggagggc aatggagtag     2160
caactgatgt accaacggca accaaaagat ggggttttcg agctggtgtt ccaccaaagg    2220
tggtaaattg cgaagctgga gaatgggctg agaactgtta taacctggct ataaagaaag    2280
ttgatggtag tgagtgccta ccagaagccc ctgagggagt gagggatttt ccccgttgcc    2340
gctatgtaca caaagtctca ggaactggac catgcccagg aggactcgcc tttcacaaag    2400
aaggagcctt cttcctgtat gaccgactcg catcaacaat catttatcgg ggtacaacct    2460
ttgccgaagg agttattgca tttctgatct tgcctaaggc gcgaaaggat ttttccagt     2520 ctcctccatt gcatgagcct gccaacatga ccacggatcc ctccagttac tatcacacga    2580
caacaataaa ctacgtggtt gataattttg gaaccaacac cacagagttt ctgttccaag    2640
tcgatcattt gacgtatgtg cagctcgagg caagattcac accacaattc cttgtcctcc    2700
taaatgaaac catctactct gataaccgca gaagtaacac aacaggaaaa ctaatctgga    2760
aaataaatcc cactgttgat accagcatgg gtgagtgggc tttctgggaa aataaaaaaa    2820
acttcacaaa aacccttca agtgaagagt tgtctttcgt acctgtacca gaaacccaga    2880
accaggtcct tgacacgaca gcgacggtct ctcctcccat ctccgcccac aaccacgcag    2940
ccgaagacca caaagaattg gtttcagagg attccactcc agtggttcag atgcaaaaca    3000
tcaagggaaa ggacacaatg ccaaccacag tgacgggtgt accaacaacc acaccctctc    3060
catttccaat caatgctcgc aacactgatc ataccaaatc atttatcggc ctggaggggc    3120
cccaagaaga ccacagcacc acacagcctg ccaagaccac cagccaacca accaacagca    3180
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtg ccattccaag agccgtgcac cccgacgaac    3360
tcagtggacc tggcttcctg acgaacacaa tacggggggt tacaaatctc ctgacaggat    3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720
gatggggagg aacatgtcac attctagggc ctgattgttg cattgaaccc caagattgga    3780
ccaaaaatat cactgataaa attgatcaaa taatccatga ctttgtcgat aataatcttc    3840
caaatcagaa tgatggcagc aactggtgga ctggatggaa acaatgggtt cctgctggaa    3900
taggaatcac aggagtaatc attgctatta ttgctttgct gtgcatttgc aaattcatgc    3960
tttgaactaa tatagcatca tactttaagc cgaattctag accaggccct ggatccagat    4020
ctgctgtgcc ttctagttgc cagccatctg ttgtttgccc ctccccgtg ccttccttga     4080 ccctggaagg tgccactccc actgtccttt cctaataaaa tgaggaaatt gcatcgcatt    4140
gtctgagtag tgtcattct attctggggg gtggggtggg gcaggacagc aagggggagg    4200
attgggaaga caatagcagg catgctgggg atgcggtggg ctctatgggt acccaggtgc    4260
```

-continued

```
tgaagaattg acccggttcc tcctgggcca gaaagaagca ggcacatccc cttctctgtg     4320
acacaccctg tccacgcccc tggttcttag ttccagcccc actcatagga cactcatagc     4380
tcaggagggc tccgccttca atcccacccg ctaaagtact tggagcggtc tctccctccc     4440
tcatcagccc accaaaccaa acctagcctc aagagtggg  aagaaattaa agcaagatag     4500
gctattaagt gcagagggag agaaaatgcc tccaacatgt gaggaagtaa tgagagaaat     4560
catagaattt cttccgcttc ctcgctcact gactcgctgc gctcggtcgt tcggctgcgg     4620
cgagcggtat cagctcactc aaaggcggta atacggttat ccacagaatc aggggataac     4680
gcaggaaaga acatgtgagc aaaaggccag caaaaggcca ggaaccgtaa aaaggccgcg     4740
ttgctggcgt ttttccatag gctccgcccc cctgacgagc atcacaaaaa tcgacgctca     4800
agtcagaggt ggcgaaaccc gacaggacta taaagatacc aggcgtttcc ccctggaagc     4860
tccctcgtgc gctctcctgt tccgaccctg ccgcttaccg gatacctgtc cgcctttctc     4920
ccttcgggaa gcgtggcgct ttctcatagc tcacgctgta ggtatctcag ttcggtgtag     4980
gtcgttcgct ccaagctggg ctgtgtgcac gaaccccccg ttcagcccga ccgctgcgcc     5040
ttatccggta actatcgtct tgagtccaac ccggtaagac acgacttatc gccactggca     5100
gcagccactg gtaacaggat tagcagagcg aggtatgtag gcggtgctac agagttcttg     5160
aagtggtggc ctaactacgg ctacactaga agaacagtat ttggtatctg cgctctgctg     5220
aagccagtta ccttcggaaa aagagttggt agctcttgat ccggcaaaca aaccaccgct     5280
ggtagcggtg ttttttgt  ttgcaagcag cagattacgc gcagaaaaaa aggatctcaa     5340
gaagatcctt tgatctttc  tacggggtct gacgctcagt ggaacgaaaa ctcacgttaa     5400
gggattttgg tcatgagatt atcaaaaagg atcttcacct agatcctttt aaattaaaaa     5460
tgaagtttta aatcaatcta agtatatat  gagtaaactt ggtctgacag ttaccaatgc     5520
ttaatcagtg aggcacctat ctcagcgatc tgtctatttc gttcatccat agttgcctga     5580
ctcgggggg  ggggcgctg  aggtctgcct cgtgaagaag gtgttgctga ctcataccag     5640
gcctgaatcg ccccatcatc cagccagaaa gtgagggagc cacggttgat gagagctttg     5700
ttgtaggtgg accagttggt gattttgaac ttttgctttg ccacgaacg  gtctgcgttg     5760
tcgggaagat gcgtgatctg atccttcaac tcagcaaaag ttcgatttat tcaacaaagc     5820
cgccgtcccg tcaagtcagc gtaatgctct gccagtgtta caaccaatta accaattctg     5880
attagaaaaa ctcatcgagc atcaaatgaa actgcaattt attcatatca ggattatcaa     5940
taccatattt ttgaaaaagc cgtttctgta atgaaggaga aaactcaccg aggcagttcc     6000
ataggatggc aagatcctgg tatcggtctg cgattccgac tcgtccaaca tcaatacaac     6060
ctattaattt cccctcgtca aaataaggt  tatcaagtga gaaatcacca tgagtgacga     6120
ctgaatccgg tgagaatggc aaaagcttat gcatttcttt ccagacttgt tcaacaggcc     6180
agccattacg ctcgtcatca aaatcactcg catcaaccaa accgttattc attcgtgatt     6240
gcgcctgagc gagacgaaat acgcgatcgc tgttaaaagg acaattacaa acaggaatcg     6300
aatgcaaccg gcgcaggaac actgccagcg catcaacaat attttcacct gaatcaggat     6360
attcttctaa tacctggaat gctgttttcc cggggatcgc agtggtgagt aaccatgcat     6420
catcaggagt acggataaaa tgcttgatgg tcggaagagg cataaattcc gtcagccagt     6480
ttagtctgac catctcatct gtaacatcat tggcaacgct acctttgcca tgtttcagaa     6540
acaactctgg cgcatcgggc ttcccataca atcgatagat tgtcgcacct gattgcccga     6600
cattatcgcg agcccattta tacccatata aatcagcatc catgttggaa tttaatcgcg     6660
```

```
gcctcgagca agacgtttcc cgttgaatat ggctcataac accccttgta ttactgttta    6720
tgtaagcaga cagttttatt gttcatgatg atatatttttt atcttgtgca atgtaacatc    6780
agagattttg agacacaacg tggctttccc cccccccca ttattgaagc atttatcagg    6840
gttattgtct catgagcgga tacatatttg aatgtattta gaaaaataaa caaatagggg    6900
ttccgcgcac atttccccga aaagtgccac ctgacgtcta agaaaccatt attatcatga    6960
cattaaccta taaaaatagg cgtatcacga ggccctttcg tc                      7002

<210> SEQ ID NO 17
<211> LENGTH: 7036
<212> TYPE: DNA
<213> ORGANISM: Artificial Sequence
<220> FEATURE:
<223> OTHER INFORMATION: Synthetic Construct pVR1012 x/s Ebola GP(IC)

<400> SEQUENCE: 17
tcgcgcgttt cggtgatgac ggtgaaaacc tctgacacat gcagctcccg gagacggtca      60
cagcttgtct gtaagcggat gccggagcca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgaccccccg cccattgacg tcaataatga cgtatgttcc     480
catagtaacg ccaatagggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgttttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccctttggc    1080 tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg gctcgcacgc gctgacgcag atggaagact taaggcagcg    1680
gcagaagaag atgcaggcag ctgagttgtt gtattctgat aagagtcaga ggtaactccc    1740
```

```
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga attcggcttc    1920
taatcacagt caccatggga gcgtcaggga ttctgcaatt gccccgtgag cgcttcagga    1980
aaacatcttt ctttgtttgg gtaataatcc tattccataa agtcttttca atcccgttgg    2040
gggttgtaca caacaatacc ctacaagtga gtgatattga caagtttgtg tgccgagaca    2100
aactctcttc aactagccaa ttgaagtcag tcggggttgaa cttggagggc aatggagtag    2160
caactgatgt accaacggca accaaaagat ggggttttcg agctggtgtt ccaccaaagg    2220
tggtaaattg cgaagctgga gaatgggctg agaactgtta taacctggct ataaagaaag    2280
ttgatggtag tgagtgccta ccagaagccc ctgagggagt gagggatttt ccccgttgcc    2340
gctatgtaca caaagtctca ggaactggac catgcccagg aggactcgcc tttcacaaag    2400
aaggagcctt cttcctgtat gaccgactcg catcaacaat catttatcgg ggtacaacct    2460
ttgccgaagg agttattgca tttctgatct tgcctaaggc gcgaaaggat tttttccagt    2520
ctcctccatt gcatgagcct gccaacatga ccacggatcc ctccagttac tatcacacga    2580
caacaataaa ctacgtggtt gataattttg gaaccaacac cacagagttt ctgttccaag    2640
tcgatcattt gacgtatgtg cagctcgagg caagattcac accacaattc cttgtcctcc    2700
taaatgaaac catctactct gataaccgca gaagtaacac aacaggaaaa ctaatctgga    2760
aaataaatcc cactgttgat accagcatgg gtgagtgggc tttctgggaa aataaaaaaa    2820
acttcacaaa aacccttca agtgaagagt tgtctttcgt acctgtacca gaaacccaga    2880
accaggtcct tgacacgaca gcgacggtct ctcctcccat ctccgccac aaccacgcag    2940 ccgaagacca caaagaattg gtttcagagg attccactcc agtggttcag atgcaaaaca    3000 tcaagggaaaa ggacacaatg ccaaccacag tgacgggtgt accaacaacc acaccctctc    3060
catttccaat caatgctcgc aacactgatc ataccaaatc atttatcggc ctggaggggc    3120
cccaagaaga ccacagcacc acacagcctg ccaagaccac cagccaacca accaacagca    3180
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtg ccattccaag agccgtgcac cccgacgaac    3360
tcagtggacc tggcttcctg acgaacacaa tacgggggt tacaaatctc ctgacaggat    3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720 gatgggagg aacatgtcac attctagggc ctgattgttg cattgaaccc caagattgga    3780
ccaaaaatat cactgataaa attgatcaaa taatccatga ctttgtcgat aataatcttc    3840
caaatcagaa tgatggcagc aactggtgga ctggatggaa acaatgggtt cctgctggaa    3900
taggaatcac aggagtaatc attgctatta ttgcttgct gtgcatttgc aaattcatgc    3960
tttgaactaa tatagcatca tactttaagc cgaattctag accaggccct ggatccagat    4020
ctgctgtgcc ttctagttgc cagccatctg ttgtttgccc ctcccccgtg ccttccttga    4080
ccctggaagg tgccactccc actgtccttt cctaataaaa tgaggaaatt gcatcgcatt    4140
```

```
gtctgagtag gtgtcattct attctggggg gtggggtggg gcaggacagc aaggggggagg    4200 attgggaaga caatagcagg catgctgggg atgcggtggg ctctatgggt acccaggtgc    4260
tgaagaattg acccggttcc tcctgggcca gaaagaagca ggcacatccc cttctctgtg    4320
acacaccctg tccacgcccc tggttcttag ttccagcccc actcatagga cactcatagc    4380
tcaggagggc tccgccttca atcccacccg ctaaagtact tggagcggtc tctccctccc    4440
tcatcagccc accaaaccaa acctagcctc aagagtgggg aagaaattaa agcaagatag    4500
gctattaagt gcagagggag agaaaatgcc tccaacatgt gaggaagtaa tgagagaaat    4560
catagaattt taaggccatg atttaaggcc atcatggcct taatcttccg cttcctcgct    4620
cactgactcg ctgcgctcgg tcgttcggct gcggcgagcg gtatcagctc actcaaaggc    4680
ggtaatacgg ttatccacag aatcagggga taacgcagga agaacatgt gagcaaaagg    4740 ccagcaaaag gccaggaacc gtaaaaaggc cgcgttgctg gcgttttttcc ataggctccg    4800 ccccctgac gagcatcaca aaaatcgacg ctcaagtcag aggtggcgaa acccgacagg    4860
actataaaga taccaggcgt ttcccctgg aagctccctc gtgcgctctc ctgttccgac    4920
cctgccgctt accggatacc tgtccgcctt tctcccttcg ggaagcgtgg cgctttctca    4980
tagctcacgc tgtaggtatc tcagttcggt gtaggtcgtt cgctccaagc tgggctgtgt    5040
gcacgaaccc cccgttcagc ccgaccgctg cgccttatcc ggtaactatc gtcttgagtc    5100
caacccggta agacacgact tatcgccact ggcagcagcc actggtaaca ggattagcag    5160
agcgaggtat gtaggcggtg ctacagagtt cttgaagtgg tggcctaact acggctacac    5220
tagaagaaca gtatttggta tctgcgctct gctgaagcca gttaccttcg gaaaaagagt    5280
tggtagctct tgatccggca aacaaaccac cgctggtagc ggtggttttt ttgtttgcaa    5340
gcagcagatt acgcgcagaa aaaaaggatc tcaagaagat cctttgatct tttctacggg    5400
gtctgacgct cagtggaacg aaaactcacg ttaagggatt ttggtcatga gattatcaaa    5460
aaggatcttc acctagatcc ttttaaatta aaaatgaagt tttaaatcaa tctaaagtat    5520
atatgagtaa acttggtctg acagttacca atgcttaatc agtgaggcac ctatctcagc    5580
gatctgtcta tttcgttcat ccatagttgc ctgactcggg ggggggggc gctgaggtct    5640 gcctcgtgaa aaggtgttg ctgactcata ccaggcctga atcgccccat catccagcca    5700
gaaagtgagg gagccacggt tgatgagagc tttgttgtag gtggaccagt tggtgatttt    5760
gaacttttgc tttgccacgg aacggtctgc gttgtcggga agatgcgtga tctgatcctt    5820
caactcagca aaagttcgat ttattcaaca aagccgccgt cccgtcaagt cagcgtaatg    5880
ctctgccagt gttacaacca attaaccaat tctgattaga aaaactcatc gagcatcaaa    5940
tgaaactgca atttattcat atcaggatta tcaataccat attttttgaaa aagccgtttc    6000 tgtaatgaag gagaaaactc accgaggcag ttccatagga tggcaagatc ctggtatcgg    6060
tctgcgattc cgactcgtcc aacatcaata caacctatta atttcccctc gtcaaaaata    6120
aggttatcaa gtgagaaatc accatgagtg acgactgaat ccggtgagaa tggcaaaagc    6180
ttatgcattt ctttccagac ttgttcaaca ggccagccat tacgctcgtc atcaaaatca    6240
ctcgcatcaa ccaaaccgtt attcattcgt gattgcgcct gagcgagacg aaatacgcga    6300
tcgctgttaa aaggacaatt acaaacagga tcgaatgca accggcgcag gaacactgcc    6360
agcgcatcaa caatatttc acctgaatca ggatattctt ctaatacctg gaatgctgtt    6420
ttcccgggga tcgcagtggt gagtaaccat gcatcatcag gagtacggat aaaatgcttg    6480
atggtcggaa gaggcataaa ttccgtcagc cagtttagtc tgaccatctc atctgtaaca    6540
```

-continued

| | |
|---|---|
| tcattggcaa cgctaccttt gccatgtttc agaaacaact ctggcgcatc gggcttccca | 6600 |
| tacaatcgat agattgtcgc acctgattgc ccgacattat cgcgagccca tttataccca | 6660 |
| tataaatcag catccatgtt ggaatttaat cgcggcctcg agcaagacgt ttcccgttga | 6720 |
| atatggctca taacacccct tgtattactg tttatgtaag cagacagttt tattgttcat | 6780 |
| gatgatatat ttttatcttg tgcaatgtaa catcagagat tttgagacac aacgtggctt | 6840 |
| tccccccccc cccattattg aagcatttat cagggttatt gtctcatgag cggatacata | 6900 |
| tttgaatgta tttagaaaaa taaacaaata ggggttccgc gcacatttcc ccgaaaagtg | 6960 |
| ccacctgacg tctaagaaac cattattatc atgacattaa cctataaaaa taggcgtatc | 7020 |
| acgaggccct ttcgtc | 7036 |

<210> SEQ ID NO 18
<211> LENGTH: 6885
<212> TYPE: DNA
<213> ORGANISM: Artificial Sequence
<220> FEATURE:
<223> OTHER INFORMATION: Synthetic Construct pVR1012-GP(IC) delta TM

<400> SEQUENCE: 18

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg gggccgggaa cggtgcattg gaacgcggat | 1020 |
| tccccgtgcc aagagtgacg taagtaccgc ctatagactc tataggcaca ccctttggc | 1080 |
| tcttatgcat gctatactgt ttttggcttg gggcctatac ccccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tattttaca | 1320 |
| ggatggggtc ccatttatta tttacaaatt cacatataca acaacgccgt ccccgtgcc | 1380 |
| cgcagttttt attaaacata gcgtgggatc tccacgcgaa tctcgggtac gtgttccgga | 1440 |
| catgggctct ctctccggtag cggcggagct tccacatccg agccctggtc ccatgcctcc | 1500 |
| agcggctcat ggtcgctcgg cagctccttg ctcctaacag tggaggccag acttaggcac | 1560 |

```
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga attcggcttc   1920
taatcacagt caccatggga gcgtcaggga ttctgcaatt gccccgtgag cgcttcagga   1980
aaacatcttt ctttgtttgg gtaataatcc tattccataa agtctttca atcccgttgg    2040 gggttgtaca caacaatacc ctacaagtga gtgatattga caagtttgtg tgccgagaca   2100
aactctcttc aactagccaa ttgaagtcag tcgggttgaa cttggagggc aatggagtag   2160
caactgatgt accaacggca accaaaagat ggggttttcg agctggtgtt ccaccaaagg   2220
tggtaaattg cgaagctgga gaatgggctg agaactgtta taacctggct ataaagaaag   2280
ttgatggtag tgagtgccta ccagaagccc ctgagggagt gagggatttt ccccgttgcc   2340
gctatgtaca caaagtctca ggaactggac catgcccagg aggactcgcc tttcacaaag   2400
aaggagcctt cttcctgtat gaccgactcg catcaacaat catttatcgg ggtacaacct   2460
ttgccgaagg agttattgca tttctgatct tgcctaaggc gcgaaaggat ttttccagt    2520 ctcctccatt gcatgagcct gccaacatga ccacggatcc ctccagttac tatcacacga   2580
caacaataaa ctacgtggtt gataattttg gaaccaacac cacagagttt ctgttccaag   2640
tcgatcattt gacgtatgtg cagctcgagg caagattcac accacaattc cttgtcctcc   2700
taaatgaaac catctactct gataaccgca gaagtaacac aacaggaaaa ctaatctgga   2760
aaataaatcc cactgttgat accagcatgg gtgagtgggc tttctgggaa aataaaaaaa   2820
acttcacaaa aacccttca agtgaagagt tgtctttcgt acctgtacca gaaacccaga   2880
accaggtcct tgacacgaca gcgacggtct ctcctcccat ctccgccac aaccacgcag    2940 ccgaagacca caaagaattg gtttcagagg attccactcc agtggttcag atgcaaaaca   3000
tcaagggaaa ggacacaatg ccaaccacag tgacgggtgt accaacaacc acaccctctc   3060
catttccaat caatgctcgc aacactgatc ataccaaatc atttatcggc ctggaggggc   3120
cccaagaaga ccacagcacc acacagcctg ccaagaccac cagccaacca accaacagca   3180
cagaatcgac gacactaaac ccaacatcag agccctccag tagaggcacg ggaccatcca   3240
gccccacggt ccccaacacc acagaaagcc acgccgaact tggcaagaca accccaacca   3300
cactcccaga acagcacact gccgccagtg ccattccaag agccgtgcac cccgacgaac   3360
tcagtggacc tggcttcctg acgaacacaa tacggggggt tacaaatctc ctgacaggat   3420
ccagaagaaa gcgaagggat gtcactccca atacacaacc caaatgcaac ccaaacctgc   3480
actattggac agccttggat gagggtgctg ccataggttt agcctggata ccatacttcg   3540
ggccagcagc tgagggaatt tacactgaag gcataatgga gaatcaaaat ggattgatct   3600
gtggattgag gcagctggcc aacgaaacga cacaagctct tcaattgttc ttaagggcaa   3660
ctactgagtt gcgtacattc tctatactaa atcggaaagc aatagacttc ttgctccaaa   3720
gatggggagg aacatgtcac attctagggc ctgattgttg cattgaaccc caagattgga   3780
ccaaaaatat cactgataaa attgatcaaa taatccatga ctttgtcgat aataatcttc   3840
caaatcagaa tgatggcagg gccgcatcgt gactgactga cgatctgcct cgcggatcca   3900
gatctgctgt gccttctagt tgccagccat ctgttgtttg ccctcccccc gtgccttcct   3960
```

```
tgaccctgga aggtgccact cccactgtcc tttcctaata aaatgaggaa attgcatcgc   4020
attgtctgag taggtgtcat tctattctgg ggggtgggt  ggggcaggac agcaagggg    4080 aggattggga agacaatagc aggcatgctg gggatgcggt gggctctatg ggtacccagg   4140
tgctgaagaa ttgacccggt tcctcctggg ccagaaagaa gcaggcacat cccttctct    4200 gtgacacacc ctgtccacgc ccctggttct tagttccagc cccactcata ggacactcat   4260
agctcaggag ggctccgcct tcaatcccac ccgctaaagt acttggagcg gtctctccct   4320
ccctcatcag cccaccaaac caaacctagc ctccaagagt gggaagaaat taaagcaaga   4380
taggctatta agtgcagagg gagagaaaat gcctccaaca tgtgaggaag taatgagaga   4440
aatcatagaa tttcttccgc ttcctcgctc actgactcgc tgcgctcggt cgttcggctg   4500
cggcgagcgt atcagctca  ctcaaaggcg gtaatacgg  tatccacaga atcaggggat   4560
aacgcaggaa agaacatgtg agcaaaaggc cagcaaaagg ccaggaaccg taaaaaggcc   4620
gcgttgctgg cgttttttcca taggctccgc cccctgacg  agcatcacaa aaatcgacgc   4680
tcaagtcaga ggtggcgaaa cccgacagga ctataaagat accaggcgtt tccccctgga   4740
agctccctcg tgcgctctcc tgttccgacc ctgccgctta ccggatacct gtccgccttt   4800
ctcccttcgg gaagcgtggc gctttctcat agctcacgct gtaggtatct cagttcggtg   4860
taggtcgttc gctccaagct gggctgtgtg cacgaacccc ccgttcagcc cgaccgctgc   4920
gccttatccg gtaactatcg tcttgagtcc aacccggtaa gacacgactt atcgccactg   4980
gcagcagcca ctggtaacag gattagcaga gcgaggtatg taggcggtgc tacagagttc   5040
ttgaagtggt ggcctaacta cggctacact agaagaacag tatttggtat ctgcgctctg   5100
ctgaagccag ttaccttcgg aaaaagagtt ggtagctctt gatccggcaa acaaaccacc   5160
gctggtagcg gtggtttttt tgtttgcaag cagcagatta cgcgcagaaa aaaggatct    5220 caagaagatc ctttgatctt ttctacgggg tctgacgctc agtggaacga aaactcacgt   5280
taagggattt tggtcatgag attatcaaaa aggatcttca cctagatcct tttaaattaa   5340
aaatgaagtt ttaaatcaat ctaaagtata tatgagtaaa cttggtctga cagttaccaa   5400
tgcttaatca gtgaggcacc tatctcagcg atctgtctat ttcgttcatc catagttgcc   5460
tgactcgggg ggggggggcg ctgaggtctg cctcgtgaag aaggtgttgc tgactcatac   5520
caggcctgaa tcgccccatc atccagccag aaagtgaggg agccacggtt gatgagagct   5580
ttgttgtagg tggaccagtt ggtgattttg aacttttgct ttgccacgga acggtctgcg   5640
ttgtcgggaa gatgcgtgat ctgatccttc aactcagcaa aagttcgatt tattcaacaa   5700
agccgccgtc ccgtcaagtc agcgtaatgc tctgccagtg ttacaaccaa ttaaccaatt   5760
ctgattagaa aaactcatcg agcatcaaat gaaactgcaa tttattcata tcaggattat   5820
caataccata tttttgaaaa agccgtttct gtaatgaagg agaaaactca ccgaggcagt   5880
tccataggat ggcaagatcc tggtatcggt ctgcgattcc gactcgtcca acatcaatac   5940
aacctattaa tttcccctcg tcaaaaataa ggttatcaag tgagaaatca ccatgagtga   6000
cgactgaatc cggtgagaat ggcaaaagct tatgcatttc tttccagact tgttcaacag   6060
gccagccatt acgctcgtca tcaaaatcac tcgcatcaac caaaccgtta ttcattcgtg   6120
attgcgcctg agcgagacga atacgcgat  cgctgttaaa aggacaatta caaacaggaa   6180
tcgaatgcaa ccggcgcagg aacactgcca gcgcatcaac aatattttca cctgaatcag   6240
gatattcttc taatacctgg aatgctgttt tcccggggat cgcagtggtg agtaaccatg   6300
catcatcagg agtacggata aaatgcttga tggtcggaag aggcataaat tccgtcagcc   6360
```

```
agtttagtct gaccatctca tctgtaacat cattggcaac gctacctttg ccatgtttca    6420
gaaacaactc tggcgcatcg ggcttcccat acaatcgata gattgtcgca cctgattgcc    6480
cgacattatc gcgagcccat ttatacccat ataaatcagc atccatgttg gaatttaatc    6540
gcggcctcga gcaagacgtt tcccgttgaa tatggctcat aacacccctt gtattactgt    6600
ttatgtaagc agacagtttt attgttcatg atgatatatt tttatcttgt gcaatgtaac    6660
atcagagatt tgagacaca acgtggcttt ccccccccc ccattattga agcatttatc    6720
agggttattg tctcatgagc ggatacatat ttgaatgtat ttagaaaaat aaacaaatag    6780
gggttccgcg cacatttccc cgaaaagtgc cacctgacgt ctaagaaacc attattatca    6840
tgacattaac ctataaaaat aggcgtatca cgaggccctt tcgtc                   6885
```

<210> SEQ ID NO 19
<211> LENGTH: 6889
<212> TYPE: DNA
<213> ORGANISM: Artificial Sequence
<220> FEATURE:
<223> OTHER INFORMATION: Synthetic Construct pVR1012x/s Ebola GP(IC)
      (dTM)

<400> SEQUENCE: 19

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca cccctttggc    1080
tcttatgcat gctatactgt ttttggcttg ggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca    1320 ggatgggtc ccattattta tttacaaatt cacatatca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
```

```
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gataattctc taatcacagt catcatggga    1920
gcgtcaggga ttctgcaatt gccccgtgag cgcttcagga aaacatcttt ctttgtttgg    1980
gtaataatcc tattccataa agtctttttca atcccgttgg gggttgtaca caacaatacc    2040
ctacaagtga gtgatattga caagtttgtg tgccgagaca aactctcttc aactagccaa    2100
ttgaagtcag tcgggttgaa cttggagggc aatggagtag caactgatgt accaacggca    2160
accaaaagat ggggttttcg agctggtgtt ccaccaaagg tggtaaatta cgaagctgga    2220
gaatgggctg agaactgtta taacctggct ataagaaaag ttgatggtag tgagtgccta    2280
ccagaagccc ctgagggagt gagggatttt ccccgttgcc gctatgtaca caaagtctca    2340
ggaactggac catgcccagg aggactcgcc tttcacaaag aaggagcctt cttcctgtat    2400
gaccgactcg catcaacaat catttatcgg ggtacaacct tgccgaagg agttattgca     2460 tttctgatct tgcctaaggc gcgaaaggat ttttccagt ctcctccatt gcatgagcct      2520
gccaacatga ccacggatcc ctccagttac tatcacacga caacaataaa ctacgtggtt    2580
gataattttg gaaccaacac cacagagttt ctgttccaag tcgatcattt gacgtatgtg    2640
cagctcgagg caagattcac accacaattc cttgtcctcc taaatgaaac catctactct    2700
gataaccgca gaagtaacac aacaggaaaa ctaatctgga aaataaatcc cactgttgat    2760
accagcatgg gtgagtgggc tttctgggaa aataaaaaaa cttcacaaaa acccttcaa    2820 gtgaagagtt gtcttcgta cctgtaccag aaacccagaa ccaggtcctt gacacgacag     2880
cgacggtctc tcctcccatc tccgcccaca accacgcagg cgaagaccac aaagaattgg    2940
tttcagagga ttccactcca gtggttcaga tgcaaaacat caagggaaag gacacaatgc    3000
caaccacagt gacgggtgta ccaacaacca caccctctcc atttccaatc aatgctcgca    3060
acactgatca taccaaatca tttatcggcc tggaggggcc ccaagaagac cacagcacca    3120
cacagcctgc caagaccacc agccaaccaa ccaacagcac agaatcgacg acactaaacc    3180
caacatcaga gccctccagt agaggcacgg gaccatccag ccccacggtc cccaacacca    3240
cagaaagcca cgccgaactt ggcaagacaa ccccaaccac actcccagaa cagcacactg    3300
ccgccagtgc cattccaaga gccgtgcacc ccgacgaact cagtggacct ggcttcctga    3360
cgaacacaat acgggggtg acaaatctcc tgacaggatc cagaagaaag cgaagggatg    3420
tcactcccaa tacacaaccc aaatgcaacc caaacctgca ctattggaca gccttggatg    3480
agggtgctgc cataggttta gcctggatac catacttcgg gccagcagct gagggaattt    3540
acactgaagg cataatggag aatcaaaatg gattgatctg tggattgagg cagctggcca    3600
acgaaacgac acaagctctt caattgttct taagggcaac tactgagttg cgtacattct    3660
ctatactaaa tcggaaagca atagacttct tgctccaaag atggggagga acatgtcaca    3720
ttctagggcc tgattgttgc attgaacccc aagattggca caaaaatatc actgataaaa    3780
ttgatcaaat aatccatgac tttgtcgata taatcttcc aaatcagaat gatggcagca    3840
actggtggac tggatggaaa caatggtgaa gatctgctgt gccttctagt tgccagccat    3900
ctgttgtttg cccctccccc gtgccttcct tgaccctgga aggtgccact cccactgtcc    3960
```

```
tttcctaata aaatgaggaa attgcatcgc attgtctgag taggtgtcat tctattctgg    4020
gggtgtgggt ggggcaggac agcaagggg aggattggga agacaatagc aggcatgctg     4080 gggatgcgt gggctctatg ggtacccagg tgctgaagaa ttgacccggt tcctcctggg     4140
ccagaaagaa gcaggcacat ccccttctct gtgacacacc ctgtccacgc cctggttct     4200 tagttccagc cccactcata ggacactcat agctcaggag gctccgcct tcaatcccac     4260 ccgctaaagt acttggagcg gtctctccct ccctcatcag cccaccaaac caaacctagc    4320
ctccaagagt gggaagaaat taaagcaaga taggctatta agtgcagagg gagagaaaat    4380
gcctccaaca tgtgaggaag taatgagaga aatcatagaa ttttaaggcc atgatttaag    4440
gccatcatgg ccttaatctt ccgcttcctc gctcactgac tcgctgcgct cggtcgttcg    4500
gctgcggcga gcggtatcag ctcactcaaa ggcggtaata cggttatcca cagaatcagg    4560
ggataacgca ggaaagaaca tgtgagcaaa aggccagcaa aaggccagga accgtaaaaa    4620
ggccgcgttg ctggcgtttt tccataggct ccgcccccct gacgagcatc acaaaaatcg    4680
acgctcaagt cagaggtggc gaaacccgac aggactataa agataccagg cgtttccccc    4740
tggaagctcc ctcgtgcgct ctcctgttcc gaccctgccg cttaccggat acctgtccgc    4800
ctttctccct tcgggaagcg tggcgctttc tcatagctca cgctgtaggt atctcagttc    4860
ggtgtaggtc gttcgctcca agctgggctg tgtgcacgaa ccccccgttc agcccgaccg    4920
ctgcgcctta tccggtaact atcgtcttga gtccaacccg gtaagacacg acttatcgcc    4980
actggcagca gccactggta acaggattag cagagcgagg tatgtaggcg gtgctacaga    5040
gttcttgaag tggtggccta actacggcta cactagaaga acagtatttg gtatctgcgc    5100
tctgctgaag ccagttacct tcggaaaaag agttggtagc tcttgatccg gcaaacaaac    5160
caccgctggt agcggtggtt tttttgtttg caagcagcag attacgcgca gaaaaaaagg    5220
atctcaagaa gatcctttga tcttttctac ggggtctgac gctcagtgga acgaaaactc    5280
acgttaaggg attttggtca tgagattatc aaaaaggatc ttcacctaga tccttttaaa    5340
ttaaaaatga agttttaaat caatctaaag tatatatgag taaacttggt ctgacagtta    5400
ccaatgctta atcagtgagg cacctatctc agcgatctgt ctatttcgtt catccatagt    5460
tgcctgactc cccccccgggg ggcgctgagg tctgcctcgt gaagaaggtg ttgctgactc    5520
ataccaggcc tgaatcgccc catcatccag ccagaaagtg agggagccac ggttgatgag    5580
agctttgttg taggtggacc agttggtgat tttgaacttt tgctttgcca cggaacggtc    5640
tgcgttgtcg ggaagatgcg tgatctgatc cttcaactca gcaaaagttc gatttattca    5700
acaaagccgc cgtcccgtca agtcagcgta atgctctgcc agtgttacaa ccaattaacc    5760
aattctgatt agaaaaactc atcgagcatc aaatgaaact gcaatttatt catatcagga    5820
ttatcaatac catattttg aaaaagccgt ttctgtaatg aaggagaaaa ctcaccgagg    5880
cagttccata ggatggcaag atcctggtat cggtctgcga ttccgactcg tccaacatca    5940
atacaaccta ttaatttccc ctcgtcaaaa ataaggttat caagtgagaa atcaccatga    6000
gtgacgactg aatccggtga agtgggcaaa agcttatgca tttctttcca gacttgttca    6060
acaggccagc cattacgctc gtcatcaaaa tcactcgcat caaccaaacc gttattcatt    6120
cgtgattgcg cctgagcgag acgaaatacg cgatcgctgt taaaaggaca attacaaaca    6180
ggaatcgaat gcaaccggcg caggaacact gccagcgcat caacaatatt ttcacctgaa    6240
tcaggatatt cttctaatac ctggaatgct gttttcccgg ggatcgcagt ggtgagtaac    6300
catgcatcat caggagtacg gataaaatgc ttgatggtcg gaagaggcat aaattccgtc    6360
```

| agccagttta gtctgaccat ctcatctgta acatcattgg caacgctacc tttgccatgt | 6420 |
| ttcagaaaca actctggcgc atcgggcttc ccatacaatc gatagattgt cgcacctgat | 6480 |
| tgcccgacat tatcgcgagc ccatttatac ccatataaat cagcatccat gttggaattt | 6540 |
| aatcgcggcc tcgagcaaga cgtttcccgt tgaatatggc tcataacacc ccttgtatta | 6600 |
| ctgtttatgt aagcagacag ttttattgtt catgatgata tatttttatc ttgtgcaatg | 6660 |
| taacatcaga gattttgaga cacaacgtgg ctttcccccc cccccatta ttgaagcatt | 6720 |
| tatcagggtt attgtctcat gagcggatac atatttgaat gtatttagaa aaataaacaa | 6780 |
| ataggggttc cgcgcacatt tccccgaaaa gtgccacctg acgtctaaga aaccattatt | 6840 |
| atcatgacat aacctataa aaataggcgt atcacgaggc cctttcgtc | 6889 |

<210> SEQ ID NO 20
<211> LENGTH: 8146
<212> TYPE: DNA
<213> ORGANISM: Artificial Sequence
<220> FEATURE:
<223> OTHER INFORMATION: Synthetic Construct pAdApt EbolaGP(IC)(dTM)

<400> SEQUENCE: 20

| ttaattaacc gcaattctca tgtttgacag cttatcatca tcaataatat accttatttt | 60 |
| ggattgaagc caatatgata atgagggggt ggagtttgtg acgtggcgcg gggcgtggga | 120 |
| acggggcggg tgacgtagta gtgtggcgga agtgtgatgt tgcaagtgtg gcggaacaca | 180 |
| tgtaagcgac ggatgtggca aaagtgacgt ttttggtgtg cgccggtgta cacaggaagt | 240 |
| gacaatttc gcgcggtttt aggcggatgt tgtagtaaat ttgggcgtaa ccgagtaaga | 300 |
| tttggccatt ttcgcgggaa aactgaataa gaggaagtga atctgaata attttgtgtt | 360 |
| actcatagcg cgtaatattt gtctagggcc gcggggactt tgaccgttta cgtggagact | 420 |
| cgcccaggtt ttttctcag gtgttttccg cgttccgggt caaagttggc gttttattat | 480 |
| tatagtcagt acgtaccagt gcactggcct agagcggccc cattgcatac gttgtatcca | 540 |
| tatcataata tgtacattta tattggctca tgtccaacat taccgccatg ttgacattga | 600 |
| ttattgacta gttattaata gtaatcaatt acggggtcat tagttcatag cccatatatg | 660 |
| gagttccgcg ttacataact tacggtaaat ggcccgcctg gctgaccgcc caacgacccc | 720 |
| cgcccattga cgtcaataat gacgtatgtt cccatagtaa cgccaatagg gactttccat | 780 |
| tgacgtcaat gggtggagta tttacggtaa actgcccact tggcagtaca tcaagtgtat | 840 |
| catatgccaa gtacgccccc tattgacgtc aatgacggta aatggcccgc ctggcattat | 900 |
| gcccagtaca tgaccttatg ggactttcct acttggcagt acatctacgt attagtcatc | 960 |
| gctattacca tggtgatgcg gttttggcag tacatcaatg ggcgtggata gcggtttgac | 1020 |
| tcacgggat ttccaagtct ccaccccatt gacgtcaatg ggagtttgtt ttggcaccaa | 1080 |
| aatcaacggg actttccaaa atgtcgtaac aactccgccc cattgacgca atgggcggt | 1140 |
| aggcgtgtac ggtgggaggt ctatataagc agagctcgtt tagtgaaccg tcagatcgcc | 1200 |
| tggagacgcc atccacgctg ttttgacctc catagaagac accgggaccg atccagcctc | 1260 |
| cgtcaccgtc gtcgacacgt gtgatcagat aattctctaa tcacagtcat catgggagcg | 1320 |
| tcagggattc tgcaattgcc ccgtgagcgc ttcaggaaaa catctttctt tgtttgggta | 1380 |
| ataatcctat tccataaagt ctttttcaatc ccgttggggg ttgtacacaa caataccta | 1440 |
| caagtgagtg atattgacaa gtttgtgtgc cgagacaaac tctcttcaac tagccaattg | 1500 |
| aagtcagtcg ggttgaactt ggagggcaat ggagtagcaa ctgatgtacc aacggcaacc | 1560 |

```
aaaagatggg gttttcgagc tggtgttcca ccaaaggtgg taaattacga agctggagaa   1620
tgggctgaga actgttataa cctggctata agaaagttg atggtagtga gtgcctacca    1680
gaagccctg agggagtgag ggattttccc cgttgccgct atgtacacaa agtctcagga    1740
actggaccat gcccaggagg actcgccttt cacaaagaag gagccttctt cctgtatgac   1800
cgactcgcat caacaatcat ttatcggggt acaacctttg ccgaaggagt tattgcattt   1860
ctgatcttgc ctaaggcgcg aaaggatttt ttccagtctc ctccattgca tgagcctgcc   1920
aacatgacca cggatccctc cagttactat cacacgacaa caataaacta cgtggttgat   1980
aattttggaa ccaacaccac agagtttctg ttccaagtcg atcatttgac gtatgtgcag   2040
ctcgaggcaa gattcacacc acaattcctt gtcctcctaa atgaaaccat ctactctgat   2100
aaccgcagaa gtaacacaac aggaaaacta atctggaaaa taaatcccac tgttgatacc   2160
agcatgggtg agtgggcttt ctggaaaaat aaaaaaactt cacaaaaacc ctttcaagtg   2220
aagagttgtc tttcgtacct gtaccagaaa cccagaacca ggtccttgac acgacagcga   2280
cggtctctcc tcccatctcc gcccacaacc acgcaggcga agaccacaaa gaattggttt   2340
cagaggattc cactccagtg gttcagatgc aaaacatcaa gggaaaggac acaatgccaa   2400
ccacagtgac gggtgtacca acaaccacac cctctccatt tccaatcaat gctcgcaaca   2460
ctgatcatac caaatcattt atcggcctgg aggggcccca agaagaccac agcaccacac   2520
agcctgccaa gaccaccagc caaccaacca acagcacaga atcgacgaca ctaaacccaa   2580
catcagagcc ctccagtaga ggcacgggac catccagccc cacggtcccc aacaccacag   2640
aaagccacgc cgaacttggc aagacaaccc caaccacact cccagaacag cacactgccg   2700
ccagtgccat tccaagagcc gtgcacccc g acgaactcag tggacctggc ttcctgacga   2760
acacaatacg gggggtgaca atctcctga caggatccag aagaaagcga agggatgtca    2820
ctcccaatac acaacccaaa tgcaacccaa acctgcacta ttggacagcc ttggatgagg   2880
gtgctgccat aggtttagcc tggataccat acttcgggcc agcagctgag ggaatttaca   2940
ctgaaggcat aatggagaat caaaatggat tgatctgtgg attgaggcag ctggccaacg   3000
aaacgacaca agctcttcaa ttgttcttaa gggcaactac tgagttgcgt acattctcta   3060
tactaaatcg gaaagcaata gacttcttgc tccaaagatg gggaggaaca tgtcacattc   3120
tagggcctga ttgttgcatt gaaccccaag attggaccaa aaatatcact gataaaattg   3180
atcaaataat ccatgacttt gtcgataata atcttccaaa tcagaatgat ggcagcaact   3240
ggtggactgg atgaaacaa tggtgaagat ccagatctgc tgtgccttct agttgccagc    3300
catctgttgt ttgcccctcc ccgtgcctt ccttgaccct ggaaggtgcc actcccactg     3360
tcctttccta ataaaatgag gaaattgcat cgcattgtct gagtaggtgt cattctattc   3420
tggggggtgg ggtggggcag cacagcaagg gggaggattg ggaagacaat agcaggcatg   3480
ctggggatgc ggtgggctct atgggtaccc agggccgcat aacttcgtat aatgtatgct   3540
atacgaagtt ataagatctg tactgaaatg tgtgggcgtg gcttaagggt gggaaagaat   3600
atataaggtg ggggtcttat gtagttttgt atctgttttg cagcagccgc cgccgccatg   3660
agcaccaact cgtttgatgg aagcattgtg agctcatatt tgacaacgcg catgcccca    3720
tgggccgggg tgcgtcagaa tgtgatgggc tccagcattg atggtcgccc cgtcctgccc   3780
gcaaactcta ctaccttgac ctacgagacc gtgtctggaa cgccgttgga gactgcagcc   3840
tccgccgccc cttcagccgc tgcagccacc gcccgcggga ttgtgactga cttgctttc   3900
ctgagcccgc ttgcaagcag tgcagcttcc cgttcatccg cccgcgatga caagttgacg   3960
```

```
gctcttttgg cacaattgga ttctttgacc cgggaactta atgtcgtttc tcagcagctg    4020
ttggatctgc gccagcaggt ttctgccctg aaggcttcct cccctcccaa tgcggtttaa    4080
aacataaata aaaaaccaga ctctgtttgg atttggatca agcaagtgtc ttgctgtctt    4140
tatttagggg ttttgcgcgc gcggtaggcc cgggaccagc ggtctcggtc gttgagggtc    4200
ctgtgtattt tttccaggac gtggtaaagg tgactctgga tgttcagata catgggcata    4260
agcccgtctc tggggtggag gtagcaccac tgcagagctt catgctgcgg ggtggtgttg    4320
tagatgatcc agtcgtagca ggagcgctgg gcgtggtgcc taaaaatgtc tttcagtagc    4380
aagctgattg ccaggggcag gcccttggtg taagtgttta caaagcggtt aagctgggat    4440
gggtgcatac gtggggatat gagatgcatc ttggactgta ttttaggtt ggctatgttc     4500 ccagccatat ccctccgggg attcatgttg tgcagaacca ccagcacagt gtatccggtg    4560
cacttgggaa atttgtcatg tagcttagaa ggaaatgcgt ggaagaactt ggagacgccc    4620
ttgtgacctc caagattttc catgcattcg tccataatga tggcaatggg cccacgggcg    4680
gcggcctggg cgaagatatt tctgggatca ctaacgtcat agttgtgttc caggatgaga    4740
tcgtcatagg ccattttac aaagcgcggg cggagggtgc cagactgcgg tataatggtt      4800
ccatccggcc caggggcgta gttaccctca cagatttgca tttcccacgc tttgagttca    4860 gatggggga tcatgtctac ctgcggggcg atgaagaaaa cggtttccgg ggtaggggag     4920
atcagctggg aagaaagcag gttcctgagc agctgcgact taccgcagcc ggtgggcccg    4980
taaatcacac ctattaccgg ctgcaactgg tagttaagag agctgcagct gccgtcatcc    5040
ctgagcaggg gggccacttc gttaagcatg tccctgactc gcatgttttc cctgaccaaa    5100
tccgccagaa ggcgctcgcc gcccagcgat agcagttctt gcaaggaagc aaagtttttc    5160
aacggtttga gaccgtccgc cgtaggcatg cttttgagcg tttgaccaag cagttccagg    5220
cggtcccaca gctcggtcac ctgctctacg gcatctcgat ccagcatatc tcctcgtttc    5280
gcgggttggg gcggctttcg ctgtacggca gtagtcggtg ctcgtccaga cgggccaggg    5340
tcatgtcttt ccacgggcgc agggtcctcg tcagcgtagt ctgggtcacg gtgaaggggt    5400
gcgctccggg ctgcgcgctg gccagggtgc gcttgaggct ggtcctgctg gtgctgaagc    5460
gctgccggtc ttcgccctgc gcgtcggcca ggtagcattt gaccatggtg tcatagtcca    5520 gccccctccgc ggcgtggccc ttggcgcgca gcttgcccct tggaggaggcg ccgcacgagg   5580 ggcagtgcag acttttgagg gcgtagagct tgggcgcgag aaataccgat tccggggagt    5640
aggcatccgc gccgcaggcc ccgcagacgg tctcgcattc cacgagccag gtgagctctg    5700
gccgttcggg gtcaaaaacc aggtttcccc catgcttttt gatgcgtttc ttacctctgg    5760
tttccatgag ccggtgtcca cgctcggtga cgaaaaggct gtccgtgtcc ccgtatacag    5820
acttgagagg cctgtcctcg agcggtgttc cgcggtcctc ctcgtataga aactcggacc    5880
actctgagac aaaggctcgc gtccaggcca gcacgaagga ggctaagtgg gagggtagc     5940 ggtcgttgtc cactaggggg tccactcgct ccagggtgtg aagacacatg tcgccctctt    6000
cggcatcaag gaaggtgatt ggtttgtagg tgtaggccac gtgaccgggt gttcctgaag    6060
gggggctata aaggggggtg ggggcgcgtt cgtcctcact ctcttccgca tcgctgtctg    6120
cgagggccag ctgttggggt gagtcgacgc gaggctggat ggccttcccc attatgattc    6180
ttctcgcttc cggcggcatc gggatgcccg cgttgcaggc catgctgtcc aggcaggtag    6240
atgacgacca tcagggacag cttcaaggcc agcaaaaggc caggaaccgt aaaaaggccg    6300
cgttgctggc gtttttccat aggctccgcc ccctgacga gcatcacaaa aatcgacgct      6360
```

```
caagtcagag gtggcgaaac ccgacaggac tataaagata ccaggcgttt ccccctggaa    6420
gctccctcgt gcgctctcct gttccgaccc tgccgcttac cggatacctg tccgcctttc    6480
tcccttcggg aagcgtggcg ctttctcata gctcacgctg taggtatctc agttcggtgt    6540
aggtcgttcg ctccaagctg ggctgtgtgc acgaaccccc cgttcagccc gaccgctgcg    6600
ccttatccgg taactatcgt cttgagtcca acccggtaag acacgactta tcgccactgg    6660
cagcagccac tggtaacagg attagcagag cgaggtatgt aggcggtgct acagagttct    6720
tgaagtggtg gcctaactac ggctacacta aggacagt atttggtatc tgcgctctgc      6780
tgaagccagt taccttcgga aaagagttg gtagctcttg atccggcaaa caaaccaccg     6840
ctggtagcgg tggtttttt gtttgcaagc agcagattac gcgcagaaaa aaggatctc      6900 aagaagatcc tttgatcttt tctacggggt ctgacgctca gtggaacgaa aactcacgtt    6960
aagggatttt ggtcatgaga ttatcaaaaa ggatcttcac ctagatcctt ttaaattaaa    7020
aatgaagttt taaatcaatc taagtatat atgagtaaac ttggtctgac agttaccaat     7080
gcttaatcag tgaggcacct atctcagcga tctgtctatt tcgttcatcc atagttgcct    7140
gactccccgt cgtgtagata actacgtac gggagggctt accatctggc cccagtgctg     7200
caatgatacc gcgagaccca cgctcaccgg ctccagattt atcagcaata aaccagccag    7260
ccggaagggc cgagcgcaga gtggtcctg caactttatc cgcctccatc cagtctatta     7320
attgttgccg ggaagctaga gtaagtagtt cgccagttaa tagtttgcgc aacgttgttg    7380
ccattgctgc aggcatcgtg gtgtcacgct cgtcgtttgg tatggcttca ttcagctccg    7440
gttcccaacg atcaaggcga gttacatgat cccccatgtt gtgcaaaaaa gcggttagct    7500
ccttcggtcc tccgatcgtt gtcagaagta agttggccgc agtgttatca ctcatggtta    7560
tggcagcact gcataattct cttactgtca tgccatccgt aagatgcttt tctgtgactg    7620
gtgagtactc aaccaagtca ttctgagaat agtgtatgcg gcgaccgagt tgctcttgcc    7680
cggcgtcaac acgggataat accgcgccac atagcagaac tttaaaagtg ctcatcattg    7740
gaaaacgttc ttcggggcga aaactctcaa ggatcttacc gctgttgaga tccagttcga    7800
tgtaacccac tcgtgcaccc aactgatctt cagcatcttt tactttcacc agcgtttctg    7860
ggtgagcaaa aacaggaagg caaaatgccg caaaaaaggg aataagggcg acacggaaat    7920
gttgaatact catactcttc cttttcaat attattgaag catttatcag ggttattgtc     7980
tcatgagcgg atacatattt gaatgtattt agaaaaataa acaaataggg gttccgcgca    8040
catttccccg aaaagtgcca cctgacgtct aagaaaccat tattatcatg acattaacct    8100
ataaaaatag gcgtatcacg aggccctttc gtcttcaaga attgtt                   8146
```

<210> SEQ ID NO 21
<211> LENGTH: 7023
<212> TYPE: DNA
<213> ORGANISM: Artificial Sequence
<220> FEATURE:
<223> OTHER INFORMATION: Synthetic Construct pVR1012x/s-SGP(IC)

<400> SEQUENCE: 21

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg       120
ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg     300
```

```
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccg cccattgacg tcaataatga cgtatgttcc     480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg ggcctatac acccccgctt ccttatgcta    1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt ccccgtgcc    1380 cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga attcggcttc   1920
taatcacagt caccatggga gcgtcaggga ttctgcaatt gccccgtgag cgcttcagga   1980
aaacatcttt ctttgtttgg gtaataatcc tattccataa agtcttttca atcccgttgg   2040
gggttgtaca caacaatacc ctacaagtga gtgatattga caagtttgtg tgccgagaca   2100
aactctcttc aactagccaa ttgaagtcag tcgggttgaa cttggagggc aatggagtag   2160
caactgatgt accaacggca accaaaagat ggggttttcg agctggtgtt ccaccaaagg   2220
tggtaaattg cgaagctgga gaatgggctg agaactgtta taacctggct ataaagaaag   2280
ttgatggtag tgagtgccta ccagaagccc ctgagggagt gagggatttt ccccgttgcc   2340
gctatgtaca caaagtctca ggaactggac catgcccagg aggactcgcc tttcacaaag   2400
aaggagcctt cttcctgtat gaccgactcg catcaacaat catttatcgg ggtacaacct   2460
ttgccgaagg agttattgca tttctgatct tgcctaaggc gcgaaggat ttttccagt     2520 ctcctccatt gcatgagcct gccaacatga ccacggatcc ctccagttac tatcacacga   2580
caacaataaa ctacgtggtt gataattttg gaaccaacac cacagagttt ctgttccaag   2640
tcgatcattt gacgtatgtg cagctcgagg caagattcac accacaattc cttgtcctcc   2700
```

```
taaatgaaac catctactct gataaccgca gaagtaacac aacaggaaaa ctaatctgga    2760
aaataaatcc cactgttgat accagcatgg gtgagtgggc tttctgggaa aataaaaaaa    2820
acttcacaaa aacccttca agtgaagagt tgtctttcgt acctgtacca gaaacccaga    2880
```
*(line 2880: note "aaccctttca" reading)*
```
accaggtcct tgacacgaca gcgacggtct ctcctcccat ctccgccac aaccacgcag    2940 ccgaagacca caaagaattg gtttcagagg attccactcc agtggttcag atgcaaaaca    3000
tcaagggaaa ggacacaatg ccaaccacag tgacgggtgt accaacaacc acccctctc    3060 catttccaat caatgctcgc aacactgatc ataccaaatc atttatcggc ctggaggggc    3120
cccaagaaga ccacagcacc acacagcctg ccaagaccac cagccaacca accaacagca    3180
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtg ccattccaag agccgtgcac cccgacgaac    3360
tcagtggacc tggcttcctg acgaacacaa tacgggggt tacaaatctc ctgacaggat    3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720 gatgggggagg aacatgtcac attctagggc ctgattgttg cattgaaccc caagattgga    3780
ccaaaaatat cactgataaa attgatcaaa taatccatga cttttgtcgat aataatcttc    3840 caaatcagaa tgatggcagc aactggtgga ctggatggaa acaatgggtt cctgctggaa    3900
taggaatcac aggagtaatc attgctatta ttgctttgct gtgcatttgc aaattcatgc    3960
tttgaactaa tatagcatca tacttttaagc cgaattctag accaggccct ggatccagat    4020
ctgctgtgcc ttctagttgc cagccatctg ttgttgccc ctccccgtg ccttccttga    4080 ccctggaagg tgccactccc actgtccttt cctaataaaa tgaggaaatt gcatcgcatt    4140
gtctgagtag gtgtcattct attctggggg gtggggtggg gcaggacagc aaggggggagg    4200 attgggaaga caatagcagg catgctgggg atgcggtggg ctctatgggt acccaggtgc    4260
tgaagaattg acccggttcc tcctgggcca gaaagaagca ggcacatccc cttctctgtg    4320
acacaccctg tccacgcccc tggttcttag ttccagcccc actcatagga cactcatagc    4380
tcaggagggc tccgccttca atcccacccg ctaaagtact tggagcggtc tctccctccc    4440
tcatcagccc accaaaccaa acctagcctc caagagtggg aagaaattaa agcaagatag    4500
gctattaagt gcagagggag agaaatgcc tccaacatgt gaggaagtaa tgagagaaat    4560
catagaattt taaggccatc atggccttaa tcttccgctt cctcgctcac tgactcgctg    4620
cgctcggtcg ttcggctgcg cgagcggta tcagctcact caaaggcggt aatacggtta    4680
tccacagaat caggggataa cgcaggaaag aacatgtgag caaaaggcca gcaaaaggcc    4740
aggaaccgta aaaaggccgc gttgctggcg tttttccata ggctccgccc ccctgacgag    4800
catcacaaaa atcgacgctc aagtcagagg tggcgaaacc cgacaggact ataaagatac    4860
caggcgtttc ccccctggaag ctccctcgtg cgctctcctg ttccgaccct gccgcttacc    4920
ggatacctgt ccgcctttct cccttcggga agcgtggcgc tttctcatag ctcacgctgt    4980
aggtatctca gttcggtgta ggtcgttcgc tccaagctgg gctgtgtgca cgaaccccc    5040 gttcagcccg accgctgcgc cttatccggt aactatcgtc ttgagtccaa cccggtaaga    5100
```

```
cacgacttat cgccactggc agcagccact ggtaacagga ttagcagagc gaggtatgta      5160
ggcggtgcta cagagttctt gaagtggtgg cctaactacg gctacactag aagaacagta      5220
tttggtatct gcgctctgct gaagccagtt accttcggaa aaagagttgg tagctcttga      5280
tccggcaaac aaaccaccgc tggtagcggt ggttttttg tttgcaagca gcagattacg       5340
cgcagaaaaa aaggatctca agaagatcct ttgatctttt ctacgggtc tgacgctcag       5400 tggaacgaaa actcacgtta agggattttg gtcatgagat tatcaaaaag gatcttcacc      5460
tagatccttt taaattaaaa atgaagtttt aaatcaatct aaagtatata tgagtaaact      5520
tggtctgaca gttaccaatg cttaatcagt gaggcaccta tctcagcgat ctgtctattt      5580
cgttcatcca tagttgcctg actcgggggg gggggcgct gaggtctgcc tcgtgaagaa       5640
ggtgttgctg actcatacca ggcctgaatc gccccatcat ccagccagaa agtgagggag      5700
ccacggttga tgagagcttt gttgtaggtg gaccagttgg tgattttgaa cttttgcttt      5760
gccacggaac ggtctgcgtt gtcgggaaga tgcgtgatct gatccttcaa ctcagcaaaa      5820
gttcgattta ttcaacaaag ccgccgtccc gtcaagtcag cgtaatgctc tgccagtgtt      5880
acaaccaatt aaccaattct gattagaaaa actcatcgag catcaaatga actgcaatt      5940 tattcatatc aggattatca ataccatatt tttgaaaaag ccgtttctgt aatgaaggag      6000
aaaactcacc gaggcagttc cataggatgg caagatcctg gtatcggtct gcgattccga      6060
ctcgtccaac atcaatacaa cctattaatt cccctcgtc aaaaataagg ttatcaagtg       6120
agaaatcacc atgagtgacg actgaatccg gtgagaatgg caaaagctta tgcatttctt      6180
tccagacttg ttcaacaggc cagccattac gctcgtcatc aaaatcactc gcatcaacca      6240
aaccgttatt cattcgtgat tgcgcctgag cgagacgaaa tacgcgatcg ctgttaaaag      6300
gacaattaca acaggaatc gaatgcaacc ggcgcaggaa cactgccagc gcatcaacaa       6360
tattttcacc tgaatcagga tattcttcta atacctggaa tgctgttttc ccggggatcg      6420
cagtggtgag taaccatgca tcatcaggag tacggataaa atgcttgatg gtcggaagag      6480
gcataaattc cgtcagccag tttagtctga ccatctcatc tgtaacatca ttggcaacgc      6540
tacctttgcc atgtttcaga aacaactctg gcgcatcggg cttcccatac aatcgataga      6600
ttgtcgcacc tgattgcccg acattatcgc gagcccattt ataccatat aaatcagcat       6660 ccatgttgga atttaatcgc ggcctcgagc aagacgtttc ccgttgaata tggctcataa      6720
caccccttgt attactgttt atgtaagcag acagttttat tgttcatgat gatatatttt      6780
tatcttgtgc aatgtaacat cagagatttt gagacacaac gtggctttcc ccccccccc       6840 attattgaag catttatcag ggttattgtc tcatgagcgg atacatattt gaatgtattt      6900
agaaaaataa acaaataggg gttccgcgca catttccccg aaaagtgcca cctgacgtct      6960
aagaaaccat tattatcatg acattaacct ataaaatag gcgtatcacg aggccctttc       7020
gtc                                                                    7023
```

<210> SEQ ID NO 22
<211> LENGTH: 7295
<212> TYPE: DNA
<213> ORGANISM: Artificial Sequence
<220> FEATURE:
<223> OTHER INFORMATION: Synthetic Construct pVR1012-NP

<400> SEQUENCE: 22

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
```

```
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca cgaccccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccccttggc    1080
tcttatgcat gctatactgt ttttggcttg gggcctatac accccgcttc cttatgcta    1140
taggtgatgg tatagcttag cctataggtg tgggttattg accattattg ccactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatccagatc gatccgagta tggattctcg tcctcagaaa atctggatgg cgccgagtct    1980
cactgaatct gacatggatt accacaagat cttgacagca ggtctgtccg ttcaacaggg    2040
gattgttcgg caaagagtca tcccagtgta tcaagtaaac aatcttgaag aaatttgcca    2100
acttatcata caggcctttg aagcaggtgt tgattttcaa gagagtgcgg acagtttcct    2160
tctcatgctt tgtcttcatc atgcgtacca gggagattac aaacttttct tggaaagtgg    2220
cgcagtcaag tatttggaag ggcacggggtt ccgttttgaa gtcaagaagc gtgatggagt    2280
gaagcgcctt gaggaattgc tgccagcagt atctagtgga aaaaacatta agagaacact    2340
tgctgccatg ccggaagagg agacaactga agctaatgcc ggtcagtttc tctccttgc    2400
aagtctattc cttccgaaat tggtagtagg agaaaaggct tgccttgaga aggttcaaag    2460
gcaaattcaa gtacatgcag agcaaggact gatacaatat ccaacagctt ggcaatcagt    2520
```

```
aggacacatg atggtgattt tccgtttgat gcgaacaaat tttctgatca aatttctcct   2580
aatacaccaa gggatgcaca tggttgccgg gcatgatgcc aacgatgctg tgatttcaaa   2640
ttcagtggct caagctcgtt tttcaggctt attgattgtc aaaacagtac ttgatcatat   2700
cctacaaaag acagaacgag gagttcgtct ccatcctctt gcaaggaccg ccaaggtaaa   2760
aaatgaggtg aactccttta aggctgcact cagctccctg gccaagcatg gagagtatgc   2820
tcctttcgcc cgacttttga acctttctgg agtaaataat cttgagcatg gtcttttccc   2880
tcaactatcg gcaattgcac tcggagtcgc cacagcacac gggagtaccc tcgcaggagt   2940
aaatgttgga gaacagtatc aacaactcag agaggctgcc actgaggctg agaagcaact   3000
ccaacaatat gcagagtctc gcgaacttga ccatcttgga cttgatgatc aggaaaagaa   3060
aattcttatg aacttccatc agaaaaagaa cgaaatcagc ttccagcaaa caaacgctat   3120
ggtaactcta agaaaagagc gcctggccaa gctgacagaa gctatcactg ctgcgtcact   3180
gcccaaaaca agtggacatt acgatgatga tgacgacatt ccctttccag acccatcaa    3240 tgatgacgac aatcctggcc atcaagatga tgatccgact gactcacagg atacgaccat   3300
tcccgatgtg gtggttgatc ccgatgatgg aagctacggc gaataccaga gttactcgga   3360
aaacggcatg aatgcaccag atgacttggt cctattcgat ctagacgagg acgacgagga   3420
cactaagcca gtgcctaata gatcgaccaa gggtggacaa cagaagaaca gtcaaaaggg   3480
ccagcatata gagggcagac agacacaatc caggccaatt caaaatgtcc caggccctca   3540
cagaacaatc caccacgcca gtgcgccact cacggacaat gacagaagaa atgaaccctc   3600
cggctcaacc agccctcgca tgctgacacc aattaacgaa gaggcagacc cactggacga   3660
tgccgacgac gagacgtcta gccttccgcc cttggagtca gatgatgaag agcaggacag   3720
ggacggaact tccaaccgca cacccactgt cgccccaccg gctcccgtat acagagatca   3780
ctctgaaaag aaagaactcc cgcaagacga gcaacaagat caggaccaca ctcaagaggc   3840
caggaaccag gacagtgaca acacccagtc agaacactct tttgaggaga tgtatcgcca   3900
cattctaaga tcacagggggc catttgatgc tgttttgtat tatcatatga tgaaggatga   3960
gcctgtagtt ttcagtacca gtgatggcaa agagtacacg tatccagact cccttgaaga   4020
ggaatatcca ccatggctca ctgaaaaaga ggctatgaat gaagagaata gatttgttac   4080
attggatggt caacaatttt attggccggt gatgaatcac aagaataaat tcatggcaat   4140
cctgcaacat catcagtgaa tgagcatgga acaatgggat gattcaaccg acaaatagct   4200
aacattaagt agtcaaggaa cgaaaacagg aagaatttt gatgtctaag gtgtgaatta    4260
ttatcacaat aaaagtgatt cttatttttg aatttgggcg agctcgaatt gatctgctgt   4320
gccttctagt tgccagccat ctgttgtttg cccctccccc gtgccttcct tgaccctgga   4380
aggtgccact cccactgtcc tttcctaata aaatgaggaa attgcatcgc attgtctgag   4440
taggtgtcat tctattctgg ggggtggggt ggggcaggac agcaagggggg aggattggga   4500 agacaatagc aggcatgctg gggatgcggt gggctctatg gtacccagg tgctgaagaa    4560 ttgacccggt tcctcctggg ccagaaagaa gcaggcacat ccccttctct gtgacacacc   4620
ctgtccacgc ccctggttct tagttccagc cccactcata ggacactcat agctcaggag   4680
ggctccgcct tcaatcccac ccgctaaagt acttggagcg gtctctcccct ccctcatcag   4740 cccaccaaac caaacctagc ctccaagagt gggaagaaat taaagcaaga taggctatta   4800
agtgcagagg gagagaaaat gcctccaaca tgtgaggaag taatgagaga aatcatagaa   4860
tttcttccgc ttcctcgctc actgactcgc tgcgctcggt cgttcggctg cggcgagcgg   4920
```

```
tatcagctca ctcaaaggcg gtaatacggt tatccacaga atcagggat aacgcaggaa     4980
agaacatgtg agcaaaaggc cagcaaaagg ccaggaaccg taaaaaggcc gcgttgctgg     5040
cgtttttcca taggctccgc cccctgacg agcatcacaa aaatcgacgc tcaagtcaga     5100
ggtggcgaaa cccgacagga ctataaagat accaggcgtt tccccctgga agctccctcg     5160
tgcgctctcc tgttccgacc ctgccgctta ccggatacct gtccgccttt ctcccttcgg     5220
gaagcgtggc gctttctcat agctcacgct gtaggtatct cagttcggtg taggtcgttc     5280
gctccaagct gggctgtgtg cacgaaccc cgttcagcc cgaccgctgc gccttatccg     5340
gtaactatcg tcttgagtcc aacccggtaa gacacgactt atcgccactg gcagcagcca     5400
ctggtaacag gattagcaga gcgaggtatg taggcggtgc tacagagttc ttgaagtggt     5460
ggcctaacta cggctacact agaagaacag tatttggtat ctgcgctctg ctgaagccag     5520
ttaccttcgg aaaaagagtt ggtagctctt gatccggcaa acaaaccacc gctggtagcg     5580
gtggtttttt tgtttgcaag cagcagatta cgcgcagaaa aaaggatct caagaagatc     5640
ctttgatctt ttctacgggg tctgacgctc agtggaacga aaactcacgt taagggattt     5700
tggtcatgag attatcaaaa aggatcttca cctagatcct tttaaattaa aaatgaagtt     5760
ttaaatcaat ctaaagtata tatgagtaaa cttggtctga cagttaccaa tgcttaatca     5820
gtgaggcacc tatctcagcg atctgtctat ttcgttcatc catagttgcc tgactcgggg     5880
ggggggggcg ctgaggtctg cctcgtgaag aaggtgttgc tgactcatac caggcctgaa     5940
tcgccccatc atccagccag aaagtgaggg agccacggtt gatgagagct tgttgtagg     6000
tggaccagtt ggtgattttg aacttttgct ttgccacgga acggtctgcg ttgtcgggaa     6060
gatgcgtgat ctgatccttc aactcagcaa agttcgatt tattcaacaa agccgccgtc     6120
ccgtcaagtc agcgtaatgc tctgccagtg ttacaaccaa ttaaccaatt ctgattagaa     6180
aaactcatcg agcatcaaat gaaactgcaa tttattcata tcaggattat caataccata     6240
tttttgaaaa agccgtttct gtaatgaagg agaaaactca ccgaggcagt tccataggat     6300
ggcaagatcc tggtatcggt ctgcgattcc gactcgtcca acatcaatac aacctattaa     6360
tttcccctcg tcaaaaataa ggttatcaag tgagaaatca ccatgagtga cgactgaatc     6420
cggtgagaat ggcaaaagct tatgcatttc tttccagact tgttcaacag gccagccatt     6480
acgctcgtca tcaaaatcac tcgcatcaac caaaccgtta ttcattcgtg attgcgcctg     6540
agcgagacga atacgcgat cgctgttaaa aggacaatta caaacaggaa tcgaatgcaa     6600
ccggcgcagg aacactgcca gcgcatcaac aatattttca cctgaatcag gatattcttc     6660
taatacctgg aatgctgttt tcccggggat cgcagtggtg agtaaccatg catcatcagg     6720
agtacggata aaatgcttga tggtcggaag aggcataaat tccgtcagcc agtttagtct     6780
gaccatctca tctgtaacat cattggcaac gctacctttg ccatgtttca gaaacaactc     6840
tggcgcatcg gcttcccat acaatcgata gattgtcgca cctgattgcc cgacattatc     6900
gcgagcccat ttatacccat ataaatcagc atccatgttg gaatttaatc gcggcctcga     6960
gcaagacgtt tcccgttgaa tatggctcat aacaccccctt gtattactgt ttatgtaagc     7020
agacagtttt attgttcatg atgatatatt tttatcttgt gcaatgtaac atcagagatt     7080
ttgagacaca acgtggcttt cccccccccc ccattattga agcatttatc agggttattg     7140
tctcatgagc ggatacatat ttgaatgtat ttagaaaaat aaacaaatag gggttccgcg     7200
cacatttccc cgaaaagtgc cacctgacgt ctaagaaacc attattatca tgacattaac     7260
ctataaaaat aggcgtatca cgaggccctt tcgtc                                7295
```

<210> SEQ ID NO 23
<211> LENGTH: 7329
<212> TYPE: DNA
<213> ORGANISM: Artificial Sequence
<220> FEATURE:
<223> OTHER INFORMATION: Synthetic Construct pVR1012x/s Ebola-NP

<400> SEQUENCE: 23

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcaggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcagattgg | 240 |
| ctattggcca | ttgcatacgt | tgtatccata | tcataatatg | tacatttata | ttggctcatg | 300 |
| tccaacatta | ccgccatgtt | gacattgatt | attgactagt | tattaatagt | aatcaattac | 360 |
| ggggtcatta | gttcatagcc | catatatgga | gttccgcgtt | acataactta | cggtaaatgg | 420 |
| cccgcctggc | tgaccgccca | acgacccccg | cccattgacg | tcaataatga | cgtatgttcc | 480 |
| catagtaacg | ccaataggga | ctttccattg | acgtcaatgg | gtggagtatt | tacggtaaac | 540 |
| tgcccacttg | gcagtacatc | aagtgtatca | tatgccaagt | acgccccta | ttgacgtcaa | 600 |
| tgacggtaaa | tggcccgcct | ggcattatgc | ccagtacatg | accttatggg | actttcctac | 660 |
| ttggcagtac | atctacgtat | tagtcatcgc | tattaccatg | gtgatgcggt | tttggcagta | 720 |
| catcaatggg | cgtggatagc | ggtttgactc | acggggattt | ccaagtctcc | accccattga | 780 |
| cgtcaatggg | agtttgtttt | ggcaccaaaa | tcaacgggac | tttccaaaat | gtcgtaacaa | 840 |
| ctccgcccca | ttgacgcaaa | tgggcggtag | gcgtgtacgg | tgggaggtct | atataagcag | 900 |
| agctcgttta | gtgaaccgtc | agatcgcctg | gagacgccat | ccacgctgtt | ttgacctcca | 960 |
| tagaagacac | cgggaccgat | ccagcctccg | cggccgggaa | cggtgcattg | gaacgcggat | 1020 |
| tccccgtgcc | aagagtgacg | taagtaccgc | ctatagactc | tataggcaca | cccctttggc | 1080 |
| tcttatgcat | gctatactgt | ttttggcttg | gggcctatac | accccgctt | ccttatgcta | 1140 |
| taggtgatgg | tatagcttag | cctataggtg | tgggttattg | accattattg | accactcccc | 1200 |
| tattggtgac | gatactttcc | attactaatc | cataacatgg | ctctttgcca | caactatctc | 1260 |
| tattggctat | atgccaatac | tctgtccttc | agagactgac | acggactctg | tattttaca | 1320 |
| ggatggggtc | ccatttatta | tttacaaatt | cacatataca | acaacgccgt | ccccgtgcc | 1380 |
| cgcagttttt | attaaacata | gcgtgggatc | tccacgcgaa | tctcgggtac | gtgttccgga | 1440 |
| catgggctct | tctccggtag | cggcggagct | tccacatccg | agccctggtc | catgcctcc | 1500 |
| agcggctcat | ggtcgctcgg | cagctccttg | ctcctaacag | tggaggccag | acttaggcac | 1560 |
| agcacaatgc | ccaccaccac | cagtgtgccg | cacaaggccg | tggcggtagg | gtatgtgtct | 1620 |
| gaaaatgagc | gtggagattg | ggctcgcacg | gctgacgcag | atgaagact | taaggcagcg | 1680 |
| gcagaagaag | atgcaggcag | ctgagttgtt | gtattctgat | aagagtcaga | ggtaactccc | 1740 |
| gttgcggtgc | tgttaacggt | ggagggcagt | gtagtctgag | cagtactcgt | tgctgccgcg | 1800 |
| cgcgccacca | gacataatag | ctgacagact | aacagactgt | tcctttccat | gggtctttc | 1860 |
| tgcagtcacc | gtcgtcgaca | cgtgtgatca | gatatcgcgg | ccgctctaga | ccaggccctg | 1920 |
| gatccagatc | gatccgagta | tggattctcg | tcctcagaaa | atctggatgg | cgccgagtct | 1980 |
| cactgaatct | gacatggatt | accacaagat | cttgacagca | ggtctgtccg | ttcaacaggg | 2040 |
| gattgttcgg | caaagagtca | tcccagtgta | tcaagtaaac | aatcttgaag | aaatttgcca | 2100 |

```
acttatcata caggcctttg aagcaggtgt tgattttcaa gagagtgcgg acagtttcct      2160
tctcatgctt tgtcttcatc atgcgtacca gggagattac aaactttct tggaaagtgg       2220 cgcagtcaag tatttggaag ggcacgggtt ccgttttgaa gtcaagaagc gtgatggagt      2280
gaagcgcctt gaggaattgc tgccagcagt atctagtgga aaaaacatta agagaacact      2340
tgctgccatg ccggaagagg agacaactga agctaatgcc ggtcagtttc tctcctttgc     2400
aagtctattc cttccgaaat tggtagtagg agaaaaggct tgccttgaga aggttcaaag      2460
gcaaattcaa gtacatgcag agcaaggact gatacaatat ccaacagctt ggcaatcagt     2520
aggacacatg atggtgattt ccgtttgat gcgaacaaat tttctgatca aatttctcct      2580
aatacaccaa gggatgcaca tggttgccgg gcatgatgcc aacgatgctg tgatttcaaa     2640
ttcagtggct caagctcgtt tttcaggctt attgattgtc aaaacagtac ttgatcatat     2700
cctacaaaag acagaacgag gagttcgtct ccatcctctt gcaaggaccg ccaaggtaaa     2760
aaatgaggtg aactcctta aggctgcact cagctccctg gccaagcatg gagagtatgc       2820
tcctttcgcc cgactttga accttttctgg agtaaataat cttgagcatg gtcttttccc     2880
tcaactatcg gcaattgcac tcggagtcgc cacagcacac gggagtaccc tcgcaggagt    2940
aaatgttgga gaacagtatc aacaactcag agaggctgcc actgaggctg agaagcaact    3000
ccaacaatat gcagagtctc gcgaacttga ccatcttgga cttgatgatc aggaaaagaa    3060
aattcttatg aacttccatc agaaaagaa cgaaatcagc ttccagcaaa caaacgctat      3120
ggtaactcta agaaaagagc gcctggccaa gctgacagaa gctatcactg ctgcgtcact     3180
gcccaaaaca gtggacatt acgatgatga tgacgacatt ccctttccag acccatcaa      3240 tgatgacgac aatcctggcc atcaagatga tgatccgact gactcacagg atacgaccat    3300
tcccgatgtg gtggttgatc ccgatgatgg aagctacggc gaataccaga gttactcgga    3360
aaacggcatg aatgcaccag atgacttggt cctattcgat ctagacgagg acgacgagga    3420
cactaagcca gtgcctaata gatcgaccaa gggtggacaa cagaagaaca gtcaaaggg     3480 ccagcatata gagggcagac agacacaatc caggccaatt caaaatgtcc caggccctca    3540
cagaacaatc caccacgcca gtgcgccact cacggacaat gacagaagaa atgaaccctc    3600
cggctcaacc agccctcgca tgctgacacc aattaacgaa gaggcagacc cactggacga    3660
tgccgacgac gagacgtcta gccttccgcc cttggagtca gatgatgaag agcaggacag    3720
ggacggaact tccaaccgca cacccactgt cgcccaccg gctcccgtat acagagatca    3780
ctctgaaaag aaagaactcc cgcaagacga gcaacaagat caggaccaca ctcaagaggc    3840
caggaaccag gacagtgaca acacccagtc agaacactct tttgaggaga tgtatcgcca    3900
cattctaaga tcacaggggc catttgatgc tgttttgtat tatcatatga tgaaggatga    3960
gcctgtagtt ttcagtacca gtgatggcaa agagtacacg tatccagact cccttgaaga    4020
ggaatatcca ccatggctca ctgaaaaaga ggctatgaat gaagagaata gatttgttac    4080
attggatggt caacaatttt attggccggt gatgaatcac aagaataaat tcatggcaat    4140
cctgcaacat catcagtgaa tgagcatgga acaatgggat gattcaaccg acaaatagct    4200
aacattaagt agtcaaggaa cgaaaacagg aagaattttt gatgtctaag gtgtgaatta    4260
ttatcacaat aaaagtgatt cttatttttg aatttgggcg agctcgaatt gatctgctgt    4320
gccttctagt tgccagccat ctgttgtttg ccccctcccc gtgccttcct tgaccctgga    4380
aggtgccact cccactgtcc tttcctaata aaatgaggaa attgcatcgc attgtctgag    4440
taggtgtcat tctattctgg ggggtggggt ggggcaggac agcaagggg aggattggga    4500
```

```
agacaatagc aggcatgctg gggatgcggt gggctctatg ggtacccagg tgctgaagaa   4560
ttgacccggt tcctcctggg ccagaaagaa gcaggcacat ccccttctct gtgacacacc   4620
ctgtccacgc ccctggttct tagttccagc cccactcata ggacactcat agctcaggag   4680
ggctccgcct tcaatcccac ccgctaaagt acttggagcg gtctctccct ccctcatcag   4740
cccaccaaac caaacctagc ctccaagagt gggaagaaat taaagcaaga taggctatta   4800
agtgcagagg gagagaaaat gcctccaaca tgtgaggaag taatgagaga aatcatagaa   4860
ttttaaggcc atgatttaag gccatcatgg ccttaatctt ccgcttcctc gctcactgac   4920
tcgctgcgct cggtcgttcg gctgcggcga gcggtatcag ctcactcaaa ggcggtaata   4980
cggttatcca cagaatcagg ggataacgca ggaaagaaca tgtgagcaaa aggccagcaa   5040
aaggccagga accgtaaaaa ggccgcgttg ctggcgtttt tccataggct ccgcccccct   5100
gacgagcatc acaaaaatcg acgctcaagt cagaggtggc gaaacccgac aggactataa   5160
agataccagg cgtttccccc tggaagctcc ctcgtgcgct ctcctgttcc gaccctgccg   5220
cttaccggat acctgtccgc ctttctccct tcgggaagcg tggcgctttc tcatagctca   5280
cgctgtaggt atctcagttc ggtgtaggtc gttcgctcca agctgggctg tgtgcacgaa   5340
ccccccgttc agcccgaccg ctgcgcctta tccggtaact atcgtcttga gtccaacccg   5400
gtaagacacg acttatcgcc actggcagca gccactggta acaggattag cagagcgagg   5460
tatgtaggcg gtgctacaga gttcttgaag tggtggccta actacggcta cactagaaga   5520
acagtatttg gtatctgcgc tctgctgaag ccagttacct tcggaaaaag agttggtagc   5580
tcttgatccg gcaaacaaac caccgctggt agcggtggtt tttttgtttg caagcagcag   5640
attacgcgca gaaaaaaagg atctcaagaa gatcctttga tcttttctac ggggtctgac   5700
gctcagtgga acgaaaactc acgttaaggg attttggtca tgagattatc aaaaaggatc   5760
ttcacctaga tccttttaaa ttaaaaatga agttttaaat caatctaaag tatatatgag   5820
taaacttggt ctgacagtta ccaatgctta atcagtgagg cacctatctc agcgatctgt   5880
ctatttcgtt catccatagt tgcctgactc ccccgggggg ggcgctgagg tctgcctcgt   5940
gaagaaggtg ttgctgactc ataccaggcc tgaatcgccc catcatccag ccagaaagtg   6000
agggagccac ggttgatgag agctttgttg taggtggacc agttggtgat tttgaacttt   6060
tgctttgcca cggaacggtc tgcgttgtcg ggaagatgcg tgatctgatc cttcaactca   6120 gcaaagttc  gatttattca acaaagccgc cgtcccgtca agtcagcgta atgctctgcc   6180
agtgttacaa ccaattaacc aattctgatt agaaaaactc atcgagcatc aaatgaaact   6240
gcaatttatt catatcagga ttatcaatac catattttg  aaaaagccgt ttctgtaatg   6300
aaggagaaaa ctcaccgagg cagttccata ggatggcaag atcctggtat cggtctgcga   6360
ttccgactcg tccaacatca atacaaccta ttaatttccc ctcgtcaaaa ataaggttat   6420
caagtgagaa atcaccatga gtgacgactg aatccggtga agatggcaaa agcttatgca   6480
tttctttcca gacttgttca acaggccagc cattacgctc gtcatcaaaa tcactcgcat   6540
caaccaaacc gttattcatt cgtgattgcg cctgagcgag acgaaatacg cgatcgctgt   6600
taaaaggaca attacaaaca ggaatcgaat gcaaccggcg caggaacact gccagcgcat   6660
caacaatatt ttcacctgaa tcaggatatt cttctaatac ctggaatgct gttttcccgg   6720
ggatcgcagt ggtgagtaac catgcatcat caggagtacg gataaaatgc ttgatggtcg   6780
gaagaggcat aaattccgtc agccagttta gtctgaccat ctcatctgta acatcattgg   6840
caacgctacc tttgccatgt ttcagaaaca actctggcgc atcgggcttc ccatacaatc   6900
```

| | |
|---|---|
| gatagattgt cgcacctgat tgcccgacat tatcgcgagc ccatttatac ccatataaat | 6960 |
| cagcatccat gttggaattt aatcgcggcc tcgagcaaga cgtttcccgt tgaatatggc | 7020 |
| tcataacacc ccttgtatta ctgtttatgt aagcagacag ttttattgtt catgatgata | 7080 |
| tatttttatc ttgtgcaatg taacatcaga gattttgaga cacaacgtgg ctttcccccc | 7140 |
| cccccattta ttgaagcatt tatcaggatt attgtctcat gagcggatac atatttgaat | 7200 |
| gtatttagaa aaataaacaa ataggggttc cgcgcacatt tccccgaaaa gtgccacctg | 7260 |
| acgtctaaga aaccattatt atcatgacat aacctataa aataggcgt atcacgaggc | 7320 |
| cctttcgtc | 7329 |

<210> SEQ ID NO 24
<211> LENGTH: 6148
<212> TYPE: DNA
<213> ORGANISM: Artificial Sequence
<220> FEATURE:
<223> OTHER INFORMATION: Synthetic Construct pVR1012-VP35

<400> SEQUENCE: 24

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga cttccattg acgtcaatgg gtggagtatt tacggtaaac | 540 |
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca cccctttggc | 1080 |
| tcttatgcat gctatactgt ttttggcttg gggcctatac accccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tatttttaca | 1320 |
| ggatggggtc ccatttatta tttacaaatt cacatataca acaacgccgt ccccgtgcc | 1380 |
| cgcagttttt attaaacata gcgtgggatc tccacgcgaa tctcgggtac gtgttccgga | 1440 |
| catgggctct ctccggtag cggcggagct tccacatccg agccctggtc ccatgcctcc | 1500 |
| agcggctcat ggtcgctcgg cagctccttg ctcctaacag tggaggccag acttaggcac | 1560 |
| agcacaatgc ccaccaccac cagtgtgccg cacaaggccg tggcggtagg gtatgtgtct | 1620 |

```
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgaattct ctagcactcg aagcttattg tcttcaatgt aaaagaaaag    1920
ctggtctaac aagatgacaa ctagaacaaa gggcagggc catactgcgg ccacgactca     1980
aaacgacaga atgccaggcc ctgagctttc gggctggatc tctgagcagc taatgaccgg    2040
aagaattcct gtaagcgaca tcttctgtga tattgagaac aatccaggat tatgctacgc    2100
atcccaaatg caacaaacga agccaaaccc gaagacgcgc aacagtcaaa cccaaacgga    2160
cccaatttgc aatcatagtt ttgaggaggt agtacaaaca ttggcttcat tggctactgt    2220
tgtgcaacaa caaaccatcg catcagaatc attagaacaa cgcattacga gtcttgagaa    2280
tggtctaaag ccagtttatg atatggcaaa aacaatctcc tcattgaaca gggtttgtgc    2340
tgagatggtt gcaaaatatg atcttctggt gatgacaacc ggtcgggcaa cagcaaccgc    2400
tgcggcaact gaggcttatt gggccgaaca tggtcaacca ccacctggac catcacttta    2460
tgaagaaagt gcgattcggg gtaagattga atctagagat gagaccgtcc ctcaaagtgt    2520
tagggaggca ttcaacaatc taaacagtac cacttcacta actgaggaaa attttgggaa    2580
acctgacatt tcggcaaagg atttgagaaa cattatgtat gatcacttgc ctggttttgg    2640
aactgctttc caccaattag tacaagtgat ttgtaaattg ggaaaagata gcaactcatt    2700
ggacatcatt catgctgagt tccaggccag cctggctgaa ggagactctc ctcaatgtgc    2760
cctaattcaa attacaaaaa gagttccaat cttccaagat gctgctccat ctgtcatcca    2820
catccgcttt cgaggtgaca ttccccgagc ttgccagaaa agcttgcgtc cagtcccacc    2880
atcgcccaag attgatcgag gttgggatgt gtttttcagc ttcaagatgg taaaacactt    2940
ggactcaaaa tttgagccaa tctcccttcc ctccgaaaga ggcgaataat agcagaggct    3000
tcaactgctg aactataggg tacgttacat taatgataca cttgtgagta tcagccctgg    3060
ataatataag tcaattaaac gaccaagata aaattgttca tatctcgcta gcagcttaaa    3120
atataaatgt aataggagct atatctctga caggggatc cagatctgct gtgccttcta    3180
gttgccagcc atctgttgtt tgcccctccc ccgtgccttc cttgaccctg gaaggtgcca    3240
ctcccactgt cctttcctaa taaaatgagg aaattgcatc gcattgtctg agtaggtgtc    3300
attctattct ggggggtggg gtggggcagc acagcaaggg ggaggattgg gaagacaata    3360
gcaggcatgc tggggatgcg gtgggctcta tgggtaccca ggtgctgaag aattgacccg    3420
gttcctcctg ggccagaaag aagcaggcac atccccttct ctgtgacaca ccctgtccac    3480 gccctggtt cttagttcca gccccactca taggacactc atagctcagg agggctccgc      3540
cttcaatccc acccgctaaa gtacttggag cggtctctcc ctccctcatc agcccaccaa    3600
accaaaccta gcctccaaga gtgggaagaa attaaagcaa gataggctat taagtgcaga    3660
gggagagaaa atgcctccaa catgtgagga agtaatgaga gaaatcatag aatttcttcc    3720
gcttcctcgc tcactgactc gctgcgctcg tcgttcggc tgcggcgagc ggtatcagct      3780
cactcaaagg cggtaatacg gttatccaca gaatcagggg ataacgcagg aaagaacatg    3840
tgagcaaaag gccagcaaaa ggccaggaac cgtaaaaagg ccgcgttgct ggcgtttttc    3900
cataggctcc gcccccctga cgagcatcac aaaaatcgac gctcaagtca gaggtggcga    3960
aacccgacag gactataaag ataccaggcg tttccccctg gaagctccct cgtgcgctct    4020
```

```
cctgttccga ccctgccgct taccggatac ctgtccgcct ttctcccttc gggaagcgtg    4080
gcgctttctc aatgctcacg ctgtaggtat ctcagttcgg tgtaggtcgt tcgctccaag    4140
ctgggctgtg tgcacgaacc ccccgttcag cccgaccgct gcgccttatc cggtaactat    4200
cgtcttgagt ccaacccggt aagacacgac ttatcgccac tggcagcagc cactggtaac    4260
aggattagca gagcgaggta tgtaggcggt gctacagagt tcttgaagtg gtggcctaac    4320
tacggctaca ctagaaggac agtatttggt atctgcgctc tgctgaagcc agttaccttc    4380
ggaaaaagag ttggtagctc ttgatccggc aaacaaacca ccgctggtag cggtggtttt    4440
tttgtttgca agcagcagat tacgcgcaga aaaaaggat ctcaagaaga tcctttgatc    4500
ttttctacgg ggtctgacgc tcagtggaac gaaaactcac gttaagggat tttggtcatg    4560
agattatcaa aaaggatctt cacctagatc cttttaaatt aaaaatgaag ttttaaatca    4620
atctaaagta tatatgagta aacttggtct gacagttacc aatgcttaat cagtgaggca    4680
cctatctcag cgatctgtct atttcgttca tccatagttg cctgactccg gggggggggg    4740
gcgctgaggt ctgcctcgtg aagaaggtgt tgctgactca taccaggcct gaatcgcccc    4800
atcatccagc cagaaagtga gggagccacg gttgatgaga gctttgttgt aggtggacca    4860
gttggtgatt ttgaactttt gctttgccac ggaacggtct gcgttgtcgg gaagatgcgt    4920
gatctgatcc ttcaactcag caaaagttcg atttattcaa caaagccgcc gtcccgtcaa    4980
gtcagcgtaa tgctctgcca gtgttacaac caattaacca attctgatta gaaaaactca    5040
tcgagcatca aatgaaactg caatttattc atatcaggat tatcaatacc atatttttga    5100
aaaagccgtt tctgtaatga aggagaaaac tcaccgaggc agttccatag gatggcaaga    5160
tcctggtatc ggtctgcgat tccgactcgt ccaacatcaa taaacctat taatttcccc    5220 tcgtcaaaaa taaggttatc aagtgagaaa tcaccatgag tgacgactga atccggtgag    5280
aatggcaaaa gcttatgcat ttctttccag acttgttcaa caggccagcc attacgctcg    5340
tcatcaaaat cactcgcatc aaccaaaccg ttattcattc gtgattgcgc ctgagcgaga    5400
cgaaatacgc gatcgctgtt aaaaggacaa ttacaaacag gaatcgaatg caaccggcgc    5460
aggaacactg ccagcgcatc aacaatattt tcacctgaat caggatattc ttctaatacc    5520
tggaatgctg ttttcccggg gatcgcagtg gtgagtaacc atgcatcatc aggagtacgg    5580
ataaaatgct tgatggtcgg aagaggcata aattccgtca gccagtttag tctgaccatc    5640
tcatctgtaa catcattggc aacgctacct ttgccatgtt tcagaaacaa ctctggcgca    5700
tcgggcttcc catacaatcg atagattgtc gcacctgatt gcccgacatt atcgcgagcc    5760
catttatacc catataaatc agcatccatg ttggaattta atcgcggcct cgagcaagac    5820
gtttcccgtt gaatatggct cataacaccc cttgtattac tgtttatgta agcagacagt    5880
tttattgttc atgatgatat ttttttatct tgtgcaatgt aacatcagag attttgagac    5940
acaacgtggc tttccccccc ccccccattat tgaagcattt atcagggtta ttgtctcatg    6000
agcggataca tatttgaatg tatttagaaa aataaacaaa tagggggtcc gcgcacattt    6060
ccccgaaaag tgccacctga cgtctaagaa accattatta tcatgacatt aacctataaa    6120
aataggcgta tcacgaggcc ctttcgtc                                      6148
```

<210> SEQ ID NO 25  
<211> LENGTH: 10783  
<212> TYPE: DNA  
<213> ORGANISM: Artificial Sequence  
<220> FEATURE:  
<223> OTHER INFORMATION: Synthetic Construct pAD/CMV-GP(dTM)(Z-CITE-S)

<400> SEQUENCE: 25

```
ttaattaacc gcaattctca tgtttgacag cttatcatca tcaataatat accttatttt      60
ggattgaagc caatatgata atgagggggt ggagtttgtg acgtggcgcg ggcgtggga      120
acggggcggg tgacgtagta gtgtggcgga agtgtgatgt tgcaagtgtg gcggaacaca     180
tgtaagcgac ggatgtggca aaagtgacgt ttttggtgtg cgccggtgta cacaggaagt     240
gacaattttc gcgcggtttt aggcggatgt tgtagtaaat ttgggcgtaa ccgagtaaga     300
tttggccatt ttcgcgggaa aactgaataa gaggaagtga aatctgaata attttgtgtt     360
actcatagcg cgtaatattt gtctagggcc gcggggactt tgaccgttta cgtggagact     420
cgcccaggtg ttttttctcag gtgttttccg cgttccgggt caaagttggc gttttattat     480
tatagtcagt acgtaccagt gcactggcct agagcggccc cattgcatac gttgtatcca     540
tatcataata tgtacattta tattggctca tgtccaacat taccgccatg ttgacattga     600
ttattgacta gttattaata gtaatcaatt acggggtcat tagttcatag cccatatatg     660
gagttccgcg ttacataact tacggtaaat ggcccgcctg gctgaccgcc caacgacccc     720
cgcccattga cgtcaataat gacgtatgtt cccatagtaa cgccaatagg gactttccat     780
tgacgtcaat gggtggagta tttacggtaa actgcccact tggcagtaca tcaagtgtat     840
catatgccaa gtacgccccc tattgacgtc aatgacggta aatggcccgc ctggcattat     900
gcccagtaca tgaccttatg ggactttcct acttggcagt acatctacgt attagtcatc     960
gctattacca tggtgatgcg gttttggcag tacatcaatg ggcgtggata gcggtttgac    1020
tcacggggat ttccaagtct ccaccccatt gacgtcaatg ggagtttgtt ttggcaccaa    1080
aatcaacggg actttccaaa atgtcgtaac aactccgccc cattgacgca atgggcggt     1140
aggcgtgtac ggtgggaggt ctatataagc agagctcgtt tagtgaaccg tcagatcgcc    1200
tggagacgcc atccacgctg ttttgacctc catagaagac accggaccg atccagcctc     1260
cgtcaccgtc gtcgacacgt gtgatcagat ctagaccagg ccctggatcg atccaacaac    1320
acaatgggcg ttacaggaat attgcagtta cctcgtgatc gattcaagag gacatcattc    1380
tttctttggg taattatcct tttccaaaga acattttcca tcccacttgg agtcatccac    1440
aatagcacat tacaggttag tgatgtcgac aaactagttt gtcgtgacaa actgtcatcc    1500
acaaatcaat tgagatcagt tggactgaat ctcgaaggga atggagtggc aactgacgtg    1560
ccatctgcaa ctaaaagatg gggcttcagg tccggtgtcc caccaaaggt ggtcaattat    1620
gaagctggtg aatgggctga aaactgctac aatcttgaaa tcaaaaaacc tgacgggagt    1680
gagtgtctac cagcagcgcc agacgggatt cggggcttcc cccggtgccg gtatgtgcac    1740
aaagtatcag gaacgggacc gtgtgccgga gactttgcct tccataaaga gggtgctttc    1800
ttcctgtatg atcgacttgc ttccacagtt atctaccgag gaacgacttt cgctgaaggt    1860
gtcgttgcat ttctgatact gccccaagct aagaaggact tcttcagctc accccttg     1920
agagagccgg tcaatgcaac ggaggacccg tctagtggct actattctac cacaattaga    1980
tatcaggcta ccggttttgg aaccaatgag acagagtact tgttcgaggt tgacaatttg    2040
acctacgtcc aacttgaatc aagattcaca ccacagtttc tgctccagct gaatgagaca    2100
atatatacaa gtgggaaaag gagcaatacc acggaaaaac taatttggaa ggtcaacccc    2160
gaaattgata caacaatcgg ggagtgggcc ttctgggaaa ctaaaaaaaa cctcactaga    2220
aaaattcgca gtgaagagtt gtctttcaca gttgtatcaa acggagccaa aaacatcagt    2280
ggtcagagtc cggcgcgaac ttcttccgac ccagggacca acacaacaac tgaagaccac    2340
```

```
aaaatcatgg cttcagaaaa ttcctctgca atggttcaag tgcacagtca aggaagggaa    2400
gctgcagtgt cgcatctaac aaccccttgcc acaatctcca cgagtcccca atccctcaca    2460
accaaaccag gtccggacaa cagcacccat aatacacccg tgtataaact tgacatctct    2520
gaggcaactc aagttgaaca acatcaccgc agaacagaca acgacagcac agcctccgac    2580
actccctctg ccacgaccgc agccggaccc caaaagcag agaacaccaa cacgagcaag    2640
agcactgact tcctggaccc cgccaccaca acaagtcccc aaaaccacag cgagaccgct    2700
ggcaacaaca acactcatca ccaagatacc ggagaagaga gtgccagcag cgggaagcta    2760
ggcttaatta ccaatactat tgctggagtc gcaggactga tcacaggcgg gagaagaact    2820
cgaagagaag caattgtcaa tgctcaaccc aaatgcaacc ctaatttaca ttactggact    2880
actcaggatg aaggtgctgc aatcggactg gcctggatac catatttcgg gccagcagcc    2940
gagggaattt acatagaggg gctaatgcac aatcaagatg gtttaatctg tgggttgaga    3000
cagctggcca acgagacgac tcaagctctt caactgttcc tgagagccac aactgagcta    3060
cgcacctttt caatcctcaa ccgtaaggca attgatttct tgctgcagcg atggggcggc    3120
acatgccaca ttctgggacc ggactgctgt atcgaaccac atgattggac caagaacata    3180
acagacaaaa ttgatcagat tattcatgat tttgttgata aaacccttcc ggaccagggg    3240
gacaatgaca attggtggac aggatggaga caatggatgg ccgcatcgtg actgactgac    3300
gatctgcctc gcgagatcaa ttccgcccct ctccctcccc ccccctaac gttactggcc    3360 gaagccgctt ggaataaggc cggtgtgcgt ttgtctatat gttatttcc accatattgc    3420 cgtctttggg caatgtgagg gcccggaaac ctggccctgt cttcttgacg agcattccta    3480
ggggtctttc ccctctcgcc aaaggaatgc aaggtctgtt gaatgtcgtg aaggaagcag    3540
ttcctctgga agcttcttga agacaaacaa cgtctgtagc gaccctttgc aggcagcgga    3600
accccccacc tggcgacagg tgcctctgcg gccaaaagcc acgtgtataa gatacacctg    3660
caaaggcggc acaaccccag tgccacgttg tgagttggat agttgtggaa agagtcaaat    3720
ggctctcctc aagcgtattc aacaagggc tgaaggatgc ccagaaggta ccccattgta    3780
tgggatctga tctggggcct cggtgcacat gctttacatg tgtttagtcg aggttaaaaa    3840
acgtctaggc cccccgaacc acggggacgt ggttttcctt tgaaaaacac gatgataata    3900
tggccacaac catggagggt cttagcctac tccaattgcc cagagataaa tttcgaaaaa    3960
gctctttctt tgtttgggtc atcatcttat ttcaaaaggc cttttccatg cctttgggtg    4020
ttgtgaccaa cagcacttta gaagtaacag agattgacca gctagtctgc aaggatcatc    4080
ttgcatccac tgaccagctg aaatcagttg gtctcaacct cgaggggagc ggagtatcta    4140
ctgatatccc atctgcgaca aagcgttggg gcttcagatc tggtgtgcct cccaaggtgg    4200
tcagctatga agcaggagaa tgggctgaaa attgctacaa tcttgaaata aagaagccgg    4260
acgggagcga atgcttaccc ccaccgccgg atggtgtcag aggctttcca aggtgccgct    4320
atgttcacaa agcccaagga accgggcct gcccggtga ctatgccttt cacaaggatg    4380
gagctttctt cctctatgac aggctggctt caactgtaat ttacagagga gtcaattttg    4440 ctgaggggt aattgcattc ttgatattgg ctaaaccaaa ggaaacgttc cttcaatcac    4500
cccccattcg agaggcagta aactacactg aaaatacatc aagttactat gccacatcct    4560
acttggagta cgaaatcgaa aattttggtg ctcaacactc cacgacccct ttcaaaatta    4620
acaataatac ttttgttctt ctggacaggc cccacacgcc tcagttcctt ttccagctga    4680
atgataccat tcaccttcac caacagttga gcaacacaac tgggaaacta atttggacac    4740
```

```
tagatgctaa tatcaatgct gatattggtg aatgggcttt ttgggaaaat aaaaaaaatc    4800
tctccgaaca actacgtgga gaagagctgt ctttcgaaac tttatcgctc aacgagacag    4860
aagacgatga tgcgacatcg tcgagaacta caaagggaag aatctccgac cgggccacca    4920
ggaagtattc ggacctggtt ccaaaggatt ccctgggat ggtttcattg cacgtaccag     4980
aaggggaaac aacattgccg tctcagaatt cgacagaagg tcgaagagta gatgtgaata    5040
ctcaggaaac tatcacagag acaactgcaa caatcatagg cactaacggt aacaacatgc    5100
agatctccac catcgggaca ggactgagct ccagccaaat cctgagttcc tcaccgacca    5160
tggcaccaag ccctgagact cagacctcca caacctacac accaaaacta ccagtgatga    5220
ccaccgagga accaacaaca ccaccgagaa actctcctgg ctcaacaaca gaagcaccca    5280
ctctcaccac cccagagaat ataacaacag cggttaaaac tgttttgcca caagagtcca    5340
caagcaacgg tctaataact tcaacagtaa cagggattct tgggagcctt ggacttcgaa    5400
aacgcagcag aagacaagtt aacaccaggg ccacgggtaa atgcaatccc aacttacact    5460
actggactgc acaagaacaa cataatgctg ctgggattgc ctggatcccg tactttggac    5520
cgggtgcaga aggcatatac actgaaggcc ttatgcacaa ccaaaatgcc ttagtctgtg    5580
gactcagaca acttgcaaat gaaacaactc aagctctgca gcttttctta agggccacga    5640
cggagctgcg gacatatacc atactcaata ggaaggccat agatttcctt ctgcgacgat    5700
ggggcgggac atgtaggatc ctgggaccag attgttgcat tgagccacat gattggacca    5760
aaaacatcac tgataaaatc aaccaaatca tccatgattt catcgacaac cctttaccca    5820
atcaggataa tgatgataat tggtggacgg gctggagaca gtggatcccg gccgcatcgt    5880
gactgactga cgatctgcct cgcggatcca gatctgctgt gccttctagt tgccagccat    5940
ctgttgtttg cccctccccc gtgccttcct tgaccctgga aggtgccact cccactgtcc    6000
tttcctaata aaatgaggaa attgcatcgc attgtctgag taggtgtcat tctattctgg    6060
ggggtggggt ggggcagcac agcaagggg aggattggga agacaatagc aggcatgctg     6120
gggatgcggt gggctctatg ggtacccagg gccgcataac ttcgtataat gtatgctata    6180
cgaagttata agatctgtac tgaaatgtgt gggcgtggct taagggtggg aaagaatata    6240
taaggtgggg gtcttatgta gttttgtatc tgttttgcag cagccgccgc cgccatgagc    6300
accaactcgt ttgatggaag cattgtgagc tcatatttga caacgcgcat gccccatgg     6360 gccggggtgc gtcagaatgt gatgggctcc agcattgatg gtcgccccgt cctgcccgca    6420
aactctacta ccttgaccta cgagaccgtg tctggaacgc cgttggagac tgcagcctcc    6480
gccgccgctt cagccgctgc agccaccgcc cgcgggattg tgactgactt tgctttcctg    6540
agcccgcttg caagcagtgc agcttcccgt tcatccgccc gcgatgacaa gttgacggct    6600
cttttggcac aattggattc tttgacccgg gaacttaatg tcgtttctca gcagctgttg    6660
gatctgcgcc agcaggtttc tgccctgaag gcttcctccc ctcccaatgc ggtttaaaac    6720
ataaataaaa aaccagactc tgtttggatt tggatcaagc aagtgtcttg ctgtctttat    6780
ttaggggttt tgcgcgcgcg gtaggcccgg gaccagcggt ctcggtcgtt gagggtcctg    6840 tgtattttt ccaggacgtg gtaaaggtga ctctggatgt tcagatacat gggcataagc     6900
ccgtctctgg ggtggaggta gcaccactgc agagcttcat gctgcgggt ggtgttgtag     6960 atgatccagt cgtagcagga gcgctgggcg tggtgcctaa aaatgtcttt cagtagcaag    7020
ctgattgcca ggggcaggcc cttggtgtaa gtgtttacaa agcggttaag ctgggatggg    7080
tgcatacgtg gggatatgag atgcatcttg gactgtattt ttaggttggc tatgttccca    7140
```

```
gccatatccc tccggggatt catgttgtgc agaaccacca gcacagtgta tccggtgcac    7200
ttgggaaatt tgtcatgtag cttagaagga aatgcgtgga agaacttgga gacgcccttg    7260
tgacctccaa gattttccat gcattcgtcc ataatgatgg caatgggccc acgggcggcg    7320
gcctgggcga agatatttct gggatcacta acgtcatagt tgtgttccag gatgagatcg    7380
tcataggcca ttttacaaa gcgcgggcgg agggtgccag actgcggtat aatggttcca     7440
tccggcccag gggcgtagtt accctcacag atttgcattt cccacgcttt gagttcagat    7500 gggggatca tgtctacctg cggggcgatg aagaaaacgg tttccggggt aggggagatc     7560
agctgggaag aaagcaggtt cctgagcagc tgcgacttac cgcagccggt gggcccgtaa    7620
atcacaccta ttaccggctg caactggtag ttaagagagc tgcagctgcc gtcatccctg    7680
agcagggggg ccacttcgtt aagcatgtcc ctgactcgca tgttttccct gaccaaatcc    7740
gccagaaggc gctcgccgcc cagcgatagc agttcttgca aggaagcaaa gttttcaac     7800 ggtttgagac cgtccgccgt aggcatgctt ttgagcgttt gaccaagcag ttccaggcgg    7860
tcccacagct cggtcacctg ctctacggca tctcgatcca gcatatctcc tcgtttcgcg    7920
ggttggggcg gctttcgctg tacggcagta gtcggtgctc gtccagacgg ccagggtca    7980 tgtctttcca cgggcgcagg gtcctcgtca gcgtagtctg ggtcacggtg aaggggtgcg    8040
ctccgggctg cgcgctggcc agggtgcgct tgaggctggt cctgctggtg ctgaagcgct    8100
gccggtcttc gccctgcgcg tcggccaggt agcatttgac catggtgtca tagtccagcc    8160
cctccgcggc gtgccccttg gcgcgcagct gcccttgga ggaggcgccg cacgaggggc     8220
agtgcagact tttgagggcg tagagcttgg gcgcgagaaa taccgattcc ggggagtagg    8280
catccgcgcc gcaggccccg cagacggtct cgcattccac gagccaggtg agctctggcc    8340
gttcggggtc aaaaaccagg tttcccccat gcttttgat gcgtttctta cctctggttt     8400
ccatgagccg gtgtccacgc tcggtgacga aaaggctgtc cgtgtcccg tatacagact     8460 tgagaggcct gtcctcgagc ggtgttccgc ggtcctcctc gtatagaaac tcggaccact    8520
ctgagacaaa ggctcgcgtc caggccagca cgaaggaggc taagtgggag gggtagcggt    8580
cgttgtccac taggggtcc actcgctcca gggtgtgaag acacatgtcg ccctcttcgg     8640
catcaaggaa ggtgattggt ttgtaggtgt aggccacgtg accgggtgtt cctgaagggg    8700
ggctataaaa gggggtgggg gcgcgttcgt cctcactctc ttccgcatcg ctgtctgcga    8760
gggccagctg ttggggtgag tcgacgcgag gctggatggc cttccccatt atgattcttc    8820
tcgcttccgg cggcatcggg atgcccgcgt tgcaggccat gctgtccagg caggtagatg    8880
acgaccatca gggacagctt caaggccagc aaaaggccag gaaccgtaaa aaggccgcgt    8940
tgctggcgtt tttccatagg ctccgccccc ctgacgagca tcacaaaaat cgacgctcaa    9000
gtcagaggtg gcgaaacccg acaggactat aaagatacca ggcgtttccc cctggaagct    9060
ccctcgtgcg ctctcctgtt ccgaccctgc cgcttaccgg atacctgtcc gcctttctcc    9120
cttcgggaag cgtggcgctt tctcatagct cacgctgtag gtatctcagt tcggtgtagg    9180
tcgttcgctc caagctgggc tgtgtgcacg aacccccgt tcagcccgac cgctgcgcct     9240
tatccggtaa ctatcgtctt gagtccaacc cggtaagaca cgacttatcg ccactggcag    9300
cagccactgg taacaggatt agcagagcga ggtatgtagg cggtgctaca gagttcttga    9360
agtggtggcc taactacggc tacactagaa ggacagtatt tggtatctgc gctctgctga    9420
agccagttac cttcggaaaa agagttggta gctcttgatc cggcaaacaa accaccgctg    9480
gtagcggtgg ttttttttgtt tgcaagcagc agattacgcg cagaaaaaaa ggatctcaag    9540
```

```
aagatccttt gatcttttct acggggtctg acgctcagtg gaacgaaaac tcacgttaag    9600
ggattttggt catgagatta tcaaaaagga tcttcaccta gatccttta aattaaaaat    9660 gaagttttaa atcaatctaa agtatatatg agtaaacttg gtctgacagt taccaatgct    9720
taatcagtga ggcacctatc tcagcgatct gtctatttcg ttcatccata gttgcctgac    9780
tccccgtcgt gtagataact acgatacggg agggcttacc atctggcccc agtgctgcaa    9840
tgataccgcg agacccacgc tcaccggctc cagatttatc agcaataaac cagccagccg    9900
gaagggccga gcgcagaagt ggtcctgcaa ctttatccgc ctccatccag tctattaatt    9960
gttgccggga agctagagta agtagttcgc cagttaatag tttgcgcaac gttgttgcca   10020
ttgctgcagg catcgtggtg tcacgctcgt cgtttggtat ggcttcattc agctccggtt   10080
cccaacgatc aaggcgagtt acatgatccc ccatgttgtg caaaaaagcg gttagctcct   10140
tcggtcctcc gatcgttgtc agaagtaagt tggccgcagt gttatcactc atggttatgg   10200
cagcactgca taattctctt actgtcatgc catccgtaag atgcttttct gtgactggtg   10260
agtactcaac caagtcattc tgagaatagt gtatgcggcg accgagttgc tcttgcccgg   10320
cgtcaacacg ggataatacc gcgccacata gcagaacttt aaaagtgctc atcattggaa   10380
aacgttcttc ggggcgaaaa ctctcaagga tcttaccgct gttgagatcc agttcgatgt   10440
aacccactcg tgcacccaac tgatcttcag catcttttac tttcaccagc gtttctgggt   10500
gagcaaaaac aggaaggcaa atgccgcaa aaagggaat aagggcgaca cggaaatgtt   10560
gaatactcat actcttcctt tttcaatatt attgaagcat ttatcagggt tattgtctca   10620
tgagcggata catatttgaa tgtatttaga aaaataaaca aataggggtt ccgcgcacat   10680
ttccccgaaa agtgccacct gacgtctaag aaaccattat tatcatgaca ttaacctata   10740
aaaataggcg tatcacgagg ccctttcgtc ttcaagaatt gtt                      10783

<210> SEQ ID NO 26
<211> LENGTH: 8338
<212> TYPE: DNA
<213> ORGANISM: Artificial Sequence
<220> FEATURE:
<223> OTHER INFORMATION: Synthetic Construct pAdApt Ebola GP(S)

<400> SEQUENCE: 26
ttaattaacc gcaattctca tgtttgacag cttatcatca tcaataatat accttatttt      60
ggattgaagc caatatgata atgagggggt ggagtttgtg acgtggcgcg ggcgtgggga     120
acggggcggg tgacgtagta gtgtggcgga agtgtgatgt tgcaagtgtg gcggaacaca     180
tgtaagcgac ggatgtggca aaagtgacgt ttttggtgtg cgccggtgta cacaggaagt     240 gacaatttc gcgcggtttt aggcggatgt tgtagtaaat ttgggcgtaa ccgagtaaga     300
tttggccatt ttcgcgggaa aactgaataa gaggaagtga atctgaata attttgtgtt     360 actcatagcg cgtaatattt gtctagggcc gcggggactt tgaccgttta cgtggagact     420
cgcccaggtg ttttctcag gtgttttccg cgttccgggt caaagttggc gttttattat     480
tatagtcagt acgtaccagt gcactggcct agagcggccc cattgcatac gttgtatcca     540
tatcataata tgtacattta tattggctca tgtccaacat taccgccatg ttgacattga     600
ttattgacta gttattaata gtaatcaatt acggggtcat tagttcatag cccatatatg     660
gagttccgcg ttacataact tacggtaaat ggcccgcctg gctgaccgcc caacgacccc     720
cgcccattga cgtcaataat gacgtatgtt cccatagtaa cgccaatagg gactttccat     780
tgacgtcaat gggtggagta tttacggtaa actgcccact tggcagtaca tcaagtgtat     840
```

```
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ccagtgtgat ggatatctgc   1320
agaattcggc ttatcttcag gatctcgcca tggagggtct tagcctactc caattgccca   1380
gagataaatt tcgaaaaagc tctttctttg tttgggtcat catcttattt caaaaggcct   1440
tttccatgcc tttgggtgtt gtgaccaaca gcactttaga agtaacagag attgaccagc   1500
tagtctgcaa ggatcatctt gcatccactg accagctgaa atcagttggt ctcaacctcg   1560
aggggagcgg agtatctact gatatcccat ctgcgacaaa gcgttggggc ttcagatctg   1620
gtgtgcctcc caaggtggtc agctatgaag caggagaatg ggctgaaaat tgctacaatc   1680
ttgaaataaa gaagccggac gggagcgaat gcttaccccc accgccggat ggtgtcagag   1740
gctttccaag gtgccgctat gttcacaaag cccaaggaac cgggccctgc ccgggtgact   1800
atgcctttca caaggatgga gctttcttcc tctatgacag gctggcttca actgtaattt   1860
acagaggagt caattttgct gagggggtaa ttgcattctt gatattggct aaaccaaagg   1920
aaacgttcct tcaatcaccc cccattcgag aggcagtaaa ctacactgaa aatacatcaa   1980
gttactatgc cacatcctac ttggagtacg aaatcgaaaa ttttggtgct caacactcca   2040 cgacccttttt caaaattaac aataatactt ttgttcttct ggacaggccc cacacgcctc   2100
agttcctttt ccagctgaat gataccattc accttcacca acagttgagc aacacaactg   2160
ggaaactaat ttggacacta gatgctaata tcaatgctga tattggtgaa tgggcttttt   2220
gggaaaataa aaaaaatctc tccgaacaac tacgtggaga agagctgtct ttcgaaactt   2280
tatcgctcaa cgagacagaa gacgatgatg cgacatcgtc gagaactaca aagggaagaa   2340
tctccgaccg ggccaccagg aagtattcgg acctggttcc aaaggattcc cctgggatgg   2400
tttcattgca cgtaccagaa ggggaaacaa cattgccgtc tcagaattcg acagaaggtc   2460
gaagagtaga tgtgaatact caggaaacta tcacagagac aactgcaaca atcataggca   2520
ctaacggtaa caacatgcag atctccacca tcgggacagg actgagctcc agccaaatcc   2580
tgagttcctc accgaccatg gcaccaagcc ctgagactca gacctccaca acctacacac   2640
caaaactacc agtgatgacc accgaggaac caacaacacc accgagaaac tctcctggct   2700
caacaacaga agcacccact ctcaccaccc cagagaatat aacaacagcg gttaaaactg   2760
ttttgccaca agagtccaca agcaacggtc taataacttc aacagtaaca gggattcttg   2820
ggagccttgg acttcgaaaa cgcagcagaa gacaagttaa caccagggcc acgggtaaat   2880
gcaatcccaa cttacactac tggactgcac aagaacaaca taatgctgct gggattgcct   2940
ggatcccgta ctttggaccg ggtgcagaag gcatatacac tgaaggcctt atgcacaacc   3000
aaaatgcctt agtctgtgga ctcagacaac ttgcaaatga aacaactcaa gctctgcagc   3060
ttttcttaag ggccacgacg gagctgcgga catataccat actcaatagg aaggccatag   3120
atttccttct gcgacgatgg ggcgggacat gtaggatcct gggaccagat tgttgcattg   3180
agccacatga ttggaccaaa aacatcactg ataaaatcaa ccaaatcatc catgatttca   3240
```

```
tcgacaaccc tttacccaat caggataatg atgataattg gtggacgggc tggagacagt    3300
ggatccctgc aggaataggc attactggaa ttattattgc aatcattgct cttctttgcg    3360
tctgcaagct gctttgttga atatcaagcc gaattccagc acactggcgg ccgttactag    3420
tggatccgag ctcggatcca agctctagac caggccctgg atccagatct gctgtgcctt    3480
ctagttgcca gccatctgtt gtttgcccct ccccgtgcc ttccttgacc ctggaaggtg     3540
ccactcccac tgtcctttcc taataaaatg aggaaattgc atcgcattgt ctgagtaggt    3600
gtcattctat tctgggggt ggggtggggc aggacagcaa gggggaggat tgggaagaca     3660
atagcaggca tgctggggat gcggtgggct ctatgggtac ccagggccgc ataacttcgt    3720
ataatgtatg ctatacgaag ttataagatc tgtactgaaa tgtgtgggcg tggcttaagg    3780
gtgggaaaga atatataagg tgggggtctt atgtagtttt gtatctgttt tgcagcagcc    3840
gccgccgcca tgagcaccaa ctcgtttgat ggaagcattg tgagctcata tttgacaacg    3900
cgcatgcccc catgggccgg ggtgcgtcag aatgtgatgg gctccagcat tgatggtcgc    3960
cccgtcctgc ccgcaaactc tactaccttg acctacgaga ccgtgtctgg aacgccgttg    4020
gagactgcag cctccgccgc cgcttcagcc gctgcagcca ccgcccgcgg gattgtgact    4080
gactttgctt tcctgagccc gcttgcaagc agtgcagctt cccgttcatc cgcccgcgat    4140
gacaagttga cggctctttt ggcacaattg gattctttga cccgggaact taatgtcgtt    4200
tctcagcagc tgttggatct gcgccagcag gtttctgccc tgaaggcttc ctcccctccc    4260
aatgcggttt aaaacataaa taaaaaacca gactctgttt ggatttggat caagcaagtg    4320
tcttgctgtc tttatttagg ggttttgcgc gcgcggtagg cccgggacca gcggtctcgg    4380
tcgttgaggg tcctgtgtat ttttttccagg acgtggtaaa ggtgactctg gatgttcaga    4440
tacatgggca taagcccgtc tctggggtgg aggtagcacc actgcagagc ttcatgctgc    4500
ggggtggtgt tgtagatgat ccagtcgtag caggagcgct gggcgtggtg cctaaaaatg    4560
tctttcagta gcaagctgat tgccaggggc aggcccttgg tgtaagtgtt tacaaagcgg    4620
ttaagctggg atgggtgcat acgtggggat atgagatgca tcttggactg tatttttagg    4680
ttggctatgt tcccagccat atccctccgg ggattcatgt tgtgcagaac caccagcaca    4740
gtgtatccgg tgcacttggg aaatttgtca tgtagcttag aaggaaatgc gtggaagaac    4800
ttggagacgc ccttgtgacc tccaagattt tccatgcatt cgtccataat gatggcaatg    4860
ggcccacggg cggcggcctg ggcgaagata tttctgggat cactaacgtc atagttgtgt    4920
tccaggatga gatcgtcata ggccatttt acaaagcgcg gcggagggt gccagactgc      4980 ggtataatgg ttccatccgg cccaggggcg tagttaccct cacagatttg catttcccac    5040
gctttgagtt cagatggggg gatcatgtct acctgcgggg cgatgaagaa aacggtttcc    5100
ggggtagggg agatcagctg ggaagaaagc aggttcctga gcagctgcga cttaccgcag    5160
ccggtgggcc cgtaaatcac acctattacc ggctgcaact ggtagttaag agagctgcag    5220
ctgccgtcat ccctgagcag gggggccact tcgttaagca tgtccctgac tcgcatgttt    5280
tccctgacca aatccgccag aaggcgctcg ccgcccagca atagcagttc ttgcaaggaa    5340
gcaaagtttt tcaacggttt gagaccgtcc gccgtaggca tgcttttgag cgtttgacca    5400
agcagttcca ggcggtccca cagctcggtc acctgctcta cggcatctcg atccagcata    5460
tctcctcgtt tcgcgggttg gggcggcttt cgctgtacgg cagtagtcgg tgctcgtcca    5520
gacgggccag ggtcatgtct ttccacgggc gcagggtcct cgtcagcgta gtctgggtca    5580
cggtgaaggg gtgcgctccg ggctgcgcgc tggccagggt gcgcttgagg ctggtcctgc    5640
```

```
tggtgctgaa gcgctgccgg tcttcgccct gcgcgtcggc caggtagcat ttgaccatgg   5700
tgtcatagtc cagcccctcc gcggcgtggc ccttggcgcg cagcttgccc ttggaggagg   5760
cgccgcacga ggggcagtgc agacttttga gggcgtagag cttgggcgcg agaaataccg   5820
attccgggga gtaggcatcc gcgccgcagg ccccgcagac ggtctcgcat ccacgagcc    5880 aggtgagctc tggccgttcg gggtcaaaaa ccaggtttcc cccatgcttt ttgatgcgtt   5940
tcttacctct ggtttccatg agccggtgtc cacgctcggt gacgaaaagg ctgtccgtgt   6000
ccccgtatac agacttgaga ggcctgtcct cgagcggtgt tccgcggtcc tcctcgtata   6060
gaaactcgga ccactctgag acaaaggctc gcgtccaggc cagcacgaag gaggctaagt   6120
gggaggggta gcggtcgttg tccactaggg ggtccactcg ctccagggtg tgaagacaca   6180
tgtcgccctc ttcggcatca aggaaggtga ttggtttgta ggtgtaggcc acgtgaccgg   6240
gtgttcctga aggggggcta taaaaggggg tggggggcgcg ttcgtcctca ctctcttccg   6300
catcgctgtc tgcgagggcc agctgttggg gtgagtcgac gcgaggctgg atggccttcc   6360
ccattatgat tcttctcgct tccggcggca tcgggatgcc cgcgttgcag gccatgctgt   6420
ccaggcaggt agatgacgac catcagggac agcttcaagg ccagcaaaag gccaggaacc   6480
gtaaaaaggc cgcgttgctg gcgttttttcc ataggctccg ccccctgac gagcatcaca   6540 aaaatcgacg ctcaagtcag aggtggcgaa acccgacagg actataaaga taccaggcgt   6600
ttccccctgg aagctccctc gtgcgctctc ctgttccgac cctgccgctt accggatacc   6660
tgtccgcctt tctcccttcg ggaagcgtgg cgctttctca tagctcacgc tgtaggtatc   6720
tcagttcggt gtaggtcgtt cgctccaagc tgggctgtgt gcacgaaccc cccgttcagc   6780
ccgaccgctg cgccttatcc ggtaactatc gtcttgagtc aacccggta agacacgact   6840 tatcgccact ggcagcagcc actggtaaca ggattagcag agcgaggtat gtaggcggtg   6900
ctacagagtt cttgaagtgg tggcctaact acggctacac tagaaggaca gtatttggta   6960
tctgcgctct gctgaagcca gttaccttcg gaaaaagagt tggtagctct tgatccggca   7020
aacaaaccac cgctggtagc ggtggttttt ttgtttgcaa gcagcagatt acgcgcagaa   7080
aaaaaggatc tcaagaagat cctttgatct tttctacggg gtctgacgct cagtggaacg   7140
aaaactcacg ttaagggatt ttggtcatga gattatcaaa aaggatcttc acctagatcc   7200
ttttaaatta aaaatgaagt tttaaatcaa tctaaagtat atatgagtaa acttggtctg   7260
acagttacca atgcttaatc agtgaggcac ctatctcagc gatctgtcta tttcgttcat   7320
ccatagttgc ctgactcccc gtcgtgtaga taactacgat acgggagggc ttaccatctg   7380
gccccagtgc tgcaatgata ccgcgagacc cacgctcacc ggctccagat ttatcagcaa   7440
taaaccagcc agccggaagg gccgagcgca gaagtggtcc tgcaacttta tccgcctcca   7500
tccagtctat taattgttgc cgggaagcta gagtaagtag ttcgccagtt aatagtttgc   7560
gcaacgttgt tgccattgct gcaggcatcg tggtgtcacg ctcgtcgttt ggtatggctt   7620
cattcagctc cggttcccaa cgatcaaggc gagttacatg atcccccatg ttgtgcaaaa   7680
aagcggttag ctccttcggt cctccgatcg ttgtcagaag taagttggcc gcagtgttat   7740
cactcatggt tatggcagca ctgcataatt ctcttactgt catgccatcc gtaagatgct   7800
tttctgtgac tggtgagtac tcaaccaagt cattctgaga atagtgtatg cggcgaccga   7860
gttgctcttg cccggcgtca acacgggata ataccgcgcc acatagcaga actttaaaag   7920
tgctcatcat tggaaaacgt tcttcggggc gaaaactctc aaggatctta ccgctgttga   7980
gatccagttc gatgtaaccc actcgtgcac ccaactgatc ttcagcatct tttactttca   8040
```

```
ccagcgtttc tgggtgagca aaaacaggaa ggcaaaatgc cgcaaaaaag ggaataaggg    8100
cgacacggaa atgttgaata ctcatactct tccttttttca atattattga agcatttatc   8160
agggttattg tctcatgagc ggatacatat ttgaatgtat ttagaaaaat aaacaaatag    8220
gggttccgcg cacatttccc cgaaaagtgc cacctgacgt ctaagaaacc attattatca    8280
tgacattaac ctataaaaat aggcgtatca cgaggccctt tcgtcttcaa gaattgtt     8338

<210> SEQ ID NO 27
<211> LENGTH: 8221
<212> TYPE: DNA
<213> ORGANISM: Artificial Sequence
<220> FEATURE:
<223> OTHER INFORMATION: Synthetic Construct pAdApt Ebola GP(S)(dTM)

<400> SEQUENCE: 27
ttaattaacc gcaattctca tgtttgacag cttatcatca tcaataatat accttatttt    60
ggattgaagc caatatgata atgaggggggt ggagtttgtg acgtggcgcg gggcgtggga   120
acggggcggg tgacgtagta gtgtggcgga agtgtgatgt tgcaagtgtg gcggaacaca   180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga   300
tttggccatt ttcgcgggaa aactgaataa gaggaagtga aatctgaata attttgtgtt   360
actcatagcg cgtaatattt gtctagggcc gcggggactt tgaccgttta cgtggagact   420
cgcccaggtg ttttttctcag gtgttttccg cgttccgggt caaagttggc gttttattat   480
tatagtcagt acgtaccagt gcactggcct agagcggccc cattgcatac gttgtatcca   540
tatcataata tgtacattta tattggctca tgtccaacat taccgccatg ttgacattga   600
ttattgacta gttattaata gtaatcaatt acggggtcat tagttcatag cccatatatg   660
gagttccgcg ttacataact tacggtaaat ggcccgcctg gctgaccgcc caacgacccc   720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac    1020
tcacggggat ttccaagtct ccaccccatt gacgtcaatg ggagtttgtt ttggcaccaa   1080
aatcaacggg actttccaaa atgtcgtaac aactccgccc cattgacgca atgggcggt    1140 aggcgtgtac ggtgggaggt ctatataagc agagctcgtt tagtgaaccg tcagatcgcc    1200
tggagacgcc atccacgctg ttttgacctc catagaagac accgggaccg atccagcctc    1260
cgtcaccgtc gtcgacacgt gtgatcagat atcgcggccg ccagtgtgat ggatatctgc    1320
agaattcggc ttatcttcag gatctcgcca tggagggtct tagcctactc caattgccca    1380
gagataaatt tcgaaaaagc tctttctttg tttgggtcat catcttattt caaaaggcct    1440
tttccatgcc tttgggtgtt gtgaccaaca gcacttttaga agtaacagag attgaccagc    1500
tagtctgcaa ggatcatctt gcatccactg accagctgaa atcagttggt ctcaacctcg    1560
aggggagcgg agtatctact gatatcccat ctgcgacaaa gcgttgggc ttcagatctg     1620 gtgtgcctcc caaggtggtc agctatgaag caggagaatg ggctgaaaat tgctacaatc   1680
ttgaaataaa gaagccggac gggagcgaat gcttaccccc accgccggat ggtgtcagag    1740
gctttccaag gtgccgctat gttcacaaag cccaaggaac cgggccctgc ccgggtgact    1800
```

```
atgcctttca caaggatgga gctttcttcc tctatgacag gctggcttca actgtaattt    1860
acagaggagt caattttgct gaggggggtaa ttgcattctt gatattggct aaaccaaagg    1920
aaacgttcct tcaatcaccc cccattcgag aggcagtaaa ctacactgaa aatacatcaa    1980
gttactatgc cacatcctac ttggagtacg aaatcgaaaa ttttggtgct caacactcca    2040
cgaccctttt caaaattaac aataatactt ttgttcttct ggacaggccc cacacgcctc    2100
agttcctttt ccagctgaat gataccattc accttcacca acagttgagc aacacaactg    2160
ggaaactaat ttggacacta gatgctaata tcaatgctga tattggtgaa tgggcttttt    2220
gggaaaataa aaaaaatctc tccgaacaac tacgtggaga agagctgtct ttcgaaactt    2280
tatcgctcaa cgagacagaa gacgatgatg cgacatcgtc gagaactaca aagggaagaa    2340
tctccgaccg ggccaccagg aagtattcgg acctggttcc aaaggattcc cctgggatgg    2400
tttcattgca cgtaccagaa ggggaaacaa cattgccgtc tcagaattcg acagaaggtc    2460
gaagagtaga tgtgaatact caggaaacta tcacagadac aactgcaaca atcataggca    2520
```

```
gtgtcttgct gtctttattt aggggttttg cgcgcgcggt aggcccggga ccagcggtct    4260
cggtcgttga gggtcctgtg tatttttcc aggacgtggt aaaggtgact ctggatgttc    4320
agatacatgg gcataagccc gtctctgggg tggaggtagc accactgcag agcttcatgc    4380
tgcggggtgg tgttgtagat gatccagtcg tagcaggagc gctgggcgtg gtgcctaaaa    4440
atgtctttca gtagcaagct gattgccagg ggcaggccct tggtgtaagt gtttacaaag    4500
cggttaagct gggatgggtg catacgtggg gatatgagat gcatcttgga ctgtatttt     4560 aggttggcta tgttcccagc catatccctc cggggattca tgttgtgcag aaccaccagc    4620
acagtgtatc cggtgcactt gggaaatttg tcatgtagct tagaaggaaa tgcgtggaag    4680
aacttggaga cgcccttgtg acctccaaga ttttccatgc attcgtccat aatgatggca    4740
atgggcccac gggcggcggc ctgggcgaag atatttctgg gatcactaac gtcatagttg    4800
tgttccagga tgagatcgtc ataggccatt tttacaaagc gcgggcggag ggtgccagac    4860
tgcggtataa tggttccatc cggcccaggg gcgtagttac cctcacagat ttgcatttcc    4920
cacgctttga gttcagatgg ggggatcatg tctacctgcg gggcgatgaa gaaaacggtt    4980
tccggggtag gggagatcag ctgggaagaa agcaggttcc tgagcagctg cgacttaccg    5040
cagccggtgg gcccgtaaat cacacctatt accggctgca actggtagtt aagagagctg    5100
cagctgccgt catccctgag cagggggggcc acttcgttaa gcatgtccct gactcgcatg    5160 ttttcctga ccaaatccgc cagaaggcgc tcgccgccca gcgatagcag ttcttgcaag    5220
gaagcaaagt ttttcaacgg tttgagaccg tccgccgtag gcatgctttt gagcgtttga    5280
ccaagcagtt ccaggcggtc ccacagctcg gtcacctgct ctacggcatc tcgatccagc    5340
atatctcctc gtttcgcggg ttggggcggc tttcgctgta cggcagtagt cggtgctcgt    5400
ccagacgggc cagggtcatg tctttccacg ggcgcagggt cctcgtcagc gtagtctggg    5460
tcacggtgaa ggggtgcgct ccgggctgcg cgctggccag ggtgcgcttg aggctggtcc    5520
tgctggtgct gaagcgctgc cggtcttcgc cctgcgcgtc ggccaggtag catttgacca    5580
tggtgtcata gtccagcccc tccgcggcgt ggcccttggc gcgcagcttg cccttggagg    5640
aggcgccgca cgaggggcag tgcagacttt tgagggcgta gagcttgggc gcgagaaata    5700
ccgattccgg ggagtaggca tccgcgccgc aggcccccgca gacggtctcg cattccacga    5760
gccaggtgag ctctggccgt cgggggtcaa aaaccaggtt tcccccatgc tttttgatgc    5820
gtttcttacc tctggtttcc atgagccggt gtccacgctc ggtgacgaaa aggctgtccg    5880
tgtccccgta tacagacttg agaggcctgt cctcgagcgg tgttccgcgg tcctcctcgt    5940
atagaaactc ggaccactct gagacaaagg ctcgcgtcca ggccagcacg aaggaggcta    6000
agtgggaggg gtagcggtcg ttgtccacta gggggtccac tcgctccagg gtgtgaagac    6060
acatgtcgcc ctcttcggca tcaaggaagg tgattggttt gtaggtgtag gccacgtgac    6120
cgggtgttcc tgaagggggg ctataaaagg gggtgggggc gcgttcgtcc tcactctctt    6180
ccgcatcgct gtctgcgagg gccagctgtt ggggtgagtc gacgcgaggc tggatggcct    6240
tccccattat gattcttctc gcttccggcg gcatcgggat gcccgcgttg caggccatgc    6300
tgtccaggca ggtagatgac gaccatcagg gacagcttca aggccagcaa aaggccagga    6360
accgtaaaaa ggccgcgttg ctggcgtttt tccataggct ccgcccccct gacgagcatc    6420
acaaaaatcg acgctcaagt cagaggtggc gaaacccgac aggactataa agataccagg    6480
cgtttccccc tggaagctcc ctcgtgcgct ctcctgttcc gaccctgccg cttaccggat    6540
acctgtccgc ctttctccct tcgggaagcg tggcgctttc tcatagctca cgctgtaggt    6600
```

| | |
|---|---|
| atctcagttc ggtgtaggtc gttcgctcca agctgggctg tgtgcacgaa ccccccgttc | 6660 |
| agcccgaccg ctgcgcctta tccggtaact atcgtcttga gtccaacccg gtaagacacg | 6720 |
| acttatcgcc actggcagca gccactggta acaggattag cagagcgagg tatgtaggcg | 6780 |
| gtgctacaga gttcttgaag tggtggccta actacggcta cactagaagg acagtatttg | 6840 |
| gtatctgcgc tctgctgaag ccagttacct tcggaaaaag agttggtagc tcttgatccg | 6900 |
| gcaaacaaac caccgctggt agcggtggtt ttttttgtttg caagcagcag attacgcgca | 6960 |
| gaaaaaaagg atctcaagaa gatcctttga tcttttctac ggggtctgac gctcagtgga | 7020 |
| acgaaaactc acgttaaggg attttggtca tgagattatc aaaaaggatc ttcacctaga | 7080 |
| tccttttaaa ttaaaaatga agttttaaat caatctaaag tatatatgag taaacttggt | 7140 |
| ctgacagtta ccaatgctta atcagtgagg cacctatctc agcgatctgt ctatttcgtt | 7200 |
| catccatagt tgcctgactc cccgtcgtgt agataactac gatacgggag ggcttaccat | 7260 |
| ctggccccag tgctgcaatg ataccgcgag acccacgctc accggctcca gatttatcag | 7320 |
| caataaaacca gccagccgga agggccgagc gcagaagtgg tcctgcaact ttatccgcct | 7380 |
| ccatccagtc tattaattgt tgccgggaag ctagagtaag tagttcgcca gttaatagtt | 7440 |
| tgcgcaacgt tgttgccatt gctgcaggca tcgtggtgtc acgctcgtcg tttggtatgg | 7500 |
| cttcattcag ctccggttcc caacgatcaa ggcgagttac atgatccccc atgttgtgca | 7560 |
| aaaaagcggt tagctccttc ggtcctccga tcgttgtcag aagtaagttg gccgcagtgt | 7620 |
| tatcactcat ggttatggca gcactgcata attctcttac tgtcatgcca tccgtaagat | 7680 |
| gcttttctgt gactggtgag tactcaacca agtcattctg agaatagtgt atgcggcgac | 7740 |
| cgagttgctc ttgcccggcg tcaacacggg ataataccgc gccacatagc agaactttaa | 7800 |
| aagtgctcat cattggaaaa cgttcttcgg ggcgaaaact ctcaaggatc ttaccgctgt | 7860 |
| tgagatccag ttcgatgtaa cccactcgtg cacccaactg atcttcagca tcttttactt | 7920 |
| tcaccagcgt ttctgggtga gcaaaaacag gaaggcaaaa tgccgcaaaa aagggaataa | 7980 |
| gggcgacacg gaaatgttga atactcatac tcttcctttt tcaatattat tgaagcattt | 8040 |
| atcagggtta ttgtctcatg agcggataca tatttgaatg tatttagaaa aataaacaaa | 8100 |
| taggggttcc gcgcacattt ccccgaaaag tgccacctga cgtctaagaa accattatta | 8160 |
| tcatgacatt aacctataaa aataggcgta tcacgaggcc ctttcgtctt caagaattgt | 8220 |
| t | 8221 |

<210> SEQ ID NO 28
<211> LENGTH: 8439
<212> TYPE: DNA
<213> ORGANISM: Artificial Sequence
<220> FEATURE:
<223> OTHER INFORMATION: Synthetic Construct pAdApt Ebola GP(Z)

<400> SEQUENCE: 28

| | |
|---|---|
| ttaattaacc gcaattctca tgtttgacag cttatcatca tcaataatat accttatttt | 60 |
| ggattgaagc caatatgata atgaggggggt ggagtttgtg acgtggcgcg gggcgtggga | 120 |
| acggggcggg tgacgtagta gtgtggcgga agtgtgatgt tgcaagtgtg gcggaacaca | 180 |
| tgtaagcgac ggatgtggca aaagtgacgt ttttggtgtg cgccggtgta cacaggaagt | 240 |
| gacaatttc gcgcggtttt aggcggatgt tgtagtaaat ttgggcgtaa ccgagtaaga | 300 |
| tttggccatt ttcgcgggaa aactgaataa gaggaagtga aatctgaata attttgtgtt | 360 |
| actcatagcg cgtaatattt gtctagggcc gcggggactt tgaccgttta cgtggagact | 420 |

```
cgcccaggtg ttttcctcag gtgttttccg cgttccgggt caaagttggc gtttattat      480
tatagtcagt acgtaccagt gcactggcct agagcggccc cattgcatac gttgtatcca      540
tatcataata tgtacattta tattggctca tgtccaacat taccgccatg ttgacattga      600
ttattgacta gttattaata gtaatcaatt acggggtcat tagttcatag cccatatatg      660
gagttccgcg ttacataact tacggtaaat ggcccgcctg gctgaccgcc caacgacccc      720
cgcccattga cgtcaataat gacgtatgtt cccatagtaa cgccaatagg gactttccat      780
tgacgtcaat gggtggagta tttacggtaa actgcccact tggcagtaca tcaagtgtat      840
catatgccaa gtacgccccc tattgacgtc aatgacggta aatggcccgc ctggcattat      900
gcccagtaca tgaccttatg gactttcct acttggcagt acatctacgt attagtcatc      960
gctattacca tggtgatgcg gttttggcag tacatcaatg ggcgtggata gcggtttgac     1020
tcacggggat ttccaagtct ccaccccatt gacgtcaatg ggagtttgtt ttggcaccaa     1080
aatcaacggg actttccaaa atgtcgtaac aactccgccc cattgacgca aatgggcggt     1140
aggcgtgtac ggtgggaggt ctatataagc agagctcgtt tagtgaaccg tcagatcgcc     1200
tggagacgcc atccacgctg ttttgacctc catagaagac accgggaccg atccagcctc     1260
cgtcaccgtc gtcgacacgt gtgatcagat atcgcggccg ctctagacca ggccctggat     1320
cgatccaaca acacaatggg cgttacagga atattgcagt tacctcgtga tcgattcaag     1380
aggacatcat tctttctttg ggtaattatc cttttccaaa gaacattttc catcccactt     1440
ggagtcatcc acaatagcac attacaggtt agtgatgtcg acaaactagt ttgtcgtgac     1500
aaactgtcat ccacaaatca attgagatca gttggactga atctcgaagg gaatggagtg     1560
gcaactgacg tgccatctgc aactaaaaga tggggcttca ggtccggtgt cccaccaaag     1620
gtggtcaatt atgaagctgg tgaatgggct gaaaactgct acaatcttga aatcaaaaaa     1680
cctgacggga gtgagtgtct accagcagcg ccagacggga ttcggggctt ccccggtgc     1740
cggtatgtgc acaaagtatc aggaacggga ccgtgtgccg gagactttgc cttccataaa     1800
gagggtgctt tcttcctgta tgatcgactt gcttccacag ttatctaccg aggaacgact     1860
ttcgctgaag gtgtcgttgc atttctgata ctgccccaag ctaagaagga cttcttcagc     1920
tcacacccct tgagagagcc ggtcaatgca acgaggacc cgtctagtgg ctactattct      1980
accacaatta gatatcaggc taccggtttt ggaaccaatg agacagagta cttgttcgag     2040
gttgacaatt tgacctacgt ccaacttgaa tcaagattca caccacagtt tctgctccag     2100
ctgaatgaga caatatatac aagtgggaaa aggagcaata ccacgggaaa actaatttgg     2160
aaggtcaacc ccgaaattga tacaacaatc ggggagtggg ccttctggga aactaaaaaa     2220
aacctcacta gaaaaattcg cagtgaagag ttgtctttca cagttgtatc aaacggagcc     2280
aaaaacatca gtggtcagag tccggcgcga acttcttccg acccagggac caacacaaca     2340
actgaagacc acaaaatcat ggcttcagaa aattcctctg caatggttca agtgcacagt     2400
caaggaaggg aagctgcagt gtcgcatcta acaaccttg ccacaatctc cacgagtccc     2460
caatccctca caaccaaacc aggtccggac aacagcaccc ataatacacc cgtgtataaa     2520
cttgacatct ctgaggcaac tcaagttgaa caacatcacc gcagaacaga caacgacagc     2580
acagcctccg acactccctc tgccacgacc gcagccggac cccaaaaagc agagaacacc     2640
aacacgagca agagcactga cttcctggac ccgccacca caacaagtcc ccaaaaccac     2700
agcgagaccg ctggcaacaa caacactcat caccaagata ccggagaaga gagtgccagc     2760
agcgggaagc taggcttaat taccaatact attgctggag tcgcaggact gatcacaggc     2820
```

```
gggagaagaa ctcgaagaga agcaattgtc aatgctcaac ccaaatgcaa ccctaattta    2880
cattactgga ctactcagga tgaaggtgct gcaatcggac tggcctggat accatatttc    2940
gggccagcag ccgagggaat ttacatagag gggctaatgc acaatcaaga tggtttaatc    3000
tgtgggttga dacagctggc caacgagacg actcaagctc ttcaactgtt cctgagagcc    3060
acaactgagc tacgcacctt ttcaatcctc aaccgtaagg caattgattt cttgctgcag    3120
cgatggggcg gcacatgcca cattctggga ccggactgct gtatcgaacc acatgattgg    3180
accaagaaca taacagacaa aattgatcag attattcatg attttgttga taaaaccctt    3240
ccggaccagg gggacaatga caattggtgg acaggatgga gacaatggat accggcaggt    3300
attggagtta caggcgttgt aattgcagtt atcgctttat tctgtatatg caaatttgtc    3360
ttttagtttt tcttcagatt gcttcatgga aaagctcagc ctcaaatcaa tgaaaccagg    3420
atttaattat atggattact tgaatctaag attacttgac aaatgataat ataatacact    3480
ggagctttaa acatagccaa tgtgattcta actcctttaa actcacagtt aatcataaac    3540
aaggtttgag gtaccgagct cgaattgatc tgctgtgcct tctagttgcc agccatctgt    3600
tgtttgcccc tcccccgtgc cttccttgac cctggaaggt gccactccca ctgtcctttc    3660
ctaataaaat gaggaaattg catcgcattg tctgagtagg tgtcattcta ttctgggggg    3720
tggggtgggg caggacagca aggggagga ttggaagac aatagcaggc atgctgggga    3780
tgcggtgggc tctatgggta cccagggccg cataacttcg tataatgtat gctatacgaa    3840
gttataagat ctgtactgaa atgtgtgggc gtggcttaag ggtgggaaag aatatataag    3900 gtggggtct tatgtagttt tgtatctgtt ttgcagcagc cgccgccgcc atgagcacca    3960
actcgtttga tggaagcatt gtgagctcat atttgacaac gcgcatgccc ccatgggccg    4020
gggtgcgtca gaatgtgatg ggctccagca ttgatggtcg ccccgtcctg cccgcaaact    4080
ctactacctt gacctacgag accgtgtctg gaacgccgtt ggagactgca gcctccgccg    4140
ccgcttcagc cgctgcagcc accgcccgcg ggattgtgac tgactttgct ttcctgagcc    4200
cgcttgcaag cagtgcagct tcccgttcat ccgcccgcga tgacaagttg acggctcttt    4260
tggcacaatt ggattctttg acccgggaac ttaatgtcgt ttctcagcag ctgttggatc    4320
tgcgccagca ggtttctgcc ctgaaggctt cctcccctcc caatgcggtt taaaacataa    4380
ataaaaaacc agactctgtt tggatttgga tcaagcaagt gtcttgctgt ctttatttag    4440
gggttttgcg cgcgcggtag gcccgggacc agcggtctcg gtcgttgagg gtcctgtgta    4500
ttttttccag gacgtggtaa aggtgactct ggatgttcag atacatgggc ataagcccgt    4560
ctctggggtg gaggtagcac cactgcagag cttcatgctg cggggtggtg ttgtagatga    4620
tccagtcgta gcaggagcgc tgggcgtggt gcctaaaaat gtctttcagt agcaagctga    4680
ttgccagggg caggcccttg gtgtaagtgt ttacaaagcg gttaagctgg gatgggtgca    4740
tacgtgggga tatgagatgc atcttggact gtatttttag gttggctatg ttcccagcca    4800
tatccctccg gggattcatg ttgtgcagaa ccaccagcac agtgtatccg gtgcacttgg    4860
gaaatttgtc atgtagctta gaaggaaatg cgtggaagaa cttggagacg cccttgtgac    4920
ctccaagatt ttccatgcat tcgtccataa tgatggcaat gggccacacg gcggcggcct    4980
gggcgaagat atttctggga tcactaacgt catagttgtg ttccaggatg agatcgtcat    5040
aggccatttt tacaaagcgc gggcggaggg tgccagactg cggtataatg gttccatccg    5100
gcccaggggc gtagttaccc tcacagattt gcatttccca cgctttgagt tcagatgggg    5160
ggatcatgtc tacctgcggg gcgatgaaga aaacggtttc cggggtaggg gagatcagct    5220
```

```
gggaagaaag caggttcctg agcagctgcg acttaccgca gccggtgggc ccgtaaatca    5280
cacctattac cggctgcaac tggtagttaa gagagctgca gctgccgtca tccctgagca    5340
ggggggccac ttcgttaagc atgtccctga ctcgcatgtt ttccctgacc aaatccgcca    5400
gaaggcgctc gccgcccagc gatagcagtt cttgcaagga agcaaagttt ttcaacggtt    5460
tgagaccgtc cgccgtaggc atgcttttga gcgtttgacc aagcagttcc aggcggtccc    5520
acagctcggt cacctgctct acggcatctc gatccagcat atctcctcgt ttcgcgggtt    5580
ggggcggctt tcgctgtacg gcagtagtcg gtgctcgtcc agacgggcca gggtcatgtc    5640
tttccacggg cgcagggtcc tcgtcagcgt agtctgggtc acggtgaagg ggtgcgctcc    5700
gggctgcgcg ctggccaggg tgcgcttgag gctggtcctg ctggtgctga agcgctgccg    5760
gtcttcgccc tgcgcgtcgg ccaggtagca tttgaccatg gtgtcatagt ccagcccctc    5820
cgcggcgtgg cccttggcgc gcagcttgcc cttggaggag gcgccgcacg aggggcagtg    5880
cagacttttg agggcgtaga gcttgggcgc gagaaatacc gattccgggg agtaggcatc    5940
cgcgccgcag gccccgcaga cggtctcgca ttccacgagc caggtgagct ctggccgttc    6000
ggggtcaaaa accaggtttc ccccatgctt tttgatgcgt ttcttacctc tggtttccat    6060
gagccggtgt ccacgctcgg tgacgaaaag gctgtccgtg tccccgtata cagacttgag    6120
aggcctgtcc tcgagcggtg ttccgcggtc ctcctcgtat agaaactcgg accactctga    6180
gacaaaggct cgcgtccagg ccagcacgaa ggaggctaag tgggaggggt agcggtcgtt    6240
gtccactagg gggtccactc gctccagggt gtgaagacac atgtcgccct cttcggcatc    6300
aaggaaggtg attggtttgt aggtgtaggc cacgtgaccg ggtgttcctg aaggggggct    6360
ataaaagggg gtggggcgc gttcgtcctc actctcttcc gcatcgctgt ctgcgagggc    6420
cagctgttgg ggtgagtcga cgcgaggctg gatggccttc cccattatga ttcttctcgc    6480
ttccggcggc atcgggatgc ccgcgttgca ggccatgctg tccaggcagg tagatgacga    6540
ccatcaggga cagcttcaag gccagcaaaa ggccaggaac cgtaaaaagg ccgcgttgct    6600 ggcgttttc cataggctcc gcccccctga cgagcatcac aaaaatcgac gctcaagtca    6660
gaggtggcga acccgacag gactataaag ataccaggcg tttccccctg gaagctccct    6720
cgtgcgctct cctgttccga ccctgccgct taccggatac ctgtccgcct ttctcccttc    6780
gggaagcgtg gcgctttctc atagctcacg ctgtaggtat ctcagttcgg tgtaggtcgt    6840
tcgctccaag ctgggctgtg tgcacgaacc ccccgttcag cccgaccgct gcgccttatc    6900
cggtaactat cgtcttgagt ccaacccggt aagacacgac ttatcgccac tggcagcagc    6960
cactggtaac aggattagca gagcgaggta tgtaggcggt gctacagagt tcttgaagtg    7020
gtggcctaac tacggctaca ctagaaggac agtatttggt atctgcgctc tgctgaagcc    7080
agttaccttc ggaaaaagag ttggtagctc ttgatccggc aaacaaacca ccgctggtag    7140
cggtggtttt tttgtttgca agcagcagat tacgcgcaga aaaaaggat ctcaagaaga    7200 tcctttgatc ttttctacgg ggtctgacgc tcagtggaac gaaaactcac gttaagggat    7260
tttggtcatg agattatcaa aaaggatctt cacctagatc cttttaaatt aaaaatgaag    7320
ttttaaatca atctaaagta tatatgagta aacttggtct gacagttacc aatgcttaat    7380
cagtgaggca cctatctcag cgatctgtct atttcgttca tccatagttg cctgactccc    7440
cgtcgtgtag ataactacga tacgggaggg cttaccatct ggccccagtg ctgcaatgat    7500
accgcgagac ccacgctcac cggctccaga tttatcagca ataaaccagc cagccggaag    7560
ggccgagcgc agaagtggtc ctgcaacttt atccgcctcc atccagtcta ttaattgttg    7620
```

```
ccgggaagct agagtaagta gttcgccagt taatagtttg cgcaacgttg ttgccattgc    7680
tgcaggcatc gtggtgtcac gctcgtcgtt tggtatggct tcattcagct ccggttccca    7740
acgatcaagg cgagttacat gatcccccat gttgtgcaaa aaagcggtta gctccttcgg    7800
tcctccgatc gttgtcagaa gtaagttggc cgcagtgtta tcactcatgg ttatggcagc    7860
actgcataat tctcttactg tcatgccatc cgtaagatgc ttttctgtga ctggtgagta    7920
ctcaaccaag tcattctgag aatagtgtat gcggcgaccg agttgctctt gcccggcgtc    7980
aacacgggat aataccgcgc cacatagcag aactttaaaa gtgctcatca ttggaaaacg    8040
ttcttcgggg cgaaaactct caaggatctt accgctgttg agatccagtt cgatgtaacc    8100
cactcgtgca cccaactgat cttcagcatc ttttactttc accagcgttt ctgggtgagc    8160
aaaaacagga aggcaaaatg ccgcaaaaaa gggaataagg gcgacacgga aatgttgaat    8220
actcatactc ttcctttttc aatattattg aagcatttat cagggttatt gtctcatgag    8280
cggatacata tttgaatgta tttagaaaaa taaacaaata ggggttccgc gcacatttcc    8340
ccgaaaagtg ccacctgacg tctaagaaac cattattatc atgacattaa cctataaaaa    8400
taggcgtatc acgaggccct ttcgtcttca agaattgtt                          8439
```

<210> SEQ ID NO 29
<211> LENGTH: 8199
<212> TYPE: DNA
<213> ORGANISM: Artificial Sequence
<220> FEATURE:
<223> OTHER INFORMATION: Synthetic Construct pAdApt Ebola GP(Z)(dTM)

<400> SEQUENCE: 29

```
ttaattaacc gcaattctca tgtttgacag cttatcatca tcaataatat accttatttt      60
ggattgaagc caatatgata atgaggggt ggagtttgtg acgtggcgcg gggcgtggga     120
acggggcggg tgacgtagta gtgtggcgga agtgtgatgt tgcaagtgtg gcggaacaca     180
tgtaagcgac ggatgtggca aaagtgacgt ttttggtgtg cgccggtgta cacaggaagt     240
gacaattttc gcgcggtttt aggcggatgt tgtagtaaat ttgggcgtaa ccgagtaaga     300
tttggccatt ttcgcgggaa aactgaataa gaggaagtga atctgaata attttgtgtt     360 actcatagcg cgtaatattt gtctagggcc gcggggactt tgaccgttta cgtggagact     420
cgcccaggtg ttttttctcag gtgttttccg cgttccgggt caaagttggc gttttattat     480
tatagtcagt acgtaccagt gcactggcct agagcggccc cattgcatac gttgtatcca     540
tatcataata tgtacattta tattggctca tgtccaacat taccgccatg ttgacattga     600
ttattgacta gttattaata gtaatcaatt acggggtcat tagttcatag cccatatatg     660
gagttccgcg ttacataact tacggtaaat ggcccgcctg gctgaccgcc caacgacccc     720
cgcccattga cgtcaataat gacgtatgtt cccatagtaa cgccaatagg gactttccat     780
tgacgtcaat gggtggagta tttacggtaa actgcccact tggcagtaca tcaagtgtat     840
catatgccaa gtacgccccc tattgacgtc aatgacggta aatggcccgc ctggcattat     900
gcccagtaca tgaccttatg ggactttcct acttggcagt acatctacgt attagtcatc     960
gctattacca tggtgatgcg gttttggcag tacatcaatg ggcgtggata gcggtttgac    1020
tcacggggat ttccaagtct ccaccccatt gacgtcaatg ggagtttgtt ttggcaccaa    1080
aatcaacggg actttccaaa atgtcgtaac aactccgccc cattgacgca atgggcggt     1140 aggcgtgtac ggtgggaggt ctatataagc agagctcgtt tagtgaaccg tcagatcgcc    1200
tggagacgcc atccacgctg ttttgacctc catagaagac accgggaccg atccagcctc    1260
```

-continued

| | |
|---|---|
| cgtcaccgtc gtcgacacgt gtgatcagat atcgcggccg ctctagacca ggccctggat | 1320 |
| cgatccaaca acacaatggg cgttacagga atattgcagt tacctcgtga tcgattcaag | 1380 |
| aggacatcat tctttctttg ggtaattatc cttttccaaa gaacattttc catcccactt | 1440 |
| ggagtcatcc acaatagcac attacaggtt agtgatgtcg acaaactagt ttgtcgtgac | 1500 |
| aaactgtcat ccacaaatca attgagatca gttggactga atctcgaagg gaatggagtg | 1560 |
| gcaactgacg tgccatctgc aactaaaaga tggggcttca ggtccggtgt cccaccaaag | 1620 |
| gtggtcaatt atgaagctgg tgaatgggct gaaaactgct acaatcttga aatcaaaaaa | 1680 |
| cctgacggga gtgagtgtct accagcagcg ccagacggga ttcggggctt ccccggtgc | 1740 |
| cggtatgtgc acaaagtatc aggaacggga ccgtgtgccg gagactttgc cttccataaa | 1800 |
| gagggtgctt tcttcctgta tgatcgactt gcttccacag ttatctaccg aggaacgact | 1860 |
| ttcgctgaag gtgtcgttgc atttctgata ctgccccaag ctaagaagga cttcttcagc | 1920 |
| tcacacccct tgagagagcc ggtcaatgca acggaggacc cgtctagtgg ctactattct | 1980 |
| accacaatta gatatcaggc taccggtttt ggaaccaatg agacagagta cttgttcgag | 2040 |
| gttgacaatt tgacctacgt ccaacttgaa tcaagattca caccacagtt tctgctccag | 2100 |
| ctgaatgaga caatatatac aagtgggaaa aggagcaata ccacgggaaa actaatttgg | 2160 |
| aaggtcaacc ccgaaattga tacaacaatc ggggagtggg ccttctggga aactaaaaaa | 2220 |
| aacctcacta gaaaaattcg cagtgaagag ttgtctttca cagttgtatc aaacggagcc | 2280 |
| aaaaacatca gtggtcagag tccggcgcga acttcttccg acccagggac caacacaaca | 2340 |
| actgaagacc acaaaatcat ggcttcagaa aattcctctg caatggttca agtgcacagt | 2400 |
| caaggaaggg aagctgcagt gtcgcatcta acaacccttg ccacaatctc cacgagtccc | 2460 |
| caatccctca caaccaaacc aggtccggac aacagcaccc ataatacacc cgtgtataaa | 2520 |
| cttgacatct ctgaggcaac tcaagttgaa caacatcacc gcagaacaga caacgacagc | 2580 |
| acagcctccg acactccctc tgccacgacc gcagccggac cccaaaagc agagaacacc | 2640 |
| aacacgagca agagcactga cttcctggac cccgccacca caacaagtcc ccaaaaccac | 2700 |
| agcgagaccg ctggcaacaa caacactcat caccaagata ccggagaaga gagtgccagc | 2760 |
| agcgggaagc taggcttaat taccaatact attgctggag tcgcaggact gatcacaggc | 2820 |
| gggagaagaa ctcgaagaga agcaattgtc aatgctcaac ccaaatgcaa ccctaattta | 2880 |
| cattactgga ctactcagga tgaaggtgct gcaatcggac tggcctggat accatatttc | 2940 |
| gggccagcag ccgagggaat ttacatagag gggctaatgc acaatcaaga tggtttaatc | 3000 |
| tgtgggttga cagctggc caacgagacg actcaagctc ttcaactgtt cctgagagcc | 3060 |
| acaactgagc tacgcacctt ttcaatcctc aaccgtaagg caattgattt cttgctgcag | 3120 |
| cgatggggcg gcacatgcca cattctggga ccggactgct gtatcgaacc acatgattgg | 3180 |
| accaagaaca taacagacaa aattgatcag attattcatg attttgttga taaaaccctt | 3240 |
| ccggaccagg gggacaatga caattggtgg acaggatgga gacaatggat ggccgcatcg | 3300 |
| tgactgactg acgatctgcc tcgcgagatc tgctgtgcct tctagttgcc agccatctgt | 3360 |
| tgtttgcccc tccccgtgcc ttccttgac cctggaaggt gccactccca ctgtcctttc | 3420 |
| ctaataaaat gaggaaattg catcgcattg tctgagtagg tgtcattcta ttctgggggg | 3480 |
| tggggtgggg caggacagca agggggagga ttgggaagac aatagcaggc atgctgggga | 3540 |
| tgcggtgggc tctatgggta cccagggccg cataacttcg tataatgtat gctatacgaa | 3600 |
| gttataagat ctgtactgaa atgtgtgggc gtggcttaag ggtgggaaag aatatataag | 3660 |

```
gtgggggtct tatgtagttt tgtatctgtt ttgcagcagc cgccgccgcc atgagcacca   3720
actcgtttga tggaagcatt gtgagctcat atttgacaac gcgcatgccc ccatgggccg   3780
gggtgcgtca gaatgtgatg ggctccagca ttgatggtcg ccccgtcctg cccgcaaact   3840
ctactacctt gacctacgag accgtgtctg gaacgccgtt ggagactgca gcctccgccg   3900
ccgcttcagc cgctgcagcc accgcccgcg ggattgtgac tgactttgct ttcctgagcc   3960
cgcttgcaag cagtgcagct tcccgttcat ccgcccgcga tgacaagttg acggctcttt   4020
tggcacaatt ggattctttg acccgggaac ttaatgtcgt ttctcagcag ctgttggatc   4080
tgcgccagca ggtttctgcc ctgaaggctt cctcccctcc caatgcggtt taaaacataa   4140
ataaaaaacc agactctgtt tggatttgga tcaagcaagt gtcttgctgt ctttatttag   4200
gggttttgcg cgcgcggtag gcccgggacc agcggtctcg gtcgttgagg gtcctgtgta   4260 tttttttccag gacgtggtaa aggtgactct ggatgttcag atacatgggc ataagcccgt   4320
ctctggggtg gaggtagcac cactgcagag cttcatgctg cggggtggtg ttgtagatga   4380
tccagtcgta gcaggagcgc tgggcgtggt gcctaaaaat gtctttcagt agcaagctga   4440
ttgccagggg caggcccttg gtgtaagtgt ttacaaagcg gttaagctgg gatgggtgca   4500
tacgtgggga tatgagatgc atcttggact gtattttag gttggctatg ttcccagcca   4560
tatccctccg gggattcatg ttgtgcagaa ccaccagcac agtgtatccg gtgcacttgg   4620
gaaatttgtc atgtagctta aaggaaatg cgtggaagaa cttggagacg cccttgtgac   4680
ctccaagatt ttccatgcat tcgtccataa tgatggcaat gggcccacgg gcggcggcct   4740
gggcgaagat atttctggga tcactaacgt catagttgtg ttccaggatg agatcgtcat   4800
aggccatttt tacaaagcgc gggcggaggg tgccagactg cggtataatg gttccatccg   4860
gcccaggggc gtagttaccc tcacagattt gcatttccca cgctttgagt tcagatgggg   4920
ggatcatgtc tacctgcggg gcgatgaaga aaacggtttc cggggtaggg gagatcagct   4980
gggaagaaag caggttcctg agcagctgcg acttaccgca gccggtgggc ccgtaaatca   5040
cacctattac cggctgcaac tggtagttaa gagagctgca gctgccgtca tccctgagca   5100
ggggggccac ttcgttaagc atgtccctga ctcgcatgtt ttccctgacc aaatccgcca   5160
gaaggcgctc gccgcccagc gatagcagtt cttgcaagga agcaaagttt ttcaacggtt   5220
tgagaccgtc cgccgtaggc atgcttttga gcgtttgacc aagcagttcc aggcggtccc   5280
acagctcggt cacctgctct acggcatctc gatccagcat atctcctcgt ttcgcgggtt   5340
ggggcggctt tcgctgtacg gcagtagtcg gtgctcgtcc agacgggcca gggtcatgtc   5400
tttccacggg cgcagggtcc tcgtcagcgt agtctgggtc acggtgaagg ggtgcgctcc   5460
gggctgcgcg ctggccaggg tgcgcttgag gctggtcctg ctggtgctga agcgctgccg   5520
gtcttcgccc tgcgcgtcgg ccaggtagca tttgaccatg gtgtcatagt ccagcccctc   5580
cgcggcgtgg cccttggcgc gcagcttgcc cttgaggag gcgccgcacg aggggcagtg   5640 cagactttg agggcgtaga gcttgggcgc gagaaatacc gattccgggg agtaggcatc   5700
cgcgccgcag gccccgcaga cggtctcgca ttccacgagc caggtgagct ctggccgttc   5760
ggggtcaaaa accaggtttc ccccatgctt tttgatgcgt ttcttacctc tggtttccat   5820
gagccggtgt ccacgctcgg tgacgaaaag gctgtccgtg tccccgtata cagacttgag   5880
aggcctgtcc tcgagcggtg ttccgcggtc ctcctcgtat agaaactcgg accactctga   5940
gacaaaggct cgcgtccagg ccagcacgaa ggaggctaag tgggaggggt agcggtcgtt   6000
gtccactagg gggtccactc gctccagggt gtgaagacac atgtcgccct cttcggcatc   6060
```

```
aaggaaggtg attggtttgt aggtgtaggc cacgtgaccg ggtgttcctg aagggggct     6120
ataaaaggg  gtgggggcgc gttcgtcctc actctcttcc gcatcgctgt ctgcgagggc    6180
cagctgttgg ggtgagtcga cgcgaggctg atggccttc cccattatga ttcttctcgc     6240
ttccggcggc atcgggatgc ccgcgttgca ggccatgctg tccaggcagg tagatgacga    6300
ccatcaggga cagcttcaag gccagcaaaa ggccaggaac cgtaaaaagg ccgcgttgct    6360
ggcgttttc  cataggctcc gccccctga  cgagcatcac aaaaatcgac gctcaagtca    6420
gaggtggcga acccgacag  gactataaag ataccaggcg tttccccctg gaagctccct    6480
cgtgcgctct cctgttccga ccctgccgct taccggatac ctgtccgcct ttctcccttc    6540
gggaagcgtg cgctttctc  atagctcacg ctgtaggtat ctcagttcgg tgtaggtcgt    6600
tcgctccaag ctgggctgtg tgcacgaacc ccccgttcag cccgaccgct gcgccttatc    6660
cggtaactat cgtcttgagt ccaacccggt aagacacgac ttatcgccac tggcagcagc    6720
cactggtaac aggattagca gagcgaggta tgtaggcggt gctacagagt tcttgaagtg    6780
gtggcctaac tacggctaca ctagaaggac agtatttggt atctgcgctc tgctgaagcc    6840
agttaccttc ggaaaaagag ttggtagctc ttgatccggc aaacaaacca ccgctggtag    6900
cggtggtttt tttgtttgca agcagcagat tacgcgcaga aaaaaggat  ctcaagaaga    6960
tcctttgatc ttttctacgg ggtctgacgc tcagtggaac gaaaactcac gttaagggat    7020
tttggtcatg agattatcaa aaaggatctt cacctagatc cttttaaatt aaaaatgaag    7080
ttttaaatca atctaaagta tatatgagta aacttggtct gacagttacc aatgcttaat    7140
cagtgaggca cctatctcag cgatctgtct atttcgttca tccatagttg cctgactccc    7200
cgtcgtgtag ataactacga tacgggaggg cttaccatct ggccccagtg ctgcaatgat    7260
accgcgagac ccacgctcac cggctccaga tttatcagca ataaaccagc cagccggaag    7320
ggccgagcgc agaagtggtc ctgcaacttt atccgcctcc atccagtcta ttaattgttg    7380
ccgggaagct agagtaagta gttcgccagt taatagtttg cgcaacgttg ttgccattgc    7440
tgcaggcatc gtggtgtcac gctcgtcgtt tggtatggct tcattcagct ccggttccca    7500
acgatcaagg cgagttacat gatccccat  gttgtgcaaa aaagcggtta gctccttcgg    7560
tcctccgatc gttgtcagaa gtaagttggc cgcagtgtta tcactcatgg ttatggcagc    7620
actgcataat tctcttactg tcatgccatc cgtaagatgc ttttctgtga ctggtgagta    7680
ctcaaccaag tcattctgag aatagtgtat gcggcgaccg agttgctctt gcccggcgtc    7740
aacacgggat aataccgcgc cacatagcag aactttaaaa gtgctcatca ttggaaaacg    7800
ttcttcgggg cgaaaactct caaggatctt accgctgttg agatccagtt cgatgtaacc    7860
cactcgtgca cccaactgat cttcagcatc ttttactttc accagcgttt ctgggtgagc    7920
aaaaacagga aggcaaaatg ccgcaaaaaa gggaataagg gcgacacgga atgttgaat    7980
actcatactc ttcctttttc aatattattg aagcatttat cagggttatt gtctcatgag    8040
cggatacata tttgaatgta tttagaaaaa taaacaaata ggggttccgc gcacatttcc    8100
ccgaaaagtg ccacctgacg tctaagaaac cattattatc atgacattaa cctataaaaa    8160
taggcgtatc acgaggccct ttcgtcttca agaattgtt                           8199
```

<210> SEQ ID NO 30
<211> LENGTH: 7778
<212> TYPE: DNA
<213> ORGANISM: Artificial Sequence
<220> FEATURE:
<223> OTHER INFORMATION: Synthetic Construct pVR1012 Marburg

<400> SEQUENCE: 30

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca cgacccccg cccattgacg tcaataatga cgtatgttcc      480
catagtaacg ccaataggga ctttccattg acgtcaatgg gtggagtatt tacggtaaac      540
tgcccacttg gcagtacatc aagtgtatca tatgccaagt acgccccta ttgacgtcaa      600
tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt tgacctcca      960
tagaagacac cgggaccgat ccagcctccg cggccgggaa cggtgcattg gaacgcggat      1020
tccccgtgcc aagagtgacg taagtaccgc ctatagactc tataggcaca ccccttggc      1080
tcttatgcat gctatactgt ttttggcttg gggcctatac accccgctt ccttatgcta      1140
taggtgatgg tatagcttag cctataggtg tgggttattg accattattg accactcccc      1200
tattggtgac gatactttcc attactaatc cataacatgg ctctttgcca caactatctc      1260
tattggctat atgccaatac tctgtccttc agagactgac acggactctg tattttaca      1320
ggatggggtc ccatttatta tttacaaatt cacatataca acaacgccgt ccccgtgcc      1380
cgcagttttt attaaacata gcgtgggatc tccacgcgaa tctcgggtac gtgttccgga      1440
catgggctct tctccggtag cggcggagct tccacatccg agccctggtc ccatgcctcc      1500
agcggctcat ggtcgctcgg cagctccttg ctcctaacag tggaggccag acttaggcac      1560
agcacaatgc ccaccaccac cagtgtgccg cacaaggccg tggcgtagg gtatgtgtct      1620
gaaaatgagc gtggagattg ggctcgcacg gctgacgcag atggaagact taaggcagcg      1680
gcagaagaag atgcaggcag ctgagttgtt gtattctgat aagagtcaga ggtaactccc      1740
gttgcggtgc tgttaacggt ggagggcagt gtagtctgag cagtactcgt tgctgccgcg      1800
cgcgccacca gacataatag ctgacagact aacagactgt tcctttccat gggtctttc      1860
tgcagtcacc gtcgtcgaca cgtgtgatca gatatcgcgg ccgctctaga gtcgaatgaa      1920
gaacattaat tgctgggtaa aagtgattaa tttctttaaa tttgaccaga ataatatttt      1980
gtcagtgaat atattctcat atcacttgat taaaaacaga aaattaccct aacatgaaga      2040
ccacatgttt ccttatcagt cttatcttaa ttcaagggac aaaaaatctc cccatttag      2100
agatagctag taataatcaa ccccaaaatg tggattcggt atgctccgga actctccaga      2160
agacagaaga cgtccatctg atgggattca cactgagtgg gcaaaaagtt gctgattccc      2220
cttttggagc atccaagcga tgggcttca ggacaggtgt acctcccaag aatgttgagt      2280
acacagaggg ggaggaagcc aaaacatgct acaatataag tgtaacggat ccctctggaa      2340
```

```
aatccttgct gttagatcct cctaccaaca tccgtgacta tcctaaatgc aaaactatcc   2400
atcatattca aggtcaaaac cctcatgcac aggggatcgc ccttcattta tggggagcat   2460
tttttctgta tgatcgcatt gcctccacaa caatgtaccg aggcaaagtc ttcactgaag   2520
ggaacatagc agctatgatt gtcaataaga cagtgcacaa aatgattttc tcgcggcaag   2580
gacaagggta ccgtcatatg aatctgactt ctactaataa atattggaca agtagtaacg   2640
gaacgcaaac gaatgacact ggatgtttcg gcgctcttca agaatacaat tctacaaaga   2700
accaaacatg tgctccgtcc aaaataccct caccactgcc cacagcccgt ccggagatca   2760
aactcacaag caccccaact gatgccacca aactcaatac cacggaccca agcagtgatg   2820
atgaggacct cgcaacatcc ggctcagggt ccggagaacg agaacccac acaacttctg   2880 atgcggtcac caagcaaggg ctttcatcaa caatgccacc cactccctca ccacaaccaa   2940
gcacgccaca gcaaggagga acaacacaca accattccca agatgctgtg actgaactag   3000
acaaaaataa cacaactgca caaccgtcca tgccccctca taacactacc acaatctcta   3060
ctaacaacac ctccaaacac aacttcagca ctctctctgc accattacaa aacaccacca   3120
atgacaacac acagagcaca atcactgaaa atgagcaaac cagtgccccc tcgataacaa   3180
ccctgcctcc aacgggaaat cccaccacag caaagagcac cagcagcaaa aaaggccccg   3240
ccacaacggc accaaacacg acaaatgagc atttcaccag tcctccccc accccagct    3300 cgactgcaca acatcttgta tatttcagaa gaaagcgaag tatcctctgg agggaaggcg   3360
acatgttccc ttttctggat gggttaataa atgctccaat tgattttgac ccagttccaa   3420
atacaaaaac aatctttgat gaatcctcta gttctggtgc ctcggctgag gaagatcaac   3480
atgcctcccc caatattagt ttaactttat cttattttcc taatataaat gagaacactg   3540
cctactctgg agaaaatgag aatgattgtg atgcagagtt aagaatttgg agcgttcagg   3600
aggatgacct ggccgcaggg ctcagttgga taccgttttt tggccctgga attgaaggac   3660
tttacactgc tgttttaatt aaaaatcaaa acaatttggt ctgcaggttg aggcgtctag   3720
ccaatcaaac tgccaaatcc ttggaactct tattgagagt cacaactgag gaaagaacat   3780
tctccttaat caatagacat gctattgact ttctactcac aagatgggga ggaacatgca   3840
aagtgcttgg acctgattgt tgcatcggga tagaagactt gtccaaaaat atttcagagc   3900
aaattgacca aattaaaaag gacgaacaaa agagggac tggttggggt ctgggtggta    3960
aatggtggac atccgactgg ggtgttctta ctaacttggg cattttgcta ctattatcca   4020
tagctgtctt gattgctcta tcctgtattt gtcgtatctt tactaaatat atcggataac   4080
gttaaatgtg taatgattag gactttagga caattgctac tgagcccttt tctaatctac   4140
tgaaatcaac ttgggagatt tttaagaagc tgataactta atgtgaatca atagtttatg   4200
tattatcgat tattatggtt tgatattcaa ttgttattat tgtcaggagt gacctttct    4260 atttgatgca ttaatgtttt aaactacctc ttaagccttt gagggcgtcc caatatgtgc   4320 gtagggtta atttaaaggg atttcttatt gtacagtttt ctgtattact tatttgggct    4380
tgaagacata gttaagattt gccgaaatgc tctccagtca attccatccc ctctcagaaa   4440
agacgtgctg ttcaaagagt cttaatttat aaccaactat tgcaagaatt aatttacttt   4500
ttccgttata cttagttaca ttaatctttt gactgttcag cattattaac gacttgtctt   4560
aattcaatcg ttcggatgaa attcataagg aaaaatgagc ctccttcccc ctattctggg   4620
ctgagaaaat ttctccttatc cgcctaaaat cagatctgtt aggtcatggg tccttcataa   4680
tctgtttgag catgaatatt gatgaaatga ccaaatgata gtgcatttgt atagactcaa   4740
```

```
ttatccttta ttaagaaaaa tcgacctgca ggcatgcaag cttcaggatc cagatctgct    4800
gtgccttcta gttgccagcc atctgttgtt tgcccctccc ccgtgccttc cttgaccctg    4860
gaaggtgcca ctcccactgt cctttcctaa taaaatgagg aaattgcatc gcattgtctg    4920
agtaggtgtc attctattct ggggggtggg gtggggcagc acagcaaggg ggaggattgg    4980
gaagacaata gcaggcatgc tggggatgcg gtgggctcta tgggtaccca ggtgctgaag    5040
aattgacccg gttcctcctg ggccagaaag aagcaggcac atcccttcct ctgtgacaca    5100
ccctgtccac gccctggtt cttagttcca gccccactca taggacactc atagctcagg    5160
agggctccgc cttcaatccc acccgctaaa gtacttggag cggtctctcc ctccctcatc    5220
agcccaccaa accaaaccta gcctccaaga gtgggaagaa attaaagcaa gataggctat    5280
taagtgcaga gggagagaaa atgcctccaa catgtgagga agtaatgaga gaaatcatag    5340
aatttcttcc gcttcctcgc tcactgactc gctgcgctcg gtcgttcggc tgcggcgagc    5400
ggtatcagct cactcaaagg cggtaatacg gttatccaca gaatcagggg ataacgcagg    5460
aaagaacatg tgagcaaaag gccagcaaaa ggccaggaac cgtaaaaagg ccgcgttgct    5520
ggcgttttc cataggctcc gcccccctga cgagcatcac aaaaatcgac gctcaagtca    5580
gaggtggcga aacccgacag gactataaag ataccaggcg tttccccctg gaagctccct    5640
cgtgcgctct cctgttccga ccctgccgct taccggatac ctgtccgcct ttctcccttc    5700
gggaagcgtg gcgctttctc aatgctcacg ctgtaggtat ctcagttcgg tgtaggtcgt    5760
tcgctccaag ctgggctgtg tgcacgaacc ccccgttcag cccgaccgct gcgccttatc    5820
cggtaactat cgtcttgagt ccaacccggt aagacacgac ttatcgccac tggcagcagc    5880
cactggtaac aggattagca gagcgaggta tgtaggcggt gctacagagt tcttgaagtg    5940
gtggcctaac tacggctaca ctagaaggac agtatttggt atctgcgctc tgctgaagcc    6000
agttaccttc ggaaaaagag ttggtagctc ttgatccggc aaacaaacca ccgctggtag    6060
cggtggtttt tttgtttgca agcagcagat tacgcgcaga aaaaaaggat ctcaagaaga    6120
tcctttgatc ttttctacgg ggtctgacgc tcagtggaac gaaaactcac gttaagggat    6180
tttggtcatg agattatcaa aaaggatctt cacctagatc cttttaaatt aaaaatgaag    6240
ttttaaatca atctaaagta tatatgagta aacttggtct gacagttacc aatgcttaat    6300
cagtgaggca cctatctcag cgatctgtct atttcgttca tccatagttg cctgactccg    6360
ggggggggg gcgctgaggt ctgcctcgtg aagaaggtgt tgctgactca taccaggcct    6420
gaatcgcccc atcatccagc cagaaagtga gggagccacg gttgatgaga gctttgttgt    6480
aggtggacca gttggtgatt ttgaactttt gctttgccac ggaacggtct gcgttgtcgg    6540
gaagatgcgt gatctgatcc ttcaactcag caaaagttcg atttattcaa caaagccgcc    6600
gtcccgtcaa gtcagcgtaa tgctctgcca gtgttacaac caattaacca attctgatta    6660
gaaaaactca tcgagcatca aatgaaactg caatttattc atatcaggat tatcaatacc    6720
atattttga aaagccgtt tctgtaatga aggagaaaac tcaccgaggc agttccatag    6780
gatggcaaga tcctggtatc ggtctgcgat tccgactcgt ccaacatcaa tacaacctat    6840
taatttcccc tcgtcaaaaa taaggttatc aagtgagaaa tcaccatgag tgacgactga    6900
atccggtgag aatggcaaaa gcttatgcat ttctttccag acttgttcaa caggccagcc    6960
attacgctcg tcatcaaaat cactcgcatc aaccaaaccg ttattcattc gtgattgcgc    7020
ctgagcgaga cgaaatacgc gatcgctgtt aaaaggacaa ttacaaacag gaatcgaatg    7080
caaccggcgc aggaacactg ccagcgcatc aacaatattt tcacctgaat caggatattc    7140
```

-continued

| | |
|---|---|
| ttctaatacc tggaatgctg ttttcccggg gatcgcagtg gtgagtaacc atgcatcatc | 7200 |
| aggagtacgg ataaaatgct tgatggtcgg aagaggcata aattccgtca gccagtttag | 7260 |
| tctgaccatc tcatctgtaa catcattggc aacgctacct ttgccatgtt tcagaaacaa | 7320 |
| ctctggcgca tcgggcttcc catacaatcg atagattgtc gcacctgatt gcccgacatt | 7380 |
| atcgcgagcc catttatacc catataaatc agcatccatg ttggaattta atcgcggcct | 7440 |
| cgagcaagac gtttcccgtt gaatatggct cataacaccc cttgtattac tgtttatgta | 7500 |
| agcagacagt tttattgttc atgatgatat attttttatct tgtgcaatgt aacatcagag | 7560 |
| attttgagac acaacgtggc tttccccccc ccccattat tgaagcattt atcagggtta | 7620 |
| ttgtctcatg agcggataca tatttgaatg tatttagaaa aataaacaaa taggggttcc | 7680 |
| gcgcacattt ccccgaaaag tgccacctga cgtctaagaa accattatta tcatgacatt | 7740 |
| aacctataaa aataggcgta tcacgaggcc ctttcgtc | 7778 |

<210> SEQ ID NO 31
<211> LENGTH: 7005
<212> TYPE: DNA
<213> ORGANISM: Artificial Sequence
<220> FEATURE:
<223> OTHER INFORMATION: Synthetic Construct pVR1012x/s Marburg GP(dTM)

<400> SEQUENCE: 31

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagggA ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccctttggc | 1080 |
| tcttatgcat gctatactgt ttttggcttg ggcctatac accccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tattttttaca | 1320 |
| ggatggggtc ccatttatta tttacaaatt cacatataca acaacgccgt cccccgtgcc | 1380 |
| cgcagttttt attaaacata gcgtgggatc tccacgcgaa tctcgggtac gtgttccgga | 1440 |

```
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga gtcgaatgaa    1920
gaacattaat tgctgggtaa aagtgattaa tttctttaaa tttgaccaga ataatatttt    1980
gtcagtgaat atattctcat atcacttgat taaaaacaga aaattaccct aacatgaaga    2040
ccacatgttt ccttatcagt cttatcttaa ttcaagggac aaaaaatctc cccattttag    2100
agatagctag taataatcaa ccccaaaatg tggattcggt atgctccgga actctccaga    2160
agacagaaga cgtccatctg atgggattca cactgagtgg gcaaaaagtt gctgattccc    2220 cttttggaggc atccaagcga tgggctttca ggacaggtgt acctcccaag aatgttgagt    2280
acacagaggg ggaggaagcc aaaacatgct acaatataag tgtaacggat ccctctggaa    2340
aatccttgct gttagatcct cctaccaaca tccgtgacta tcctaaatgc aaaactatcc    2400
atcatattca aggtcaaaac cctcatgcac aggggatcgc ccttcattta tggggagcat    2460
tttttctgta tgatcgcatt gcctccacaa caatgtaccg aggcaaagtc ttcactgaag    2520
ggaacatagc agctatgatt gtcaataaga cagtgcacaa aatgattttc tcgcggcaag    2580
gacaagggta ccgtcatatg aatctgactt ctactaataa atattggaca agtagtaacg    2640
gaacgcaaac gaatgacact ggatgtttcg gcgctcttca agaatacaat tctacaaaga    2700
accaaacatg tgctccgtcc aaaataccte caccactgcc cacagcccgt ccggagatca    2760
aactcacaag caccccaact gatgccacca aactcaatac cacggaccca agcagtgatg    2820
atgaggacct cgcaacatcc ggctcagggt ccggagaacg agaacccac acaacttctg     2880 atgcggtcac caagcaaggg ctttcatcaa caatgccacc cactccctca ccacaaccaa    2940
gcacgccaca gcaaggagga acaacacaa ccattcccca agatgctgtg actgaactag     3000
acaaaaataa cacaactgca caaccgtcca tgcccctca taacactacc acaatctcta     3060
ctaacaacac ctccaaacac aacttcagca ctctctctgc accattacaa acaccacca     3120 atgacaacac acagagcaca atcactgaaa atgagcaaac cagtgccccc tcgataacaa    3180
ccctgcctcc aacgggaaat cccaccacag caaagagcac cagcagcaaa aaaggccccg    3240
ccacaacggc accaaacacg acaaatgagc atttcaccag tcctcccccc accccagct     3300 cgactgcaca acatcttgta tatttcagaa gaaagcgaag tatcctctgg agggaaggcg    3360
acatgttccc ttttctggat gggttaataa atgctccaat tgattttgac ccagttccaa    3420
atacaaaaac aatctttgat gaatcctcta gttctggtgc ctcggctgag aagatcaac     3480 atgcctcccc caatattagt ttaactttat cttattttcc taatataaat gagaacactg    3540
cctactctgg agaaaatgag aatgattgtg atgcagagtt aagaatttgg agcgttcagg    3600
aggatgacct ggccgcaggg ctcagttgga taccgttttt tggccctgga attgaaggac    3660
tttacactgc tgtttaatt aaaaatcaaa acaatttggt ctgcaggttg aggcgtctag     3720
ccaatcaaac tgccaaatcc ttggaactct tattgagagt cacaactgag gaaagaacat    3780
tctccttaat caatagacat gctattgact ttctactcac aagatgggga ggaacatgca    3840
```

```
aagtgcttgg acctgattgt tgcatcggga tagaagactt gtccaaaaat atttcagagc   3900
aaattgacca aattaaaaag gacgaacaaa aagagggac tggttggggt ctgggtggta    3960
aatggtggac atccgactgg ggttaagatc tgctgtgcct tctagttgcc agccatctgt   4020
tgtttgcccc tcccccgtgc cttccttgac cctggaaggt gccactccca ctgtcctttc   4080
ctaataaaat gaggaaattg catcgcattg tctgagtagg tgtcattcta ttctggggg    4140
tggggtgggg caggacagca agggggagga ttggaagac aatagcaggc atgctgggga    4200
tgcggtgggc tctatgggta cccaggtgct gaagaattga cccggttcct cctgggccag   4260
aaagaagcag gcacatcccc ttctctgtga cacaccctgt ccacgcccct ggttcttagt   4320
tccagcccca ctcataggac actcatagct caggagggct ccgccttcaa tcccacccgc   4380
taaagtactt ggagcggtct ctccctccct catcagccca ccaaaccaaa cctagcctcc   4440
aagagtggga agaaattaaa gcaagatagg ctattaagtg cagagggaga gaaaatgcct   4500
ccaacatgtg aggaagtaat gagagaaatc atagaatttt aaggccatga tttaaggcca   4560
tcatggcctt aatcttccgc ttcctcgctc actgactcgc tgcgctcggt cgttcggctg   4620
cggcgagcgg tatcagctca ctcaaaggcg gtaatacggt tatccacaga atcagggat    4680
aacgcaggaa agaacatgtg agcaaaaggc cagcaaaagg ccaggaaccg taaaaaggcc   4740
gcgttgctgg cgttttttcca taggctccgc cccctgacg agcatcacaa aaatcgacgc    4800
tcaagtcaga ggtggcgaaa cccgacagga ctataaagat accaggcgtt ccccctgga    4860
agctccctcg tgcgctctcc tgttccgacc ctgccgctta ccggatacct gtccgccttt   4920
ctcccttcgg gaagcgtggc gctttctcat agctcacgct gtaggtatct cagttcggtg   4980
taggtcgttc gctccaagct gggctgtgtg cacgaacccc ccgttcagcc cgaccgctgc   5040
gccttatccg gtaactatcg tcttgagtcc aacccggtaa gacacgactt atcgccactg   5100
gcagcagcca ctggtaacag gattagcaga gcgaggtatg taggcggtgc tacagagttc   5160
ttgaagtggt ggcctaacta cggctacact agaagaacag tatttggtat ctgcgctctg   5220
ctgaagccag ttaccttcgg aaaaagagtt ggtagctctt gatccggcaa acaaaccacc   5280
gctggtagcg gtggtttttt tgtttgcaag cagcagatta cgcgcagaaa aaaggatct   5340
caagaagatc ctttgatctt ttctacgggg tctgacgctc agtggaacga aaactcacgt   5400
taagggattt tggtcatgag attatcaaaa aggatcttca cctagatcct ttaaattaa    5460
aaatgaagtt ttaaatcaat ctaaagtata tatgagtaaa cttggtctga cagttaccaa   5520
tgcttaatca gtgaggcacc tatctcagcg atctgtctat ttcgttcatc catagttgcc   5580
tgactcgggg ggggggggcg ctgaggtctg cctcgtgaag aaggtgttgc tgactcatac   5640
caggcctgaa tcgccccatc atccagccag aaagtgaggg agccacggtt gatgagagct   5700
ttgttgtagg tggaccagtt ggtgattttg aacttttgct ttgccacgga acggtctgcg   5760
ttgtcgggaa gatgcgtgat ctgatccttc aactcagcaa agttcgatt tattcaacaa    5820
agccgccgtc ccgtcaagtc agcgtaatgc tctgccagtg ttacaaccaa ttaaccaatt   5880
ctgattagaa aaactcatcg agcatcaaat gaaactgcaa tttattcata tcaggattat   5940
caataccata tttttgaaaa agccgtttct gtaatgaagg agaaaactca ccgaggcagt   6000
tccataggat ggcaagatcc tggtatcggt ctgcgattcc gactcgtcca acatcaatac   6060
aacctattaa tttccctcg tcaaaaataa ggttatcaag tgagaaatca ccatgagtga    6120
cgactgaatc cggtgagaat ggcaaaagct tatgcatttc tttccagact tgttcaacag   6180
gccagccatt acgctcgtca tcaaaatcac tcgcatcaac caaaccgtta ttcattcgtg   6240
```

```
attgcgcctg agcgagacga aatacgcgat cgctgttaaa aggacaatta caaacaggaa    6300
tcgaatgcaa ccggcgcagg aacactgcca gcgcatcaac aatattttca cctgaatcag    6360
gatattcttc taatacctgg aatgctgttt tcccggggat cgcagtggtg agtaaccatg    6420
catcatcagg agtacggata aaatgcttga tggtcggaag aggcataaat tccgtcagcc    6480
agtttagtct gaccatctca tctgtaacat cattggcaac gctacctttg ccatgtttca    6540
gaaacaactc tggcgcatcg ggcttcccat acaatcgata gattgtcgca cctgattgcc    6600
cgacattatc gcgagcccat ttatacccat ataaatcagc atccatgttg gaatttaatc    6660
gcggcctcga gcaagacgtt tcccgttgaa tatggctcat aacacccctt gtattactgt    6720
ttatgtaagc agacagtttt attgttcatg atgatatatt tttatcttgt gcaatgtaac    6780
atcagagatt ttgagacaca acgtggcttt ccccccccc ccattattga agcatttatc    6840 aggggttattg tctcatgagc ggatacatat ttgaatgtat ttagaaaaat aaacaaatag    6900
gggttccgcg cacatttccc cgaaaagtgc cacctgacgt ctaagaaacc attattatca    6960
tgacattaac ctataaaaat aggcgtatca cgaggccctt tcgtc                    7005

<210> SEQ ID NO 32
<211> LENGTH: 8256
<212> TYPE: DNA
<213> ORGANISM: Artificial Sequence
<220> FEATURE:
<223> OTHER INFORMATION: Synthetic Construct pAdApt Marburg GP(dTM)

<400> SEQUENCE: 32
ttaattaacc gcaattctca tgtttgacag cttatcatca tcaataatat accttatttt      60
ggattgaagc caatatgata atgagggggt ggagtttgtg acgtggcgcg gggcgtggga     120
acggggcggg tgacgtagta gtgtggcgga agtgtgatgt tgcaagtgtg gcggaacaca     180
tgtaagcgac ggatgtggca aaagtgacgt ttttggtgtg cgccggtgta cacaggaagt     240
gacaattttc gcgcggtttt aggcggatgt tgtagtaaat ttgggcgtaa ccgagtaaga     300
tttggccatt ttcgcgggaa aactgaataa gaggaagtga atctgaata attttgtgtt      360 actcatagcg cgtaatattt gtctagggcc gcggggactt tgaccgttta cgtggagact     420
cgcccaggtg ttttttctcag gtgttttccg cgttccgggt caaagttggc gttttattat     480
tatagtcagt acgtaccagt gcactggcct agagcggccc cattgcatac gttgtatcca     540
tatcataata tgtacattta tattggctca tgtccaacat taccgccatg ttgacattga     600
ttattgacta gttattaata gtaatcaatt acggggtcat tagttcatag cccatatatg     660
gagttccgcg ttacataact tacggtaaat ggcccgcctg gctgaccgcc caacgacccc     720
cgcccattga cgtcaataat gacgtatgtt cccatagtaa cgccaatagg gactttccat     780
tgacgtcaat gggtggagta tttacggtaa actgcccact tggcagtaca tcaagtgtat     840
catatgccaa gtacgccccc tattgacgtc aatgacggta aatggcccgc ctggcattat     900
gcccagtaca tgaccttatg ggactttcct acttggcagt acatctacgt attagtcatc     960
gctattacca tggtgatgcg gttttggcag tacatcaatg ggcgtggata gcggtttgac    1020
tcacggggat ttccaagtct ccaccccatt gacgtcaatg ggagtttgtt ttggcaccaa    1080
aatcaacggg actttccaaa atgtcgtaac aactccgccc cattgacgca atgggcggt    1140 aggcgtgtac ggtgggaggt ctatataagc agagctcgtt tagtgaaccg tcagatcgcc    1200
tggagacgcc atccacgctg ttttgacctc catagaagac accgggaccg atccagcctc    1260
cgtcaccgtc gtcgacacgt gtgatcagat atcgcggccg ctctagagtc gaatgaagaa    1320
```

```
cattaattgc tgggtaaaag tgattaattt ctttaaattt gaccagaata atattttgtc    1380
agtgaatata ttctcatatc acttgattaa aaacagaaaa ttaccctaac atgaagacca    1440
catgtttcct tatcagtctt atcttaattc aagggacaaa aaatctcccc attttagaga    1500
tagctagtaa taatcaaccc caaaatgtgg attcggtatg ctccggaact ctccagaaga    1560
cagaagacgt ccatctgatg ggattcacac tgagtgggca aaaagttgct gattcccctt    1620
tggaggcatc caagcgatgg gctttcagga caggtgtacc tcccaagaat gttgagtaca    1680
cagaggggga ggaagccaaa acatgctaca atataagtgt aacggatccc tctggaaaat    1740
ccttgctgtt agatcctcct accaacatcc gtgactatcc taaatgcaaa actatccatc    1800
atattcaagg tcaaacccct catgcacagg ggatcgccct tcatttatgg ggagcatttt    1860
ttctgtatga tcgcattgcc tccacaacaa tgtaccgagg caaagtcttc actgaaggga    1920
acatagcagc tatgattgtc aataagacag tgcacaaaat gattttctcg cggcaaggac    1980
aagggtaccg tcatatgaat ctgacttcta ctaataaata ttggacaagt agtaacggaa    2040
cgcaaacgaa tgacactgga tgtttcggcg ctcttcaaga atacaattct acaaagaacc    2100
aaacatgtgt tccgtccaaa atacctccac cactgcccac agcccgtccg gagatcaaac    2160
tcacaagcac cccaactgat gccaccaaac tcaataccac ggacccaagc agtgatgatg    2220
aggacctcgc aacatccggc tcagggtccg gagaacgaga accccacaca acttctgatg    2280
cggtcaccaa gcaagggctt tcatcaacaa tgccacccac tccctcacca caaccaagca    2340
cgccacagca aggaggaaac aacacaaacc attcccaaga tgctgtgact gaactagaca    2400
aaaataacac aactgcacaa ccgtccatgc cccctcataa cactaccaca atctctacta    2460
acaacacctc caaacacaac ttcagcactc tctctgcacc attacaaaac accaccaatg    2520
acaacacaca gagcacaatc actgaaaatg agcaaaccag tgcccccctcg ataacaaccc    2580 tgcctccaac gggaaatccc accacagcaa agagcaccag cagcaaaaaa ggccccgcca    2640
caacggcacc aaaacacgaca aatgagcatt tcaccagtcc tcccccccacc cccagctcga    2700 ctgcacaaca tcttgtatat ttcagaagaa agcgaagtat cctctggagg gaaggcgaca    2760
tgttcccttt tctggatggg ttaataaatg ctccaattga ttttgaccca gttccaaata    2820
caaaaacaat ctttgatgaa tcctctagtt ctggtgcctc ggctgaggaa gatcaacatg    2880
cctcccccaa tattagttta actttatctt attttcctaa tataaatgag aacactgcct    2940
actctggaga aaatgagaat gattgtgatg cagagttaag aatttggagc gttcaggagg    3000
atgacctggc cgcagggctc agttggatac cgttttttgg ccctggaatt gaaggacttt    3060
acactgctgt tttaattaaa aatcaaaaca atttggtctg caggttgagg cgtctagcca    3120
atcaaactgc caaatccttg gaactcttat tgagagtcac aactgaggaa agaacattct    3180
ccttaatcaa tagacatgct attgactttc tactcacaag atggggagga acatgcaaag    3240
tgcttggacc tgattgttgc atcgggatag aagacttgtc caaaaatatt tcagagcaaa    3300
ttgaccaaat taaaaaggac gaacaaaaag aggggactgg ttgggggtctg ggtggtaaat    3360 ggtggacatc cgactgggt taagatctgc tgtgccttct agttgccagc catctgttgt    3420
ttgcccctcc cccgtgcctt ccttgaccct ggaaggtgcc actcccactg tcctttccta    3480
ataaaatgag gaaattgcat cgcattgtct gagtaggtgt cattctattc tggggggtgg    3540
ggtggggcag cacagcaagg gggaggattg ggaagacaat agcaggcatg ctggggatgc    3600
ggtgggctct atgggtaccc agggccgcat aacttcgtat aatgtatgct atacgaagtt    3660
ataagatctg tactgaaatg tgtgggcgtg gcttaagggt gggaagaat atataaggtg    3720
```

```
ggggtcttat gtagttttgt atctgttttg cagcagccgc cgccgccatg agcaccaact    3780
cgtttgatgg aagcattgtg agctcatatt tgacaacgcg catgccccca tgggccgggg    3840
tgcgtcagaa tgtgatgggc tccagcattg atggtcgccc cgtcctgccc gcaaactcta    3900
ctaccttgac ctacgagacc gtgtctggaa cgccgttgga gactgcagcc tccgccgccg    3960
cttcagccgc tgcagccacc gcccgcggga ttgtgactga ctttgctttc ctgagcccgc    4020
ttgcaagcag tgcagcttcc cgttcatccg cccgcgatga caagttgacg gctcttttgg    4080
cacaattgga ttctttgacc cgggaactta atgtcgtttc tcagcagctg ttggatctgc    4140
gccagcaggt ttctgccctg aaggcttcct cccctcccaa tgcggtttaa acataaata    4200
aaaaaccaga ctctgtttgg atttggatca agcaagtgtc ttgctgtctt tatttagggg    4260
ttttgcgcgc gcggtaggcc cgggaccagc ggtctcggtc gttgagggtc ctgtgtattt    4320
tttccaggac gtggtaaagg tgactctgga tgttcagata catgggcata agcccgtctc    4380
tggggtggag gtagcaccac tgcagagctt catgctgcgg ggtggtgttg tagatgatcc    4440
agtcgtagca ggagcgctgg gcgtggtgcc taaaaatgtc tttcagtagc aagctgattg    4500
ccaggggcag gcccttggtg taagtgttta caaagcggtt aagctgggat gggtgcatac    4560
gtggggatat gagatgcatc ttggactgta ttttaggtt ggctatgttc ccagccatat    4620
ccctccgggg attcatgttg tgcagaacca ccagcacagt gtatccggtg cacttgggaa    4680
atttgtcatg tagcttagaa ggaaatgcgt ggaagaactt ggagacgccc ttgtgacctc    4740
caagattttc catgcattcg tccataatga tggcaatggg cccacgggcg gcggcctggg    4800
cgaagatatt tctgggatca ctaacgtcat agttgtgttc caggatgaga tcgtcatagg    4860
ccattttac aaagcgcggg cggagggtgc cagactgcgg tataatggtt ccatccggcc    4920
caggggcgta gttaccctca cagatttgca tttcccacgc tttgagttca gatgggggga    4980
tcatgtctac ctgcggggcg atgaagaaaa cggtttccgg ggtaggggag atcagctggg    5040
aagaaagcag gttcctgagc agctgcgact taccgcagcc ggtgggcccg taaatcacac    5100
ctattaccgg ctgcaactgg tagttaagag agctgcagct gccgtcatcc ctgagcaggg    5160
gggccacttc gttaagcatg tccctgactc gcatgttttc cctgaccaaa tccgccagaa    5220
ggcgctcgcc gcccagcgat agcagttctt gcaaggaagc aaagttttc aacggtttga    5280
gaccgtccgc cgtaggcatg cttttgagcg tttgaccaag cagttccagg cggtcccaca    5340
gctcggtcac ctgctctacg gcatctcgat ccagcatatc tcctcgtttc gcgggttggg    5400
gcggctttcg ctgtacggca gtagtcggtg ctcgtccaga cgggccaggg tcatgtcttt    5460
ccacgggcgc agggtcctcg tcagcgtagt ctgggtcacg gtgaaggggt gcgctccggg    5520
ctgcgcgctg gccagggtgc gcttgaggct ggtcctgctg gtgctgaagc gctgccggtc    5580
ttcgccctgc gcgtcggcca ggtagcattt gaccatggtg tcatagtcca gcccctccgc    5640
ggcgtggccc ttggcgcgca gcttgccctt ggaggaggcg ccgcacgagg ggcagtgcag    5700
acttttgagg gcgtagagct ggggcgcgag aaataccgat tccggggagt aggcatccgc    5760
gccgcaggcc ccgcagacgg tctcgcattc cacgagccag gtgagctctg gccgttcggg    5820
gtcaaaaacc aggtttcccc catgcttttt gatgcgtttc ttacctctgg tttccatgag    5880
ccggtgtcca cgctcggtga cgaaaaggct gtccgtgtcc ccgtatacag acttgagagg    5940
cctgtcctcg agcggtgttc cgcggtcctc ctcgtataga aactcggacc actctgagac    6000
aaaggctcgc gtccaggcca gcacgaagga ggctaagtgg gaggggtagc ggtcgttgtc    6060
cactagggg tccactcgct ccagggtgtg aagacacatg tcgccctctt cggcatcaag    6120
```

```
gaaggtgatt ggtttgtagg tgtaggccac gtgaccgggt gttcctgaag gggggctata    6180 aaaggggtg ggggcgcgtt cgtcctcact ctcttccgca tcgctgtctg cgagggccag     6240 ctgttgggt gagtcgacgc gaggctggat ggccttcccc attatgattc ttctcgcttc     6300
cggcggcatc gggatgcccg cgttgcaggc catgctgtcc aggcaggtag atgacgacca    6360
tcagggacag cttcaaggcc agcaaaaggc caggaaccgt aaaaaggccg cgttgctggc    6420 gttttttccat aggctccgcc ccctgacga gcatcacaaa aatcgacgct caagtcagag    6480
gtggcgaaac ccgacaggac tataaagata ccaggcgttt ccccctggaa gctccctcgt    6540
gcgctctcct gttccgaccc tgccgcttac cggatacctg tccgcctttc tcccttcggg    6600
aagcgtggcg ctttctcata gctcacgctg taggtatctc agttcggtgt aggtcgttcg    6660
ctccaagctg ggctgtgtgc acgaaccccc cgttcagccc gaccgctgcg ccttatccgg    6720
taactatcgt cttgagtcca acccggtaag acacgactta tcgccactgg cagcagccac    6780
tggtaacagg attagcagag cgaggtatgt aggcggtgct acagagttct tgaagtggtg    6840
gcctaactac ggctacacta aaggacagt atttggtatc tgcgctctgc tgaagccagt     6900
taccttcgga aaaagagttg gtagctcttg atccggcaaa caaaccaccg ctggtagcgg    6960 tggtttttt gtttgcaagc agcagattac gcgcagaaaa aaaggatctc aagaagatcc     7020
tttgatcttt tctacggggt ctgacgctca gtggaacgaa aactcacgtt aagggatttt    7080
ggtcatgaga ttatcaaaaa ggatcttcac ctagatcctt ttaaattaaa aatgaagttt    7140
taaatcaatc taaagtatat atgagtaaac ttggtctgac agttaccaat gcttaatcag    7200
tgaggcacct atctcagcga tctgtctatt tcgttcatcc atagttgcct gactccccgt    7260
cgtgtagata actacgatac gggagggctt accatctggc cccagtgctg caatgatacc    7320
gcgagaccca cgctcaccgg ctccagattt atcagcaata accagccag ccggaagggc     7380 cgagcgcaga gtggtcctg caactttatc cgcctccatc cagtctatta attgttgccg     7440
ggaagctaga gtaagtagtt cgccagttaa tagtttgcgc aacgttgttg ccattgctgc    7500
aggcatcgtg gtgtcacgct cgtcgtttgg tatggcttca ttcagctccg gttcccaacg    7560
atcaaggcga gttacatgat cccccatgtt gtgcaaaaaa gcggttagct ccttcggtcc    7620
tccgatcgtt gtcagaagta agttggccgc agtgttatca ctcatggtta tggcagcact    7680
gcataattct cttactgtca tgccatccgt aagatgcttt tctgtgactg gtgagtactc    7740
aaccaagtca ttctgagaat agtgtatgcg gcgaccgagt tgctcttgcc cggcgtcaac    7800
acgggataat accgcgccac atagcagaac tttaaaagtg ctcatcattg gaaaacgttc    7860
ttcggggcga aaactctcaa ggatcttacc gctgttgaga tccagttcga tgtaacccac    7920
tcgtgcaccc aactgatctt cagcatcttt tactttcacc agcgtttctg ggtgagcaaa    7980
aacaggaagg caaaatgccg caaaaaaggg aataagggcg acacggaaat gttgaatact    8040
catactcttc ctttttcaat attattgaag catttatcag ggttattgtc tcatgagcgg    8100
atacatattt gaatgtattt agaaaaataa acaaataggg gttccgcgca catttccccg    8160
aaaagtgcca cctgacgtct aagaaaccat tattatcatg acattaacct ataaaaatag    8220
gcgtatcacg aggccctttc gtcttcaaga attgtt                             8256
```

<210> SEQ ID NO 33
<211> LENGTH: 6447
<212> TYPE: DNA
<213> ORGANISM: Artificial Sequence
<220> FEATURE:
<223> OTHER INFORMATION: Synthetic Construct pVR1012x/s Lassa GP

<400> SEQUENCE: 33

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca cgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg aacgcggat    1020
tccccgtgcc aagagtgacg taagtaccgc ctatagactc tataggcaca ccccttttggc    1080
tcttatgcat gctatactgt ttttggcttg gggcctatac accccgctt ccttatgcta    1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt ccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga atttaggatt    1920
gcgcttttag agattcacta ctagttagga attcctaaat catggggcag attattacat    1980
tctttcaaga agtgccacat gtaatagagg aagtcatgaa cattgtgcta attgcgcttt    2040
ctctattggc aatcttgaag ggcttgtata acatcgctac atgtgggatt attggattgg    2100
ttgccttttt attcttgtgt ggcaagtctt gttccctaac ccttaaaggg ggatatgagc    2160
tgcaaaacctt agaattaaat atggagaccc taaacatgac catgccctta tcatgcacca    2220
agaacagcag tcatcattac ataagagtgg gcaatgagac tggattagaa ttgacttaa    2280
ctaacaccag cattataaat cacaaatttt gcaacttatc cgatgctcac aaaaagaatc    2340
```

```
tttatgatca tgctctcatg agcatcatct caacattcca tctatccatt ccaaacttca   2400
atcagtatga agccatgagt tgtgatttca atggagggaa aatcagtgtg caatacaacc   2460
tctctcattc ctatgctggg gatgcggccg aacactgtgg gacagttgcc aacggagtgt   2520
tgcaaacatt tatgagaatg gcctggggtg gaagatacat tgcattagac tcaggaaagg   2580
gaaactggga ctgtataatg accagctacc agtacctgat aattcaaaat acaacatggg   2640
aggaccactg ccaattctca agaccgtctc ctatcgggta ccttggcctt tgtcacaaa    2700
ggacaagaga tatatatata agtaggaggc tcttggggac cttcacctgg acattgtcag   2760
attctgaggg caatgaaaca ccaggtggtt attgtttaac caggtggatg ctaattgaag   2820
cagaactcaa gtgttttggg aatacagctg tggcaaaatg caatgagaag catgatgagg   2880
agttttgtga catgctgaga ttgtttgatt tcaacaagca agcaatccgt aggttgaagg   2940
ctgaggccca gatgagtatt caattaataa ataaagccgt gaatgcctta atcaatgatc   3000
aattaatcat gaagaaccat ttaagagaca tcatgggcat tccctactgc aattacagca   3060
agtattggta ccttaatcat actagtagcg ggagaacatc actaccaaag tgttggctta   3120
tatccaatgg gtcatatcta aatgaaaccc agttctctga tgacatagaa cagcaagccg   3180
acaatatgat cacagagatg cttcagaaag aatacattga agacaagggg aaaacgccct   3240
tgggactagt ggacattttc atctttagca caagctttta tctgatcagc attttcttgc   3300
atttaattaa aatccctaca catcgacaca tcgttgggaa accctgtccc aaaccccata   3360
gactaaatca catgggagta tgttcctgtg gactgtacaa acaccctggt gttccaacaa   3420
agtggaagag atagggatcc agatctgctg tgccttctag ttgccagcca tctgttgttt   3480
gccccctccc cgtgccttcc ttgaccctgg aaggtgccac tcccactgtc ctttcctaat   3540
aaaatgagga aattgcatcg cattgtctga gtaggtgtca ttctattctg ggggtgggg    3600
tggggcagga cagcaagggg gaggattggg aagacaatag caggcatgct ggggatgcgg   3660
tgggctctat gggtacccag gtgctgaaga attgacccgg ttcctcctgg gccagaaaga   3720
agcaggcaca tccccttctc tgtgacacac cctgtccacg ccctggttc ttagttccag    3780
ccccactcat aggacactca tagctcagga gggctccgcc ttcaatccca cccgctaaag   3840
tacttggagc ggtctctccc tccctcatca gcccaccaaa ccaaacctag cctccaagag   3900
tgggaagaaa ttaaagcaag ataggctatt aagtgcagag ggagagaaaa tgcctccaac   3960
atgtgaggaa gtaatgagag aaatcataga attttaaggc catcatggcc ttaatcttcc   4020
gcttcctcgc tcactgactc gctgcgctcg gtcgttcggc tgcggcgagc ggtatcagct   4080
cactcaaagg cggtaatacg gttatccaca gaatcagggg ataacgcagg aaagaacatg   4140
tgagcaaaag gccagcaaaa ggccaggaac cgtaaaaagg ccgcgttgct ggcgtttttc   4200
cataggctcc gcccccctga cgagcatcac aaaaatcgac gctcaagtca gaggtggcga   4260
aacccgacag gactataaag ataccaggcg tttccccctg gaagctccct cgtgcgctct   4320
cctgttccga ccctgccgct taccggatac ctgtccgcct ttctcccttc gggaagcgtg   4380
gcgctttctc atagctcacg ctgtaggtat ctcagttcgg tgtaggtcgt tcgctccaag   4440
ctgggctgtg tgcacgaacc ccccgttcag cccgaccgct gcgccttatc cggtaactat   4500
cgtcttgagt ccaacccggt aagacacgac ttatcgccac tggcagcagc cactggtaac   4560
aggattagca gagcgaggta tgtaggcggt gctacagagt tcttgaagtg gtggcctaac   4620
tacggctaca ctagaagaac agtatttggt atctgcgctc tgctgaagcc agttaccttc   4680
ggaaaaagag ttggtagctc ttgatccggc aaacaaacca ccgctggtag cggtggtttt   4740
```

| | |
|---|---:|
| tttgtttgca agcagcagat tacgcgcaga aaaaaggat ctcaagaaga tcctttgatc | 4800 |
| ttttctacgg ggtctgacgc tcagtggaac gaaaactcac gttaagggat tttggtcatg | 4860 |
| agattatcaa aaaggatctt cacctagatc cttttaaatt aaaaatgaag ttttaaatca | 4920 |
| atctaaagta tatatgagta aacttggtct gacagttacc aatgcttaat cagtgaggca | 4980 |
| cctatctcag cgatctgtct atttcgttca tccatagttg cctgactcgg ggggggggg | 5040 |
| cgctgaggtc tgcctcgtga agaaggtgtt gctgactcat accaggcctg aatcgcccca | 5100 |
| tcatccagcc agaaagtgag ggagccacgg ttgatgagag ctttgttgta ggtggaccag | 5160 |
| ttggtgattt tgaacttttg ctttgccacg gaacggtctg cgttgtcggg aagatgcgtg | 5220 |
| atctgatcct tcaactcagc aaagttcga tttattcaac aaagccgccg tcccgtcaag | 5280 |
| tcagcgtaat gctctgccag tgttacaacc aattaaccaa ttctgattag aaaaactcat | 5340 |
| cgagcatcaa atgaaactgc aatttattca tatcaggatt atcaatacca tattttttgaa | 5400 |
| aaagccgttt ctgtaatgaa ggagaaaact caccgaggca gttccatagg atggcaagat | 5460 |
| cctggtatcg gtctgcgatt ccgactcgtc aacatcaat acaacctatt aatttccct | 5520 |
| cgtcaaaaat aaggttatca agtgagaaat caccatgagt gacgactgaa tccggtgaga | 5580 |
| atggcaaaag cttatgcatt tctttccaga cttgttcaac aggccagcca ttacgctcgt | 5640 |
| catcaaaatc actcgcatca accaaaccgt tattcattcg tgattgcgcc tgagcgagac | 5700 |
| gaaatacgcg atcgctgtta aaaggacaat tacaaacagg aatcgaatgc aaccggcgca | 5760 |
| ggaacactgc cagcgcatca acaatatttt cacctgaatc aggatattct tctaatacct | 5820 |
| ggaatgctgt ttcccgggg atcgcagtgg tgagtaacca tgcatcatca ggagtacgga | 5880 |
| taaaatgctt gatggtcgga agaggcataa attccgtcag ccagtttagt ctgaccatct | 5940 |
| catctgtaac atcattggca acgctacctt tgccatgttt cagaaacaac tctggcgcat | 6000 |
| cgggcttccc atacaatcga tagattgtcg cacctgattg cccgacatta tcgcgagccc | 6060 |
| atttataccc atataaatca gcatccatgt tggaatttaa tcgcggcctc gagcaagacg | 6120 |
| tttcccgttg aatatggctc ataacacccc ttgtattact gtttatgtaa gcagacagtt | 6180 |
| ttattgttca tgatgatata ttttatctt gtgcaatgta acatcagaga ttttgagaca | 6240 |
| caacgtggct ttcccccccc ccccattatt gaagcattta tcagggttat tgtctcatga | 6300 |
| gcggatacat atttgaatgt atttagaaaa ataaacaaat aggggttccg cgcacatttc | 6360 |
| cccgaaaagt gccacctgac gtctaagaaa ccattattat catgacatta acctataaaa | 6420 |
| ataggcgtat cacgaggccc tttcgtc | 6447 |

<210> SEQ ID NO 34
<211> LENGTH: 6258
<212> TYPE: DNA
<213> ORGANISM: Artificial Sequence
<220> FEATURE:
<223> OTHER INFORMATION: Synthetic Construct pVR1012x/s Lassa GP(dTM)

<400> SEQUENCE: 34

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |

```
ggggtcatta gttcatagcc catatatgga gttccgcgtt acataactta cggtaaatgg    420
cccgcctggc tgaccgccca acgaccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac accccgcctt ccttatgcta   1140
taggtgatgg tatagcttag cctataggtg tgggttattg accattattg ccactcccc    1200
tattggtgac gatactttcc attactaatc cataacatgg ctctttgcca caactatctc   1260
tattggctat atgccaatac tctgtccttc agagactgac acggactctg tattttaca    1320
ggatggggtc ccatttatta tttacaaatt cacatataca acaacgccgt ccccgtgcc    1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgca atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtctttc    1860
tgcagtcacc gtcgtcgaca cgtgtgatca gatatcgcgg ccgctctaga atttaggatt   1920
gcgcttttag agattcacta ctagttagga attcctaaat catggggcag attattacat   1980
tctttcaaga agtgccacat gtaatagagg aagtcatgaa cattgtgcta attgcgcttt   2040
ctctattggc aatcttgaag ggcttgtata acatcgctac atgtgggatt attggattgg   2100
ttgccttttt attcttgtgt ggcaagtctt gttccctaac ccttaaaggg ggatatgagc   2160
tgcaaacctt agaattaaat atggagaccc taaacatgac catgccctta tcatgcacca   2220
agaacagcag tcatcattac ataagagtgg gcaatgagac tggattagaa ttgactttaa   2280
ctaacaccag cattataaat cacaaatttt gcaacttatc cgatgctcac aaaaagaatc   2340
tttatgatca tgctctcatg agcatcatct caacattcca tctatccatt ccaaacttca   2400
atcagtatga agccatgagt tgtgatttca atggaggaa aatcagtgtg caatacaacc   2460
tctctcattc ctatgctggg gatgcggccg aacactgtgg gacagttgcc aacggagtgt   2520
tgcaaacatt tatgagaatg gcctggggtg aagatacat tgcattagac tcaggaaagg   2580
gaaactggga ctgtataatg accagctacc agtacctgat aattcaaaat acaacatggg   2640
aggaccactc ccaattctca agaccgtctc tatcggta ccttggcctt ttgtcacaaa   2700
ggacaagaga tatatatata agtaggaggc tcttgggac cttcacctgg acattgtcag   2760
```

```
attctgaggg caatgaaaca ccaggtggtt attgtttaac caggtggatg ctaattgaag    2820
cagaactcaa gtgttttggg aatacagctg tggcaaaatg caatgagaag catgatgagg    2880
agttttgtga catgctgaga ttgtttgatt tcaacaagca agcaatccgt aggttgaagg    2940
ctgaggccca gatgagtatt caattaataa ataaagccgt gaatgcctta atcaatgatc    3000
aattaatcat gaagaaccat ttaagagaca tcatgggcat tccctactgc aattacagca    3060
agtattggta ccttaatcat actagtagcg ggagaacatc actaccaaag tgttggctta    3120
tatccaatgg gtcatatcta aatgaaaccc agttctctga tgacatagaa cagcaagccg    3180
acaatatgat cacagagatg cttcagaaag aatacattga agacaagggg aaaacgccct    3240
tgtagggatc cagatctgct gtgccttcta gttgccagcc atctgttgtt tgcccctccc    3300
ccgtgccttc cttgaccctg gaaggtgcca ctcccactgt cctttcctaa taaaatgagg    3360
aaattgcatc gcattgtctg agtaggtgtc attctattct ggggggtggg gtggggcagg    3420
acagcaaggg ggaggattgg gaagacaata gcaggcatgc tggggatgcg gtgggctcta    3480
tgggtaccca ggtgctgaag aattgacccg gttcctcctg gccagaaag aagcaggcac     3540 atcccctcct ctgtgacaca ccctgtccac gcccctggtt cttagttcca gccccactca    3600
taggacactc atagctcagg agggctccgc cttcaatccc acccgctaaa gtacttggag    3660
cggtctctcc ctccctcatc agcccaccaa accaaaccta gcctcaagsa gtgggaagaa    3720
attaaagcaa gataggctat taagtgcaga gggagagaaa atgcctccaa catgtgagga    3780
agtaatgaga gaaatcatag aattttaagg ccatcatggc cttaatcttc cgcttcctcg    3840
ctcactgact cgctgcgctc ggtcgttcgg ctgcggcgag cggtatcagc tcactcaaag    3900
gcggtaatac ggttatccac agaatcaggg gataacgcag gaaagaacat gtgagcaaaa    3960
ggccagcaaa aggccaggaa ccgtaaaaag gccgcgttgc tggcgttttt ccataggctc    4020 cgccccctg acgagcatca caaaaatcga cgctcaagtc agaggtggcg aaacccgaca     4080
ggactataaa gataccaggc gtttccccct ggaagctccc tcgtgcgctc tcctgttccg    4140
accctgccgc ttaccggata cctgtccgcc tttctccctt cgggaagcgt ggcgctttct    4200
catagctcac gctgtaggta tctcagttcg gtgtaggtcg ttcgctccaa gctgggctgt    4260
gtgcacgaac cccccgttca gcccgaccgc tgcgccttat ccggtaacta tcgtcttgag    4320
tccaacccgg taagacacga cttatcgcca ctggcagcag ccactggtaa caggattagc    4380
agagcgaggt atgtaggcgg tgctacagag ttcttgaagt ggtggcctaa ctacggctac    4440
actagaagaa cagtatttgg tatctgcgct ctgctgaagc cagttacctt cggaaaaaga    4500
gttggtagct cttgatccgg caaacaaacc accgctggta gcggtggttt ttttgtttgc    4560
aagcagcaga ttacgcgcag aaaaaaagga tctcaagaag atcctttgat cttttctacg    4620
gggtctgacg ctcagtggaa cgaaaactca cgttaaggga ttttggtcat gagattatca    4680
aaaaggatct tcacctagat ccttttaaat taaaaatgaa gttttaaatc aatctaaagt    4740
atatatgagt aaacttggtc tgacagttac caatgcttaa tcagtgaggc acctatctca    4800
gcgatctgtc tatttcgttc atccatagtt gcctgactcg ggggggggg gcgctgaggt     4860 ctgcctcgtg aagaaggtgt tgctgactca taccaggcct gaatcgcccc atcatccagc    4920
cagaaagtga gggagccacg gttgatgaga gctttgttgt aggtggacca gttggtgatt    4980
ttgaactttt gctttgccac ggaacggtct gcgttgtcgg aagatgcgt gatctgatcc     5040 ttcaactcag caaaagttcg atttattcaa caaagccgcc gtcccgtcaa gtcagcgtaa    5100
tgctctgcca gtgttacaac caattaacca attctgatta gaaaaactca tcgagcatca    5160
```
aatgaaactg caatttattc atatcaggat tatcaatacc atatttttga aaaagccgtt 5220
tctgtaatga aggagaaaac tcaccgaggc agttccatag gatggcaaga tcctggtatc 5280
ggtctgcgat tccgactcgt ccaacatcaa tacaacctat taatttcccc tcgtcaaaaa 5340
taaggttatc aagtgagaaa tcaccatgag tgacgactga atccggtgag aatggcaaaa 5400
gcttatgcat ttctttccag acttgttcaa caggccagcc attacgctcg tcatcaaaat 5460
cactcgcatc aaccaaaccg ttattcattc gtgattgcgc ctgagcgaga cgaaatacgc 5520
gatcgctgtt aaaaggacaa ttacaaacag gaatcgaatg caaccggcgc aggaacactg 5580
ccagcgcatc aacaatattt tcacctgaat caggatattc ttctaatacc tggaatgctg 5640
ttttcccggg gatcgcagtg gtgagtaacc atgcatcatc aggagtacgg ataaaatgct 5700
tgatggtcgg aagaggcata aattccgtca gccagtttag tctgaccatc tcatctgtaa 5760
catcattggc aacgctacct ttgccatgtt tcagaaacaa ctctggcgca tcgggcttcc 5820
catacaatcg atagattgtc gcacctgatt gcccgacatt atcgcgagcc catttatacc 5880
catataaatc agcatccatg ttggaattta atcgcggcct cgagcaagac gtttcccgtt 5940
gaatatggct cataacaccc cttgtattac tgtttatgta agcagacagt tttattgttc 6000
atgatgatat atttttatct tgtgcaatgt aacatcagag attttgagac acaacgtggc 6060
tttccccccc cccccattat tgaagcattt atcagggtta ttgtctcatg agcggataca 6120
tatttgaatg tatttagaaa aataaacaaa taggggttcc gcgcacattt ccccgaaaag 6180
tgccacctga cgtctaagaa accattatta tcatgacatt aacctataaa aataggcgta 6240
tcacgaggcc ctttcgtc 6258

<210> SEQ ID NO 35
<211> LENGTH: 7711
<212> TYPE: DNA
<213> ORGANISM: Artificial Sequence
<220> FEATURE:
<223> OTHER INFORMATION: Synthetic Construct pAdApt Lassa GP

<400> SEQUENCE: 35
ttaattaacc gcaattctca tgtttgacag cttatcatca tcaataatat accttatttt 60
ggattgaagc caatatgata atgagggggt ggagtttgtg acgtggcgcg gggcgtggga 120
acggggcggg tgacgtagta gtgtggcgga agtgtgatgt tgcaagtgtg gcggaacaca 180
tgtaagcgac ggatgtggca aaagtgacgt ttttggtgtg cgccggtgta cacaggaagt 240
gacaattttc gcgcggtttt aggcggatgt tgtagtaaat ttgggcgtaa ccgagtaaga 300
tttggccatt ttcgcgggaa aactgaataa gaggaagtga aatctgaata attttgtgtt 360
actcatagcg cgtaatattt gtctagggcc gcggggactt tgaccgttta cgtggagact 420
cgcccaggtg tttttctcag gtgttttccg cgttccgggt caaagttggc gttttattat 480
tatagtcagt acgtaccagt gcactggcct agagcggccc cattgcatac gttgtatcca 540
tatcataata tgtacattta tattggctca tgtccaacat taccgccatg ttgacattga 600
ttattgacta gttattaata gtaatcaatt acggggtcat tagttcatag cccatatatg 660
gagttccgcg ttacataact tacggtaaat ggcccgcctg gctgaccgcc caacgacccc 720
cgcccattga cgtcaataat gacgtatgtt cccatagtaa cgccaatagg gactttccat 780
tgacgtcaat gggtggagta tttacggtaa actgcccact tggcagtaca tcaagtgtat 840
catatgccaa gtacgccccc tattgacgtc aatgacggta aatggcccgc ctggcattat 900
gcccagtaca tgaccttatg ggactttcct acttggcagt acatctacgt attagtcatc 960

-continued

```
gctattacca tggtgatgcg gttttggcag tacatcaatg gcggtgggata gcggtttgac    1020
tcacggggat ttccaagtct ccaccccatt gacgtcaatg ggagtttgtt ttggcaccaa    1080
aatcaacggg actttccaaa atgtcgtaac aactccgccc cattgacgca aatgggcggt    1140
aggcgtgtac ggtgggaggt ctatataagc agagctcgtt tagtgaaccg tcagatcgcc    1200
tggagacgcc atccacgctg ttttgacctc catagaagac accgggaccg atccagcctc    1260
cgtcaccgtc gtcgacacgt gtgatcagat atcgcggccg ctctagaatt taggattgcg    1320
cttttagaga ttcactacta gttaggaatt cctaaatcat ggggcagatt attacattct    1380
ttcaagaagt gccacatgta atagaggaag tcatgaacat tgtgctaatt gcgctttctc    1440
tattggcaat cttgaagggc ttgtataaca tcgctacatg tgggattatt ggattggttg    1500
cctttttatt cttgtgtggc aagtcttgtt ccctaacccct taaaggggga tatgagctgc    1560
aaaccttaga attaaatatg gagaccctaa acatgaccat gcccttatca tgcaccaaga    1620
acagcagtca tcattacata agagtgggca atgagactgg attagaattg actttaacta    1680
acaccagcat tataaatcac aaattttgca acttatccga tgctcacaaa aagaatcttt    1740
atgatcatgc tctcatgagc atcatctcaa cattccatct atccattcca aacttcaatc    1800
agtatgaagc catgagttgt gatttcaatg gagggaaaat cagtgtgcaa tacaacctct    1860
ctcattccta tgctggggat gcggccgaac actgtgggac agttgccaac ggagtgttgc    1920
aaacatttat gagaatggcc tggggtggaa gatacattgc attagactca ggaaagggaa    1980
actgggactg tataatgacc agctaccagt acctgataat tcaaaataca acatgggagg    2040
accactgcca attctcaaga ccgtctccta tcgggtacct tggccttttg tcacaaagga    2100
caagagatat atatataagt aggaggctct tggggacctt cacctggaca ttgtcagatt    2160
ctgagggcaa tgaaacacca ggtggttatt gtttaaccag gtggatgcta attgaagcag    2220
aactcaagtg ttttgggaat acagctgtgg caaaatgcaa tgagaagcat gatgaggagt    2280
tttgtgacat gctgagattg tttgatttca acaagcaagc aatccgtagg ttgaaggctg    2340
aggcccagat gagtattcaa ttaataaata agccgtgaa tgccttaatc aatgatcaat    2400
taatcatgaa gaaccattta agagacatca tgggcattcc ctactgcaat tacagcaagt    2460
attggtacct taatcatact agtagcggga gaacatcact accaaagtgt tggcttatat    2520
ccaatgggtc atatctaaat gaaacccagt tctctgatga catagaacag caagccgaca    2580
atatgatcac agagatgctt cagaaagaat acattgaaag acaagggaaa acgcccttgg    2640
gactagtgga catttcatc tttagcacaa gcttttatct gatcagcatt ttcttgcatt    2700
taattaaaat ccctacacat cgacacatcg ttgggaaacc ctgtcccaaa ccccatagac    2760
taaatcacat gggagtatgt tcctgtggac tgtacaaaca ccctggtgtt ccaacaaagt    2820
ggaagagata gggatccaga tctgctgtgc cttctagttg ccagccatct gttgtttgcc    2880
cctcccccgt gccttccttg accctggaag gtgccactcc cactgtcctt tcctaataaa    2940
atgaggaaat tgcatcgcat tgtctgagta ggtgtcattc tattctgggg ggtgggggtgg    3000
ggcagcacag caaggggggag gattgggaag acaaatagcag gcatgctggg gatgcggtgg    3060
gctctatggg tacccaggggc cgcataactt cgtataatgt atgctatacg aagttataag    3120
atctgtactg aaatgtgtgg gcgtggctta agggtgggaa agaatatata aggtgggggt    3180
cttatgtagt tttgtatctg ttttgcagca gccgccgccg ccatgagcac caactcgttt    3240
gatgaaagca ttgtgagctc atatttgaca acgcgcatgc ccccatgggc cggggtgcgt    3300
cagaatgtga tgggctccag cattgatggt cgccccgtcc tgcccgcaaa ctctactacc    3360
```

```
ttgacctacg agaccgtgtc tggaacgccg ttggagactg cagcctccgc cgccgcttca   3420
gccgctgcag ccaccgcccg cgggattgtg actgactttg ctttcctgag cccgcttgca   3480
agcagtgcag cttcccgttc atccgcccgc gatgacaagt tgacggctct tttggcacaa   3540
ttggattctt tgacccggga acttaatgtc gtttctcagc agctgttgga tctgcgccag   3600
caggtttctg ccctgaaggc ttcctcccct cccaatgcgg tttaaaacat aaataaaaaa   3660
ccagactctg tttggatttg gatcaagcaa gtgtcttgct gtctttattt aggggttttg   3720
cgcgcgcggt aggcccggga ccagcggtct cggtcgttga gggtcctgtg tattttttcc   3780
aggacgtggt aaaggtgact ctggatgttc agatacatgg gcataagccc gtctctgggg   3840
tggaggtagc accactgcag agcttcatgc tgcggggtgg tgttgtagat gatccagtcg   3900
tagcaggagc gctgggcgtg gtgcctaaaa atgtctttca gtagcaagct gattgccagg   3960
ggcaggccct tggtgtaagt gtttacaaag cggttaagct gggatgggtg catacgtggg   4020
gatatgagat gcatcttgga ctgtatttt aggttggcta tgttcccagc catatccctc   4080
cggggattca tgttgtgcag aaccaccagc acagtgtatc cggtgcactt gggaaatttg   4140
tcatgtagct tagaaggaaa tgcgtggaag aacttggaga cgcccttgtg acctccaaga   4200
ttttccatgc attcgtccat aatgatggca atgggcccac gggcggcggc ctgggcgaag   4260
atatttctgg gatcactaac gtcatagttg tgttccagga tgagatcgtc ataggccatt   4320
tttacaaagc gcgggcggag ggtgccagac tgcggtataa tggttccatc cggcccaggg   4380
gcgtagttac cctcacagat ttgcatttcc cacgctttga gttcagatgg ggggatcatg   4440
tctacctgcg gggcgatgaa gaaaacggtt ccgggtag gggagatcag ctgggaagaa   4500
agcaggttcc tgagcagctg cgacttaccg cagccgtgg gcccgtaaat cacacctatt   4560
accggctgca actggtagtt aagagagctg cagctgccgt catccctgag caggggggcc   4620
acttcgttaa gcatgtccct gactcgcatg ttttccctga ccaaatccgc cagaaggcgc   4680
tcgccgccca gcgatagcag ttcttgcaag gaagcaaagt ttttcaacgg tttgagaccg   4740
tccgccgtag gcatgctttt gagcgtttga ccaagcagtt ccaggcggtc ccacagctcg   4800
gtcacctgct ctacggcatc tcgatccagc atatctcctc gtttcgcggg ttggggcggc   4860
tttcgctgta cggcagtagt cggtgctcgt ccagacgggc cagggtcatg tctttccacg   4920
ggcgcagggt cctcgtcagc gtagtctggg tcacggtgaa ggggtgcgct ccgggctgcg   4980
cgctggccag ggtgcgcttg aggctggtcc tgctggtgct gaagcgctgc cggtcttcgc   5040
cctgcgcgtc ggccaggtag catttgacca tggtgtcata gtccagcccc tccgcggcgt   5100
ggcccttggc gcgcagcttg cccttggagg aggcgccgca cgaggggcag tgcagacttt   5160
tgagggcgta gagcttgggc gcgagaaata ccgattccgg ggagtaggca tccgcgccgc   5220
aggccccgca gacggtctcg cattccacga gccaggtgag ctctggccgt tcggggtcaa   5280
aaaccaggtt tcccccatgc ttttgatgc gtttcttacc tctggtttcc atgagccggt   5340
gtccacgctc ggtgacgaaa aggctgtccg tgtccccgta tacagacttg agaggcctgt   5400
cctcgagcgg tgttccgcgg tcctcctcgt atagaaactc ggaccactct gagacaaagg   5460
ctcgcgtcca ggccagcacg aaggaggcta agtgggaggg gtagcggtcg ttgtccacta   5520
gggggtccac tcgctccagg gtgtgaagac acatgtcgcc ctcttcggca tcaaggaagg   5580
tgattggttt gtaggtgtag gccacgtgac cgggtgttcc tgaagggggg ctataaaagg   5640 gggtggggc gcgttcgtcc tcactctctt ccgcatcgct gtctgcgagg ccagctgtt   5700 ggggtgagtc gacgcgaggc tggatggcct tccccattat gattcttctc gcttccggcg   5760
```
gcatcgggat gcccgcgttg caggccatgc tgtccaggca ggtagatgac gaccatcagg 5820
gacagcttca aggccagcaa aaggccagga accgtaaaaa ggccgcgttg ctggcgtttt 5880
tccataggct ccgcccccct gacgagcatc acaaaaatcg acgctcaagt cagaggtggc 5940
gaaacccgac aggactataa agataccagg cgtttccccc tggaagctcc ctcgtgcgct 6000
ctcctgttcc gaccctgccg cttaccggat acctgtccgc ctttctccct tcgggaagcg 6060
tggcgctttc tcatagctca cgctgtaggt atctcagttc ggtgtaggtc gttcgctcca 6120
agctgggctg tgtgcacgaa ccccccgttc agcccgaccg ctgcgcctta tccggtaact 6180
atcgtcttga gtccaacccg gtaagacacg acttatcgcc actggcagca gccactggta 6240
acaggattag cagagcgagg tatgtaggcg gtgctacaga gttcttgaag tggtggccta 6300
actacggcta cactagaagg acagtatttg gtatctgcgc tctgctgaag ccagttacct 6360
tcggaaaaag agttggtagc tcttgatccg gcaaacaaac caccgctggt agcggtggtt 6420
tttttgtttg caagcagcag attacgcgca gaaaaaaagg atctcaagaa gatcctttga 6480
tcttttctac ggggtctgac gctcagtgga acgaaaactc acgttaaggg attttggtca 6540
tgagattatc aaaaaggatc ttcacctaga tccttttaaa ttaaaaatga agttttaaat 6600
caatctaaag tatatatgag taaacttggt ctgacagtta ccaatgctta atcagtgagg 6660
cacctatctc agcgatctgt ctatttcgtt catccatagt tgcctgactc cccgtcgtgt 6720
agataactac gatacgggag ggcttaccat ctggccccag tgctgcaatg ataccgcgag 6780
acccacgctc accggctcca gatttatcag caataaacca gccagccgga agggccgagc 6840
gcagaagtgg tcctgcaact ttatccgcct ccatccagtc tattaattgt tgccgggaag 6900
ctagagtaag tagttcgcca gttaatagtt tgcgcaacgt tgttgccatt gctgcaggca 6960
tcgtggtgtc acgctcgtcg tttggtatgg cttcattcag ctccggttcc caacgatcaa 7020
ggcgagttac atgatccccc atgttgtgca aaaaagcggt tagctccttc ggtcctccga 7080
tcgttgtcag aagtaagttg gccgcagtgt tatcactcat ggttatggca gcactgcata 7140
attctcttac tgtcatgcca tccgtaagat gcttttctgt gactggtgag tactcaacca 7200
agtcattctg agaatagtgt atgcggcgac cgagttgctc ttgcccggcg tcaacacggg 7260
ataataccgc gccacatagc agaactttaa aagtgctcat cattggaaaa cgttcttcgg 7320
ggcgaaaact ctcaaggatc ttaccgctgt tgagatccag ttcgatgtaa cccactcgtg 7380
cacccaactg atcttcagca tcttttactt tcaccagcgt ttctgggtga gcaaaaacag 7440
gaaggcaaaa tgccgcaaaa aagggaataa gggcgacacg gaaatgttga atactcatac 7500
tcttcctttt tcaatattat tgaagcattt atcagggtta ttgtctcatg agcggataca 7560
tatttgaatg tatttagaaa aataaacaaa taggggttcc gcgcacattt ccccgaaaag 7620
tgccacctga cgtctaagaa accattatta tcatgacatt aacctataaa aataggcgta 7680
tcacgaggcc ctttcgtctt caagaattgt t 7711

<210> SEQ ID NO 36
<211> LENGTH: 7522
<212> TYPE: DNA
<213> ORGANISM: Artificial Sequence
<220> FEATURE:
<223> OTHER INFORMATION: Synthetic Construct pAdApt Lassa GP(dTM)

<400> SEQUENCE: 36
ttaattaacc gcaattctca tgtttgacag cttatcatca tcaataatat accttatttt 60
ggattgaagc caatatgata atgagggggt ggagtttgtg acgtggcgcg gggcgtggga 120

-continued

```
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg ttttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020 tcacgggat ttccaagtct ccaccccatt gacgtcaatg ggagtttgtt ttggcaccaa   1080
aatcaacggg actttccaaa atgtcgtaac aactccgccc cattgacgca atgggcggt   1140 aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagaatt taggattgcg   1320
cttttagaga ttcactacta gttaggaatt cctaaatcat ggggcagatt attacattct   1380
ttcaagaagt gccacatgta atagaggaag tcatgaacat tgtgctaatt gcgctttctc   1440
tattggcaat cttgaagggc ttgtataaca tcgctacatg tgggattatt ggattggttg   1500
cctttttatt cttgtgtggc aagtcttgtt ccctaaccct taaaggggga tatgagctgc   1560
aaaccttaga attaaatatg gagaccctaa acatgaccat gcccttatca tgcaccaaga   1620
acagcagtca tcattacata agagtgggca atgagactgg attagaattg actttaacta   1680
acaccagcat tataaatcac aaattttgca acttatccga tgctcacaaa aagaatcttt   1740
atgatcatgc tctcatgagc atcatctcaa cattccatct atccattcca aacttcaatc   1800
agtatgaagc catgagttgt gatttcaatg gagggaaaat cagtgtgcaa tacaacctct   1860
ctcattccta tgctggggat gcggccgaac actgtgggac agttgccaac ggagtgttgc   1920
aaacatttat gagaatggcc tggggtggaa gatacattgc attagactca ggaaagggaa   1980
actgggactg tataatgacc agctaccagt acctgataat tcaaaataca acatgggagg   2040
accactgcca attctcaaga ccgtctccta tcgggtacct tggccttttg tcacaaagga   2100
caagagatat atatataagt aggaggctct tggggacctt cacctggaca ttgtcagatt   2160
ctgagggcaa tgaaacacca ggtggttatt gtttaaccag gtggatgcta attgaagcag   2220
aactcaagtg ttttgggaat acagctgtgg caaaatgcaa tgagaagcat gatgaggagt   2280
tttgtgacat gctgagattg tttgatttca acaagcaagc aatccgtagg ttgaaggctg   2340
aggcccagat gagtattcaa ttaataaata agccgtgaa tgccttaatc aatgatcaat   2400
taatcatgaa gaaccattta agagacatca tgggcattcc ctactgcaat tacagcaagt   2460
attggtacct taatcatact agtagcggga gaacatcact accaaagtgt tggcttatat   2520
```

```
ccaatgggtc atatctaaat gaaacccagt tctctgatga catagaacag caagccgaca    2580
atatgatcac agagatgctt cagaaagaat acattgaaag acaagggaaa acgcccttgt    2640
agggatccag atctgctgtg ccttctagtt gccagccatc tgttgtttgc ccctcccccg    2700
tgccttcctt gaccctggaa ggtgccactc ccactgtcct ttcctaataa aatgaggaaa    2760
ttgcatcgca ttgtctgagt aggtgtcatt ctattctggg gggtggggtg gggcagcaca    2820 gcaagggggga ggattgggaa gacaatagca ggcatgctgg ggatgcggtg ggctctatgg   2880
gtacccaggg ccgcataact tcgtataatg tatgctatac gaagttataa gatctgtact    2940
gaaatgtgtg ggcgtggctt aagggtggga aagaatatat aaggtggggg tcttatgtag    3000
ttttgtatct gttttgcagc agccgccgcc gccatgagca ccaactcgtt tgatggaagc    3060
attgtgagct catatttgac aacgcgcatg cccccatggg ccggggtgcg tcagaatgtg    3120
atgggctcca gcattgatgg tcgcccgtc ctgcccgcaa actctactac cttgacctac     3180
gagaccgtgt ctggaacgcc gttggagact gcagcctccg ccgccgcttc agccgctgca    3240
gccaccgccc gcgggattgt gactgacttt gctttcctga gcccgcttgc aagcagtgca    3300
gcttcccgtt catccgcccg cgatgacaag ttgacggctc ttttggcaca attggattct    3360
ttgacccggg aacttaatgt cgtttctcag cagctgttgg atctgcgcca gcaggtttct    3420
gccctgaagg cttcctcccc tcccaatgcg gtttaaaaca taaataaaaa accagactct    3480
gtttggattt ggatcaagca agtgtcttgc tgtctttatt taggggtttt gcgcgcgcgg    3540
taggcccggg accagcggtc tcggtcgttg agggtcctgt gtattttttc caggacgtgg    3600
taaaggtgac tctggatgtt cagatacatg ggcataagcc cgtctctggg gtggaggtag    3660
caccactgca gagcttcatg ctgcggggtg tgttgtagat gatccagtc gtagcaggag      3720 cgctgggcgt ggtgcctaaa aatgtctttc agtagcaagc tgattgccag gggcaggccc     3780
ttggtgtaag tgtttacaaa gcggttaagc tgggatgggt gcatacgtgg ggatatgaga     3840
tgcatcttgg actgtatttt taggttggct atgttcccag ccatatccct ccggggattc    3900
atgttgtgca gaaccaccag cacagtgtat ccggtgcact tgggaaattt gtcatgtagc    3960
ttagaaggaa atgcgtggaa gaacttggag acgcccttgt gacctccaag attttccatg    4020
cattcgtcca taatgatggc aatgggccca cgggcggcgg cctgggcgaa gatatttctg    4080
ggatcactaa cgtcatagtt gtgttccagg atgagatcgt cataggccat ttttacaaag    4140
cgcgggcgga gggtgccaga ctgcggtata atggttccat ccggcccagg ggcgtagtta    4200
ccctcacaga tttgcatttc ccacgctttg agttcagatg gggggatcat gtctacctgc    4260
ggggcgatga agaaaacggt tccggggta ggggagatca gctgggaaga aagcaggttc      4320
ctgagcagct gcgacttacc gcagccggtg ggcccgtaaa tcacacctat taccggctgc    4380
aactggtagt taagagagct gcagctgccg tcatccctga gcaggggggc cacttcgtta    4440
agcatgtccc tgactcgcat gttttccctg accaaatccg ccagaaggcg ctcgccgccc    4500
agcgatagca gttcttgcaa ggaagcaaag tttttcaacg gtttgagacc gtccgccgta    4560
ggcatgcttt tgagcgtttg accaagcagt tccaggcggt cccacagctc ggtcacctgc    4620
tctacggcat ctcgatccag catatctcct cgtttcgcgg gttggggcgg ctttcgctgt    4680
acggcagtag tcggtgctcg tccagacggg ccagggtcat gtctttccac gggcgcaggg    4740
tcctcgtcag cgtagtctgg gtcacggtga aggggtgcgc tccggctgc gcgctggcca     4800 gggtgcgctt gaggctggtc ctgctggtgc tgaagcgctg ccggtcttcg ccctgcgcgt    4860
cggccaggta gcatttgacc atggtgtcat agtccagccc ctccgcggcg tggcccttgg    4920
```

```
cgcgcagctt gcccttggag gaggcgccgc acgaggggca gtgcagactt ttgagggcgt    4980
agagcttggg cgcgagaaat accgattccg gggagtaggc atccgcgccg caggccccgc    5040
agacggtctc gcattccacg agccaggtga gctctggccg ttcggggtca aaaaccaggt    5100
ttcccccatg ctttttgatg cgtttcttac ctctggtttc catgagccgg tgtccacgct    5160
cggtgacgaa aaggctgtcc gtgtcccgt atacagactt gagaggcctg tcctcgagcg     5220
gtgttccgcg gtcctcctcg tatagaaact cggaccactc tgagacaaag gctcgcgtcc    5280
aggccagcac gaaggaggct aagtgggagg gtagcggtc gttgtccact agggggtcca     5340
ctcgctccag ggtgtgaaga cacatgtcgc cctcttcggc atcaaggaag gtgattggtt    5400
tgtaggtgta ggccacgtga ccgggtgttc ctgaagggg gctataaaag ggggtggggg     5460
cgcgttcgtc ctcactctct tccgcatcgc tgtctgcgag ggccagctgt tggggtgagt    5520
cgacgcgagg ctggatggcc ttccccatta tgattcttct cgcttccggc ggcatcggga    5580
tgcccgcgtt gcaggccatg ctgtccaggc aggtagatga cgaccatcag ggacagcttc    5640
aaggccagca aaaggccagg aaccgtaaaa aggccgcgtt gctggcgttt ttccataggc    5700
tccgcccccc tgacgagcat cacaaaaatc gacgctcaag tcagaggtgg cgaaacccga    5760
caggactata aagataccag gcgtttcccc ctggaagctc cctcgtgcgc tctcctgttc    5820
cgaccctgcc gcttaccgga tacctgtccg ccttctccc ttcgggaagc gtggcgcttt    5880
ctcatagctc acgctgtagg tatctcagtt cggtgtaggt cgttcgctcc aagctgggct    5940
gtgtgcacga accccccgtt cagcccgacc gctgcgcctt atccggtaac tatcgtcttg    6000
agtccaaccc ggtaagacac gacttatcgc cactggcagc agccactggt aacaggatta    6060
gcagagcgag gtatgtaggc ggtgctacag agttcttgaa gtggtggcct aactacggct    6120
acactagaag gacagtattt ggtatctgcg ctctgctgaa gccagttacc ttcggaaaaa    6180
gagttggtag ctcttgatcc ggcaaacaaa ccaccgctgg tagcggtggt ttttttgttt    6240
gcaagcagca gattacgcgc agaaaaaaag gatctcaaga agatcctttg atcttttcta    6300
cggggtctga cgctcagtgg aacgaaaact cacgttaagg gattttggtc atgagattat    6360
caaaaaggat cttcacctag atccttttaa attaaaaatg aagttttaaa tcaatctaaa    6420
gtatatatga gtaaacttgg tctgacagtt accaatgctt aatcagtgag gcacctatct    6480
cagcgatctg tctatttcgt tcatccatag ttgcctgact ccccgtcgtg tagataacta    6540
cgatacggga gggcttacca tctggcccca gtgctgcaat gataccgcga cccacgct     6600 caccggctcc agatttatca gcaataaacc agccagccgg aagggccgag cgcagaagtg    6660
gtcctgcaac tttatccgcc tccatccagt ctattaattg ttgccgggaa gctagagtaa    6720
gtagttcgcc agttaatagt ttgcgcaacg ttgttgccat tgctgcaggc atcgtggtgt    6780
cacgctcgtc gtttggtatg gcttcattca gctccggttc ccaacgatca aggcgagtta    6840
catgatcccc catgttgtgc aaaaaagcgg ttagctcctt cggtcctccg atcgttgtca    6900
gaagtaagtt ggccgcagtg ttatcactca tggttatggc agcactgcat aattctctta    6960
ctgtcatgcc atccgtaaga tgcttttctg tgactggtga gtactcaacc aagtcattct    7020
gagaatagtg tatgcggcga ccgagttgct cttgcccggc gtcaacacgg ataataccg    7080 cgccacatag cagaacttta aaagtgctca tcattggaaa acgttcttcg ggcgaaaac    7140 tctcaaggat cttaccgctg ttgagatcca gttcgatgta acccactcgt gcacccaact    7200
gatcttcagc atcttttact ttcaccagcg tttctgggtg agcaaaaaca ggaaggcaaa    7260
atgccgcaaa aaagggaata agggcgacac ggaaatgttg aatactcata ctcttccttt    7320
```

| | |
|---|---:|
| ttcaatatta ttgaagcatt tatcagggtt attgtctcat gagcggatac atatttgaat | 7380 |
| gtatttagaa aaataaacaa ataggggttc cgcgcacatt tccccgaaaa gtgccacctg | 7440 |
| acgtctaaga aaccattatt atcatgacat taacctataa aaataggcgt atcacgaggc | 7500 |
| cctttcgtct tcaagaattg tt | 7522 |

<210> SEQ ID NO 37
<211> LENGTH: 6324
<212> TYPE: DNA
<213> ORGANISM: Artificial Sequence
<220> FEATURE:
<223> OTHER INFORMATION: Synthetic Construct CMV/R Ebola GP(Z) delta
 TM/h

<400> SEQUENCE: 37

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagggA ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccttacct gaggccgcca tccacgccgg ttgagtcgcg ttctgccgcc tcccgcctgt | 1080 |
| ggtgcctcct gaactacgtc cgccgtctag gtaagtttag agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg gagggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacga tatcgccgcc atgggcgtga ccggcatcct | 1380 |
| gcagctgccc agggacaggt tcaagaggac cagcttcttc ctgtgggtga tcatcctgtt | 1440 |
| ccagaggacc ttcagcatcc ccctgggcgt gatccacaac agcaccctgc aggtgagcga | 1500 |
| cgtggacaag ctggtgtgca gggacaagct gagcagcacc aaccagctga ggagcgtggg | 1560 |
| cctgaacctg gagggcaacg gcgtggccac cgacgtgccc agcgccacca gaggtgggg | 1620 |
| cttcaggagc ggcgtgcctc caaggtggt gaactacgag gccggcgagt gggccgagaa | 1680 |
| ctgctacaac ctggagatca agaagcccga cggcagcgag tgcctgcccg ccgcccctga | 1740 |
| cggcatcagg ggcttcccca ggtgcaggta cgtgcacaag gtgagcggca ccggcccctg | 1800 |

```
cgccggcgac ttcgccttcc acaaggaggg cgccttcttc ctgtacgaca ggctggccag    1860
caccgtgatc tacaggggca ccaccttcgc cgagggcgtg gtggccttcc tgatcctgcc    1920
ccaggccaag aaggacttct tcagcagcca ccctctgagg gagcccgtga acgccaccga    1980
ggaccccagc agcggctact acagcaccac catcaggtac caggccaccg gcttcggcac    2040
caacgagacc gagtacctgt tcgaggtgga caacctgacc tacgtgcagc tggagtctag    2100
attcacccct cagttcctgc tgcagctgaa cgagaccatc tacaccagcg gcaagaggag    2160
caacaccacc ggcaagctga tctggaaggt gaaccccgag atcgacacca ccatcggcga    2220
gtgggccttc tgggagacca agaagaacct gaccaggaag atcaggagcg aggagctgag    2280
cttcaccgtc gtgagcaacg ggccaagaa catcagcggc cagagccccg ccaggaccag    2340
cagcgacccc ggcaccaaca ccaccaccga ggaccacaag atcatggcca gcgagaacag    2400
cagcgccatg gtgcaggtgc acagccaggg cagggaggcc gccgtgagcc acctgaccac    2460
cctggccacc atcagcacca gccctcagtc tttaaccacc aagcccggcc ccgacaacag    2520
cacccacaac accctgtgt acaagctgga catcagcgag gccacccagg tggagcagca    2580
ccacaggagg accgacaacg acagcaccgc cagcgacacc ccttccgcca ccaccgccgc    2640
cggccctccg aaggccgaga acaccaacac cagcaagagc accgactttc tggatcccgc    2700
caccaccacc agccctcaga accacagcga gaccgccggc aacaacaaca cccaccacca    2760
ggacaccggc gaggagagcg ccagcagcgg caagctgggc ctgatcacca acaccatcgc    2820
cggcgtggcc ggcctgatca ccggcggcag gaggaccagg agggaggcca tcgtgaacgc    2880
ccagcccaag tgcaaccca acctgcacta ctggaccacc aggacgagg cgccgccat     2940 cggcctggcc tggattccct acttcggccc cgccgccgag ggcatctaca tcgagggcct    3000
gatgcacaac caggacggcc tgatctgcgg cctgaggcag ctggcaacg agaccaccca    3060 ggccctgcag ctgttcctga gggccaccac cgagctgagg accttcagca tcctgaacag    3120
gaaggccatc gacttcctgc tgcagagagt gggcggcacc tgccacatcc tgggccccga    3180
ctgctgcatc gagccccacg actggaccaa gaacatcacc gacaagatcg accagatcat    3240
ccacgacttc gtgacaaga ccctgcccga ccagggcgac aacgacaact ggtggaccgg    3300
ctgaacacgt ggaattcaga tctgctgtgc cttctagttg ccagccatct gttgtttgcc    3360
cctcccccgt gccttccttg accctggaag gtgccactcc cactgtcctt tcctaataaa    3420
atgaggaaat tgcatcgcat tgtctgagta ggtgtcattc tattctgggg ggtggggtgg    3480
ggcaggacag caaggggag gattgggaag acaatagcag gcatgctggg gatgcggtgg    3540
gctctatggg tacccaggtg ctgaagaatt gacccggttc ctcctgggcc agaaagaagc    3600
aggcacatcc ccttctctgt gacacaccct gtccacgccc ctggttctta gttccagccc    3660
cactcatagg acactcatag ctcaggaggg ctccgccttc aatcccaccc gctaaagtac    3720
ttggagcggt ctctcctcc ctcatcagcc caccaaacca aacctagcct caagagtgg    3780 gaagaaatta aagcaagata ggctattaag tgcagaggga gagaaaatgc ctccaacatg    3840
tgaggaagta atgagagaaa tcatagaatt ttaaggccat catggcctta atcttccgct    3900
tcctcgctca ctgactcgct gcgctcggtc gttcggctgc ggcgagcggt atcagctcac    3960
tcaaaggcgg taatacggtt atccacagaa tcagggggata acgcaggaaa gaacatgtga    4020
gcaaaaggcc agcaaaaggc caggaaccgt aaaaaggccg cgttgctggc gttttttccat    4080 aggctccgcc cccctgacga gcatcacaaa aatcgacgct caagtcagag gtggcgaaac    4140
ccgacaggac tataaagata ccaggcgttt ccccctggaa gctccctcgt gcgctctcct    4200
```

```
gttccgaccc tgccgcttac cggatacctg tccgcctttc tcccttcggg aagcgtggcg    4260
ctttctcata gctcacgctg taggtatctc agttcggtgt aggtcgttcg ctccaagctg    4320
ggctgtgtgc acgaaccccc cgttcagccc gaccgctgcg ccttatccgg taactatcgt    4380
cttgagtcca acccggtaag acacgactta tcgccactgg cagcagccac tggtaacagg    4440
attagcagag cgaggtatgt aggcggtgct acagagttct tgaagtggtg gcctaactac    4500
ggctacacta agaagaacagt atttggtatc tgcgctctgc tgaagccagt taccttcgga    4560
aaaagagttg gtagctcttg atccggcaaa caaaccaccg ctggtagcgg tggttttttt    4620
gtttgcaagc agcagattac gcgcagaaaa aaaggatctc aagaagatcc tttgatcttt    4680
tctacggggt ctgacgctca gtggaacgaa aactcacgtt aagggatttt ggtcatgaga    4740
ttatcaaaaa ggatcttcac ctagatcctt ttaaattaaa aatgaagttt taaatcaatc    4800
taaagtatat atgagtaaac ttggtctgac agttaccaat gcttaatcag tgaggcacct    4860
atctcagcga tctgtctatt tcgttcatcc atagttgcct gactcggggg ggggggggcgc    4920 tgaggtctgc ctcgtgaaga aggtgttgct gactcatacc aggcctgaat cgccccatca    4980
tccagccaga aagtgaggga gccacggttg atgagagctt tgttgtaggt ggaccagttg    5040
gtgattttga acttttgctt tgccacggaa cggtctgcgt tgtcgggaag atgcgtgatc    5100
tgatccttca actcagcaaa agttcgattt attcaacaaa gccgccgtcc cgtcaagtca    5160
gcgtaatgct ctgccagtgt tacaaccaat taaccaattc tgattagaaa aactcatcga    5220
gcatcaaatg aaactgcaat ttattcatat caggattatc aataccatat ttttgaaaaa    5280
gccgtttctg taatgaagga gaaaactcac cgaggcagtt ccataggatg caagatcct    5340 ggtatcggtc tgcgattccg actcgtccaa catcaataca acctattaat ttcccctcgt    5400
caaaaataag gttatcaagt gagaaatcac catgagtgac gactgaatcc ggtgagaatg    5460
gcaaaagctt atgcatttct ttccagactt gttcaacagg ccagccatta cgctcgtcat    5520
caaaatcact cgcatcaacc aaaccgttat tcattcgtga ttgcgcctga gcgagacgaa    5580
atacgcgatc gctgttaaaa ggacaattac aaacaggaat cgaatgcaac cggcgcagga    5640
acactgccag cgcatcaaca atattttcac ctgaatcagg atattcttct aatacctgga    5700
atgctgtttt cccggggatc gcagtggtga gtaaccatgc atcatcagga gtacggataa    5760
aatgcttgat ggtcggaaga ggcataaatt ccgtcagcca gtttagtctg accatctcat    5820
ctgtaacatc attggcaacg ctacctttgc catgtttcag aaacaactct ggcgcatcgg    5880
gcttcccata caatcgatag attgtcgcac ctgattgccc gacattatcg cgagcccatt    5940
tatacccata taaatcagca tccatgttgg aatttaatcg cggcctcgag caagacgttt    6000
cccgttgaat atggctcata caccccttg tattactgtt tatgtaagca gacagtttta    6060
ttgttcatga tgatatattt ttatcttgtg caatgtaaca tcagagattt tgagacacaa    6120
cgtggctttc ccccccccc cattattgaa gcatttatca gggttattgt ctcatgagcg    6180
gatacatatt tgaatgtatt tagaaaaata acaaataagg ggttccgcgc acatttcccc    6240
gaaaagtgcc acctgacgtc taagaaacca ttattatcat gacattaacc tataaaaata    6300
ggcgtatcac gaggcccttt cgtc                                          6324
```

<210> SEQ ID NO 38
<211> LENGTH: 6868
<212> TYPE: DNA
<213> ORGANISM: Artificial Sequence
<220> FEATURE:
<223> OTHER INFORMATION: Synthetic Construct pVR1012x/s Ebola GP(Z)
      delta TM/h (P87666)

```
<400> SEQUENCE: 38
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca cgacccccg cccattgacg tcaataatga cgtatgttcc      480
catagtaacg ccaataggga ctttccattg acgtcaatgg gtggagtatt tacggtaaac     540
tgcccacttg gcagtacatc aagtgtatca tatgccaagt acgccccta ttgacgtcaa      600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca      960
tagaagacac cgggaccgat ccagcctccg cggccgggaa cggtgcattg gaacgcggat     1020
tccccgtgcc aagagtgacg taagtaccgc ctatagactc tataggcaca ccctttggc     1080
tcttatgcat gctatactgt ttttggcttg gggcctatac accccgctt ccttatgcta     1140
taggtgatgg tatagcttag cctataggtg tgggttattg accattattg accactcccc     1200
tattggtgac gatactttcc attactaatc cataacatgg ctctttgcca caactatctc     1260
tattggctat atgccaatac tctgtccttc agagactgac acggactctg tatttttaca     1320
ggatggggtc ccatttatta tttacaaatt cacatataca acaacgccgt ccccgtgcc     1380
cgcagttttt attaaacata gcgtgggatc tccacgcgaa tctcgggtac gtgttccgga     1440
catgggctct tctccggtag cggcggagct tccacatccg agccctggtc ccatgcctcc     1500
agcggctcat ggtcgctcgg cagctccttg ctcctaacag tggaggccag acttaggcac     1560
agcacaatgc ccaccaccac cagtgtgccg cacaaggccg tggcggtagg gtatgtgtct     1620
gaaaatgagc gtggagattg gctcgcacg gctgacgcag atggaagact taaggcagcg      1680
gcagaagaag atgcaggcag ctgagttgtt gtattctgat aagagtcaga ggtaactccc     1740
gttgcggtgc tgttaacggt ggagggcagt gtagtctgag cagtactcgt tgctgccgcg     1800
cgcgccacca gacataatag ctgacagact aacagactgt tccttccat gggtctttc      1860
tgcagtcacc gtcgtcgacg atatcgccgc catggagggc ctgagcctgc tgcagctgcc     1920
cagggacaag ttcaggaaga gcagcttctt cgtgtgggtg atcatcctgt tccagaaggc     1980
cttcagcatg cccctgggcg tggtgaccaa cagcaccctg gaggtgaccg agatcgacca     2040
gctggtgtgc aaggaccacc tggccagcac cgaccagctg aagagcgtgg gcctgaacct     2100
ggagggcagc ggcgtgagca ccgacatccc cagcgccacc aagaggtggg gcttcaggag     2160
cggcgtgcct ccccaggtgg tgagctacga ggccggcgag tgggccgaga ctgctacaa     2220
cctggagatc aagaagcccg acggcagcga gtgcctgcct cctcctcctg acggcgtgag     2280
gggcttcccc aggtgcaggt acgtgcacaa ggcccagggc accggcccct gccccggcga     2340
```

```
ctacgccttc cacaaggacg gcgccttctt cctgtacgac aggctggcca gcaccgtgat   2400
ctacaggggc gtgaacttcg ccgagggcgt gatcgccttc ctgatcctgg ccaagcccaa   2460
ggagaccttc ctgcagagcc ctcccatcag ggaggccgcc aactacaccg agaacaccag   2520
cagctactac gccaccagct atctagagta cgagatcgag aacttcggcg cccagcacag   2580
caccaccctg ttcaagatca acaacaacac cttcgtgctg ctggacaggc cccacacccc   2640
tcagttcctg ttccagctga cgacaccat ccagctgcac cagcagctga gcaacaccac   2700
cggcaagctg atctggaccc tggacgccaa catcaacgcc gacatcggcg agtgggcctt   2760
ctgggagaac aagaagaacc tgagcgagca gctgaggggc gaggagctga gcttcgagac   2820
cctgagcctg aacgagaccg aggacgacga cgccaccagc agcaggacca ccaagggcag   2880
gatcagcgac agggccacca ggaagtacag cgacctggtg cccaaggaca gccccggcat   2940
ggtgagcctg cacgtgcccg agggcgagac caccctgccc agccagaaca gcaccgaggg   3000
caggagggtg gacgtgaaca cccaggagac catcaccgag accaccgcca ccatcatcgg   3060
caccaacggc aacaacatgc agatcagcac catcggcacc ggcctgagca gcagccagat   3120
cctgagcagc agccccacca tggccctag ccccgagacc cagaccagca ccacctacac   3180
ccctaagctg cccgtgatga ccaccgagga gcccaccacc cctcccagga acagccccgg   3240
atccaccacc gaggccccta ccctgaccac ccctgagaac atcaccaccg ccgtgaagac   3300
cgtgtgggcc caggagagca ccagcaacgg cctgatcacc agcaccgtga ccggcatcct   3360
gggcagcctg ggcctgagga agaggagcag gaggcaggtg aacaccaggg ccaccggcaa   3420
gtgcaacccc aacctgcact actggaccgc ccaggagcag cacaacgccg ccggcatcgc   3480
ctggattccc tacttcggcc ccggcgccga gggcatctac accgagggcc tgatgcacaa   3540
ccagaacgcc ctggtgtgcg gcctgaggca gctggccaac gagaccaccc aggccctgca   3600
gctgttcctg agggccacca ccgagctgag gacctacacc atcctgaaca ggaaggccat   3660
cgacttcctg ctgaggaggt ggggcggcac ctgcaggatt ctgggccccg actgctgcat   3720
cgagccccac gactggacca agaacatcac cgacaagatc aaccagatca tccacgactt   3780
catcgacaac cctctgccca accaggacaa cgacgacaac tggtggaccg gctgaacacg   3840
tggaattcag atctgctgtg ccttctagtt gccagccatc tgttgtttgc cctccccccg   3900
tgccttcctt gaccctggaa ggtgccactc ccactgtcct ttcctaataa aatgaggaaa   3960
ttgcatcgca ttgtctgagt aggtgtcatt ctattctggg gggtgggggt gggcaggaca   4020
gcaaggggga ggattgggaa gacaatagca ggcatgctgg ggatgcggtg ggctctatgg   4080
gtacccaggt gctgaagaat tgacccggtt cctcctgggc cagaaagaag caggcacatc   4140
cccttctctg tgacacaccc tgtccacgcc cctggttctt agttccagcc ccactcatag   4200
gacactcata gctcaggagg gctccgcctt caatcccacc cgctaaagta cttggagcgg   4260
tctctccctc cctcatcagc ccaccaaacc aaacctagcc tccaagagtg ggaagaaatt   4320
aaagcaagat aggctattaa gtgcagaggg agagaaaatg cctccaacat gtgaggaagt   4380
aatgagagaa atcatagaat tttaaggcca tgatttaagg ccatcatggc cttaatcttc   4440
cgcttcctcg ctcactgact cgctgcgctc ggtcgttcgg ctgcggcgag cggtatcagc   4500
tcactcaaag gcggtaatac ggttatccac agaatcaggg gataacgcag gaaagaacat   4560
gtgagcaaaa ggccagcaaa aggccaggaa ccgtaaaaag gccgcgttgc tggcgttttt   4620
ccataggctc cgcccccctg acgagcatca caaaaatcga cgctcaagtc agaggtggcg   4680
aaacccgaca ggactataaa gataccaggc gtttccccct ggaagctccc tcgtgcgctc   4740
```

```
tcctgttccg accctgccgc ttaccggata cctgtccgcc tttctccctt cgggaagcgt   4800
ggcgctttct catagctcac gctgtaggta tctcagttcg gtgtaggtcg ttcgctccaa   4860
gctgggctgt gtgcacgaac cccccgttca gcccgaccgc tgcgccttat ccggtaacta   4920
tcgtcttgag tccaacccgg taagacacga cttatcgcca ctggcagcag ccactggtaa   4980
caggattagc agagcgaggt atgtaggcgg tgctacagag ttcttgaagt ggtggcctaa   5040
ctacggctac actagaagaa cagtatttgg tatctgcgct ctgctgaagc cagttacctt   5100
cggaaaaaga gttggtagct cttgatccgg caaacaaacc accgctggta gcggtggttt   5160
ttttgtttgc aagcagcaga ttacgcgcag aaaaaaagga tctcaagaag atcctttgat   5220
cttttctacg gggtctgacg ctcagtggaa cgaaaactca cgttaaggga ttttggtcat   5280
gagattatca aaaaggatct tcacctagat ccttttaaat taaaaatgaa gttttaaatc   5340
aatctaaagt atatatgagt aaacttggtc tgacagttac caatgcttaa tcagtgaggc   5400
acctatctca gcgatctgtc tatttcgttc atccatagtt gcctgactcg gggggggggg   5460
gcgctgaggt ctgcctcgtg aagaaggtgt tgctgactca taccaggcct gaatcgcccc   5520
atcatccagc cagaaagtga gggagccacg gttgatgaga gctttgttgt aggtggacca   5580
gttggtgatt ttgaactttt gctttgccac ggaacggtct gcgttgtcgg gaagatgcgt   5640
gatctgatcc ttcaactcag caaaagttcg atttattcaa caaagccgcc gtcccgtcaa   5700
gtcagcgtaa tgctctgcca gtgttacaac caattaacca attctgatta gaaaaactca   5760
tcgagcatca aatgaaactg caatttattc atatcaggat tatcaatacc atatttttga   5820
aaaagccgtt tctgtaatga aggagaaaac tcaccgaggc agttccatag gatggcaaga   5880
tcctggtatc ggtctgcgat tccgactcgt ccaacatcaa tacaacctat taatttcccc   5940
tcgtcaaaaa taaggttatc aagtgagaaa tcaccatgag tgacgactga atccggtgag   6000
aatggcaaaa gcttatgcat ttctttccag acttgttcaa caggccagcc attacgctcg   6060
tcatcaaaat cactcgcatc aaccaaaccg ttattcattc gtgattgcgc ctgagcgaga   6120
cgaaatacgc gatcgctgtt aaaaggacaa ttacaaacag gaatcgaatg caaccggcgc   6180
aggaacactg ccagcgcatc aacaatattt tcacctgaat caggatattc ttctaatacc   6240
tggaatgctg ttttcccggg gatcgcagtg gtgagtaacc atgcatcatc aggagtacgg   6300
ataaaatgct tgatggtcgg aagaggcata aattccgtca gccagtttag tctgaccatc   6360
tcatctgtaa catcattggc aacgctacct ttgccatgtt tcagaaacaa ctctggcgca   6420
tcgggcttcc catacaatcg atagattgtc gcacctgatt gcccgacatt atcgcgagcc   6480
catttatacc catataaatc agcatccatg ttggaattta atcgcggcct cgagcaagac   6540
gtttcccgtt gaatatggct cataacaccc cttgtattac tgtttatgta agcagacagt   6600
tttattgttc atgatgatat atttttatct tgtgcaatgt aacatcagag attttgagac   6660
acaacgtggc tttccccccc cccccattat tgaagcattt atcagggtta ttgtctcatg   6720
agcggataca tatttgaatg tatttagaaa aataaacaaa taggggttcc gcgcacattt   6780
ccccgaaaag tgccacctga cgtctaagaa accattatta tcatgacatt aacctataaa   6840
aataggcgta tcacgaggcc ctttcgtc                                      6868
```

<210> SEQ ID NO 39
<211> LENGTH: 6322
<212> TYPE: DNA
<213> ORGANISM: Artificial Sequence
<220> FEATURE:
<223> OTHER INFORMATION: Synthetic Construct CMV/R-GP(S/G)(deltaTM)/h

<400> SEQUENCE: 39

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca cgacccccg cccattgacg tcaataatga cgtatgttcc       480
catagtaacg ccaataggga ctttccattg acgtcaatgg gtggagtatt tacggtaaac      540
tgcccacttg gcagtacatc aagtgtatca tatgccaagt acgccccta ttgacgtcaa       600
tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt tgacctcca      960
tagaagacac cgggaccgat ccagcctcca tcggctcgca tctctccttc acgcgcccgc     1020
cgccttacct gaggccgcca tccacgccgg ttgagtcgcg ttctgccgcc tcccgcctgt     1080
ggtgcctcct gaactacgtc cgccgtctag gtaagtttag agctcaggtc gagaccgggc     1140
ctttgtccgg cgctcccttg gagcctacct agactcagcc ggctctccac gctttgcctg     1200
accctgcttg ctcaactcta gttaacggtg gagggcagtg tagtctgagc agtactcgtt     1260
gctgccgcgc gcgccaccag acataatagc tgacagacta acagactgtt cctttccatg     1320
ggtcttttct gcagtcaccg tcgtcgacga tatcgccgcc atggagggcc tgagcctgct     1380
gcagctgccc agggacaagt tcaggaagag cagcttcttc gtgtgggtga tcatcctgtt     1440
ccagaaggcc ttcagcatgc ccctgggcgt ggtgaccaac agcaccctgg aggtgaccga     1500
gatcgaccag ctggtgtgca aggaccacct ggccagcacc gaccagctga gagcgtggg      1560
cctgaacctg gagggcagcg gcgtgagcac cgacatcccc agcgccacca agaggtgggg     1620
cttcaggagc ggcgtgcctc ccaaggtggt gagctacgag gccggcgagt gggccgagaa     1680
ctgctacaac ctggagatca agaagcccga cggcagcgag tgcctgcctc ctcctcctga     1740
cggcgtgagg ggcttcccca ggtgcaggta cgtgcacaag gcccagggca ccggcccctg     1800
ccccggcgac tacgccttcc acaaggacgc gccttcttc ctgtacgaca ggctggccag      1860
caccgtgatc tacaggggcg tgaacttcgc cgagggcgtg atcgccttcc tgatcctggc     1920
caagcccaag gagaccttcc tgcagagccc tccatcagg gaggccgtga actacaccga      1980
gaacaccagc agctactacg ccaccagcta tctagagtac gagatcgaga acttcggcgc     2040
ccagcacagc accaccctgt tcaagatcga caacaacacc ttcgtgaggc tggacaggcc     2100
ccacaccct cagttcctgt tccagctgaa cgacaccatc cacctgcacc agcagctgag      2160
caacaccacc ggcaggctga tctggaccct ggacgccaac atcaacgccg acatcggcga     2220
gtgggcttc tggagaacaa agaagaacct gagcgagcag ctgaggggcg aggagctgag      2280
cttcgaggcc ctgagcctga acgagaccga ggacgacgac gccgccagca gcaggatcac     2340
```

```
caagggcagg atcagcgaca gggccaccag gaagtacagc gacctggtgc ccaagaacag   2400
ccccggcatg gtgcccctgc acatcccga gggcgagacc accctgccca gccagaacag   2460
caccgagggc aggagggtgg gcgtgaacac ccaggagacc atcaccgaga ccgccgccac   2520
catcatcggc accaacggca accacatgca gatcagcacc atcggcatca ggcccagcag   2580
cagccagatc cccagcagca gccccaccac cgccccctagc cccgaggccc agaccccac   2640 cacccacacc agcggaccca gcgtgatggc caccgaggag cccaccaccc ctcccggcag   2700
cagccccgga cccaccaccg aggccctac cctgaccacc cctgagaaca tcaccaccgc   2760
cgtgaagacc gtgctgcccc aggagagcac cagcaacggc ctgatcacca gcaccgtgac   2820
cggcatcctg gcagcctgg gcctgaggaa gaggagcagg aggcagacca acaccaaggc   2880
caccggcaag tgcaacccca acctgcacta ctggaccgcc caggagcagc acaacgccgc   2940
cggcatcgcc tggattccct acttcggccc cggcgccgag ggcatctaca ccgagggcct   3000
gatgcacaac agaacgccc tggtgtgcgg cctgaggcag ctggccaacg agaccaccca   3060
ggccctgcag ctgttcctga gggccaccac cgagctgagg acctacacca tcctgaacag   3120
gaaggccatc gacttcctgc tgaggaggtg gggcggcacc tgcaggattc tgggccccga   3180
ctgctgcatc gagccccacg actggaccaa gaacatcacc gacaagatca accagatcat   3240
ccacgacttc atcgacaacc ctctgcccaa ccaggacaac gacgacaact ggtggaccgg   3300
ctgaacacgt ggaattgatc tgctgtgcct tctagttgcc agccatctgt tgtttgcccc   3360 tccccgtgc cttccttgac cctggaaggt gccactccca ctgtcctttc ctaataaaat   3420
gaggaaattg catcgcattg tctgagtagg tgtcattcta ttctgggggg tgggtgggg   3480 caggacagca agggggagga ttgggaagac aatagcaggc atgctgggga tgcggtgggc   3540
tctatgggta cccaggtgct gaagaattga cccggttcct cctgggccag aaagaagcag   3600
gcacatcccc ttctctgtga cacccctgt ccacgcccct ggttcttagt tccagcccca   3660
ctcataggac actcatagct caggagggct ccgccttcaa tcccacccgc taaagtactt   3720
ggagcggtct ctccctccct catcagccca ccaaaccaaa cctagcctcc aagagtggga   3780
agaaattaaa gcaagatagg ctattaagtg cagagggaga gaaaatgcct ccaacatgtg   3840
aggaagtaat gagagaaatc atagaatttt aaggccatca tggccttaat cttccgcttc   3900
ctcgctcact gactcgctgc gctcggtcgt tcggctgcgg cgagcggtat cagctcactc   3960
aaaggcggta atacggttat ccacagaatc aggggataac gcaggaaaga acatgtgagc   4020
aaaaggccag caaaaggcca ggaaccgtaa aaaggccgcg ttgctggcgt ttttccatag   4080
gctccgcccc cctgacgagc atcacaaaaa tcgacgctca agtcagaggt ggcgaaaccc   4140
gacaggacta taaagatacc aggcgtttcc ccctggaagc tccctcgtgc gctctcctgt   4200
tccgaccctg ccgcttaccg gatacctgtc cgcctttctc ccttcgggaa gcgtggcgct   4260
ttctcatagc tcacgctgta ggtatctcag ttcggtgtag tcgttcgct ccaagctggg   4320 ctgtgtgcac gaaccccccg ttcagcccga ccgctgcgcc ttatccggta actatcgtct   4380
tgagtccaac ccggtaagac acgacttatc gccactggca gcagccactg gtaacaggat   4440
tagcagagcg aggtatgtag gcggtgctac agagttcttg aagtggtggc ctaactacgg   4500
ctacactaga agaacagtat ttggtatctg cgctctgctg aagccagtta ccttcggaaa   4560
aagagttggt agctcttgat ccggcaaaca aaccaccgct ggtagcggtg gtttttttgt   4620
ttgcaagcag cagattacgc gcagaaaaaa aggatctcaa gaagatcctt tgatcttttc   4680 tacgggtct gacgctcagt ggaacgaaaa ctcacgttaa gggattttgg tcatgagatt   4740
```

```
atcaaaaagg atcttcacct agatccttt aaattaaaaa tgaagttta aatcaatcta      4800
aagtatatat gagtaaactt ggtctgacag ttaccaatgc ttaatcagtg aggcacctat      4860
ctcagcgatc tgtctatttc gttcatccat agttgcctga ctcggggggg ggggcgctg      4920
aggtctgcct cgtgaagaag gtgttgctga ctcataccag gcctgaatcg ccccatcatc      4980
cagccagaaa gtgagggagc cacggttgat gagagctttg ttgtaggtgg accagttggt      5040
gattttgaac ttttgctttg ccacggaacg gtctgcgttg tcgggaagat gcgtgatctg      5100
atccttcaac tcagcaaaag ttcgatttat tcaacaaagc cgccgtcccg tcaagtcagc      5160
gtaatgctct gccagtgtta caaccaatta accaattctg attagaaaaa ctcatcgagc      5220
atcaaatgaa actgcaattt attcatatca ggattatcaa taccatattt ttgaaaaagc      5280
cgtttctgta atgaaggaga aaactcaccg aggcagttcc ataggatggc aagatcctgg      5340
tatcggtctg cgattccgac tcgtccaaca tcaatacaac ctattaattt cccctcgtca      5400
aaaataaggt tatcaagtga gaaatcacca tgagtgacga ctgaatccgg tgagaatggc      5460
aaaagcttat gcatttcttt ccagacttgt tcaacaggcc agccattacg ctcgtcatca      5520
aaatcactcg catcaaccaa accgttattc attcgtgatt gcgcctgagc gagacgaaat      5580
acgcgatcgc tgttaaaagg acaattacaa caggaatcg aatgcaaccg gcgcaggaac      5640
actgccagcg catcaacaat attttcacct gaatcaggat attcttctaa tacctggaat      5700
gctgttttcc cggggatcgc agtggtgagt aaccatgcat catcaggagt acggataaaa      5760
tgcttgatgg tcggaagagg cataaattcc gtcagccagt ttagtctgac catctcatct      5820
gtaacatcat tggcaacgct acctttgcca tgtttcagaa acaactctgg cgcatcgggc      5880
ttcccataca atcgatagat tgtcgcacct gattgcccga cattatcgcg agcccattta      5940
tacccatata aatcagcatc catgttggaa tttaatcgcg gcctcgagca agacgtttcc      6000
cgttgaatat ggctcataac accccttgta ttactgttta tgtaagcaga cagttttatt      6060
gttcatgatg atatattttt atcttgtgca atgtaacatc agagattttg agacacaacg      6120
tggctttccc ccccccccca ttattgaagc atttatcagg gttattgtct catgagcgga      6180
tacatatttg aatgtattta gaaaaataaa caaatagggg ttccgcgcac atttccccga      6240
aaagtgccac ctgacgtcta agaaaccatt attatcatga cattaaccta taaaaatagg      6300
cgtatcacga ggccctttcg tc                                                6322
```

<210> SEQ ID NO 40
<211> LENGTH: 6324
<212> TYPE: DNA
<213> ORGANISM: Artificial Sequence
<220> FEATURE:
<223> OTHER INFORMATION: Synthetic Construct CMV/R-GP(S, Q66798)(dTM)/h

<400> SEQUENCE: 40

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc       180
accatatgcg gtgtgaaata ccgcacagat gcgtaaggag aaaataccgc atcagattgg       240
ctattggcca ttgcatacgt tgtatccata tcataatatg tacatttata ttggctcatg       300
tccaacatta ccgccatgtt gacattgatt attgactagt tattaatagt aatcaattac       360
ggggtcatta gttcatagcc catatatgga gttccgcgtt acataactta cggtaaatgg       420
cccgcctggc tgaccgccca acgacccccg cccattgacg tcaataatga cgtatgttcc       480
```

```
catagtaacg ccaataggga cttt ccattg acgt caatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccttacct gaggccgcca tccacgccgg ttgagtcgcg ttctgccgcc tcccgcctgt   1080
ggtgcctcct gaactacgtc cgccgtctag gtaagtttag agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacga tatcgccgcc atggagggcc tgagcctgct   1380
gcagctgccc agggacaagt tcaggaagag cagcttcttc gtgtgggtga tcatcctgtt   1440
ccagaaggcc ttcagcatgc ccctgggcgt ggtgaccaac agcaccctgg aggtgaccga   1500
gatcgaccag ctggtgtgca aggaccacct ggccagcacc gaccagctga gagcgtgggg   1560
cctgaacctg gagggcagcg gcgtgagcac cgacatcccc agcgccacca gaggtgggg   1620 cttcaggagc ggcgtgcctc cccaggtggt gagctacgag gccggcgagt gggccgagaa   1680
ctgctacaac ctggagatca agaagcccga cggcagcgag tgcctgcctc ctcctcctga   1740
cggcgtgagg ggcttcccca ggtgcaggta cgtgcacaag gcccagggca ccggcccctg   1800
ccccggcgac tacgccttcc acaaggacgg cgccttcttc ctgtacgaca ggctggccag   1860
caccgtgatc tacaggggcg tgaacttcgc cgagggcgtg atcgccttcc tgatcctggc   1920
caagcccaag gagaccttcc tgcagagccc tcccatcagg gaggccgcca actacaccga   1980
gaacaccagc agctactacg ccaccagcta tctagagtac gagatcgaga acttcggcgc   2040
ccagcacagc accaccctgt tcaagatcaa caacaacacc ttcgtgctgc tggacaggcc   2100
ccacacccct cagttcctgt tccagctgaa cgacaccatc cagctgcacc agcagctgag   2160
caacaccacc ggcaagctga tctggaccct ggacgccaac atcaacgccg acatcggcga   2220
gtgggccttc tgggagaaca agaagaacct gagcgagcag ctgaggggcg aggagctgag   2280
cttcgagacc ctgagcctga cgagaccga ggacgacgac gccaccagca gcaggaccac   2340
caagggcagg atcagcgaca gggccaccag gaagtacagc gacctggtgc caaggacag   2400 ccccggcatg gtgagcctgc acgtgcccga gggcgagacc accctgccca gccagaacag   2460
caccgagggc aggagggtgg acgtgaacac ccaggagacc atcaccgaga ccaccgccac   2520
catcatcggc accaacggca acaacatgca gatcagcacc atcggcaccg gcctgagcag   2580
cagccagatc ctgagcagca gccccaccat ggccctagc cccgagaccc agaccagcac   2640
cacctacacc cctaagctgc ccgtgatgac caccgaggag cccaccaccc ctcccagaa   2700 cagccccgga tccaccaccg aggcccctac cctgaccacc cctgagaaca tcaccaccgc   2760
cgtgaagacc gtgtgggccc aggagagcac cagcaacgcc tgatcacca gcaccgtgac   2820 cggcatcctg ggcagcctgg gcctgaggaa gaggagcagg aggcaggtga acaccagggc   2880
```

-continued

```
caccggcaag tgcaaccca acctgcacta ctggaccgcc caggagcagc acaacgccgc    2940
cggcatcgcc tggattccct acttcggccc cggcgccgag ggcatctaca ccgagggcct    3000
gatgcacaac cagaacgccc tggtgtgcgg cctgaggcag ctggccaacg agaccaccca    3060
ggccctgcag ctgttcctga gggccaccac cgagctgagg acctacacca tcctgaacag    3120
gaaggccatc gacttcctgc tgaggaggtg gggcggcacc tgcaggattc tgggccccga    3180
ctgctgcatc gagccccacg actggaccaa gaacatcacc gacaagatca accagatcat    3240
ccacgacttc atcgacaacc ctctgcccaa ccaggacaac gacgacaact ggtggaccgg    3300
ctgaacacgt ggaattcaga tctgctgtgc cttctagttg ccagccatct gttgtttgcc    3360
cctcccccgt gccttccttg accctggaag gtgccactcc cactgtcctt tcctaataaa    3420
atgaggaaat tgcatcgcat tgtctgagta ggtgtcattc tattctgggg ggtggggtgg    3480
ggcaggacag caaggggag gattgggaag acaatagcag gcatgctggg gatgcggtgg    3540
gctctatggg tacccaggtg ctgaagaatt gacccggttc ctcctgggcc agaaagaagc    3600
aggcacatcc ccttctctgt gacacaccct gtccacgccc ctggttctta gttccagccc    3660
cactcatagg acactcatag ctcaggaggg ctccgccttc aatcccaccc gctaaagtac    3720
ttggagcggt ctctccctcc ctcatcagcc caccaaacca aacctagcct caagagtgg    3780
gaagaaatta aagcaagata ggctattaag tgcagaggga gagaaaatgc ctccaacatg    3840
tgaggaagta atgagagaaa tcatagaatt ttaaggccat catggcctta atcttccgct    3900
tcctcgctca ctgactcgct gcgctcggtc gttcggctgc ggcgagcggt atcagctcac    3960
tcaaaggcgg taatacggtt atccacagaa tcagggata acgcaggaaa gaacatgtga    4020
gcaaaaggcc agcaaaaggc caggaaccgt aaaaaggccg cgttgctggc gtttttccat    4080
aggctccgcc cccctgacga gcatcacaaa aatcgacgct caagtcagag gtggcgaaac    4140
ccgacaggac tataaagata ccaggcgttt ccccctggaa gctccctcgt gcgctctcct    4200
gttccgaccc tgccgcttac cggatacctg tccgcctttc tcccttcggg aagcgtggcg    4260
ctttctcata gctcacgctg taggtatctc agttcggtgt aggtcgttcg ctccaagctg    4320
ggctgtgtgc acgaaccccc cgttcagccc gaccgctgcg ccttatccgg taactatcgt    4380
cttgagtcca acccggtaag acacgactta tcgccactgg cagcagccac tggtaacagg    4440
attagcagag cgaggtatgt aggcggtgct acagagttct tgaagtggtg gcctaactac    4500
ggctacacta gaagaacagt atttggtatc tgcgctctgc tgaagccagt taccttcgga    4560
aaaagagttg gtagctcttg atccggcaaa caaaccaccg ctggtagcgg tggtttttt    4620
gtttgcaagc agcagattac gcgcagaaaa aaaggatctc aagaagatcc tttgatcttt    4680
tctacggggt ctgacgctca gtggaacgaa aactcacgtt aagggatttt ggtcatgaga    4740
ttatcaaaaa ggatcttcac ctagatcctt ttaaattaaa aatgaagttt taaatcaatc    4800
taaagtatat atgagtaaac ttggtctgac agttaccaat gcttaatcag tgaggcacct    4860
atctcagcga tctgtctatt tcgttcatcc atagttgcct gactcggggg ggggggcgc    4920
tgaggtctgc ctcgtgaaga aggtgttgct gactcatacc aggcctgaat cgccccatca    4980
tccagccaga aagtgaggga gccacggttg atgagagctt tgttgtaggt ggaccagttg    5040
gtgattttga acttttgctt tgccacgaag cggtctgcgt tgtcgggaag atgcgtgatc    5100
tgatccttca actcagcaaa agttcgattt attcaacaaa gccgccgtcc cgtcaagtca    5160
gcgtaatgct ctgccagtgt tacaaccaat taaccaattc tgattagaaa aactcatcga    5220
gcatcaaatg aaactgcaat ttattcatat caggattatc aataccatat ttttgaaaaa    5280
```

```
gccgtttctg taatgaagga gaaaactcac cgaggcagtt ccataggatg gcaagatcct   5340
ggtatcggtc tgcgattccg actcgtccaa catcaataca acctattaat ttcccctcgt   5400
caaaaataag gttatcaagt gagaaatcac catgagtgac gactgaatcc ggtgagaatg   5460
gcaaaagctt atgcatttct ttccagactt gttcaacagg ccagccatta cgctcgtcat   5520
caaaatcact cgcatcaacc aaaccgttat tcattcgtga ttgcgcctga gcgagacgaa   5580
atacgcgatc gctgttaaaa ggacaattac aaacaggaat cgaatgcaac cggcgcagga   5640
acactgccag cgcatcaaca atattttcac ctgaatcagg atattcttct aatacctgga   5700
atgctgtttt cccggggatc gcagtggtga gtaaccatgc atcatcagga gtacggataa   5760
aatgcttgat ggtcggaaga ggcataaatt ccgtcagcca gtttagtctg accatctcat   5820
ctgtaacatc attggcaacg ctacctttgc catgtttcag aaacaactct ggcgcatcgg   5880
gcttcccata caatcgatag attgtcgcac ctgattgccc gacattatcg cgagcccatt   5940
tatacccata taaatcagca tccatgttgg aatttaatcg cggcctcgag caagacgttt   6000
cccgttgaat atggctcata acaccccttg tattactgtt tatgtaagca gacagtttta   6060
ttgttcatga tgatatattt ttatcttgtg caatgtaaca tcagagattt tgagacacaa   6120
cgtggctttc cccccccccc cattattgaa gcatttatca gggttattgt ctcatgagcg   6180
gatacatatt tgaatgtatt tagaaaaata aacaaatagg ggttccgcgc acatttcccc   6240
gaaaagtgcc acctgacgtc taagaaacca ttattatcat gacattaacc tataaaaata   6300
ggcgtatcac gaggcccttt cgtc                                          6324
```

```

<210> SEQ ID NO 41
<211> LENGTH: 6236
<212> TYPE: DNA
<213> ORGANISM: Artificial Sequence
<220> FEATURE:
<223> OTHER INFORMATION: Synthetic Construct pVR1012x/s Lassa (codon
      optimized)

<400> SEQUENCE: 41
```

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
```

```
tagaagacac cgggaccgat ccagcctccg cggccgggaa cggtgcattg gaacgcggat    1020
tccccgtgcc aagagtgacg taagtaccgc ctatagactc tataggcaca ccccctttggc   1080 tcttatgcat gctatactgt ttttggcttg gggcctatac accccgctt ccttatgcta     1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt ccccgtgcc    1380 cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtctttc     1860 tgcagtcacc gtcgtcgaca cgtgtgatca gatatcgcgg ccgctctaga gatatcgccg    1920
ccatgggcca gatcgtgacc ttcttccagg aggtgcccca tgtgatcgag gaggtgatga    1980
acatcgtgct gatcgccctg agcgtgctgg ccgtgctgaa gggcctgtac aacttcgcca    2040
cctgcggcct ggtgggcctg gtgaccttcc tgctgctgtg cggcaggagc tgcaccacca    2100
gcctgtacaa gggcgtgtac gagctgcaga ccctggagct gaacatggag accctgaaca    2160
tgaccatgcc cctgagctgc accaagaaca acagccacca ctacatcatg gtgggcaacg    2220
agaccggcct ggagctaacc ctgaccaaca ccagcatcat caaccacaag ttctgcaacc    2280
tgagcgacgc ccacaagaag aacctgtacg accacgccct gatgagcatc atcagcacct    2340
tccacctgag catccccaac ttcaaccagt acgaggccat gagctgcgac ttcaacggcg    2400
gcaagatcag cgtgcagtac aacctgagcc acagctacgc cggcgacgcc gccaaccact    2460
gcggcaccgt ggccaacggc gtgctgcaga ccttcatgag gatggcctgg ggcggcagct    2520
acatcgccct ggacagcggc aggggcaact gggactgcat catgaccagc taccagtacc    2580
tgatcatcca gaacaccacc tgggaggacc actgccagtt cagcaggccc agccccatcg    2640
gctacctggg cctgctgagc cagaggacca gggacatcta catcagcagg aggctgctgg    2700
gcaccttcac ctggaccctg agcgacagcg agggcaagga cacccggc ggctactgcc      2760 tgaccaggtg gatgctgatc gaggccgagc tgaagtgctt cggcaacacc gccgtggcca    2820
agtgcaacga gaagcacgac gaggagttct gcgacatgct gaggctgttc gacttcaaca    2880
agcaggccat ccagaggctg aaggccgagg cccagatgag catccagctg atcaacaagg    2940
ccgtgaacgc cctgatcaac gaccagctga tcatgaagaa ccacctgagg gacatcatgg    3000
gcatccccta ctgcaactac agcaagtact ggtacctgaa ccacaccacc accgcagga    3060 ccagcctgcc caagtgctgg ctggtgagca acggcagcta cctgaacgag acccacttca    3120
gcgacgacat cgagcagcag gccgacaaca tgatcaccga gatgctgcag aaggagtaca    3180
tggagaggca gggcaagacc tgaacacgtg ggatccagat ctgctgtgcc ttctagttgc    3240
cagccatctt ttgtttgccc ctcccccgtg ccttccttga ccctggaagg tgccactccc    3300
actgtccttt cctaataaaa tgaggaaatt gcatcgcatt gtctgagtag gtgtcattct    3360
```

```
attctggggg gtggggtggg gcaggacagc aaggggggagg attgggaagaa caatagcagg    3420 catgctgggg atgcggtggg ctctatgggt acccaggtgc tgaagaattg acccggttcc    3480
tcctgggcca gaaagaagca ggcacatccc cttctctgtg acacaccctg tccacgcccc    3540
tggttcttag ttccagcccc actcatagga cactcatagc tcaggagggc tccgccttca    3600
atcccacccg ctaaagtact tggagcggtc tctccctccc tcatcagccc accaaaccaa    3660
acctagcctc caagagtggg aagaaattaa agcaagatag gctattaagt gcagagggag    3720
agaaaatgcc tccaacatgt gaggaagtaa tgagagaaat catagaattt taaggccatg    3780
atttaaggcc atcatggcct taatcttccg cttcctcgct cactgactcg ctgcgctcgg    3840
tcgttcggct gcggcgagcg gtatcagctc actcaaaggc ggtaatacgg ttatccacag    3900
aatcagggga taacgcagga agaacatgt gagcaaaagg ccagcaaaag gccaggaacc    3960
gtaaaaaggc cgcgttgctg gcgttttttcc ataggctccg ccccctgac gagcatcaca    4020 aaaatcgacg ctcaagtcag aggtggcgaa acccgacagg actataaaga taccaggcgt    4080
ttccccctgg aagctccctc gtgcgctctc ctgttccgac cctgccgctt accggatacc    4140
tgtccgcctt tctcccttcg ggaagcgtgg cgctttctca tagctcacgc tgtaggtatc    4200
tcagttcggt gtaggtcgtt cgctccaagc tgggctgtgt gcacgaaccc cccgttcagc    4260
ccgaccgctg cgccttatcc ggtaactatc gtcttgagtc aacccggta agacacgact    4320 tatcgccact ggcagcagcc actggtaaca ggattagcag agcgaggtat gtaggcggtg    4380
ctacagagtt cttgaagtgg tggcctaact acgctacac tagaagaaca gtatttggta    4440
tctgcgctct gctgaagcca gttaccttcg gaaaaagagt tggtagctct tgatccggca    4500
aacaaaccac cgctggtagc ggtggttttt ttgtttgcaa gcagcagatt acgcgcagaa    4560
aaaaaggatc tcaagaagat cctttgatct tttctacggg gtctgacgct cagtggaacg    4620
aaaactcacg ttaagggatt ttggtcatga gattatcaaa aaggatcttc acctagatcc    4680
ttttaaatta aaaatgaagt tttaaatcaa tctaaagtat atatgagtaa acttggtctg    4740
acagttacca atgcttaatc agtgaggcac ctatctcagc gatctgtcta tttcgttcat    4800
ccatagttgc ctgactcggg ggggggggc gctgaggtct gcctcgtgaa gaaggtgttg    4860
ctgactcata ccaggcctga atcgccccat catccagcca gaaagtgagg gagccacggt    4920
tgatgagagc tttgttgtag gtggaccagt tggtgatttt gaactttgc tttgccacgg    4980 aacggtctgc gttgtcggga agatgcgtga tctgatcctt caactcagca aaagttcgat    5040
ttattcaaca aagccgccgt cccgtcaagt cagcgtaatg ctctgccagt gttacaacca    5100
attaaccaat tctgattaga aaaactcatc gagcatcaaa tgaaactgca atttattcat    5160
atcaggatta tcaataccat attttttgaaa agccgtttc tgtaatgaag gagaaaactc    5220
accgaggcag ttccatagga tgcaagatc ctggtatcgg tctgcgattc cgactcgtcc    5280
aacatcaata caacctatta atttcccctc gtcaaaaata aggttatcaa gtgagaaatc    5340
accatgagtg acgactgaat ccggtgagaa tggcaaaagc ttatgcattt ctttccagac    5400
ttgttcaaca ggccagccat tacgctcgtc atcaaaatca ctcgcatcaa ccaaaccgtt    5460
attcattcgt gattgcgcct gagcgagacg aaatacgcga tcgctgttaa aaggacaatt    5520
acaaacagga atcgaatgca accggcgcag gaacactgcc agcgcatcaa caatattttc    5580
acctgaatca ggatattctt ctaataccct gaatgctgtt ttcccgggga tcgcagtggt    5640
gagtaaccat gcatcatcag gagtacggat aaaatgcttg atggtcggaa gaggcataaa    5700
ttccgtcagc cagtttagtc tgaccatctc atctgtaaca tcattggcaa cgctacctt    5760
```

-continued

```
gccatgtttc agaaacaact ctggcgcatc gggcttccca tacaatcgat agattgtcgc    5820
acctgattgc ccgacattat cgcgagccca tttatcccca tataaatcag catccatgtt    5880
ggaatttaat cgcggcctcg agcaagacgt ttcccgttga atatggctca taacacccct    5940
tgtattactg tttatgtaag cagacagttt tattgttcat gatgatatat ttttatcttg    6000
tgcaatgtaa catcagagat tttgagacac aacgtggctt tccccccccc cccattattg    6060
aagcatttat cagggttatt gtctcatgag cggatacata tttgaatgta tttagaaaaa    6120
taaacaaata ggggttccgc gcacatttcc ccgaaaagtg ccacctgacg tctaagaaac    6180
cattattatc atgacattaa cctataaaaa taggcgtatc acgaggccct ttcgtc        6236
```

<210> SEQ ID NO 42
<211> LENGTH: 6902
<212> TYPE: DNA
<213> ORGANISM: Artificial Sequence
<220> FEATURE:
<223> OTHER INFORMATION: Synthetic Construct pVR1012x/s Marburg (codon optimized)

<400> SEQUENCE: 42

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac accccgcctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttttaca   1320
ggatggggtc ccatttatta tttacaaatt cacatataca acaacgccgt ccccgtgcc    1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
```

```
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga gatatcgccg    1920
ccatgaagac cacctgcctg ttcatcagcc tgatcctgat ccagggcatc aagaccctgc    1980
ccatcctgga gatcgccagc aacaaccagc cccagaacgt ggacagcgtg tgcagcggca    2040
ccctgcagaa gaccgaggac gtgcacctga tgggcttcac cctgagcggc cagaaggtgg    2100
ccgacagccc tctggaggcc agcaagaggt gggccttcag gaccggcgtg cccccaaga    2160 acgtggagta caccgagggc gaggaggcca agacctgcta caacatcagc gtgaccgacc    2220
ccagcggcaa gagcctgctg ctggaccctc ccaccaacat cagggactac cctaagtgca    2280
agaccatcca ccacatccag ggccagaacc ctcacgccca gggcatcgcc ctgcacctgt    2340
ggggcgcctt cttcctgtac gacaggatcg ccagcaccac catgtacagg ggcagggtgt    2400
tcaccgaggg caacatcgcc gccatgatcg ttaacaagac cgtgcacaag atgatcttca    2460
gcaggcaggg ccagggctac aggcacatga acctgaccag caccaacaag tactggacca    2520
gcaacaacgg cacccagacc aacgacaccg gctgcttcgg cgccctgcag gagtacaaca    2580
gcaccaagaa ccagacctgc gcccccagca agatccccag cccctgcccc accgccaggc    2640
ccgagatcaa gcccaccagc accccaccg acgccaccac cctgaacacc accgacccca    2700
acaacgacga cgaggacctg atcaccagcg gcagcggcag cggcgagcag gagccctaca    2760
ccaccagcga cgccgtgacc aagcagggcc tgagcagcac catgcctcct ccccctagcc    2820
ctcagcccag caccctcag caggagggca acaacaccga ccacagccag ggcaccgtga    2880
ccgagcccaa caagaccaac accaccgccc agcccagcat gcctcctcac aacaccaccg    2940
ccatcagcac caacaacacc agcaagaaca acttcagcac cctgagcgtg agcctgcaga    3000
acaccaccaa ctacgacacc cagagcaccg ccaccgagaa cgagcagacc agcgcccct    3060 gcaagaccac cctgcctccc accggcaacc tgaccaccgc caagagcacc aacaacacca    3120 agggcccca ccaccgcc cctaacatga ccaacggcca cctgaccagc cccagcccca    3180 ccccaaccc caccacccag cacctggtgt acttcaggaa gaagaggagc atcctgtgga    3240
gggagggcga tatgttcccc ttcctggacg gcctgatcaa cgcccctatc gacttcgacc    3300
ccgtgcccaa caccaagacc atcttcgacg agagcagcag cagcggcgcc agcgccgagg    3360
aggaccagca cgccagcccc aacatcagcc tgacccctga gctacttcccc aacatcaacg    3420 agaacaccgc ctacagcggc gagaacgaga acgactgcga cgccgagctg aggatctgga    3480
gcgtgcagga ggacgacctg gccgccggcc tgagctggat cccttcttc ggccccggca    3540 tcgagggcct gtacaccgcc ggcctgatca gaaccagaa caacctggtg tgcaggctga    3600
ggaggctggc caaccagacc gccaagagcc tggagctgct gctgagggtg accaccgagg    3660
agaggacctt cagcctgatc aacaggcacg ccatcgactt cctgctgacc aggtggggcg    3720
gcacctgcaa ggtgctgggc cccgactgct gcatcggcat cgaggacctg agcaggaaca    3780
tcagcgagca gatcgaccag atcaagaagg acgagcagaa ggagggcacc ggctgggcc    3840 tgggcggcaa gtggtggacc agcgactgaa cacgtgggat ccagatctgc tgtgccttct    3900
agttgccagc catctgttgt ttgccccctcc ccgtgccctt ccttgaccct ggaaggtgcc    3960
actcccactg tccttttccta ataaaatgag gaaattgcat cgcattgtct gagtaggtgt    4020
```

```
cattctattc tgggggggtgg ggtggggcag gacagcaagg gggaggattg ggaagacaat    4080
agcaggcatg ctggggatgc ggtgggctct atgggtaccc aggtgctgaa gaattgaccc    4140
ggttcctcct gggccagaaa gaagcaggca catcccttc tctgtgacac accctgtcca    4200
cgcccctggt tcttagttcc agccccactc ataggacact catagctcag gagggctccg    4260
ccttcaatcc cacccgctaa agtacttgga gcggtctctc cctccctcat cagcccacca    4320
aaccaaacct agcctccaag agtgggaaga aattaaagca agataggcta ttaagtgcag    4380
agggagagaa aatgcctcca acatgtgagg aagtaatgag agaaatcata gaattttaag    4440
gccatgattt aaggccatca tggccttaat cttccgcttc ctcgctcact gactcgctgc    4500
gctcggtcgt tcggctgcgg cgagcggtat cagctcactc aaaggcggta atacggttat    4560
ccacagaatc agggggataac gcaggaaaga acatgtgagc aaaaggccag caaaaggcca    4620
ggaaccgtaa aaaggccgcg ttgctggcgt ttttccatag gctccgcccc cctgacgagc    4680
atcacaaaaa tcgacgctca agtcagaggt ggcgaaaccc gacaggacta taaagatacc    4740
aggcgtttcc ccctggaagc tccctcgtgc gctctcctgt tccgaccctg ccgcttaccg    4800
gatacctgtc cgcctttctc ccttcgggaa gcgtggcgct ttctcatagc tcacgctgta    4860
ggtatctcag ttcggtgtag gtcgttcgct ccaagctggg ctgtgtgcac gaaccccccg    4920
ttcagcccga ccgctgcgcc ttatccggta actatcgtct tgagtccaac ccggtaagac    4980
acgacttatc gccactggca gcagccactg gtaacaggat tagcagagcg aggtatgtag    5040
gcggtgctac agagttcttg aagtggtggc ctaactacgg ctacactaga agaacagtat    5100
ttggtatctg cgctctgctg aagccagtta ccttcggaaa aagagttggt agctcttgat    5160
ccggcaaaca aaccaccgct ggtagcggtg gtttttttgt ttgcaagcag cagattacgc    5220
gcagaaaaaa aggatctcaa gaagatcctt tgatcttttc tacggggtct gacgctcagt    5280
ggaacgaaaa ctcacgttaa gggattttgg tcatgagatt atcaaaaagg atcttcacct    5340
agatcctttt aaattaaaaa tgaagtttta atcaatcta aagtatatat gagtaaactt    5400
ggtctgacag ttaccaatgc ttaatcagtg aggcacctat ctcagcgatc tgtctatttc    5460
gttcatccat agttgcctga ctcggggggg ggggggcgctg aggtctgcct cgtgaagaag    5520
gtgttgctga ctcataccag gcctgaatcg ccccatcatc cagccagaaa gtgagggagc    5580
cacggttgat gagagctttg ttgtaggtgg accagttggt gattttgaac ttttgctttg    5640
ccacggaacg gtctgcgttg tcgggaagat gcgtgatctg atccttcaac tcagcaaaag    5700
ttcgatttat tcaacaaagc cgccgtcccg tcaagtcagc gtaatgctct gccagtgtta    5760
caaccaatta accaattctg attagaaaaa ctcatcgagc atcaaatgaa actgcaattt    5820
attcatatca ggattatcaa taccatattt ttgaaaaagc cgtttctgta atgaaggaga    5880
aaactcaccg aggcagttcc ataggatggc aagatcctgg tatcggtctg cgattccgac    5940
tcgtccaaca tcaatacaac ctattaattt cccctcgtca aaataaggt tatcaagtga    6000 gaaatcacca tgagtgacga ctgaatccgg tgagaatggc aaaagcttat gcatttcttt    6060
ccagacttgt tcaacaggcc agccattacg ctcgtcatca aaatcactcg catcaaccaa    6120
accgttattc attcgtgatt gcgcctgagc gagacgaaat acgcgatcgc tgttaaaagg    6180
acaattacaa acaggaatcg aatgcaaccg gcgcaggaac actgccagcg catcaacaat    6240
attttcacct gaatcaggat attcttctaa tacctggaat gctgttttcc cggggatcgc    6300
agtggtgagt aaccatgcat catcaggagt acggataaaa tgcttgatgg tcggaagagg    6360
cataaattcc gtcagccagt ttagtctgac catctcatct gtaacatcat tggcaacgct    6420
```

-continued

| | |
|---|---|
| acctttgcca tgtttcagaa acaactctgg cgcatcgggc ttcccataca atcgatagat | 6480 |
| tgtcgcacct gattgcccga cattatcgcg agcccattta tacccatata atcagcatc | 6540 |
| catgttggaa tttaatcgcg gcctcgagca agacgtttcc cgttgaatat ggctcataac | 6600 |
| accccttgta ttactgttta tgtaagcaga cagtttatt gttcatgatg atatattttt | 6660 |
| atcttgtgca atgtaacatc agagattttg agacacaacg tggctttccc cccccccca | 6720 |
| ttattgaagc atttatcagg gttattgtct catgagcgga tacatatttg aatgtattta | 6780 |
| gaaaaataaa caatagggg ttccgcgcac atttccccga aaagtgccac ctgacgtcta | 6840 |
| agaaaccatt attatcatga cattaaccta taaaaatagg cgtatcacga ggccctttcg | 6900 |
| tc | 6902 |

<210> SEQ ID NO 43
<211> LENGTH: 6625
<212> TYPE: DNA
<213> ORGANISM: Artificial Sequence
<220> FEATURE:
<223> OTHER INFORMATION: Synthetic Construct CMV/R Ebola NP

<400> SEQUENCE: 43

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca cgacccccg cccattgacg tcaataatga cgtatgttcc | 480 |
| catagtaacg ccaatagga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccttacct gaggccgcca tccacgccgg ttgagtcgcg ttctgccgcc tcccgcctgt | 1080 |
| ggtgcctcct gaactacgtc cgccgtctag gtaagtttag agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg gagggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacac gtgtgatcag atatcgcggc cgctctagac | 1380 |
| caggccctgg atccagatcg atccgagtat ggattctcgt cctcagaaaa tctggatggc | 1440 |
| gccgagtctc actgaatctg acatggatta ccacaagatc ttgacagcag gtctgtccgt | 1500 |
| tcaacagggg attgttcggc aaagagtcat cccagtgtat caagtaaaca atcttgaaga | 1560 |

```
aatttgccaa cttatcatac aggcctttga agcaggtgtt gattttcaag agagtgcgga    1620
cagtttcctt ctcatgcttt gtcttcatca tgcgtaccag ggagattaca aacttttctt    1680
ggaaagtggc gcagtcaagt atttggaagg cacgggttc cgttttgaag tcaagaagcg     1740
tgatggagtg aagcgccttg aggaattgct gccagcagta tctagtggaa aaacattaa    1800 gagaacactt gctgccatgc cggaagagga acaactgaa gctaatgccg gtcagtttct    1860
ctcctttgca agtctattcc ttccgaaatt ggtagtagga gaaaaggctt gccttgagaa    1920
ggttcaaagg caaattcaag tacatgcaga gcaaggactg atacaatatc aacagcttg    1980 gcaatcagta ggacacatga tggtgatttt ccgtttgatg cgaacaaatt ttctgatcaa    2040
atttctccta atacaccaag ggatgcacat ggttgccggg catgatgcca acgatgctgt    2100
gatttcaaat tcagtggctc aagctcgttt ttcaggctta ttgattgtca aaacagtact    2160
tgatcatatc ctacaaaaga cagaacgagg agttcgtctc catcctcttg caaggaccgc    2220
caaggtaaaa aatgaggtga actcctttaa ggctgcactc agctccctgg ccaagcatgg    2280
agagtatgct cctttcgccc gactttgaa ccttctgga gtaaataatc ttgagcatgg      2340 tctttccct caactatcgg caattgcact cggagtcgcc acagcacacg ggagtaccct    2400
cgcaggagta aatgttggag aacagtatca acaactcaga gaggctgcca ctgaggctga    2460
gaagcaactc caacaatatg cagagtctcg cgaacttgac catcttggac ttgatgatca    2520
ggaaaagaaa attcttatga acttccatca gaaaaagaac gaaatcagct ccagcaaac    2580 aaacgctatg gtaactctaa gaaaagagcg cctggccaag ctgacagaag ctatcactgc    2640
tgcgtcactg cccaaaacaa gtggacatta cgatgatgat gacgacatc cctttccagg    2700 acccatcaat gatgacgaca atcctggcca tcaagatgat gatccgactg actcacagga    2760
tacgaccatt cccgatgtgg tggttgatcc cgatgatgga agctacggcg aataccagag    2820
ttactcggaa aacggcatga atgcaccaga tgacttggtc ctattcgatc tagacgagga    2880
cgacgaggac actaagccag tgcctaatag atcgaccaag ggtggacaac agaagaacag    2940
tcaaaagggc cagcatatag agggcagaca gacacaatcc aggccaattc aaaatgtccc    3000
aggccctcac agaacaatcc accacgccag tgcgccactc acggacaatg acagaagaaa    3060
tgaaccctcc ggctcaacca gccctcgcat gctgacacca attaacgaag aggcagaccc    3120
actggacgat gccgacgacg agacgtctag ccttccgccc ttggagtcag atgatgaaga    3180
gcaggacagg gacggaactt ccaaccgcac acccactgtc gccccaccgg ctcccgtata    3240
cagagatcac tctgaaaaga aagaactccc gcaagacgag caacaagatc aggaccacac    3300
tcaagaggcc aggaaccagg acagtgacaa cacccagtca gaacactctt ttgaggagat    3360
gtatcgccac attctaagat cacagggcc atttgatgct gttttgtatt atcatatgat    3420
gaaggatgag cctgtagttt tcagtaccag tgatggcaaa gagtacacgt atccagactc    3480
ccttgaagag gaatatccac catggctcac tgaaaaagag gctatgaatg aagagaatag    3540
atttgttaca ttggatggtc aacaatttta ttggccggtg atgaatcaca agaataaatt    3600
catggcaatc ctgcaacatc atcagctgtg ccttctagtt gccagccatc tgttgtttgc    3660 ccctccccg tgccttcctt gaccctggaa ggtgccactc ccactgtcct ttcctaataa    3720
aatgaggaaa ttgcatcgca ttgtctgagt aggtgtcatt ctattctggg gggtggggtg    3780
gggcaggaca gcaagggga ggattgggaa gacaatagca ggcatgctgg ggatgcggtg    3840
ggctctatgg gtacccaggt gctgaagaat tgacccggtt cctcctgggc agaaagaag    3900 caggcacatc cccttctctg tgacacaccc tgtccacgcc cctggttctt agttccagcc    3960
```

```
ccactcatag gacactcata gctcaggagg gctccgcctt caatcccacc cgctaaagta   4020
cttggagcgg tctctccctc cctcatcagc ccaccaaacc aaacctagcc tccaagagtg   4080
ggaagaaatt aaagcaagat aggctattaa gtgcagaggg agagaaaatg cctccaacat   4140
gtgaggaagt aatgagagaa atcatagaat tttaaggcca tcatggcctt aatcttccgc   4200
ttcctcgctc actgactcgc tgcgctcggt cgttcggctg cggcgagcgg tatcagctca   4260
ctcaaaggcg gtaatacggt tatccacaga atcagggggat aacgcaggaa agaacatgtg   4320
agcaaaaggc cagcaaaagg ccaggaaccg taaaaaggcc gcgttgctgg cgttttccca   4380
taggctccgc cccctgacg agcatcacaa aaatcgacgc tcaagtcaga ggtggcgaaa   4440
cccgacagga ctataaagat accaggcgtt tccccctgga agctccctcg tgcgctctcc   4500
tgttccgacc ctgccgctta ccggatacct gtccgccttt ctcccttcgg gaagcgtggc   4560
gctttctcat agctcacgct gtaggtatct cagttcggtg taggtcgttc gctccaagct   4620
gggctgtgtg cacgaacccc ccgttcagcc cgaccgctgc gccttatccg gtaactatcg   4680
tcttgagtcc aacccggtaa gacacgactt atcgccactg gcagcagcca ctggtaacag   4740
gattagcaga gcgaggtatg taggcggtgc tacagagttc ttgaagtggt ggcctaacta   4800
cggctacact agaagaacag tatttggtat ctgcgctctg ctgaagccag ttaccttcgg   4860
aaaaagagtt ggtagctctt gatccggcaa acaaaccacc gctggtagcg gtggtttttt   4920
tgtttgcaag cagcagatta cgcgcagaaa aaaaggatct caagaagatc ctttgatctt   4980
ttctacgggg tctgacgctc agtggaacga aaactcacgt taagggattt tggtcatgag   5040
attatcaaaa aggatcttca cctagatcct tttaaattaa aaatgaagtt ttaaatcaat   5100
ctaaagtata tatgagtaaa cttggtctga cagttaccaa tgcttaatca gtgaggcacc   5160
tatctcagcg atctgtctat ttcgttcatc catagttgcc tgactcgggg ggggggggcg   5220
ctgaggtctg cctcgtgaag aaggtgttgc tgactcatac caggcctgaa tcgccccatc   5280
atccagccag aaagtgaggg agccacggtt gatgagagct ttgttgtagg tggaccagtt   5340
ggtgattttg aacttttgct ttgccacgga acggtctgcg ttgtcgggaa gatgcgtgat   5400
ctgatccttc aactcagcaa aagttcgatt tattcaacaa agccgccgtc ccgtcaagtc   5460
agcgtaatgc tctgccagtg ttacaaccaa ttaaccaatt ctgattagaa aaactcatcg   5520
agcatcaaat gaaactgcaa tttattcata tcaggattat caataccata ttttttgaaaa   5580 agccgtttct gtaatgaagg agaaaactca ccgaggcagt tccataggat ggcaagatcc   5640
tggtatcggt ctgcgattcc gactcgtcca acatcaatac aacctattaa tttcccctcg   5700
tcaaaaataa ggttatcaag tgagaaatca ccatgagtga cgactgaatc cggtgagaat   5760
ggcaaaagct tatgcatttc tttccagact tgttcaacag gccagccatt acgctcgtca   5820
tcaaaatcac tcgcatcaac caaaccgtta ttcattcgtg attgcgcctg agcgagacga   5880
aatacgcgat cgctgttaaa aggacaatta caaacaggaa tcgaatgcaa ccggcgcagg   5940
aacactgcca gcgcatcaac aatatttttca cctgaatcag gatattcttc taatacctgg   6000
aatgctgttt tcccggggat cgcagtggtg agtaaccatg catcatcagg agtacggata   6060
aaatgcttga tggtcggaag aggcataaat tccgtcagcc agtttagtct gaccatctca   6120
tctgtaacat cattggcaac gctacctttg ccatgtttca gaaacaactc tggcgcatcg   6180
ggcttcccat acaatcgata gattgtcgca cctgattgcc cgacattatc gcgagcccat   6240
ttatacccat ataaatcagc atccatgttg gaatttaatc gcggcctcga gcaagacgtt   6300
tcccgttgaa tatggctcat aacaccccttt gtattactgt ttatgtaagc agacagtttt   6360
```

-continued

```
attgttcatg atgatatatt tttatcttgt gcaatgtaac atcagagatt ttgagacaca    6420
acgtggcttt ccccccccc ccattattga agcatttatc agggttattg tctcatgagc    6480
ggatacatat ttgaatgtat ttagaaaaat aaacaaatag gggttccgcg cacatttccc    6540
cgaaaagtgc cacctgacgt ctaagaaacc attattatca tgacattaac ctataaaaat    6600
aggcgtatca cgaggccctt tcgtc                                         6625
```

<210> SEQ ID NO 44
<211> LENGTH: 22
<212> TYPE: DNA
<213> ORGANISM: Artificial Sequence
<220> FEATURE:
<223> OTHER INFORMATION: Ebola Sudan GP primer

<400> SEQUENCE: 44
atcttcagga tctcgccatg ga                                            22

<210> SEQ ID NO 45
<211> LENGTH: 24
<212> TYPE: DNA
<213> ORGANISM: Artificial Sequence
<220> FEATURE:
<223> OTHER INFORMATION: Ebola Sudan GP primer

<400> SEQUENCE: 45
gatattcaac aaagcagctt gcag                                          24

<210> SEQ ID NO 46
<211> LENGTH: 21
<212> TYPE: DNA
<213> ORGANISM: Artificial Sequence
<220> FEATURE:
<223> OTHER INFORMATION: Ebola Ivory Coast GP primer

<400> SEQUENCE: 46
ctaatcacag tcaccatggg a                                             21

<210> SEQ ID NO 47
<211> LENGTH: 24
<212> TYPE: DNA
<213> ORGANISM: Artificial Sequence
<220> FEATURE:
<223> OTHER INFORMATION: Ebola Ivory Coast GP primer

<400> SEQUENCE: 47
aaagtatgat gctatattag ttca                                          24

<210> SEQ ID NO 48
<211> LENGTH: 10
<212> TYPE: PRT
<213> ORGANISM: Ebola Virus

<400> SEQUENCE: 48

Gln Arg Thr Phe Ser Ile Pro Leu Gly Val
 1               5                  10

<210> SEQ ID NO 49
<211> LENGTH: 10
<212> TYPE: PRT
<213> ORGANISM: Ebola Virus

<400> SEQUENCE: 49

Arg Arg Thr Arg Arg Glu Ala Ile Val Asn
 1               5                  10

<210> SEQ ID NO 50
<211> LENGTH: 16
<212> TYPE: PRT
<213> ORGANISM: Ebola Virus

<400> SEQUENCE: 50

Gly Ala Ala Ile Gly Leu Ala Trp Ile Pro Tyr Phe Gly Pro Ala Ala
 1               5                  10                  15

<210> SEQ ID NO 51
<211> LENGTH: 5
<212> TYPE: PRT
<213> ORGANISM: Ebola Virus

<400> SEQUENCE: 51

Arg Arg Thr Arg Arg
 1               5

<210> SEQ ID NO 52
<211> LENGTH: 1087
<212> TYPE: DNA
<213> ORGANISM: Artificial Sequence
<220> FEATURE:
<223> OTHER INFORMATION: The CMV Enhancer/Promoter, R Region (HTVL-1),
      CMV IE Splicing Acceptor sequence

<400> SEQUENCE: 52
ccattgcata cgttgtatcc atatcataat atgtacattt atattggctc atgtccaaca      60
ttaccgccat gttgacattg attattgact agttattaat agtaatcaat tacgggtca     120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccacccat tgacgtcaat    540 gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc gtcagatcgc ctggagacgc catccacgct gttttgacct ccatagaaga    720
caccgggacc gatccagcct ccatcggctc gcatctctcc ttcacgcgcc cgccgcctta    780
cctgaggccg ccatccacgc cggttgagtc gcgttctgcc gcctcccgcc tgtggtgcct    840
cctgaactac gtccgccgtc taggtaagtt tagagctcag gtcgagaccg gcctttgtc    900 cggcgctccc ttggagccta cctagactca gccggctctc cacgctttgc ctgaccctgc    960
ttgctcaact ctagttaacg gtggagggca gtgtagtctg agcagtactc gttgctgccg   1020
cgcgcgccac cagacataat agctgacaga ctaacagact gttcctttcc atgggtcttt   1080
tctgcag                                                             1087